US011191822B2

(12) United States Patent
Seeberger et al.

(10) Patent No.: US 11,191,822 B2
(45) Date of Patent: Dec. 7, 2021

(54) PNEUMOCOCCAL POLYSACCHARIDE-PROTEIN CONJUGATE COMPOSITION

(71) Applicants: Max-Planck-Gesellschaft zur Förderung der Wissenschaften e.V., Munich (DE); Vaxxilon AG, Reinach (CH)

(72) Inventors: Peter H. Seeberger, Kleinmachnow (DE); Claney Lebev Pereira, Berlin (DE); Madhu Emmadi, Berlin (DE); Sharavathi Guddehalli Parameswarappa, Berlin (DE); Adam Calow, Bristol (GB); Petra Menova, Prague (CZ); Marilda Lisboa, Berlin (DE); Christopher Martin, Tuttlingen (DE); Benjamin Schumann, Berlin (DE); Fei-Fei Xu, Berlin (DE); Naeem Khan, Berlin-Britz (DE); Paulina Kaplonek, Berlin (DE); Lennart Lykke, Copenhagen (DK)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 16/312,189

(22) PCT Filed: Jun. 22, 2017

(86) PCT No.: PCT/EP2017/065469
§ 371 (c)(1),
(2) Date: Dec. 20, 2018

(87) PCT Pub. No.: WO2017/220753
PCT Pub. Date: Dec. 28, 2017

(65) Prior Publication Data
US 2019/0240309 A1 Aug. 8, 2019

Related U.S. Application Data

(63) Continuation of application No. PCT/EP2017/065469, filed on Jun. 22, 2017.

(30) Foreign Application Priority Data

Jun. 22, 2016 (EP) .................... 16175841
Jul. 12, 2016 (EP) .................... 16179133
Dec. 18, 2016 (EP) .................... 16204904

(51) Int. Cl.
*A61K 39/09* (2006.01)
*A61P 31/04* (2006.01)
*A61K 39/00* (2006.01)

(52) U.S. Cl.
CPC ............ *A61K 39/092* (2013.01); *A61P 31/04* (2018.01); *A61K 2039/55505* (2013.01); *A61K 2039/6037* (2013.01); *A61K 2039/62* (2013.01)

(58) Field of Classification Search
None
See application file for complete search history.

(56) References Cited

U.S. PATENT DOCUMENTS

| 5,057,540 A | 10/1991 | Kensil et al. |
| 5,614,382 A | 3/1997 | Metcalf |
| 5,769,047 A | 6/1998 | Zoche |
| 6,113,918 A | 9/2000 | Johnson et al. |
| 6,207,646 B1 | 3/2001 | Krieg et al. |
| 10,220,083 B2 * | 3/2019 | Seeberger .......... A61K 31/7028 |
| 2003/0147922 A1 * | 8/2003 | Capiau ................ A61K 39/092 424/244.1 |

FOREIGN PATENT DOCUMENTS

| EP | 0072513 A2 | 2/1983 |
| EP | 0161188 A2 | 11/1985 |
| EP | 0208375 A2 | 1/1987 |
| EP | 0477508 A1 | 4/1992 |
| EP | 0497524 A2 | 8/1992 |
| EP | 0497525 A2 | 8/1992 |
| EP | 0594610 B1 | 5/1994 |
| WO | WO 1990/014837 | 12/1990 |
| WO | WO 1991/018926 | 12/1991 |
| WO | WO 1992/019265 | 11/1992 |
| WO | WO 1993/013302 | 7/1993 |

(Continued)

OTHER PUBLICATIONS

Gruber et al. 2012 (Development of clinical evaluation of Prevnar 13, a 13-valent pneumococcal CRM197 conjugate vaccine; Annals of the New York Academy of Sciences 1263(1); (Year: 2012).*

(Continued)

*Primary Examiner* — Mary Maille Lyons
(74) *Attorney, Agent, or Firm* — Knobbe Martens Olson & Bear LLP

(57) ABSTRACT

The present invention relates to immunogenic compositions comprising a conjugate of a saccharide from *Streptococcus pneumoniae* serotype 8 and a carrier protein, and a mixture consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein, or a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14, and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid. Said compositions are useful for the prevention and/or treatment of diseases caused by *Streptococcus pneumoniae*.

18 Claims, 14 Drawing Sheets

(56) References Cited

FOREIGN PATENT DOCUMENTS

| WO | WO 1993/015760 | 8/1993 | | |
|---|---|---|---|---|
| WO | WO 1995/008348 | 3/1995 | | |
| WO | WO 1996/029094 | 9/1996 | | |
| WO | WO 1998/042721 | 10/1998 | | |
| WO | WO 2000/018434 | 4/2000 | | |
| WO | WO 2002/098368 | 12/2002 | | |
| WO | WO 2002/098369 | 12/2002 | | |
| WO | WO 2015/040140 | 3/2015 | | |
| WO | WO 2016/046420 | 3/2016 | | |
| WO | WO-2016046420 A1 * | 3/2016 | ............... | A61P 19/02 |

OTHER PUBLICATIONS

Grubner et al. 2012 (Development and clinical evaluation of Prevnar 13, a 13-valent pneumococcal CRM197 conjugate vaccine; Ann. NY Acad. Sci 1263: 15-26) (Year: 2012).*

Croxtall et al. 2009 (Pneumococcal Polysaccharide Protein D-Conjugate Vaccine (Synflorix; PHiD-CV) (Year: 2009).*

Plosker 2015 (13-Valent Pneumococcal Conjugate Vaccine: A Review of its Use in Adults; Drugs 75: 1535-1546). (Year: 2015).*

Scott et al. 1996 (Serogroup-Specific Epidemiology of *Streptococcus pneumoniae*: Associations with Age, Sex, and Geography in 7,000 Episodes of Invasive Disease; Clinical Infectious Diseases 22:973-981). (Year: 1996).*

Vanderkooi et al. 2011 (Community based outbreaks in Vulnerable Populations of Invasive Infections Caused by *Streptococcus pneumoniae* Serotypes 5 and 8 in Calgary Canada; PLoS One 6(12): e28547). (Year: 2011).*

De Vos 2015 (The Polysaccharide Capsule of *Streptococcus pneumonia* partially impedes MyD88-Mediated Immunity during Pneumonia in Mice; PLoS One; DOI:10.1371/journal.pone.0118181; pp. 1-12). (Year: 2015).*

Alonsodevelasco et al., "*Streptococcus pneumoniae*: Virulence Factors, Pathogenesis, and Vaccines" Microbiological Reviews (1995) 59(4):591-603.

Beshore, et al., "Preparation of Substituted Piperazinones via Tandem Reductive Amination-(N,N'-Acyl Transfer)-Cyclization" Org. Lett. (2002) 4(7):1201-1204.

Bourke et al., "The synthesis and biological evaluation of mycobacterial p-hydroxybenzoic acid derivatives (p-HBADs)" Org. Biomol. Chem. (2014) 12(7):1114-1123.

Bundle et al., "Design of a Candida albicans Disaccharide Conjugate Vaccine by Reverse Engineering a Protective Monoclonal Antibody," ACS Chem. Biol. (2012) 7:1754-1763 and Supplemental Materials.

Dagan et al., "Glycoconjugate vaccines and immune interference: A review" Vaccine (2010) 28(34):5513-5523.

Dhénin et al., "Sensitive and specific enzyme immunoassays for antigenic trisaccharide from *Bacillus anthracis* spores," Org. Biomol. Chem. (2009) 7:5184-5199.

Eller et al., "Automated Solid-Phase Synthesis of Chondroitin Sulfate Glycosaminoglycans" Angew. Chem. Int. Ed. (2013) 52(22):5858-5861.

Gruber et al., "Development and clinical evaluation of Prevnar 13, a 13-valent pneumococcal $CRM_{197}$ conjugate vaccine" Annals of the New York Academy at Sciences (2012) 1263(1):15-26.

Guan et al., "Study on Metal-Induced Reactions of α-Diazocarbonyl Glucosides," J. Org. Chem. (2012) 77:8888-8895.

Hoeprich P.D., "C14 Labelling of Diplococcus Pneumoniae" J. Bacteriology (1955) 69(6):682-688.

Hoeprich P.D. "Evaluation of an Improved Chemically Defined Medium for the Culture of *Diplococcus pneumonia*"J. Bacteriology (1957) 74(5):587-590.

Jones et al., "The Structure of the Type VIII Pneumococcus Specific Polysaccharide" J. Am. Chem. Soc. (1957) 79(11):2787-2793.

Kaeothip et al., "Glycosidation of Thioglycosides in the Presence of Bromine: Mechanism, Reactivity, and Stereoselectivity" J. Org. Chem. (2012) 77(1):291-299.

Lassaletta et al., "Silyl Group Migration in 1-O-Silyl Protected Sugars-Convenient Synthesis of 2-O-Unprotected Sugars" J. Carbohydrate Chemistry (1996) 15(2):241-254.

Mo et al., "Synthesis of the β-1,3-glucan, laminarahexaose: NMR and conformational studies" Carbohydrate Research (2009) 344(4):439-447.

Rajput et al., "Concise Synthesis of a Pentasaccharide Related to the Anti-Leishmanial Triterpenoid Saponin Isolated from Maesa balansae†," J. Org. Chem. (2008) 73:6924-6927.

Weishaupt et al., "Automated Solid-Phase Synthesis of a β-(1,3)-Glucan Dodecasaccharide" Chem. Eur. J. (2013) 19(37):12497-12503.

Yu et al., "An efficient method for the preparation of glycosides with a free C-2 hydroxyl group from thioglycosides" Tetrahedron Letters (2003) 44(52):9363-9366.

International Search Report and Written Opinion dated Aug. 31, 2017 for PCT Application No. PCT/EP2017/065469, filed Jun. 22, 2017.

International Preliminary Report on Patentability completed Oct. 9, 2018 for PCT Application No. PCT/EP2017/065469, filed Jun. 22, 2017.

\* cited by examiner

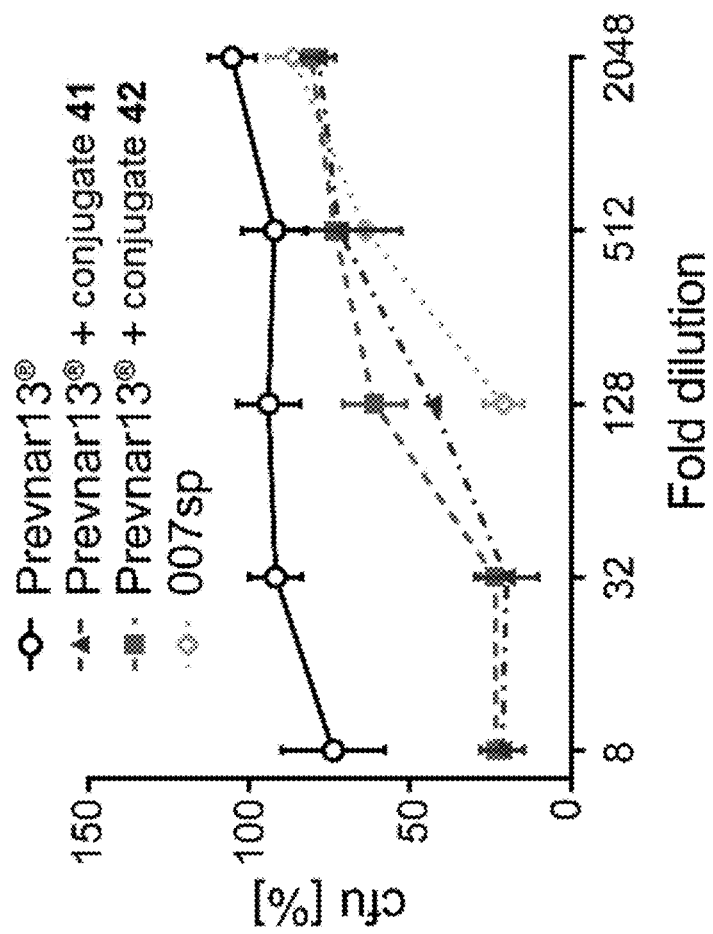

ST8

A

B

C

D

PNEUMOCOCCAL POLYSACCHARIDE-PROTEIN CONJUGATE COMPOSITION

FIELD OF THE INVENTION

The present invention relates to immunogenic compositions comprising a conjugate of a saccharide from *Streptococcus pneumoniae* serotype 8 and a carrier protein, and a mixture consisting of capsular polysaccharides from *Streptococcus pneumoniae* serotypes 1, 3, 4, 5, 6A, 6B, 7F, 9V, 14, 18C, 19A, 19F and 23F individually conjugated to CRM$_{197}$ carrier protein, or a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14, and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid. Said compositions are useful for the prevention and/or treatment of diseases caused by *Streptococcus pneumoniae*, including *Streptococcus pneumoniae* serotype 8.

BACKGROUND OF THE INVENTION

*Streptococcus pneumoniae* (*S. pneumoniae*) commonly known as pneumococci or diplococci is a human pathogenic Gram positive bacterium encapsulated with capsular polysaccharide. Based on the chemical nature of the polysaccharide capsule, pneumococci have been classified into more than 90 serotypes. Pneumococcus is a commensal bacterium that asymptomatically colonizes in the upper respiratory tract of human and is responsible for causing pneumonia, septicemia, meningitis and otitis media. Pneumococci is the most common cause of vaccine-preventable deaths in children aged <5 years and elderly peoples worldwide. Global estimates suggest that 18% of all deaths in children less than 5 years of age occur due to pneumonia.

Capsular polysaccharide is one of the major virulence factors responsible for pneumococcal pathogenesis. The spectrum of prevailing capsular types varies with age, time and geographical region, although common serotypes are consistently identified throughout the world. Globally, about 20 serotypes are associated with >80% of invasive pneumococcal disease occurring in all age groups; the 13 most common serotypes cause at least 70-75% of invasive disease in children. Pneumococcal vaccines that are currently available are capsular polysaccharide based and designed to cover the serotypes most frequently associated with invasive pneumococcal disease.

The available 23-valent polysaccharide vaccine (23-PPV) is not effective in children less than 2 years of age, while the 7-valent conjugate vaccines (7-PCV) is effective in children, but has limited serotype coverage.

To increase the serotype coverage, 10-valent conjugate vaccine containing the conjugates of the capsular polysaccharides from *S. pneumoniae* type 1, 4, 5, 6B, 7F, 9V, 14, 18C, 19F and 23F and protein D (a non-typeable *Haemophilus influenzae* protein), tetanus toxoid and diphtheria toxoid protein, and 13-valent conjugate vaccine containing the conjugates of capsular polysaccharides from *S. pneumoniae* type 1, 3, 4, 5, 6A, 6B, 7F, 9V, 14, 18C, 19A, 19F, and 23F and diphtheria CRM$_{197}$ protein have been licensed for use. The 13-valent conjugate vaccine provides comprehensive coverage for over 85% of epidemiologically important pneumococcal serotypes in the United States and throughout the world. In immunization experiments performed with this vaccine, both polysaccharide binding IgG and opsonophagocytic antibodies were elicited to each of the vaccine's 13 serotypes. The by far least-efficient serotype in the current pneumococcal conjugate vaccine is *Streptococcus pneumoniae* serotype 3 (ST3) (63.5% responders by antipolysaccharide IgG according to Table 2 in Gruber et al., ANNALS OF THE NEW YORK ACADEMY OF SCIENCES 2012, 1263, p. 15).

The international patent application WO2016046420A1 discloses synthetic saccharides derived from *S. pneumoniae* serotype 8 and the corresponding conjugates with carrier proteins. Further, the immune response raised in rabbits was evaluated with a synthetic tetrasaccharide and a synthetic hexasaccharide conjugated to the carrier protein CRM$_{197}$. All rabbits immunized with the conjugates showed a marked immune response against *S. pneumoniae* serotype 8 capsular polysaccharide.

The structure of the *S. pneumoniae* polysaccharide of serotype 8 was described by Jones et al. in J. Am. Chem. Soc. 1957, 79, p. 2787. The authors found out by acid hydrolysis that the *S. pneumoniae* polysaccharide of serotype 8 is a linear having a repeating unit of -β-D-GlcAp-(1→4)-β-D-Glcp-(1→4)-α-D-Glcp-(1→4)-α-D-Galp-(1→4)-.

The review Microbiological Rev. 1995, 59, p. 591 reports on *S. pneumoniae* virulence factors, pathogenesis and vaccines. Pneumococcal polysaccharide vaccines and pneumococcal saccharide-protein vaccines are described. Pneumococcal polysaccharide vaccines only elicit long-lasting antibodies and protection in healthy adults, while these vaccines are poorly immunogenic in children and elderly people. Pneumococcal saccharide-protein vaccines show an enhanced immunogenicity, which is assumed to be caused by the T-cell dependent antigen-character of the conjugate. Further, the immunogenicity of saccharide-protein conjugates depends on their structural characteristics, namely the saccharide length and terminal structures, the nature of the carrier protein, the ratio saccharide/protein and the coupling chemistry. Based on recent experimental results which support the fact that protection is also mediated by the removal of disintegrating pneumococci and their degradation products, the authors suggest that an effective conjugate vaccine should include the capsular polysaccharide and at least one inflammatory factor.

It is the objective of the present invention to provide an improved immunogenic composition comprising a mixture consisting of capsular polysaccharides from *Streptococcus pneumoniae* serotypes 1, 3, 4, 5, 6A, 6B, 7F, 9V, 14, 18C, 19A, 19F and 23F individually conjugated to CRM$_{197}$ carrier protein, or a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14, and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid providing protection against further serotypes and/or providing increased protection against serotypes covered with low efficiency (such as serotype 3). Immunization with the immunogenic compositions disclosed herein leads to elevated serum IgG titer and functional antibody activity. Therefore, the immunogenic compositions disclosed herein are useful for the treatment and prevention of diseases caused by *Streptococcus pneumoniae*, including *Streptococcus pneumoniae* serotype 8 in infants, children and adults.

The objective of the present invention is solved by the teaching of the independent claims. Further advantageous features, aspects and details of the invention are evident from the dependent claims, the description, the figures, and the examples of the present application.

DESCRIPTION OF THE INVENTION

It was found that immunization with a composition comprising a conjugate of a saccharide from *S. pneumoniae* serotype 8 and a carrier protein and a mixture consisting of capsular polysaccharides from *S. pneumoniae* serotypes 1, 3, 4, 5, 6A, 6B, 7F, 9V, 14, 18C, 19A, 19F and 23F individually conjugated to $CRM_{197}$ carrier protein, induces a robust immune response against the capsular polysaccharide from *Streptococcus pneumoniae* serotype 8 (see for e.g. FIGS. 1A and 2A) leading to opsonophagocytic killing of *Streptococcus pneumoniae* serotype 8 pneumococci (see for e.g. FIG. 2B), without impairing the immune response against *Streptococcus pneumoniae* serotypes 1, 3, 4, 5, 6A, 6B, 7F, 9V, 14, 18C, 19A, 19F and 23F (see for e.g. FIG. 1B to 1G) and in contrast by an unexpected increase of the immune response against *Streptococcus pneumoniae* serotypes 3. The inventors have furthermore found that immunization with a composition comprising a conjugate of a saccharide from *S. pneumoniae* serotype 8 and a carrier protein, and a mixture consisting of capsular polysaccharides from *S. pneumoniae* serotypes 1, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14, and 23F are individually conjugated to protein D, the capsular polysaccharide from *S. pneumoniae* serotype 18C is conjugated to tetanus toxoid and the capsular polysaccharide from *S. pneumoniae* serotype 19F is conjugated to diphtheria toxoid, induces also a robust immune response against the capsular polysaccharide from *Streptococcus pneumoniae* serotype 8 without impairing the immune response against *Streptococcus pneumoniae* serotypes 1, 4, 5, 6B, 7F, 9V, 14, 18C, 19F and 23F.

In addition the inventors could surprisingly show that immunogenic composition comprising a conjugate of a saccharide from *S. pneumoniae* serotype 8 and a carrier protein and a mixture consisting of capsular polysaccharides from *S. pneumoniae* serotypes 1, 3, 4, 5, 6A, 6B, 7F, 9V, 14, 18C, 19A, 19F and 23F individually conjugated to $CRM_{197}$ carrier protein; or a mixture consisting of capsular polysaccharides from *S. pneumoniae* serotypes 1, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14, and 23F are individually conjugated to protein D, the capsular polysaccharide from *S. pneumoniae* serotype 18C is conjugated to tetanus toxoid and the capsular polysaccharide from *S. pneumoniae* serotype 19F is conjugated to diphtheria toxoid produces a new and unexpected joint therapeutic effect. It seems that the conjugate of a saccharide from *S. pneumoniae* serotype 8 and the used mixtures of the other afore-mentioned conjugates lead to an additional effect that goes beyond the sum of the effects of each feature taken in isolation. When adding the conjugate of a saccharide from *S. pneumoniae* serotype 8 and a carrier protein to the mixtures of conjugates as described herein, the antibody response against *S. pneumoniae* serotype 19A is surprisingly increased. In particular, addition of the conjugate of capsular saccharide from *S. pneumoniae* serotype 8 to a mixture consisting of capsular polysaccharides from *S. pneumoniae* serotypes 1, 3, 4, 5, 6A, 6B, 7F, 9V, 14, 18C, 19A, 19F and 23F individually conjugated to $CRM_{197}$ carrier protein induces an immune response against *S. pneumoniae* serotype 3 that exceeds the immune response induced by the mixture alone, i.e. without the conjugate of a capsular saccharide from *S. pneumoniae* serotype 8 (see FIG. 8). This effect is even more unexpected as it was disclosed in the literature that adding a further serotype to the afore-mentioned mixture of conjugates decreases the overall immune response due to a higher $CRM_{197}$ loading and immune interference (see *Vaccine* 2010, 5513-5523 and US20030147922A1; Table 4-7). The same unexpected advantageous effect could be observed by adding the conjugate of a capsular saccharide from *S. pneumoniae* serotype 8 and the $CRM_{197}$ carrier protein to a mixture containing the capsular polysaccharides from *S. pneumoniae* serotypes 1, 3, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14, and 23F are individually conjugated to protein D, the capsular saccharide from *S. pneumoniae* serotype 3 is conjugated to a carrier protein such as $CRM_{197}$, the capsular polysaccharide from *S. pneumoniae* serotype 18C is conjugated to tetanus toxoid and the capsular polysaccharide from *S. pneumoniae* serotype 19F is conjugated to diphtheria toxoid.

Thus, the present invention relates to an improved immunogenic composition comprising a conjugate of a saccharide from *S. pneumoniae* serotype 8 and a carrier protein and a mixture consisting of capsular polysaccharides from *S. pneumoniae* serotypes 1, 3, 4, 5, 6A, 6B, 7F, 9V, 14, 18C, 19A, 19F and 23F individually conjugated to $CRM_{197}$ carrier protein; or a mixture consisting of capsular polysaccharides from *S. pneumoniae* serotypes 1, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14, and 23F are individually conjugated to protein D, the capsular polysaccharide from *S. pneumoniae* serotype 18C is conjugated to tetanus toxoid and the capsular polysaccharide from *S. pneumoniae* serotype 19F is conjugated to diphtheria toxoid; or a mixture consisting of capsular polysaccharides from *S. pneumoniae* serotypes 1, 3, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14, and 23F are individually conjugated to protein D, the capsular saccharide from *S. pneumoniae* serotype 3 is conjugated to a carrier protein such as $CRM_{197}$, the capsular polysaccharide from *S. pneumoniae* serotype 18C is conjugated to tetanus toxoid and the capsular polysaccharide from *S. pneumoniae* serotype 19F is conjugated to diphtheria toxoid.

Alternatively worded, the present invention relates to an immunogenic composition comprising
a) a conjugate of a saccharide from *Streptococcus pneumoniae* serotype 8 and of a carrier protein, and
b) a mixture consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein; or
b') a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

In other words the present invention refers to an immunogenic composition comprising a mixture consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein and a saccharide from *Streptococcus pneumoniae* serotype 8 conjugated to a carrier protein, preferably to the diphtheria toxoid $CRM_{197}$. Another embodiment of the present invention is an immunogenic composition comprising a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid and comprises further a saccharide from *Streptococcus pneumoniae* serotype 8 conjugated to a carrier protein, preferably to the diphtheria toxoid $CRM_{197}$.

As used herein the term "a conjugate of a saccharide from *S. pneumoniae* serotype 8 and a carrier protein" encompasses an isolated capsular polysaccharide from *S. pneumoniae* serotype 8 covalently coupled to a carrier protein, an isolated oligosaccharide from *S. pneumoniae* serotype 8 covalently coupled to a carrier protein and a conjugate of general (I).

The capsular polysaccharide from *S. pneumoniae* serotype 8 can be purchased from American Type Culture Collection (ATCC) or prepared by standard techniques known to those skilled in the art. For example, the capsular polysaccharide may be grown in a soy based medium and then purified through centrifugation, precipitation, ultra-filtration and column chromatography. Following activation, the capsular polysaccharide can be reacted with the carrier protein. In order to reduce viscosity of the polysaccharide or to improve filterability for the corresponding conjugate, the capsular polysaccharide may be sized to some degree by known methods (see for example EP497524 and EP497525) and preferably by microfluidization prior to its activation.

An isolated oligosaccharide from *S. pneumoniae* serotype 8 has typically a number of 3-10 repeating units and can be prepared by treatment of the capsular polysaccharide with appropriate chemicals or enzymes. These chemicals include, but are not limited to trifluoroacetic acid, acetic acid, fluorhydric acid, chlorhydric acid, sodium hydroxide and sodium acetate. Different time periods and temperatures may be used depending on the particular chemistry and concentration and on the resulting oligosaccharide desired. Commercially available enzymes, such as cellulase and ß-galactosidases, or isolated bacteriophage-associated endoglycans known in the art or prepared by known methods can also be used to prepare oligosaccharide from capsular polysaccharide.

The term "carrier protein" as used herein refers to a protein that is preferably non-toxic and non-reactogenic and obtainable in sufficient amount and purity. A carrier protein is amenable to standard conjugation procedures. Carrier proteins which may be used in the present invention include inactivated bacterial toxins such as tetanus toxoid (TT), pertussis toxoid (PT), cholera toxoid (CT), *E. coli* LT, *E. coli* ST, and exotoxin A from *Pseudomonas aeruginosa*. Bacterial outer membrane proteins such as outer membrane complex c (OMPC), porins, transferrin binding proteins, pneumolysin, pneumococcal surface protein A (PspA), pneumococcal adhesin protein (PsaA), C5a peptidase from Group A or Group B *streptococcus*, *Haemophilus influenzae* protein D (PD), or a member of the polyhistidine triad family (Pht) proteins, fragments or fusion proteins thereof can also be used. Other proteins, such as ovalbumin, keyhole limpet hemocyanin (KLH), bovine serum albumin (BSA) or purified protein derivative of tuberculin (PPD) can also be used as carrier proteins.

The term "protein D" as used herein refers to the *Haemophilus influenzae* protein D (PD). Protein D is surface lipoprotein having a molecular weight of about 42 kDa and which can be found in all *Haemophilus influenzae* (EP 0594610 B1). It is further potentially immunogenic. Protein D is commercially available or can be recombinantly prepared from bacterial expression systems such as genetically modified *E. coli* cells (EP 0594610 B1). Protein D may be used as a full length protein or as a fragment.

The term "tetanus toxoid" as used herein refers to the nontoxic toxoid of the tetanus toxin, which can be isolated from *Clostridium tetani*. The tetanus toxin is made nontoxic by treatment with formaldehyde. It has a molecular weight of 150 kDa and consists of two polypeptide chains. Tetanus toxoid is used as carrier in vaccines, especially in HiB conjugate vaccines.

The term "diphtheria toxoid" as used herein refers to the nontoxic toxoid of the diphtheria toxin, which is released extracellularly from *Cornyebacterium diphtheria*. The diphtheria toxin is also made nontoxic by treatment with formaldehyde. It consists of a single polypeptide chain of 62 kDa and may also be used as carrier protein.

The diphtheria toxoid $CRM_{197}$ which is a non-toxic variant (i.e. toxoid) of diphteria toxin isolated from cultures of *Corynebacterium diphteriastrain* C7 (β197) grown casamino acids and yeast extract-based medium, may also be used as carrier protein. $CRM_{197}$ is purified through ultrafiltration, ammonium sulfate precipitation, and ion-exchange chromatography. Alternatively, $CRM_{197}$ is prepared recombinantly in accordance with U.S. Pat. No. 5,614,382.

The capsular polysaccharides (CPS) from *S. pneumoniae* serotypes 1, 3, 4, 5, 6A, 6B, 7F, 9V, 14, 18C, 19A, 19F and 23F are either purchased from American Type Culture Collection (ATCC) or are isolated from bacteria and purified by known methods (see EP0072513A2) such as centrifugation, precipitation, ultra-filtration, and column chromatography. Further, they may be sized to some degree before forming conjugates with carrier proteins. Sizing of these full length capsular polysaccharides means that their size is reduced and it may be achieved by known methods (see for example EP497524 and EP497525), such as acid hydrolysis treatment, hydrogen peroxide treatment, sizing by Emulsiflex® followed by a hydrogen peroxide treatment to generate oligosaccharide fragments or preferably by microfluidization. Sizing of polysaccharides is advantageous to filtering conjugated products due to the reduced viscosity of the sized polysaccharides. Sized polysaccharides have typically a molecular weight of 130 to 400 kDa depending on the serotype.

Each of the capsular polysaccharides from *S. pneumoniae* serotypes is conjugated to a carrier protein. Thus, each capsular polysaccharide from a *S. pneumoniae* serotype is covalently coupled or linked either directly or via a spacer to a carrier protein.

A spacer as used herein is preferably bifunctional. The spacer is optionally heterobifunctional or homobifunctional, having for example a reactive amino group and a reactive carboxylic acid group, 2 reactive amino groups or two reactive carboxylic acid groups. The spacer has for example between 4 and 20, 4 and 12, 5 and 10 carbon atoms. A possible spacer is adipic acid dihydrazide (ADH). Other spacers include B-propionamido, nitrophenyl-ethylamine, haloalkyl halides, glycosidic linkages, hexane diamine and 6-aminocaproic acid.

The capsular polysaccharide can be conjugated to a carrier protein by using any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer group to an amino group on the carrier protein. For example, the spacer could be cystamine or cysteamine to give a thiolated polysaccharide, which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester (optionally made by CDAP chemistry) is coupled with hexane diamine or ADH and the amino-derivatised saccharide is conjugated to the carrier protein using carbodiimide (e.g. EDAC or EDC) chemistry via a carboxyl group on the protein carrier. Such conjugation methods are described in WO 93/15760, WO 95/08348 and WO 96/29094.

Other suitable conjugation techniques rely on the use of carbodiimides, hydrazides, active esters, norborane, p-nitrobenzoic acid, N-hydroxysuccinimide, S—NHS (N-hydroxysulfosuccinimide), EDC, TSTU (2-succinimide-1,1,3,3-tetramethyluronium tetrafluoroborate) (WO 98/42721). Conjugation may involve a carbonyl linker which may be formed by reaction of a free hydroxyl group of the saccharide with CDI (1,1'-carbonyldiimidazole) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,673,574. Other preparation methods are described in EP0161188, EP208375 and EP0477508.

A further method involves the coupling of a cyanogen bromide (or CDAP) activated saccharide derivatised with adipic acid dihydrazide (ADH) to the protein carrier by carbodiimide condensation, for example using EDAC.

In an embodiment, a hydroxyl group (preferably an activated hydroxyl group for example a hydroxyl group activated to make a cyanate ester [e.g. with CDAP]) on a saccharide is linked to an amino or carboxylic group on a protein either directly or indirectly (through a spacer). Where a spacer is present, a hydroxyl group on a saccharide is preferably linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, the pneumococcal capsular saccharide(s) is conjugated to the spacer first before the spacer is conjugated to the carrier protein. Alternatively, the spacer may be conjugated to the carrier before conjugation to the saccharide.

A combination of techniques may also be used, with some conjugates being prepared by CDAP, and some by reductive amination.

In general the following types of chemical groups on a protein carrier can be used for conjugation:

Carboxyl (for instance via aspartic acid or glutamic acid). In one embodiment this group is linked to amino groups on saccharides directly or to an amino group on a spacer with carbodiimide chemistry e.g. with EDAC.

Amino group (for instance via lysine). In one embodiment this group is linked to carboxyl groups on saccharides directly or to a carboxyl group on a spacer with carbodiimide chemistry e.g. with EDAC. In another embodiment this group is linked to hydroxyl groups activated with CDAP or CNBr on saccharides directly or to such groups on a spacer; to saccharides or spacers having an aldehyde group; to saccharides or spacers having a succinimide ester group.

Sulfhydryl (for instance via cysteine). In one embodiment this group is linked to a bromo or chloro acetylated saccharide or linker with maleimide chemistry. In one embodiment this group is activated/modified with bis diazobenzidine.

Hydroxyl group (for instance via tyrosine). In one embodiment this group is activated/modified with bis diazobenzidine.

Imidazolyl group (for instance via histidine). In one embodiment this group is activated/modified with bis diazobenzidine.

Guanidyl group (for instance via arginine).

Indolyl group (for instance via tryptophan).

On a saccharide, in general the following groups can be used for conjugation: OH, COOH or $NH_2$. Aldehyde groups can be generated after different treatments known in the art such as: periodate, acid hydrolysis, hydrogen peroxide, etc.

Examples of direct coupling approaches include, but are not limited to:

CPS-OH+CNBr or CDAP→CPS-cyanate ester+$NH_2$-carrier protein→conjugate;

CPS-aldehyde+$NH_2$-carrier protein→Schiff base+$NaCNBH_3$→conjugate;

CPS-COOH+$NH_2$-carrier protein+EDAC→conjugate;

CPS-$NH_2$+carrier protein-COOH+EDAC→conjugate;

Indirect coupling via spacer approaches include, but are not limited to:

CPS-OH+CNBr or CDAP→CPS-cyanate ester+$NH_2$—$NH_2$→CPS-$NH_2$+COOH-carrier protein+EDAC→conjugate;

CPS-OH+CNBr or CDAP→CPS-cyanate ester+$NH_2$—SH→CPS-SH+SH-carrier protein (native protein with an exposed cysteine or obtained after modification of amino groups of the protein by SPDP for instance)→CPS-S-S-carrier protein;

CPS-OH+CNBr or CDAP→CPS-cyanate ester+$NH_2$—SH→CPS-SH+maleimide-carrier protein (modification of amino groups)→conjugate;

CPS-OH+CNBr or CDAP→CPS-cyanate ester+$NH_2$—SH→CPS-SH+haloacetylated-carrier protein→conjugate;

CPS-COOH+EDAC+$NH_2$—$NH_2$→CPS-$NH_2$+EDAC+COOH-carrier protein→conjugate;

CPS-COOH+EDAC+NH$_2$—SH→CPS-SH+SH-carrier protein (native protein with an exposed cysteine or obtained after modification of amino groups of the protein by SPDP for instance)→saccharide-S-S-carrier protein;

CPS-COOH+EDAC+NH$_2$—SH→CPS-SH+maleimide-carrier protein (modification of amino groups)→conjugate;

CPS-COOH+EDAC+NH$_2$—SH→CPS-SH+haloacetylated-carrier protein→conjugate;

CPS-aldehyde+NH$_2$—NH$_2$→CPS-NH$_2$+EDAC+carrier protein-COOH→conjugate.

In a preferred embodiment, CDAP (1-cyano-dimethylaminopyridinium tetrafluoroborate) cyanylating reagent is used for the synthesis of capsular polysaccharide-protein conjugates. This coupling method avoids hydrolysis of the alkaline sensitive polysaccharides and allows direct coupling to the carrier protein. The polysaccharide is dissolved in water or a saline solution. CDAP is dissolved in acetonitrile and added immediately to the polysaccharide solution. The CDAP reacts with the hydroxyl groups of the polysaccharide to form a cyanate ester in an activation step. Afterwards, the carrier protein is added. Amino groups of lysine react with the activated polysaccharide to form an isourea covalent linkage. After the conjugation reaction, a large excess of glycine is added to quench residual activated functions. The formed conjugate is then passed through a gel permeation to remove unreacted carrier protein and residual reagents.

Another preferred conjugation method is the reductive amination, wherein the capsular polysaccharide is oxidized with sodium periodate in an activation step and subsequently brought to reaction with the amino group of a carrier protein in the presence of sodium borohydride or sodium cyanoborohydride. The reductive amination can be performed in aqueous media or in DMSO. The crude conjugate is then passed through a HA or DEAE column and filtered sterile.

Preferably, the conjugate of a saccharide from *S. pneumoniae* serotype 8 and a carrier protein is an isolated capsular polysaccharide from *S. pneumoniae* type 8 covalently coupled to CRM$_{197}$ or an isolated oligosaccharide from *S. pneumoniae* serotype 8 covalently coupled to CRM$_{197}$.

Even more preferably, the conjugate of a saccharide from *S. pneumoniae* serotype 8 and a carrier protein has the following general formula (I):

$$[V^*—U_{x+3}—U_{x+2}—U_{x+1}—U_x—O-L^1-NH—W^1]_{m1}\text{-carrier-protein1} \quad (I)$$

wherein
x is an integer selected from 1, 2, 3 and 4;

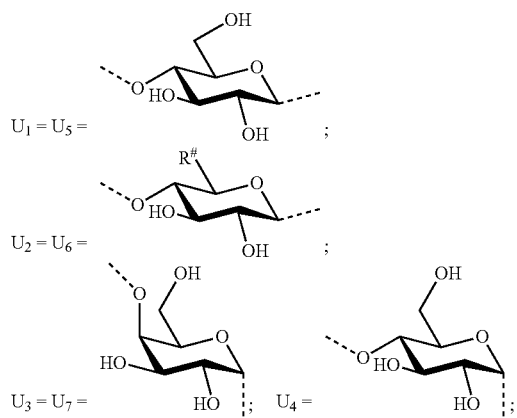

V*— represents H—, H—U$_x$— or H—U$_{x+1}$—U$_x$—;
R# represents —COOH or —CH$_2$OH;
L$^1$ represents a linker;
m1 is comprised between 2 and 18;
—W$^1$— is selected from:

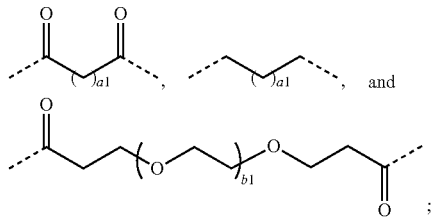

a1 represents an integer from 1 to 10;
b1 represents an integer from 1 to 4; and
carrier-protein1 is selected from CRM$_{197}$, protein D, tetanus toxoid and diphtheria toxoid.

-L$^1$- is defined as a linker and is part of the fragment —O-L$^1$-NH—. Thus, the linker -L$^1$- is bound to an oxygen atom and to the nitrogen atom of the —NH—W$^1$— fragment. It is preferred that at least two carbon atoms of the linker are between the oxygen atom and the —NH—W$^1$— fragment, like —O—C—C—NH—W$^1$—. The linker -L$^1$- can be an aliphatic chain, wherein the aliphatic chain can optionally include an aromatic chain inserted in it, or a number of heteroatoms oscillating from 0 to 10. The linker -L$^1$- preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms. The shortest atom chain between the oxygen atom (i.e. the oxygen of —O-L$^1$-NH$_2$) and the —NH—W$^1$— fragment consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the —NH—W$^1$— fragment) consists of 2 to 6 atoms, these are preferably carbon atoms. In case the shortest chain consists of 4 to 8 atoms, the chain may contain 1, 2 or 3 heteroatoms selected from O, N and S. In case the shortest chain consists of 9 to 14 atoms, the chain may contain 1, 2, 3, 4, 5, or 6 heteroatoms selected from O, N and S.

It is also preferred that the linker -L$^1$- or the shortest chain is fully or partially fluorinated. The linker -L$^1$- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L$^1$- may also contain amide (—NH—CO—, —CO—NH—) and/or urea (—NH—CO—NH—) residues and preferably only one amide or urea residue. The linker may also contain substituents and preferably two substituents, such as R$^{10}$ and R$^{11}$, or four substituents such as R$^{10}$, R$^{11}$, R$^{15}$ and R$^{14}$, which have the meanings as defined herein and which are preferably selected from: —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$, and —N(C$_2$H$_5$)$_2$.

In case the linker -L$^1$- is fluorinated, more than two substituents F are preferred.

Linker -L$^1$- is preferably selected from: —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$—O—CH$_2$—CH$_2$—O—(CH$_2$)$_2$—, —(CH$_2$)$_2$—O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$;

wherein

-L$^a$- is selected from: —(CH$_2$)$_o$—, —(CF$_2$)$_o$—, —(CH$_2$—CH$_2$—O)$_o$—C$_2$H$_4$—, —(CH$_2$—CH$_2$O)$_o$—CH$_2$—, —(CR$^{10}$R$^{11}$)$_o$—,

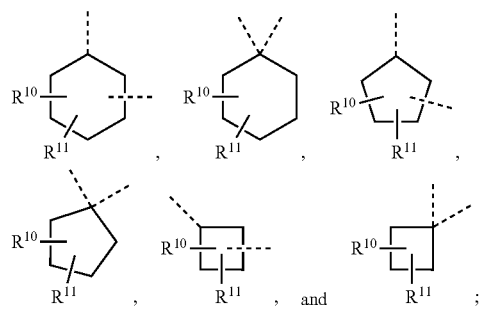

-L$^b$- and -L$^c$- are independently of each other selected from: —O—, —NH—C(O)—NH—, —NH—C(S)—NH—, —NH—C(O)—, —C(O)—NH—, —NH—C(O)—O—, —NR$^9$—, —NR$^{18}$—, —SO$_2$—,

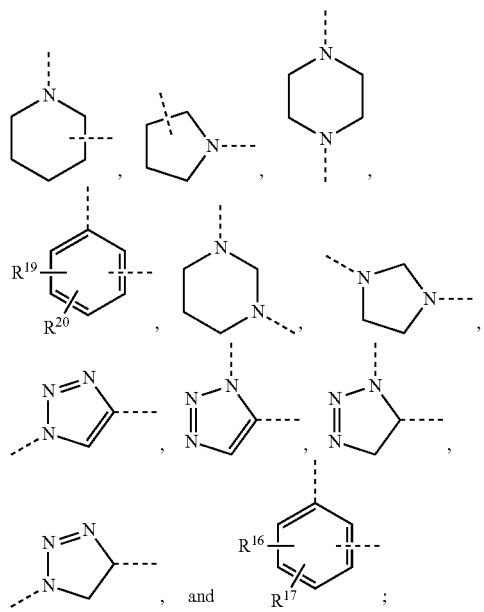

-L$^d$- represents: —(CH$_2$)$_q$—, —(CF$_2$)$_q$—, —(CR$^{12}$R$^{13}$)$_q$—, —(CH$_2$—CH$_2$—O)$_q$—C$_2$H$_4$—, —(CH$_2$—CH$_2$—O)$_q$—CH$_2$—,

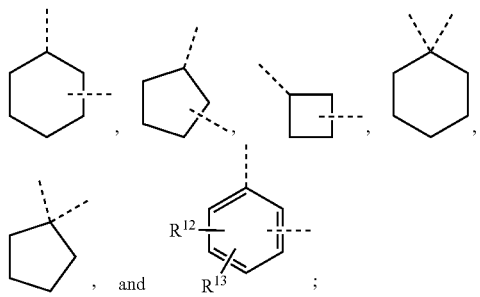

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—,

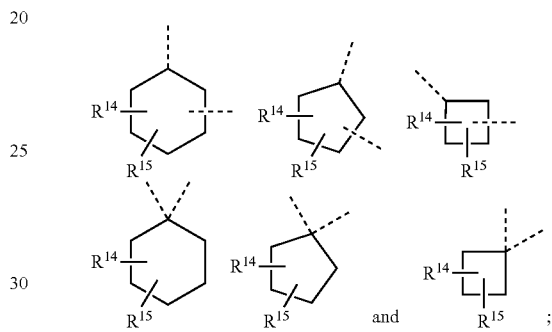

R$^9$ and R$^{18}$ are independently of each other selected from: —CH$_3$, —C$_2$H$_5$, —C$_3$H$_7$, and —C(O)CH$_3$;

R$^{10}$, R$^{11}$, R$^{12}$, R$^{13}$, R$^{14}$, R$^{15}$, R$^{16}$, R$^{17}$, R$^{19}$, R$^{20}$, R$^{21}$ and R$^{22}$ are independently of each other selected from: —H, —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$ and —N(C$_2$H$_5$)$_2$;

o, q, p1 and p2 are independently of each other an integer selected from 1, 2, 3, 4, 5, 6, 7, 8, 9, and 10.

In general formula (I), preferably x represents 3. Hence, an immunogenic composition according to the present invention, wherein the conjugate of a saccharide from S. pneumoniae serotype 8 and a carrier protein is of the following general formula (I-A):

[V*—U$_6$—U$_5$—U$_4$—U$_3$—O-L$^1$-NH—W$^1$]$_{m1}$-carrier-protein1      (I-A)

wherein

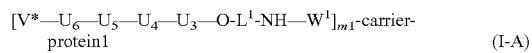

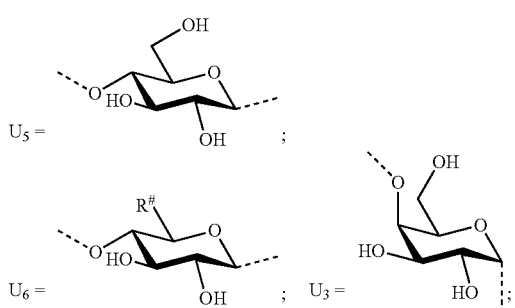

-continued

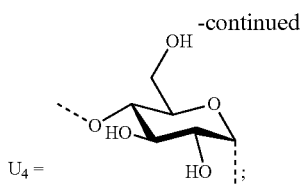

V*— represents H—, H—U$_3$— or H—U$_4$—U$_3$—;
and R$^\#$, L$^1$, m1, —W$^1$—, a1, b1 and carrier-protein1 have the meanings defined herein, is especially preferred.

In a further preferred embodiment, the residue V*— in general formula (I) represents H—. Thus, an immunogenic composition comprising a *Streptococcus pneumoniae* serotype 8 conjugate of general formula (I-B):

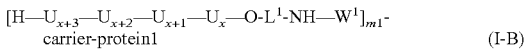
(I-B)

wherein
x is an integer selected from 1, 2, 3 and 4;

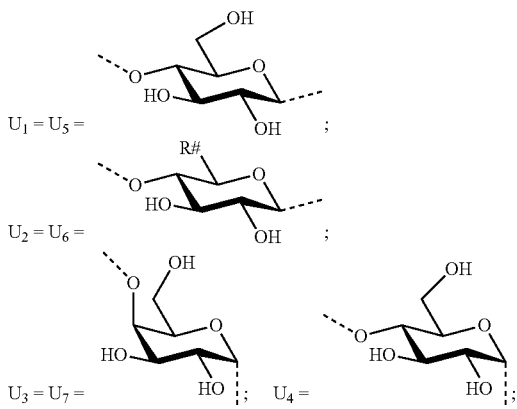

and R$^\#$, L$^1$, m1, —W$^1$—, a1, b1 and carrier-protein1 have the meanings defined herein,
and
a mixture consisting of capsular polysaccharides from *S. pneumoniae* serotypes 1, 3, 4, 5, 6A, 6B, 7F, 9V, 14, 18C, 19A, 19F and 23F individually conjugated to CRM$_{197}$ carrier protein; or
a mixture consisting of capsular polysaccharides from *S. pneumoniae* serotypes 1, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14, and 23F are individually conjugated to protein D, the capsular polysaccharide from *S. pneumoniae* serotype 18C is conjugated to tetanus toxoid and the capsular polysaccharide from *S. pneumoniae* serotype 19F is conjugated to diphtheria toxoid; is also preferred.

Even more preferred is an immunogenic composition comprising a *S. pneumoniae* serotype 8 conjugate of general formula (I-A), wherein V*— represents H—, and a mixture consisting of capsular polysaccharides from *S. pneumoniae* serotypes 1, 3, 4, 5, 6A, 6B, 7F, 9V, 14, 18C, 19A, 19F and 23F individually conjugated to CRM$_{197}$ carrier protein; or a mixture consisting of capsular polysaccharides from *S. pneumoniae* serotypes 1, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14, and 23F are individually conjugated to protein D, the capsular polysaccharide from *S. pneumoniae* serotype 18C is conjugated to tetanus toxoid and the capsular polysaccharide from *S. pneumoniae* serotype 19F is conjugated to diphtheria toxoid.

Preferably the linker -L$^1$- is selected from: -L$^a$-, -L$^a$-L$^e$-, -L$^a$-L$^b$-L$^e$-, -L$^a$-L$^d$-L$^e$-; wherein
-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;
-L$^b$- represents —O—;
-L$^d$- is selected from —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;
-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;
and o, q, p1 and p2 are independently of each other an integer selected from 1, 2, 3, 4, 5, and 6.

Therefore, the immunogenic composition of the present invention contains preferably a conjugate of a saccharide from *S. pneumoniae* serotype 8 and a carrier protein, wherein the conjugate has the general formula (I), (I-A) or (I-B), with -L- being selected from: -L$^a$-, -L$^a$-L$^e$-, -L$^a$-L$^b$-L$^e$-, and -L$^a$-L$^d$-L$^e$-; -L$^a$- being selected from: —(CH$_2$)$_o$—, —(CH$_2$—CH$_2$—O)$_o$—C$_2$H$_4$—, —(CH$_2$—CH$_2$—O)$_o$—CH$_2$—;
-L$^b$- representing —O—;
-L$^d$- being selected from: —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;
-L$^e$- being selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;
and o, q, p1 and p2 being independently of each other an integer selected from 1, 2, 3, 4, 5, and 6.

Even more preferred is an immunogenic composition comprising a conjugate of a saccharide from *S. pneumoniae* serotype 8 and a carrier protein, wherein the conjugate has the general formula (I), (I-A) or (I-B), with -L$^1$- representing —(CH$_2$)$_o$— and o being an integer selected from 2, 3, 4, 5, 6, 7 and 8.

It is also preferred that —W$^1$— represents

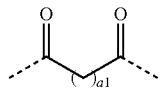

and a1 is an integer selected from 2, 3, 4, 5 and 6.

Thus, an immunogenic composition according to the present invention comprising a conjugate of a saccharide from *S. pneumoniae* serotype 8 and a carrier protein, wherein said conjugate has the general formula (I), (I-A) or (I-B), with
-L$^1$- being selected from: -L$^a$-, -L$^a$-L$^e$-, -L$^a$-L$^b$-L$^e$- and -L$^a$-L$^d$-L$^e$-;
-L$^a$- being selected from: —(CH$_2$)$_o$—, —(CH$_2$—CH$_2$—O)$_o$—C$_2$H$_4$—, —(CH$_2$—CH$_2$—O)$_o$—CH$_2$—;
-L$^b$- representing —O—;
-L$^d$- being selected from: —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;
-L$^e$- being selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;
o, q, p1 and p2 being independently of each other an integer selected from 1, 2, 3, 4, 5, and 6, and —W¹— representing

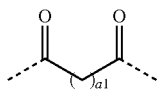

with a1 being an integer selected from 2, 3, 4, 5 and 6, is especially preferred.

Even more preferred is an immunogenic composition comprising a conjugate of general formula (I), (I-A) or (I-B), wherein -L¹- represents —(CH$_2$)$_o$—, o is an integer selected from 2, 3, 4, 5, 6, 7 and 8, —W¹— represents

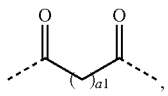

and a1 is an integer selected from 2, 3, 4, 5 and 6.

Preferably, carrier-protein1 is CRM$_{197}$. Preferably m1 is comprised between 5 and 17, even more preferably between 7 and 16, and most preferably between 8 and 15.

The inventors have surprisingly found that an immunogenic composition comprising a conjugate of general formula (I), (I-A) or (I-B) as defined above and a mixture consisting of capsular polysaccharides from S. pneumoniae serotypes 1, 3, 4, 5, 6A, 6B, 7F, 9V, 14, 18C, 19A, 19F and 23F individually conjugated to CRM$_{197}$ carrier protein, or a mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid induces in a host a robust immune response against the capsular polysaccharide from Streptococcus pneumoniae serotype 8, thereby leading to opsonophagocytic killing of Streptococcus pneumoniae serotype 8 pneumococci, without impairing the immune response against the capsular polysaccharides from the other S. pneumoniae serotypes, which are present in the immunogenic composition. Therefore, said immunogenic compositions are useful for the prevention and/or treatment of diseases caused by Streptococcus pneumoniae and are especially useful for the prevention and/or treatment of diseases caused by Streptococcus pneumoniae serotype 8 and/or serotype 3. Accordingly, one embodiment comprises the immunogenic composition of the present invention for use as a medicament and in particular for the use as a vaccine for the prevention and/or treatment of diseases caused by Streptococcus pneumoniae.

In addition, the inventors found that immunization with an immunogenic composition comprising a conjugate of a saccharide from Streptococcus pneumoniae serotype 2 and of a carrier protein as well as a conjugate of a saccharide from Streptococcus pneumoniae serotype 8 and of a carrier protein together with a mixture consisting of capsular polysaccharides from S. pneumoniae serotypes 1, 3, 4, 5, 6A, 6B, 7F, 9V, 14, 18C, 19A, 19F and 23F individually conjugated to CRM$_{197}$ carrier protein, or a mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid induces a robust immune response against the capsular polysaccharides from Streptococcus pneumoniae serotypes 2 and 8, without impairing the immune response against the capsular polysaccharides from the other S. pneumoniae serotypes, which are present in the immunogenic composition. Even by adding the two further conjugates, namely the conjugate of a saccharide from Streptococcus pneumoniae serotype 2 and a carrier protein as well as the conjugate of a saccharide from Streptococcus pneumoniae serotype 8 and a carrier protein to the afore-mentioned mixtures, namely the mixture consisting of capsular polysaccharides from S. pneumoniae serotypes 1, 3, 4, 5, 6A, 6B, 7F, 9V, 14, 18C, 19A, 19F and 23F individually conjugated to CRM$_{197}$ carrier protein, and the mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid and the mixture consisting of capsular polysaccharides from S. pneumoniae serotypes 1, 3, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular saccharide from S. pneumoniae serotype 3 is conjugated to a carrier protein such as CRM$_{197}$, the capsular polysaccharide from S. pneumoniae serotype 18C is conjugated to tetanus toxoid and the capsular polysaccharide from S. pneumoniae serotype 19F is conjugated to diphtheria toxoid the unexpected and advantageous increase in the immune response against S. pneumoniae serotype 3 as well as 19A is still obtained in a similar manner as disclosed above for the mixtures to which only the capsular polysaccharide from Streptococcus pneumoniae serotypes 8 but not 2 was added.

Therefore, a further embodiment of the present invention relates to an immunogenic composition comprising
  a) a conjugate of a saccharide from Streptococcus pneumoniae serotype 8 and of a carrier protein,
  b) a conjugate of a saccharide from Streptococcus pneumoniae serotype 2 and of a carrier protein, and
  c) a mixture consisting of capsular polysaccharides from S. pneumoniae serotypes 1, 3, 4, 5, 6A, 6B, 7F, 9V, 14, 18C, 19A, 19F and 23F individually conjugated to CRM$_{197}$ carrier protein or
  c') a mixture consisting of capsular polysaccharides from Streptococcus pneumoniae serotypes 1, 4, 5, 6B, 7F, 9V, 14, 18C, 19F and 23F individually conjugated to a carrier protein, wherein the capsular polysaccharides from Streptococcus pneumoniae serotypes 1, 4, 5, 6B, 7F, 9V, 14 and 23F are individually conjugated to protein D, the capsular polysaccharide from Streptococcus pneumoniae serotype 18C is conjugated to tetanus toxoid and the capsular polysaccharide from Streptococcus pneumoniae serotype 19F is conjugated to diphtheria toxoid.

A further embodiment of the present invention relates to an immunogenic composition comprising
  a) a conjugate of a saccharide from Streptococcus pneumoniae serotype 8 and of a carrier protein, b) a conjugate of a saccharide from *Streptococcus pneumoniae* serotype 3 and of a carrier protein,
c) a conjugate of a saccharide from *Streptococcus pneumoniae* serotype 2 and of a carrier protein, and
d) a mixture consisting of capsular polysaccharides from *S. pneumoniae* serotypes 1, 3, 4, 5, 6A, 6B, 7F, 9V, 14, 18C, 19A, 19F and 23F individually conjugated to CRM$_{197}$ carrier protein or
d') a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

A further embodiment of the present invention relates to an immunogenic composition comprising
a) a conjugate of a saccharide from *Streptococcus pneumoniae* serotype 8 and of a carrier protein,
b) a conjugate of a saccharide from *Streptococcus pneumoniae* serotype 3 and of a carrier protein, and
c) a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

A further embodiment of the present invention relates to an immunogenic composition comprising
a) a conjugate of a saccharide from *Streptococcus pneumoniae* serotype 8 and of a carrier protein,
b) a conjugate of a saccharide from *Streptococcus pneumoniae* serotype 19A and of a carrier protein, and
c) a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

One embodiment of the present invention relates to an immunogenic composition comprising
a) a conjugate of a saccharide from *Streptococcus pneumoniae* serotype 8 and of a carrier protein,
b) a conjugate of a saccharide from *Streptococcus pneumoniae* serotype 19A and of a carrier protein,
c) a conjugate of a saccharide from *Streptococcus pneumoniae* serotype 2 and of a carrier protein, and
d) a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

One embodiment of the present invention relates to an immunogenic composition comprising
a) a conjugate of a saccharide from *Streptococcus pneumoniae* serotype 8 and of a carrier protein,
b) a conjugate of a saccharide from *Streptococcus pneumoniae* serotype 6A and of a carrier protein,
c) a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

One embodiment of the present invention relates to an immunogenic composition comprising
a) a conjugate of a saccharide from *Streptococcus pneumoniae* serotype 8 and of a carrier protein,
b) a conjugate of a saccharide from *Streptococcus pneumoniae* serotype 6A and of a carrier protein,
c) a conjugate of a saccharide from *Streptococcus pneumoniae* serotype 2 and of a carrier protein, and
d) a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

One embodiment of the present invention relates to an immunogenic composition comprising
a) a conjugate of a saccharide from *Streptococcus pneumoniae* serotype 8 and of a carrier protein,
b) a conjugate of a saccharide from *Streptococcus pneumoniae* serotype 19A and of a carrier protein,
c) a conjugate of a saccharide from *Streptococcus pneumoniae* serotype 2 and of a carrier protein,
d) a conjugate of a saccharide from *Streptococcus pneumoniae* serotype 3 and of a carrier protein, and
e) a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

A further embodiment of the present invention relates to an immunogenic composition comprising
a) a conjugate of a saccharide from *Streptococcus pneumoniae* serotype 8 and of a carrier protein, b) a conjugate of a saccharide from *Streptococcus pneumoniae* serotype 3 and of a carrier protein, and c) a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

Still a further embodiment of the present invention relates to an immunogenic composition comprising a) a conjugate of a saccharide from *Streptococcus pneumoniae* serotype 8 and of a carrier protein, b) a conjugate of a saccharide from *Streptococcus pneumoniae* serotype 2 and of a carrier protein, c) a conjugate of a saccharide from *Streptococcus pneumoniae* serotype 3 and of a carrier protein, and d) a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14 and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

One embodiment of the present invention relates to an immunogenic composition comprising a mixture consisting of capsular polysaccharides from *Streptococcus pneumoniae* serotypes 1, 4, 5, 6B, 7F, 8, 9V, 14, 18C, 19F and 23F individually conjugated to $CRM_{197}$ carrier protein. Another embodiment of the present invention relates to an immunogenic composition comprising a mixture consisting of capsular polysaccharides from *Streptococcus pneumoniae* serotypes 1, 2, 4, 5, 6B, 7F, 8, 9V, 14, 18C, 19F and 23F individually conjugated to $CRM_{197}$ carrier protein. A further embodiment of the present invention relates to an immunogenic composition comprising a mixture consisting of capsular polysaccharides from *Streptococcus pneumoniae* serotypes 1, 2, 3, 4, 5, 6B, 7F, 8, 9V, 14, 18C, 19F and 23F individually conjugated to $CRM_{197}$ carrier protein. A further embodiment of the present invention relates to an immunogenic composition comprising a mixture consisting of capsular polysaccharides from *Streptococcus pneumoniae* serotypes 1, 3, 4, 5, 6B, 7F, 8, 9V, 14, 18C, 19F and 23F individually conjugated to $CRM_{197}$ carrier protein.

Preferably, the immunogenic composition according to the present invention further comprises a *Streptococcus pneumoniae* serotype 2 conjugate of the following general formula (II-C):

$$[B^*-A_{y+3}-A_{y+2}-A_{y+1}-A_y-O-L^2-NH-W^2]_{m2}\text{-carrier-protein2} \quad (II\text{-}C)$$

wherein y is an integer selected from 1, 2, 3 and 4;

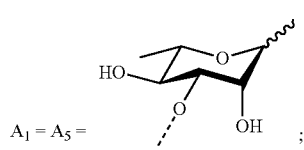

$A_1 = A_5 =$

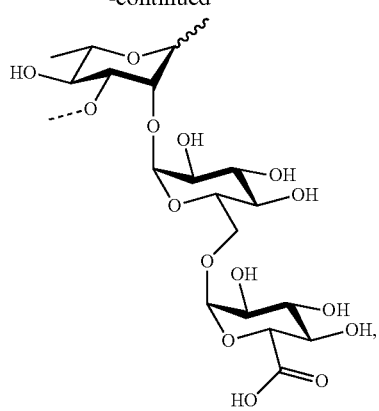

$A_2 = A_6 =$

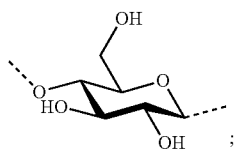

$A_3 = A_7 =$

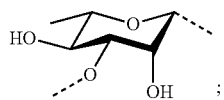

$A_4 =$ $B^*$— represents: H—, H-$A_y$-, H-$A_{y+1}$-$A_y$-, H-$A_{y+2}$-$A_{y+1}$-$A_y$- or H-$A_{y+3}$-$A_{y+2}$-$A_{y+1}$-$A_y$-;

$L^2$ represents a linker;

m2 is comprised between about 2 and about 18;

—$W^2$— is selected from:

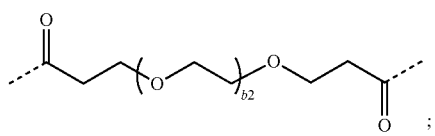

a2 represents an integer from 1 to 10;

b2 represents an integer from 1 to 4; and carrier-protein2 is selected from $CRM_{197}$, protein D, tetanus toxoid and diphtheria toxoid.

It is preferred that

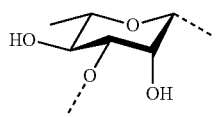

$A_1 = A_5 =$ ; and a2 represents an integer from 1 to 10;
b2 represents an integer from 1 to 4; and
carrier-protein2 is selected from $CRM_{197}$, protein D, tetanus toxoid and diphtheria toxoid.

It is more preferred that:

$A_1 = A_5 =$ 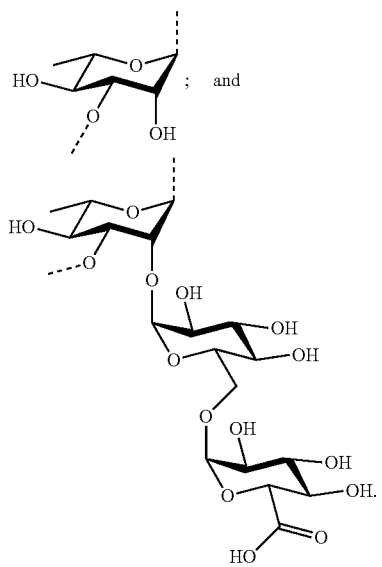 ; and $A_2 = A_6 =$

Hence more preferably, the *Streptococcus pneumoniae* serotype 2 conjugate has the following general formula (II-D):

$$[B^*-A_{y+3}-A_{y+2}-A_{y+1}-O-L^2-NH-W^2]_{m2}\text{-carrier-protein2} \tag{II-D}$$

wherein
y is an integer selected from 1, 2, 3 and 4;

$A_1 = A_5 =$ 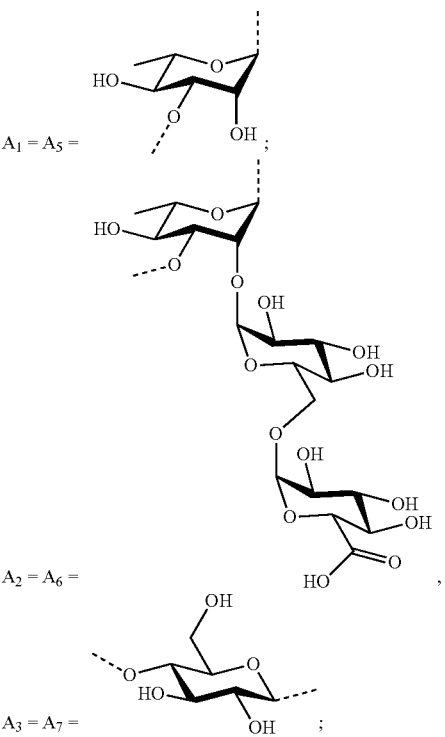

$A_2 = A_6 =$ $A_3 = A_7 =$

-continued

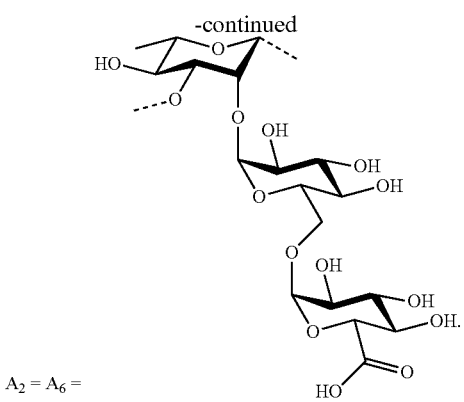

$A_2 = A_6 =$

Thus, the *Streptococcus pneumoniae* serotype 2 conjugate has preferably the following general formula (II):

$$[B^*-A_{y+3}-A_{y+2}-A_{y+1}-A_y-O-L^2-NH-W^2]_{m2}\text{-carrier-protein2} \tag{II}$$

wherein
y is an integer selected from 1, 2, 3 and 4;

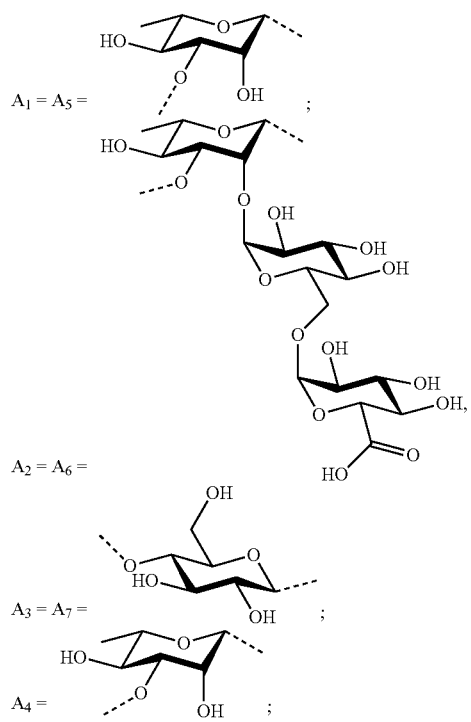

$A_1 = A_5 =$ $A_2 = A_6 =$ $A_3 = A_7 =$ $A_4 =$

B*— represents: H—, $H-A_y$-, $H-A_{y+1}-A_y$-, $H-A_{y+2}-A_{y+1}-A_y$- or $H-A_{y+3}-A_{y+2}-A_{y+1}-A_y$-;
$L^2$ represents a linker;
m2 is comprised between about 2 and about 18;
—$W^2$— is selected from:

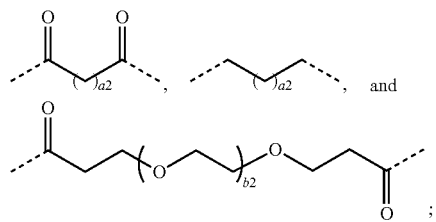

$A_4 =$ 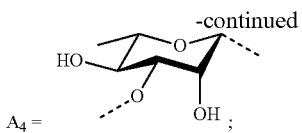

B*— represents: H—, H-$A_y$-, H-$A_{y+1}$-$A_y$-, H-$A_{y+2}$-$A_{y+1}$-$A_y$- or H-$A_{y+3}$-$A_{y+2}$-$A_{y+1}$-$A_y$-;

$L^2$ represents a linker;

m2 is comprised between about 2 and about 18;

—$W^2$— is selected from:

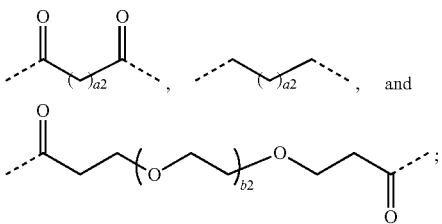

a2 represents an integer from 1 to 10;

b2 represents an integer from 1 to 4; and carrier-protein2 is selected from $CRM_{197}$, protein D, tetanus toxoid and diphtheria toxoid.

-$L^2$- is defined as a linker and is part of the fragment —O-$L^2$-NH—. Thus, the linker -$L^2$- is bound to an oxygen atom and to the nitrogen atom of the —NH—$W^2$— fragment. It is preferred that at least two carbon atoms of the linker are between the oxygen atom and the —NH—$W^2$— fragment, like —O—C—C—NH—$W^2$—. The linker -$L^2$- can be an aliphatic chain, wherein the aliphatic chain can optionally include an aromatic chain inserted in it, or a number of heteroatoms oscillating from 0 to 10.

The linker -$L^2$- preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen atom (i.e. the oxygen of —O-$L^2$-NH—) and the —NH—$W^2$— fragment consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the —NH—$W^2$— fragment) consists of 2 to 6 atoms, these are preferably carbon atoms. In case the shortest chain consists of 4 to 8 atoms, the chain may contain 1, 2 or 3 heteroatoms selected from O, N and S. In case the shortest chain consists of 9 to 14 atoms, the chain may contain 1, 2, 3, 4, 5, or 6 heteroatoms selected from O, N and S.

It is also preferred that the linker -$L^2$-, or the shortest chain is fully or partially fluorinated. The linker -$L^2$- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -$L^2$- may also contain amide (—NH—CO—, —CO—NH—) and/or urea (—NH—CO—NH—) residues and preferably only one amide or urea residue. The linker may also contain substituents and preferably two substituents, such as $R^{10}$* and $R^{11}$*, or four substituents such as $R^{10}$*, $R^{11}$*, $R^{15}$* and $R^{14}$*, which have the meanings as defined herein and which are preferably selected from: —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —C(O)—$NH_2$, —$SCH_3$, —$SC_2H_5$, —NHC(O)$CH_3$, —N($CH_3$)$_2$, and —N($C_2H_5$)$_2$.

In case the linker -$L^2$- is fluorinated, more than two substituents —F are preferred.

Linker -$L^2$- is preferably selected from: —$CH_2$—, —($CH_2$)$_2$—, —($CH_2$)$_3$—, —($CH_2$)$_4$—, —($CH_2$)$_5$—, —($CH_2$)$_6$—, —($CH_2$)$_7$—, —($CH_2$)$_8$—, —($CH_2$)$_9$—, —($CH_2$)$_{10}$—, —$CF_2$—, —($CF_2$)$_2$—, —($CF_2$)$_3$—, —($CF_2$)$_4$—, —($CF_2$)$_5$—, —($CF_2$)$_6$—, —($CF_2$)$_7$—, —($CF_2$)$_8$—, —($CF_2$)$_9$—, —($CF_2$)$_{10}$—, —($CH_2$)$_2$—O—($CH_2$)$_2$—, —$CH_2$—O—($CH_2$)$_3$—, —($CH_2$)$_3$—O—$CH_2$—$CH_2$—O—($CH_2$)$_2$—, —($CH_2$)$_2$—O—$CH_2$—, —($CH_2$)$_3$—O—($CH_2$)$_2$—, —($CH_2$)$_2$—O—($CH_2$)$_3$—, —($CH_2$)$_4$—O—$CH_2$—, —$CH_2$—O—($CH_2$)$_4$—, -$L^a$*-, -$L^a$*-$L^e$*-, -$L^a$*-$L^b$*-$L^e$*-, -$L^a$*-$L^b$*-$L^d$*-$L^c$*-$L^e$*, -$L^a$*-$L^d$*-$L^e$*-;

wherein

-$L^a$*- is selected from: —($CH_2$)$_o$*—, —($CF_2$)$_o$*—, —($CH_2$—$CH_2$—O)$_o$*—$C_2H_4$—, —($CH_2$—$CH_2$—O)$_o$*—$CH_2$—, —($CR^{10}$*$R^{11}$*)$_o$*—,

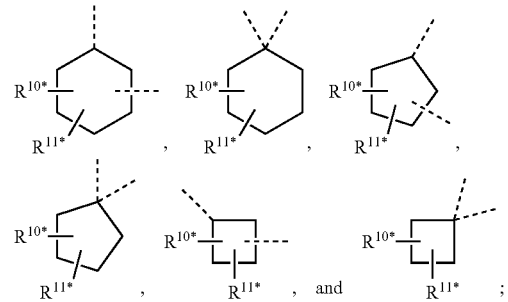

-$L^b$*- and -$L^c$*- are independently of each other selected from: —O—, —NH—C(O)—NH—, —NH—C(S)—NH—, —NH—C(O)—, —C(O)—NH—, —NH—C(O)—O—, —$NR^9$*—, —$NR^{18}$*—, —$SO_2$—,

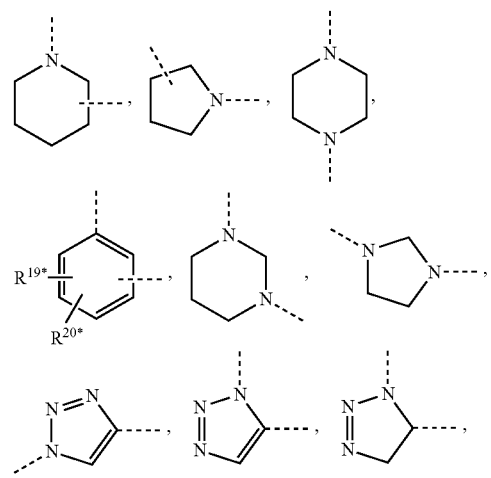

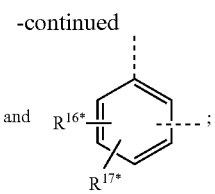

$-L^{d*}-$ represents $-(CH_2)_q*-$, $-(CF_2)_q*-$, $-(CR^{12}*R^{13}*)_q*$, $-(CH_2-CH_2-O)_q*-C_2H_4-$, $-(CH_2-CH_2-O)_q*-CH_2-$,

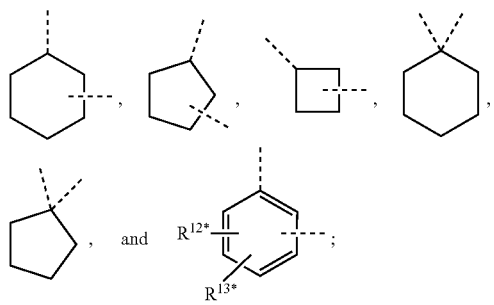

$-L^{e*}-$ is selected from: $-(CH_2)_{p1}*-$, $-(CF_2)_{p1}*-$, $-C_2H_4-(O-CH_2-CH_2)_{p1}*-$, $-CH_2-(O-CH_2-CH_2)_{p1}*-$, $-(CH_2)_{p1}*-O-(CH_2)_{p2}*-$, $-(CR^{14}*R^{15}*)_{p1}-$, $-(CR^{14}*R^{15}*)_{p1}*-O-(CR^{21}*R^{22}*)_{p2}*-$,

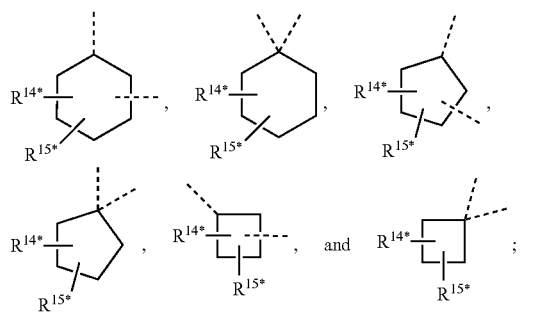

$R^{9*}$ and $R^{18*}$ are independently of each other selected from: $-CH_3$, $-C_2H_5$, $-C_3H_7$, and $-C(O)CH_3$;

$R^{10*}$, $R^{11*}$, $R^{12*}$, $R^{13*}$, $R^{14*}$, $R^{15*}$, $R^{16*}$, $R^{17*}$, $R^{19*}$, $R^{20*}$, $R^{21*}$ and $R^{22*}$ are independently of each other selected from: $-H$, $-F$, $-Cl$, $-CH_3$, $-C_2H_5$, $-C_3H_7$, $-C_5H_9$, $-C_6H_{13}$, $-OCH_3$, $-OC_2H_5$, $-CH_2F$, $-CHF_2$, $-CF_3$, $-C(O)-NH_2$, $-SCH_3$, $-SC_2H_5$, $-NHC(O)CH_3$, $-N(CH_3)_2$ and $-N(C_2H_5)_2$;

$o*$, $q*$, $p1*$ and $p2*$ are independently of each other an integer selected from 1, 2, 3, 4, 5, 6, 7, 8, 9, and 10.

Thus, another aspect of the present invention is directed to an immunogenic composition comprising a conjugate of a saccharide from *S. pneumoniae* serotype 8 and a carrier protein as defined above, a *S. pneumoniae* serotype 2 conjugate of general formula (II), (II-C) or (II-D) and a mixture consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein; or a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14, and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

In general formulae (II), (II-C) and (II-D), it is preferred that y represents 1. Thus, the immunogenic composition according to the present invention preferably contains besides the conjugate of a saccharide from *S. pneumoniae* serotype 8 and a carrier protein defined above, and a mixture consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein; or a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14, and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid, a conjugate of general formula (II-E):

$$[B*-A_4-A_3-A_2-A_1-O-L^2-NH-W^2]_{m2}\text{-carrier-protein2} \qquad (II-E)$$

wherein

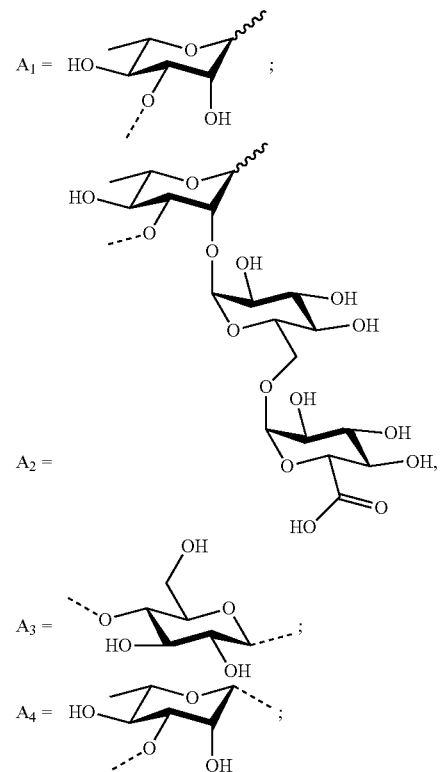

$B*$— represents $H-$, $H-A_1-$, $H-A_2-A_1-$, $H-A_3-A_2-A_1-$ or $H-A_4-A_3-A_2-A_1-$; and $L^2$, m2, $-W^2-$, a2, b2 and carrier-protein2 have the meanings defined herein.

A further preferred immunogenic composition according to the present invention contains besides the conjugate of a saccharide from *S. pneumoniae* serotype 8 and a carrier protein defined above, and a mixture consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein; or a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14, and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid, a conjugate of general formula (II-A):

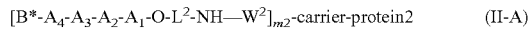

$$[B^*-A_4-A_3-A_2-A_1-O-L^2-NH-W^2]_{m2}\text{-carrier-protein2} \quad (\text{II-A})$$

wherein

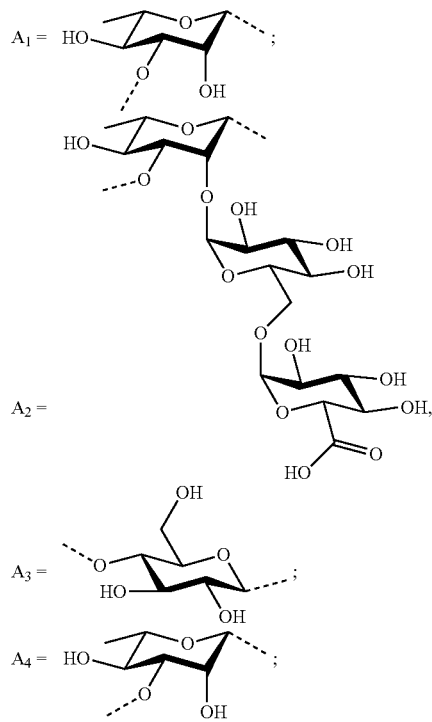

B*— represents H—, $H-A_1$-, $H-A_2-A_1$-, $H-A_3-A_2-A_1$- or $H-A_4-A_3-A_2-A_1$-; and $L^2$, m2, $-W^2-$ and carrier-protein2 have the meanings defined herein.

An especially preferred immunogenic composition according to the present invention contains besides the *S. pneumoniae* serotype 8 conjugate defined above, and a mixture consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein; or a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14, and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid, a *S. pneumoniae* serotype 2 conjugate of general formula (II-F):

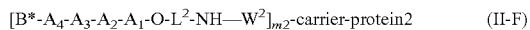

$$[B^*-A_4-A_3-A_2-A_1-O-L^2-NH-W^2]_{m2}\text{-carrier-protein2} \quad (\text{II-F})$$

wherein

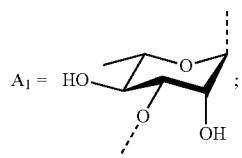

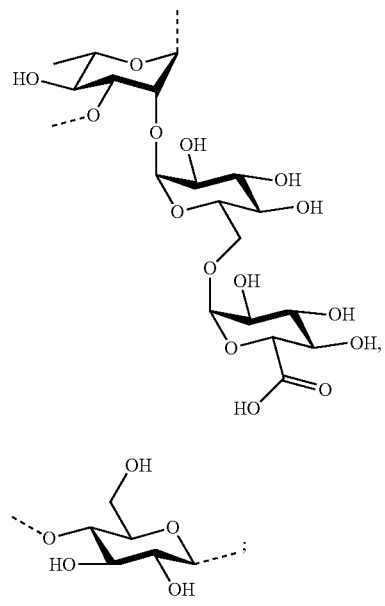

B*— represents H—, $H-A_1$-, $H-A_2-A_1$-, $H-A_3-A_2-A_1$- or $H-A_4-A_3-A_2-A_1$-; and $L^2$, m2, $-W^2-$ and carrier-protein2 have the meanings defined herein.

More preferably, the residue B*- in general formulae (II), (II-A), (II-C), (II-E) and (II-F) represents H—.

Hence, the immunogenic composition of the present invention preferably contains a *S. pneumoniae* serotype 2 conjugate of general formula (II-G):

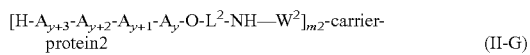

$$[H-A_{y+3}-A_{y+2}-A_{y+1}-A_y-O-L^2-NH-W^2]_{m2}\text{-carrier-protein2} \quad (\text{II-G})$$

wherein y is an integer selected from 1, 2, 3 and 4;

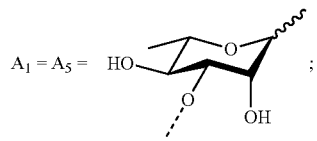

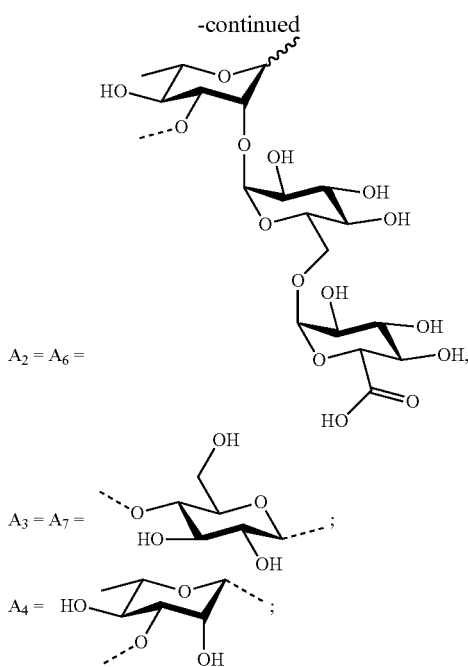

and $L^2$, m2, —$W^2$— and carrier-protein2 have the meanings defined herein.

More preferably, the immunogenic composition of the present invention contains a *S. pneumoniae* serotype 2 conjugate of general formula (II-B):

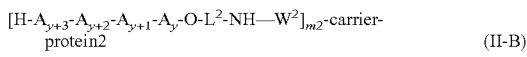
(II-B)

wherein
y is an integer selected from 1, 2, 3 and 4;

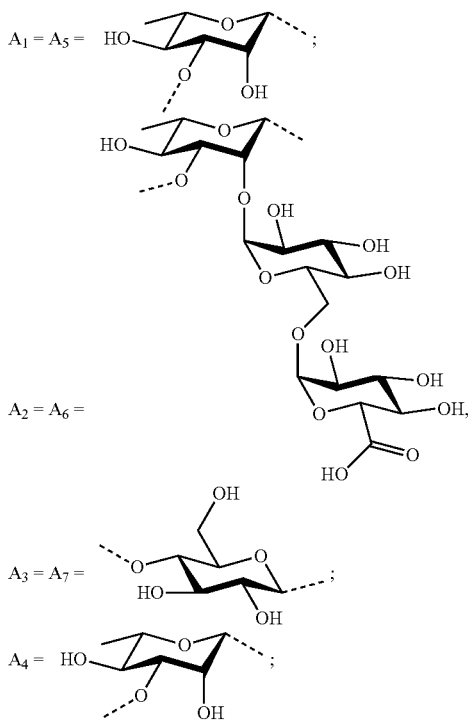

and $L^2$, m2, —$W^2$— and carrier-protein2 have the meanings defined herein.

Even more preferably, the immunogenic composition of the present invention contains a *S. pneumoniae* serotype 2 conjugate of general formula (II-H):

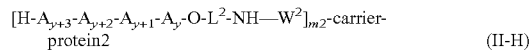
(II-H)

wherein
y is an integer selected from 1, 2, 3 and 4;

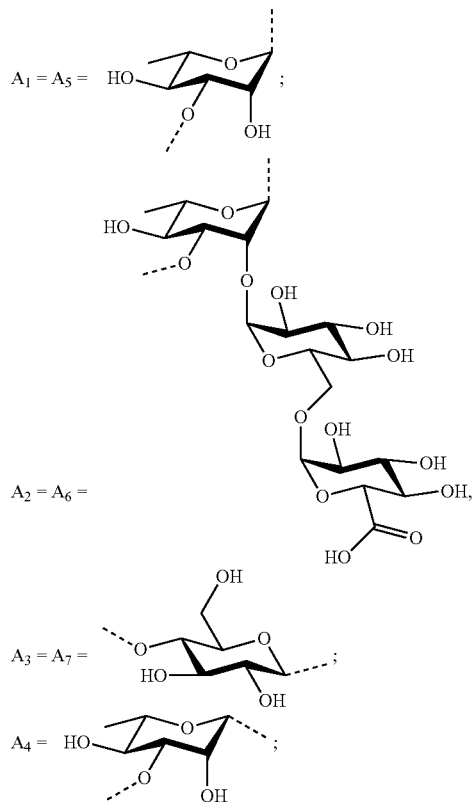

and $L^2$, m2, —$W^2$— and carrier-protein2 have the meanings defined herein.

Even more preferred is an immunogenic composition comprising a conjugate of a saccharide from *S. pneumoniae* serotype 8 and a carrier protein as defined above, a conjugate of general formula (II-A) wherein B*— represents H—, and a mixture consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein; or a mixture consisting of capsular polysaccharides from *Streptococcus pneumoniae* serotypes 1, 4, 5, 6B, 7F, 9V, 14, 18C, 19F and 23F individually conjugated to a carrier protein, wherein the capsular polysaccharides from *Streptococcus pneumoniae* serotypes 1, 4, 5, 6B, 7F, 9V, 14, and 23F are individually conjugated to protein D, the capsular polysaccharide from *Streptococcus pneumoniae* serotype 18C is conjugated to tetanus toxoid and the capsular polysaccharide from *Streptococcus pneumoniae* serotype 19F is conjugated to diphtheria toxoid.

Most preferably, the immunogenic composition of the present invention contains a *S. pneumoniae* serotype 2 conjugate of general formula (II-I)

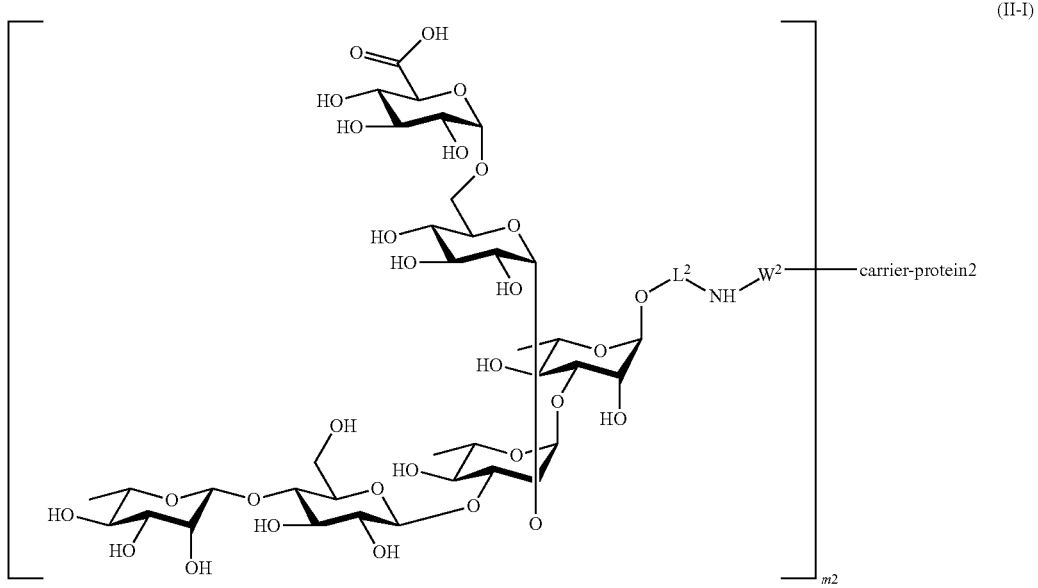

wherein $L^2$, m2, —$W^2$— and carrier-protein2 have the meanings defined herein.

Preferably the linker -$L^2$- is selected from: -$L^{a*}$-, -$L^{a*}$-$L^{e*}$-, -$L^{a*}$-$L^{b*}$-$L^{e*}$-, -$L^{a*}$-$L^{d*}$-$L^{e*}$-; wherein -$L^{a*}$- is selected from: —$(CH_2)_o{}^*$—, —$(CH_2—CH_2—O)_o{}^*—C_2H_4$—, —$(CH_2—CH_2—O)_o{}^*—CH_2$—;

-$L^{b*}$- represents —O—;

-$L^{d*}$- is selected from: —$(CH_2)_q{}^*$—, —$(CF_2)_q{}^*$—, —$(CH_2—CH_2—O)_q{}^*—C_2H_4$—, and —$(CH_2—CH_2—O)_q{}^*—CH_2$—;

-$L^{e*}$- is selected from: —$(CH_2)_{p1}{}^*$—, —$(CF_2)_{p1}{}^*$—, —$C_2H_4—(O—CH_2CH_2)_{p1*}$—, —$CH_2—(O—CH_2—CH_2)_{p1}{}^*$— and —$(CH_2)_{p1}{}^*—O—(CH_2)_{p2}{}^*$—;

and o*, q*, p1* and p2* are independently of each other an integer selected from 1, 2, 3, 4, 5, and 6.

Hence, the inventive immunogenic composition provided herein preferably contains a conjugate of general formula (II), (II-A), (II-B), (II-C), (II-D), (II-E), (II-F). (II-H), (II-I) or (II-A) with B*— being H—, wherein -$L^2$- is selected from: -$L^{a*}$-, -$L^{a*}$-$L^{e*}$-, -$L^{a*}$-$L^{b*}$-$L^{e*}$-, -$L^{a*}$-$L^{d*}$-$L^{e*}$-; wherein -$L^{a*}$- is selected from: —$(CH_2)_o{}^*$—, —$(CH_2—CH_2—O)_o{}^*—C_2H_4$—, —$(CH_2—CH_2—O)_o{}^*—CH_2$—;

-$L^{b*}$- represents —O—;

-$L^{d*}$- is selected from: —$(CH_2)_q{}^*$—, —$(CF_2)_q{}^*$—, —$(CH_2—CH_2—O)_q{}^*—C_2H_4$—, and —$(CH_2—CH_2—O)_q{}^*—CH_2$—;

-$L^{e*}$- is selected from: —$(CH_2)_{p1}{}^*$—, —$(CF_2)_{p1}{}^*$—, —$C_2H_4—(O—CH_2—CH_2)_{p1}{}^*$—, —$CH_2—(O—CH_2—CH_2)_{p1}{}^*$— and —$(CH_2)_{p1}{}^*—O—(CH_2)_{p2}{}^*$—;

and o*, q*, p1* and p2* are independently of each other an integer selected from 1, 2, 3, 4, 5, and 6.

In a more preferred embodiment, the linker -$L^2$- in general formulae (II), (II-A), (II-B), (II-C), (II-D), (II-E), (II-F). (II-H), (II-I) and (II-A) with B*— being H—, represents —$(CH_2)_o{}^*$— and o* is an integer selected from 2, 3, 4, 5, 6, 7 and 8.

It is also preferred that —$W^2$— represents

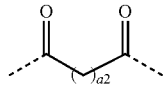

and a2 is an integer selected from 2, 3, 4, 5 and 6.

It is further preferred that the carrier-protein2 is $CRM_{197}$ and/or m2 is comprised between 4 and 15, and more preferably between 6 and 12.

Immunization with an immunogenic composition comprising a conjugate of a saccharide from S. pneumoniae serotype 8 and a carrier protein, such as a conjugate of general formula (I), (I-A) or (I-B) defined above, a conjugate of general formula (II), (II-A), (II-B), (II-C), (II-D), (II-E), (II-F), (II-H) or (II-I) as defined above, and a mixture consisting of capsular polysaccharides from S. pneumoniae serotypes 1, 3, 4, 5, 6A, 6B, 7F, 9V, 14, 18C, 19A, 19F and 23F individually conjugated to $CRM_{197}$ carrier protein, or a mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid, or a mixture consisting of capsular polysaccharides from S. pneumoniae serotypes 1, 3, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular saccharide from S. pneumoniae serotype 3 is conjugated to a carrier protein such as $CRM_{197}$, the capsular polysaccharide from S. pneumoniae serotype 18C is conjugated to tetanus toxoid and the capsular polysaccharide from S. pneumoniae serotype 19F is conjugated to diphtheria toxoid induces a robust immune response against the capsular polysaccharide from Streptococcus pneumoniae serotypes 8 and 2, thereby leading to opsonophagocytic killing of Streptococcus pneumoniae serotype 8 and 2 pneumococci, without impairing the immune response against the capsular polysaccharides from the other S. pneumoniae serotypes, which are present in the immunogenic composition and an unexpected higher immune response against the capsular polysaccharides from S. pneumoniae serotypes 3 and 19A. Therefore, said immunogenic compositions are useful for the prevention and/or treatment of diseases caused by Streptococcus pneumoniae and in particular for the prevention and/or treatment of diseases caused by Streptococcus pneumoniae serotype 8 and serotype 2 and serotype 3.

A further aspect of the present invention is directed to an improved immunogenic composition comprising a conjugate of general formula (II), (II-A), (II-B), (II-C), (II-D), (II-E), (II-F), (II-H), or (II-I) as defined above and a mixture consisting of capsular polysaccharides from S. pneumoniae serotypes 1, 3, 4, 5, 6A, 6B, 7F, 9V, 14, 18C, 19A, 19F and 23F individually conjugated to $CRM_{197}$ carrier protein; or a mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14 and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid, or a mixture consisting of capsular polysaccharides from S. pneumoniae serotypes 1, 3, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular saccharide from S. pneumoniae serotype 3 is conjugated to a carrier protein such as $CRM_{197}$, the capsular polysaccharide from S. pneumoniae serotype 18C is conjugated to tetanus toxoid and the capsular polysaccharide from S. pneumoniae serotype 19F is conjugated to diphtheria toxoid. Immunization with such immunogenic composition induces a robust immune response against the capsular polysaccharide from Streptococcus pneumoniae serotypes 2, thereby leading to opsonophagocytic killing of Streptococcus pneumoniae serotype 2 pneumococci, without impairing the immune response against the capsular polysaccharides from the other S. pneumoniae serotypes, which are present in the immunogenic composition. Therefore, said immunogenic composition is useful for the prevention and/or treatment of diseases caused by Streptococcus pneumoniae and in particular for the prevention and/or treatment of diseases caused by Streptococcus pneumoniae serotype 2.

The immunogenic compositions comprising the above-defined conjugate of a saccharide from S. pneumoniae serotype 8 and a carrier protein, the mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14 and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid, and optionally a S. pneumoniae serotype 2 conjugate of general formula (II), (II-A), (II-B), (II-C), (II-D), (II-E), (II-F), (II-H) or (II-I) as defined above, may most preferably further contain a S. pneumoniae serotype 3 conjugate of general formula (III):

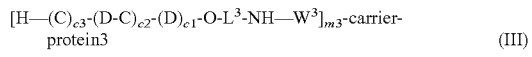

wherein

C represents:

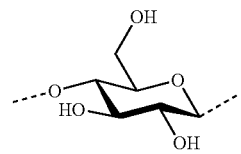

D represents

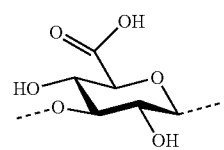

c2 is an integer selected from 1, 2, 3, 4, 5, 6, 7, 8, 9 and 10;

c1 and c3 represent independently of each other an integer selected from 0 and 1;

$L^3$ represents a linker;

m3 is comprised between about 2 and about 18;

—$W^3$— is selected from:

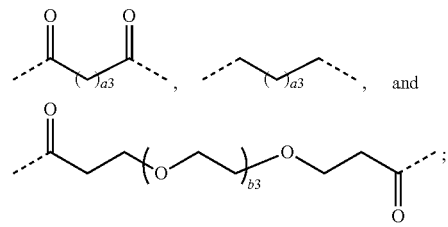

a3 represents an integer from 1 to 10;

b3 represents an integer from 1 to 4; and carrier-protein3 is selected from $CRM_{197}$, protein D, tetanus toxoid and diphtheria toxoid.

-$L^3$- is defined as a linker and is part of the fragment —O-$L^3$-NH—. Thus, the linker -$L^3$- is bound to an oxygen atom and to the nitrogen atom of the —NH—$W^3$— fragment. It is preferred that at least two carbon atoms of the linker are between the oxygen atom and the —NH—$W^3$— fragment, like —O—C—C—NH—$W^3$—. The linker -$L^3$- can be an aliphatic chain, wherein the aliphatic chain can optionally include an aromatic chain inserted in it, or a number of heteroatoms oscillating from 0 to 10. The linker -$L^3$- preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms. The shortest atom chain between the oxygen atom (i.e. the oxygen of —O-$L^3$-NH—) and the —NH—$W^3$— fragment consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the —NH—

W³— fragment) consists of 2 to 6 atoms, these are preferably carbon atoms. In case the shortest chain consists of 4 to 8 atoms, the chain may contain 1, 2 or 3 heteroatoms selected from O, N and S. In case the shortest chain consists of 9 to 14 atoms, the chain may contain 1, 2, 3, 4, 5, or 6 heteroatoms selected from O, N and S.

It is also preferred that the linker -L³-, or the shortest chain is fully or partially fluorinated. The linker -L³- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L³- may also contain amide (—NH—CO—, —CO—NH—) and/or urea (—NH—CO—NH—) residues and preferably only one amide or urea residue. The linker may also contain substituents and preferably two substituents, such as $R^{10}$ and $R^{11}$, or four substituents such as $R^{10}, R^{11}, R^{15}$ and $R^{14}$, which have the meanings as defined herein and which are preferably selected from: —F, —Cl, —CH₃, —C₂H₅, —C₃H₇, —C₅H₉, —C₆H₁₃, —OCH₃, —OC₂H₅, —CH₂F, —CHF₂, —CF₃, —C(O)—NH₂, —SCH₃, —SC₂H₅, —NHC(O)CH₃, —N(CH₃)₂, and —N(C₂H₅)₂;

In case the linker -L³- is fluorinated, more than two substituents —F are preferred.

Linker -L³- is preferably selected from: —CH₂—, —(CH₂)₂—, —(CH₂)₃—, —(CH₂)₄—, —(CH₂)₅—, —(CH₂)₆—, —(CH₂)₇—, —(CH₂)₈—, —(CH₂)₉—, —(CH₂)₁₀—, —CF₂—, —(CF₂)₂—, —(CF₂)₃—, —(CF₂)₄—, —(CF₂)₅—, —(CF₂)₆—, —(CF₂)₇—, —(CF₂)₈—, —(CF₂)₉—, —(CF₂)₁₀—, —(CH₂)₂—O—(CH₂)₂—, —CH₂—O—(CH₂)₃—, —(CH₂)₃—O—CH₂—CH₂—O—(CH₂)₂—, —(CH₂)₂—O—CH₂—, —(CH₂)₃—O—(CH₂)₂—, —(CH₂)₂—O—(CH₂)₃—, —(CH₂)₄—O—CH₂—, —CH₂—O—(CH₂)₄—, -L$^{a}$-, -L$^{a}$-L$^{e}$-, -L$^{a}$-L$^{b}$-L$^{e}$-, -L$^{a}$-L$^{b}$-L$^{d}$-L$^{c}$-L$^{e}$-, -L$^{a}$-L$^{d}$-L$^{e}$-;

wherein

-L$^{a}$- is selected from: —(CH₂)$_o$—, —(CF₂)$_o$—, —(CH₂—CH₂—O)$_o$—C₂H₄—, —(CH₂—CH₂—O)$_o$**—CH₂—, —(CR$^{10*}$R$^{11*}$)$_o$**,

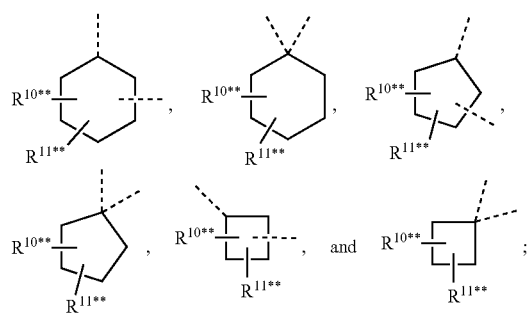

-L$^{b}$- and -L$^{c}$- are independently of each other selected from: —O—, —NH—C(O)—NH—, —NH—C(S)—NH—, —NH—C(O)—, —C(O)—NH—, —NH—C(O)—O—, —NR$^{9}$—, —NR$^{18}$—, —SO₂—,

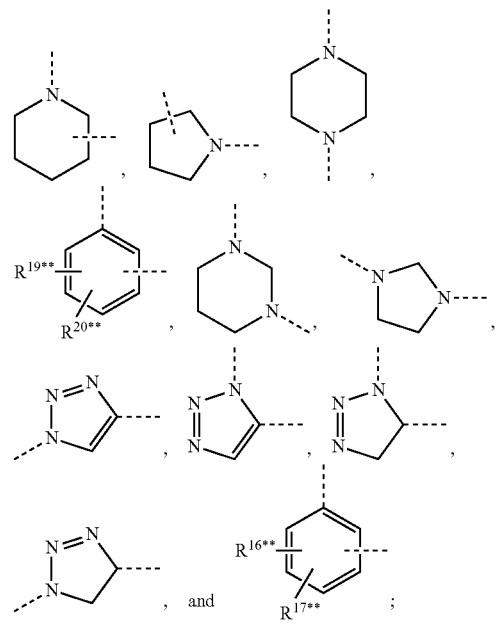

-L$^{d}$- represents: —(CH₂)$_q$—, —(CF₂)$_q$—, —(CR$^{12}$R$^{13}$)$_q$—, —(CH₂—CH₂—O)$_q$—C₂H₄—, —(CH₂—CH₂—O)$_q$—CH₂—,

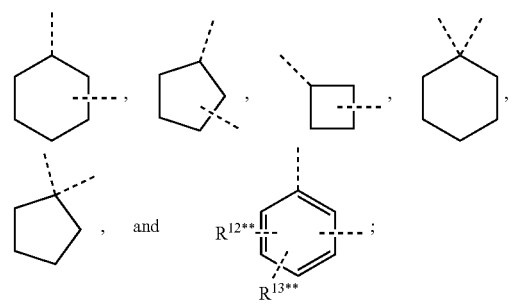

-L$^{e}$- is selected from: —(CH₂)$_{p1}$—, —(CF₂)$_{p1}$—, —C₂H₄—(O—CH₂—CH₂)$_{p1}$—, —CH₂—(O—CH₂—CH₂)$_{p1}$—, —(CH₂)$_{p1}$—O—(CH₂)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—,

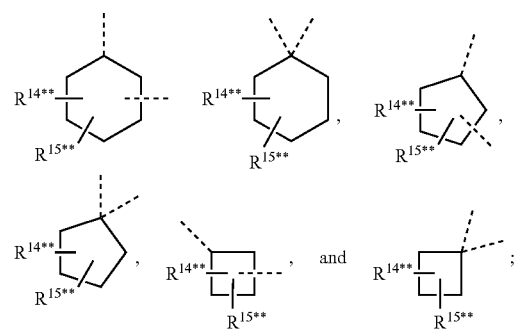

$R^{9}$ and $R^{18}$ are independently of each other selected from: —CH₃, —C₂H₅, —C₃H₇, and —C(O)CH₃;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$ and —N(C$_2$H$_5$)$_2$;

o, q, p1 and p2 are independently of each other an integer selected from 1, 2, 3, 4, 5, 6, 7, 8, 9, and 10.

In general formula (III), preferably c1 and c3 represent 0. Thus, an immunogenic composition comprising the above-defined conjugate of a saccharide from *S. pneumoniae* serotype 8 and a carrier protein, the mixture consisting of capsular polysaccharides from *S. pneumoniae* serotypes 1, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14, and 23F are individually conjugated to protein D, the capsular polysaccharide from *S. pneumoniae* serotype 18C is conjugated to tetanus toxoid and the capsular polysaccharide from *S. pneumoniae* serotype 19F is conjugated to diphtheria toxoid, optionally a *S. pneumoniae* serotype 2 conjugate of general formula (II), (II-A), (II-B), (II-C), (II-D), (II-E), (II-F), (II-H) or (II-I) as defined above, and a *S. pneumoniae* serotype 3 conjugate of general formula (III-A):

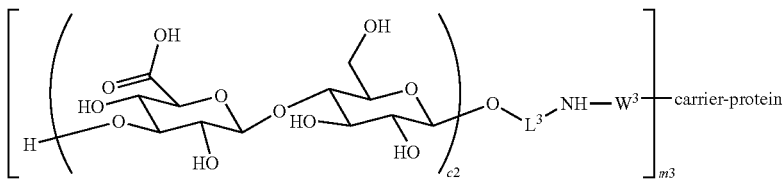

(III-A)

wherein c2, $L^3$, —$W^3$—, m3 and carrier-protein3 have the meanings defined herein, is especially preferred.

Preferably the linker -$L^3$- is selected from: -$L^{a}$-, -$L^{a}$-$L^{e}$-, -$L^{a}$-$L^{b}$-$L^{e}$-, -$L^{a}$-$L^{d}$-$L^{e}$-; wherein -$L^{a}$- is selected from: —(CH$_2$)$_o$—, —(CH$_2$—CH$_2$—O)$_o$—C$_2$H$_4$—, —(CH$_2$—CH$_2$—O)$_o$**—CH$_2$—;

-$L^{b**}$- represents —O—;

-$L^{d}$- is selected from: —(CH$_2$)$_q$—, —(CF$_2$)$_q$—, —(CH$_2$—CH$_2$—O)$_q$—C$_2$H$_4$—, and —(CH$_2$—CH$_2$—O)$_q$**—CH$_2$—;

-$L^{e}$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$**— and —(CH$_2$)$_{p1}$*—O—(CH$_2$)$_{p2}$**—;

and o, q, p1 and p2 are independently of each other an integer selected from 1, 2, 3, 4, 5, and 6.

More preferably, the linker -$L^3$- represents —(CH$_2$)$_o$— and o is an integer selected from 2, 3, 4, 5, 6, 7 and 8.

It is also preferred that —$W^3$— represents

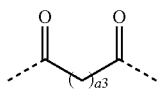

and a3 is an integer selected from 2, 3, 4, 5 and 6.

It is further preferred that the carrier-protein3 is CRM$_{197}$ and/or m3 is comprised between 3 and 14, and more preferably between 4 and 10. Moreover, it is preferred that c2 is an integer selected from 2, 3, 4 and 5, and even more preferred that c2 represents 2.

Surprisingly, it was found that immunization with an immunogenic composition comprising a conjugate of a saccharide from *S. pneumoniae* serotype 8 and a carrier protein, such as a conjugate of general formula (I), (I-A) or (I-B) defined above, a conjugate of general formula (III) or (III-A) as defined above, and a mixture consisting of capsular polysaccharides from *S. pneumoniae* serotypes 1, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14 and 23F are individually conjugated to protein D, the capsular polysaccharide from *S. pneumoniae* serotype 18C is conjugated to tetanus toxoid and the capsular polysaccharide from *S. pneumoniae* serotype 19F is conjugated to diphtheria toxoid induces a robust immune response against the capsular polysaccharide from *Streptococcus pneumoniae* serotypes 8 and 3, thereby leading to opsonophagocytic killing of *Streptococcus pneumoniae* serotype 8 and 3 pneumococci, without impairing the immune response against the capsular polysaccharides from the other *S. pneumoniae* serotypes, which are present in the immunogenic composition. Therefore, said immunogenic compositions are useful for the prevention and/or treatment of diseases caused by *Streptococcus pneumoniae* serotype 8 and serotype 3.

Furthermore, immunization with an immunogenic composition comprising a conjugate of a saccharide from *S. pneumoniae* serotype 8 and a carrier protein, such as a conjugate of general formula (I), (I-A) or (I-B) defined above, a *S. pneumoniae* serotype 2 conjugate of general formula (II), (II-A), (II-B), (II-C), (II-D), (II-E), (II-F). (II-H), or (II-I) as defined above, a *S. pneumoniae* serotype 3 conjugate of general formula (III) or (III-A) as defined above, and a mixture consisting of capsular polysaccharides from *S. pneumoniae* serotypes 1, 4, 5, 6B, 7F, 9V, 14, 18C, 19F and 23F individually conjugated to a carrier protein, wherein the capsular polysaccharides from *S. pneumoniae* serotypes 1, 4, 5, 6B, 7F, 9V, 14 and 23F are individually conjugated to protein D, the capsular polysaccharide from *S. pneumoniae* serotype 18C is conjugated to tetanus toxoid and the capsular polysaccharide from *S. pneumoniae* serotype 19F is conjugated to diphtheria toxoid induces a robust immune response against the capsular polysaccharide from *Streptococcus pneumoniae* serotypes 8, 2 and 3, thereby leading to opsonophagocytic killing of *Streptococcus pneumoniae* serotype 8, 2 and 3 pneumococci, without impairing the immune response against the capsular polysaccharides from the other *S. pneumoniae* serotypes, which are present in the immunogenic composition. Therefore, said immunogenic compositions are useful for the prevention and/or treatment of diseases caused by *Streptococcus pneumoniae* serotypes 8, 2 and 3.

A further aspect of the present invention is directed to a vaccine that comprises the inventive immunogenic composition disclosed herein, a physiologically acceptable vehicle and an adjuvant. Thus, a vaccine can be obtained by formulating the inventive immunogenic composition with a physiologically acceptable vehicle and an adjuvant by methods known in the art.

A physiologically acceptable vehicle may include non-toxic levels of alcohols and salts, 5% dextrose or other sugars, saline, and other pharmaceutically acceptable excipients, and any combination of any of these solvents. Such excipients are well known and described. Preferably used physiologically acceptable vehicles are water, buffered saline, succinic acid, polysorbate 80, polyols (e.g., glycerol, propylene glycol, liquid polyethylene glycol) and dextrose solutions.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples of immunological adjuvants include, but are not restricted to (1) aluminum salts (alum), such as aluminum hydroxide, aluminum phosphate, aluminum sulfate, etc.;
(2) oil-in-water emulsion formulations (with or without other specific immunostimulating agents such as muramyl peptides (defined below) or bacterial cell wall components), such as, for example,
   (a) MF59 (WO 90/14837), containing 5% Squalene, 0.5% Tween 80, and 0.5% Span 85 (optionally containing various amounts of MTP-PE (see below, although not required)) formulated into submicron particles using a microfluidizer such as Model 110Y microfluidizer (Microfluidics, Newton, Mass.),
   (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and
   (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);
(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);
(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyl-oxytetradecanoyl-amino]ethyl 2-deoxy-4-O-phosphono-3-O—[(R)-3-tetradecanoyloxytetra-decanoyl]-2-[(R)-3-tetradecanoyloxytetradecanoylamino-β-D-glucopyranoside, which is also known as 529 (formerly known as RC529), which is formulated as an aqueous form or as a stable emulsion, synthetic polynucleotides such as oligonucleotides containing CpG motif(s) (U.S. Pat. No. 6,207,646);
(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.;
(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with WO 00/18434 (see also WO 02/098368 and WO 02/098369), a pertussis toxin (PT), or an E. coli heat-labile toxin (LT), particularly LT-K63, LT-R72, CT-S109, PT-K9/G129 (see, e.g., WO 93/13302 and WO 92/19265); and
(7) other substances that act as immunostimulating agents to enhance the effectiveness of the composition. Muramyl peptides include, but are not limited to, N-acetyl-muramyl-L-threonyl-D-isoglutamine (thr-MDP), N-acetyl-normuramyl-L-alanine-2-(1'-2'dipalmitoyl-sn-glycero-3-hydroxyphosphoryloxy)-ethylamine (MTP-PE)1 etc.

Vaccines are preferably in aqueous form, particularly at the point of administration, but they can also be presented in non-aqueous liquid forms or in dried forms e.g. as gelatin capsules, or as lyophilisates, etc. Vaccines may include one or more preservatives, such as thiomersal or 2-phenoxyethanol. Mercury-free compositions are preferred, and preservative-free vaccines can be prepared.

Vaccines may include a physiological salt, such as a sodium salt e.g. to control tonicity. Sodium chloride (NaCl) is typical and may be present at between 1 and 20 mg/ml. Other salts that may be present include potassium chloride, potassium dihydrogen phosphate, disodium phosphate dehydrate, magnesium chloride, calcium chloride, etc.

Vaccines can have an osmolality of between 200 mOsm/kg and 400 mOsm/kg.

Vaccines may include compounds (with or without an insoluble metal salt) in plain water (e.g. w.f.i.), but will usually include one or more buffers. Typical buffers include: a phosphate buffer; a Tris buffer; a borate buffer; a succinate buffer; a histidine buffer (particularly with an aluminium hydroxide adjuvant); or a citrate buffer. Buffer salts will typically be included in the 5-20 mM range. Vaccines typically have a pH between 5.0 and 9.5 e.g. between 6.0 and 8.0. Vaccines are preferably sterile and gluten free.

Vaccines are suitable for administration to animal (and, in particular, human) patients, and thus, include both human and veterinary uses. They may be used in a method of raising an immune response in a patient, comprising the step of administering the composition to the patient. The vaccines of the present invention may be administered before a subject is exposed to a Streptococcus pneumoniae type 8 and/or after a subject is exposed to a Streptococcus pneumoniae type 8.

Vaccines may be prepared in unit dose form. In some embodiments a unit dose may have a volume of between 0.1-1.0 mL e.g. about 0.5 mL. The invention also provides a delivery device (e.g. syringe, nebulizer, sprayer, inhaler, dermal patch, etc.) containing a vaccine of the invention e.g. containing a unit dose. This device can be used to administer the composition to a vertebrate subject.

The invention also provides a sterile container (e.g. a vial) containing a vaccine of the invention e.g. containing a unit dose.

The invention also provides a unit dose of a vaccine of the invention.

The invention also provides a hermetically sealed container containing a vaccine of the invention. Suitable containers include e.g. a vial.

Vaccines of the invention may be prepared in various forms. For example, the vaccines may be prepared as injectables, either as liquid solutions or suspensions. Solid forms suitable for solution in, or suspension in, liquid vehicles prior to injection can also be prepared (e.g. a lyophilized composition or a spray-freeze dried composition). The vaccine may be prepared for topical administration e.g. as an ointment, cream or powder. The vaccine may be prepared for oral administration e.g. as a tablet or capsule, as a spray, or as a syrup (optionally flavored). The vaccine may be prepared for pulmonary administration e.g. by an inhaler, using a fine powder or a spray. The vaccine may be prepared as a suppository. The vaccine may be prepared for nasal, aural or ocular administration e.g. as a spray or drops. Injectables for intramuscular administration are typical.

The inventive vaccine comprises an effective amount of an adjuvant i.e. an amount which, when administered to an individual, either in a single dose or as part of a series, is effective for enhancing the immune response to a co-administered S. pneumoniae type 8 antigen. This amount can vary depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range that can be determined through routine trials.

Techniques for the formulation and administration of the vaccine of the present invention may be found in "Remington's Pharmaceutical Sciences" Mack Publishing Co., Easton Pa.

The amount of conjugate in each vaccine dose is selected as an amount that induces an immunoprotective response without significant, adverse effects. Such amount can vary depending upon the S. pneumoniae serotype. Preferably, each dose will comprise 0.1 to 100 µg of each capsular polysaccharide or saccharide, more preferably 0.1 to 10 µg, and most preferably 1 to 5 µg.

In one embodiment of the present invention the vaccine comprises the herein disclosed immunogenic composition, wherein each conjugate is adsorbed on aluminum phosphate.

Preferably, the vaccine comprises the S. pneumoniae serotype 8 conjugate defined above and a mixture consisting of capsular polysaccharides from S. pneumoniae serotypes 1, 3, 4, 5, 6A, 6B, 7F, 9V, 14, 18C, 19A, 19F and 23F individually conjugated to $CRM_{197}$ carrier protein, wherein each conjugate is adsorbed on aluminum phosphate. More preferably, the vaccine comprises the S. pneumoniae serotype 8 conjugate and the S. pneumoniae serotype 2 conjugate defined above and a mixture consisting of capsular polysaccharides from S. pneumoniae serotypes 1, 3, 4, 5, 6A, 6B, 7F, 9V, 14, 18C, 19A, 19F and 23F individually conjugated to $CRM_{197}$ carrier protein, wherein each conjugate is adsorbed on aluminum phosphate.

In another embodiment of the present invention the vaccine comprises the S. pneumoniae serotype 8 conjugate described herein, as well as a mixture consisting of 2.2 µg of each capsular polysaccharides from S. pneumoniae serotypes 1, 3, 4, 5, 6A, 7F, 9V, 14, 18C, 19A, 19F and 23F individually conjugated to $CRM_{197}$ carrier protein and 4.4 µg of capsular polysaccharide from S. pneumoniae serotype 6B conjugated to $CRM_{197}$ carrier protein, wherein each conjugate is adsorbed on aluminum phosphate and wherein the total amount of aluminum phosphate is 500 µg. In a further preferred embodiment, the vaccine comprises the S. pneumoniae serotype 8 conjugate and the S. pneumoniae serotype 2 conjugate described herein, as well as a mixture consisting of 2.2 µg of each capsular polysaccharides from S. pneumoniae serotypes 1, 3, 4, 5, 6A, 7F, 9V, 14, 18C, 19A, 19F and 23F individually conjugated to $CRM_{197}$ carrier protein and 4.4 µg of capsular polysaccharide from S. pneumoniae serotype 6B conjugated to $CRM_{197}$ carrier protein, wherein each conjugate is adsorbed on aluminum phosphate and wherein the total amount of aluminum phosphate is 500 µg. Preferably, the amount of S. pneumoniae serotype 8 saccharide contained in the above-disclosed vaccines is approximately 2.2 µg. Even more preferably, the amount of S. pneumoniae serotype 2 saccharide contained in the above-disclosed vaccines is approximately 2.2 µg.

In another embodiment of the present invention the vaccine comprises the S. pneumoniae serotype 8 conjugate described herein, as well as a mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid and wherein each conjugate is adsorbed on aluminum phosphate. In a more preferred embodiment of the present invention the vaccine comprises the S. pneumoniae serotype 8 conjugate and the S. pneumoniae serotype 2 conjugate described herein, as well as a mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid and wherein each conjugate is adsorbed on aluminum phosphate. In a further preferred embodiment of the present invention the vaccine comprises the S. pneumoniae serotype 8 conjugate, the S. pneumoniae serotype 2 conjugate and the S. pneumoniae serotype 3 conjugate described herein, as well as a mixture consisting of capsular polysaccharides from S. pneumoniae serotypes 1, 4, 5, 6B, 7F, 9V, 14, 18C, 19F and 23F individually conjugated to a carrier protein, wherein the capsular polysaccharides from S. pneumoniae serotypes 1, 4, 5, 6B, 7F, 9V, 14, and 23F are individually conjugated to protein D, the capsular polysaccharide from S. pneumoniae serotype 18C is conjugated to tetanus toxoid and the capsular polysaccharide from S. pneumoniae serotype 19F is conjugated to diphtheria toxoid and wherein each conjugate is adsorbed on aluminum phosphate.

Preferably, the vaccine comprises the S. pneumoniae serotype 8 conjugate disclosed herein, as well as a mixture consisting of 1 µg of capsular polysaccharides from S. pneumoniae serotypes 1, 5, 6B, 7F, 9V, 14 and 23F individually conjugated to protein D, 3 µg of capsular polysaccharide from S. pneumoniae serotype 4 conjugated to protein D, 3 µg of capsular polysaccharide from S. pneumoniae serotype 18C conjugated to tetanus toxoid and 3 µg of capsular polysaccharide from S. pneumoniae serotype 19F conjugated to diphtheria toxoid and, wherein each conjugate is adsorbed on aluminum phosphate and wherein the total amount of aluminum phosphate is 500 µg. More preferably, the vaccine comprises the S. pneumoniae serotype 8 conjugate and the S. pneumoniae serotype 2 conjugate disclosed herein, as well as a mixture consisting of 1 µg of capsular polysaccharides from S. pneumoniae serotypes 1, 5, 6B, 7F, 9V, 14, and 23F individually conjugated to protein D, 3 µg of capsular polysaccharide from S. pneumoniae serotype 4 conjugated to protein D, 3 µg of capsular polysaccharide from S. pneumoniae serotype 18C conjugated to tetanus toxoid and 3 µg of capsular polysaccharide from S. pneumoniae serotype 19F conjugated to diphtheria toxoid and, wherein each conjugate is adsorbed on aluminum phosphate and wherein the total amount of aluminum phosphate is 500 µg. Even more preferably, the vaccine comprises the S. pneumoniae serotype 8 conjugate, the S. pneumoniae serotype 2 conjugate and S. pneumoniae serotype 3 conjugate disclosed herein, as well as a mixture consisting of 1 μg of capsular polysaccharides from *S. pneumoniae* serotypes 1, 5, 6B, 7F, 9V, 14 and 23F individually conjugated to protein D, 3 μg of capsular polysaccharide from *S. pneumoniae* serotype 4 conjugated to protein D, 3 μg of capsular polysaccharide from *S. pneumoniae* serotype 18C conjugated to tetanus toxoid and 3 μg of capsular polysaccharide from *S. pneumoniae* serotype 19F conjugated to diphtheria toxoid and, wherein each conjugate is adsorbed on aluminum phosphate and wherein the total amount of aluminum phosphate is 500 μg.

Synthesis of *S. pneumoniae* Serotype 8 Conjugates of General Formula (I)

The conjugates of general formula I $$[V^*-U_{x+3}-U_{x+2}-U_{x+1}-U_x\text{O-L}^1\text{-NH-W}^1]_{m1}\text{ carrier-protein1} \quad (I)$$

wherein $V^*-$, x, $U_{x+3}$, $U_{x+2}$, $U_{x+1}$, $U_x$, $L^1$, $-W^1-$, m1 and carrier-protein1 have the meanings defined herein, can be obtained starting from a saccharide of general formula 1* and carrier-protein1 using coupling methods well known to the skilled person (see Scheme 1).

Scheme 1 Retrosynthetic analysis of the
*S. pneumoniae* serotype 8 conjugates of general formula (I).

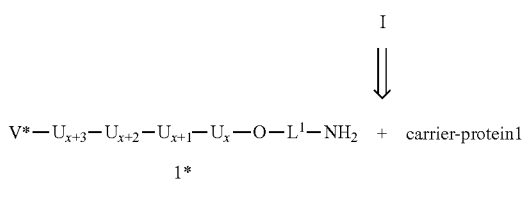

Such coupling methods include, for example, treatment of the saccharide 1* with a commercially available bifunctional spacer (Thermo Fischer, Sigma Aldrich) such as, disuccinimidyl adipate (DSA), bis-(4-nitrophenyl) adipate, bis-(4-nitrophenyl)succinate, disuccinimidyl glutarate (DSG), bis (sulfosuccinimidyl)disuccinimidyl glutarate bis (sulfosuccinimidyl)disuccinimidyl suberate (DSS), bis (sulfosuccinimidyl)suberate ($BS^3$), sebacic acid bis(N-succinimidyl) ester bis(succinimidyl)penta(ethyleneglycol), bis(succinimidyl) tetra(ethyleneglycol), in presence of a base, such as triethylamine, pyridine, followed by reaction of the resulting construct with carrier-protein1. Alternatively, saccharide 1* can be reacted with a suitable dialdehyde, such as glutaraldehyde, under reductive amination condition, and the resulting construct can be subsequently treated with the carrier-protein1 under reductive amination conditions.

A saccharide of general formula 1* can be synthesized via several synthetic routes.

For example, saccharide 1* can be assembled starting from thioglycoside building blocks BB2 (see Example C.5, precursor for the sugar fragment $U_1$, $U_5$, $U_2$ and $U_6$), BB3 (*Angew. Chem. Int. Ed.* 2013, 52, 5858; precursor for the sugar fragment $U_2$ and $U_6$), BB4 (see Example C.5, precursor for the sugar fragment $U_3$ and $U_7$) and BB5 (see Example C.5, precursor for the sugar fragment $U_4$) and functionalized solid support BB1 (*Angew. Chem. Int. Ed.* 2013, 52, 5858.) (see Scheme 2) by automated solid phase synthesis.

The synthetic process, which is summarized in Scheme 2 involves:

assembly of the desired oligosaccharide, which includes
  glycosylation with the appropriate thioglycoside (BB2, BB3, BB4 or BB5) by activation with NIS/TfOH; followed by
  removal of the temporary protecting group Fmoc by treatment with $Et_3N$;
cleavage from the solid support; and
removal of the permanent protecting groups.

Scheme 2 Automated solid phase synthesis of saccharides of general formula 1*.

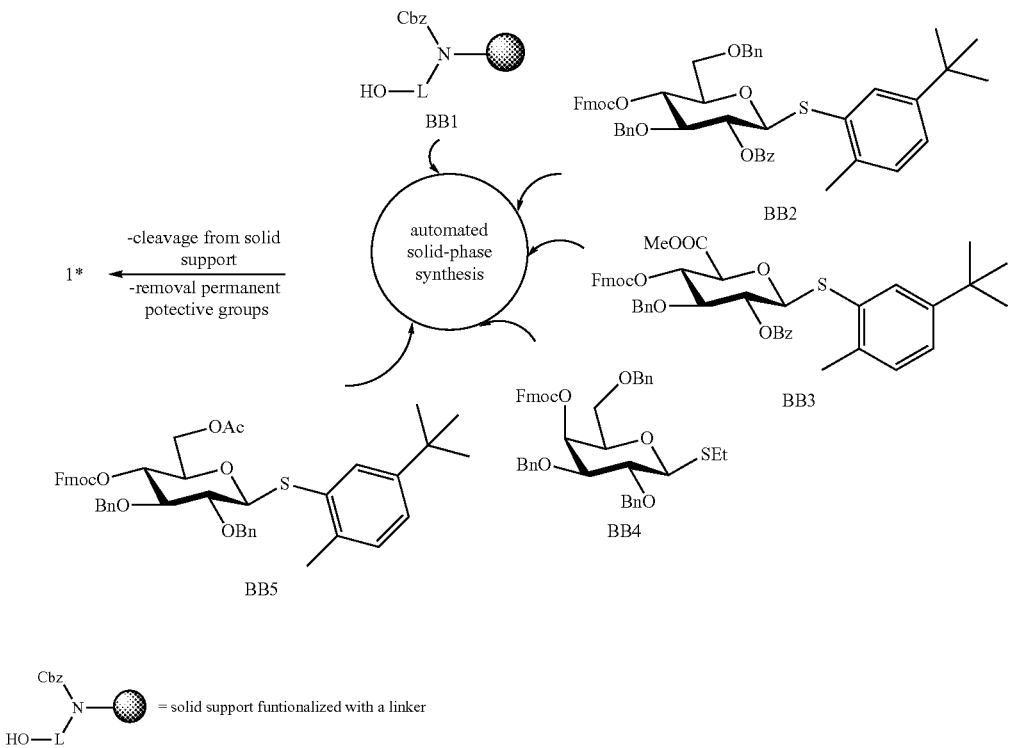

Synthesis of *S. pneumoniae* Serotype 2 Conjugates of General Formula (II-C)

The conjugates of general formula II-C

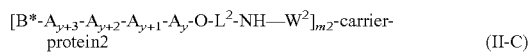
(II-C)

wherein y is an integer selected from 1, 2, 3 and 4;

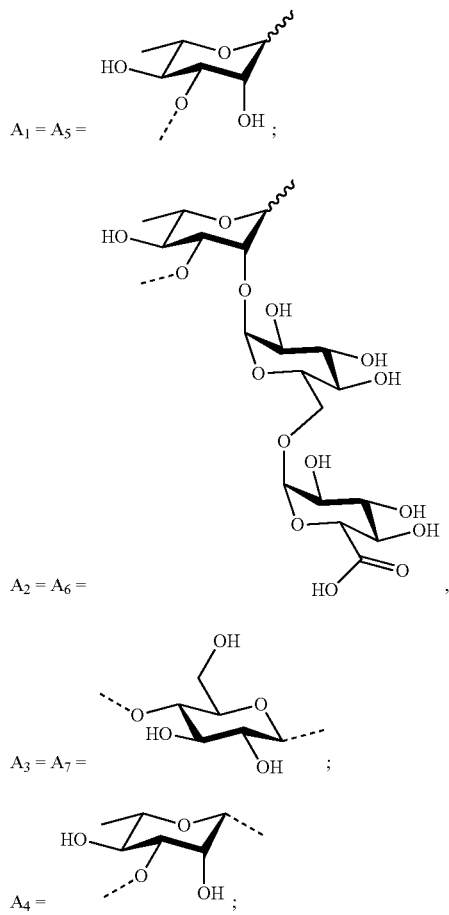

B*— represents: H—, H-$A_y$-, H-$A_{y+1}$-$A_y$-, H-$A_{y+2}$-$A_{y+1}$-$A_y$- or H-$A_{y+3}$-$A_{y+2}$-$A_{y+1}$-$A_y$-;

$L^2$ represents a linker and is defined as above;

m2 is comprised between about 2 and about 18;

—$W^2$— is selected from:

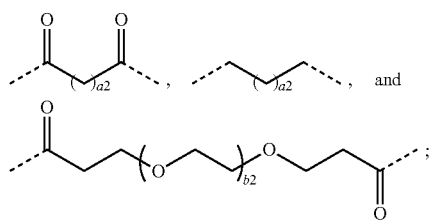

a2 represents an integer from 1 to 10;

b2 represents an integer from 1 to 4; and carrier-protein2 is selected from $CRM_{197}$, protein D, tetanus toxoid and diphtheria toxoid, can be obtained starting from a saccharide of general formula 2* and carrier-protein2 using coupling methods well known to the skilled person (see Scheme 3).

Scheme 3 Retrosynthetic analysis of the
*S. pneumoniae* serotype 2 conjugates of general formula (II-C).

II-C

⇓

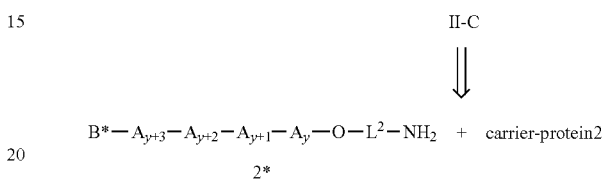

Such coupling methods include, for example, treatment of the saccharide 2* with a commercially available bifunctional spacer (Thermo Fischer, Sigma Aldrich) such as, disuccinimidyl adipate (DSA), bis-(4-nitrophenyl) adipate, bis-(4-nitrophenyl)succinate, disuccinimidyl glutarate (DSG), bis (sulfosuccinimidyl)di-succinimidyl glutarate bis (sulfosuccinimidyl)disuccinimidyl suberate (DSS), bis (sulfosuccinimidyl)suberate ($BS^3$), sebacic acid bis(N-succinimidyl) ester bis(succinimidyl)penta(ethyleneglycol), bis(succinimidyl) tetra(ethyleneglycol), in presence of a base, such as triethylamine, pyridine, followed by reaction of the resulting construct with carrier-protein2. Alternatively, saccharide 2* can be reacted with a suitable dialdehyde, such as glutaraldehyde, under reductive amination conditions, and the resulting construct can be subsequently treated with the carrier-protein2 under reductive amination conditions.

A saccharide of general formula 2* can be efficiently assembled starting from building blocks 3* (see Example A-1), 4* (see Example A-4), 5* (see Example A-1), 6*, 7* (see Example A-2), as well as amino-alcohol linker 8* as starting material (Scheme 4) and using glycosylation and deprotection method well known to the skilled person in the art. Building block 6* can be prepared from known building block 9* (Bundle D. R. et al. *ACS Chem. Biol.* 2012, 7, 1754). Conversion of building block 9* to building block 6* involves installing the Fmoc protecting group at $4^{th}$ position of the glucoside by reaction with FmocCl and pyridine in dichloromethane, followed by treatment with CAN in a mixture of acetonitrile and water, and finally installation of the trichloroacetimidate leaving group at the anomeric position by treatment with $CCl_3CN$ and DBU in dichloromethane at room temperature.

Scheme 4 Retrosynthetic analysis of saccharide of general formula 2*.

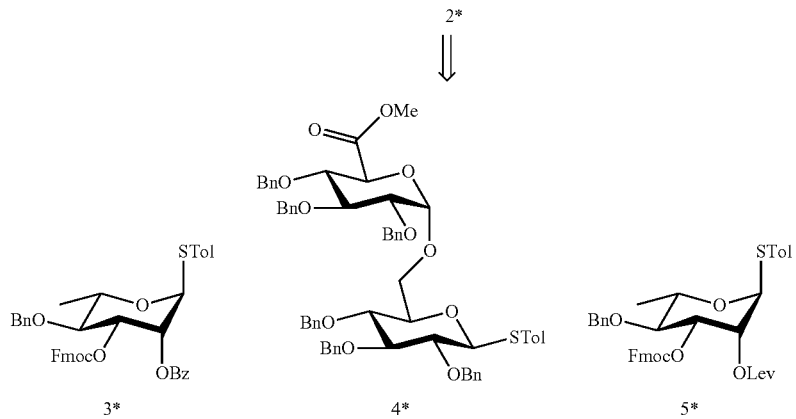

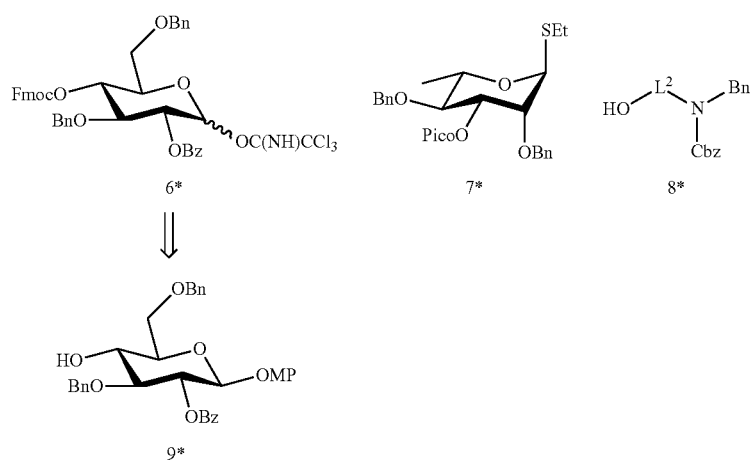

Synthesis of *S. pneumoniae* Serotype 3 Conjugates of General Formula (III)

The conjugates of general formula III $$[H—(C)_{c3}\text{-}(D\text{-}C)_{c2}\text{-}(D)_{c1}\text{-}O\text{-}L^3\text{-}NH—W^3]_{m3}\text{-carrier-protein3} \quad \text{(III)}$$

wherein C, D, c1, c2, c3, L3, m3, —$W^3$— and carrier-protein3 have the meanings defined herein, can be generated starting from saccharide 10* and carrier-protein3 using coupling methods well known to the skilled person.

Scheme 1 Retrosynthetic analysis of the *S. pneumoniae* serotype 3 conjugates of general formula (III).

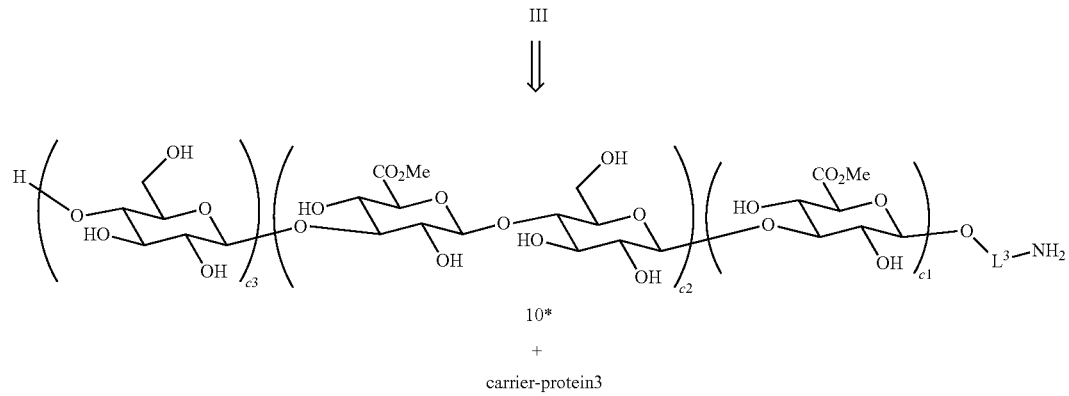

Such coupling methods include, for example, treatment of the saccharide 10* with a commercially available bifunctional spacer (Thermo Fischer, Sigma Aldrich) such as, disuccinimidyl adipate (DSA), bis-(4-nitrophenyl) adipate, bis-(4-nitrophenyl)succinate, disuccinimidyl glutarate (DSG), bis(sulfosuccinimidyl) disuccinimidyl glutarate bis (sulfosuccinimidyl)disuccinimidyl suberate (DSS), bis (sulfosuccinimidyl)suberate ($BS^3$), sebacic acid bis(N-succinimidyl) ester, bis(succinimidyl)penta(ethyleneglycol), bis (succinimidyl)tetra(ethyleneglycol), in presence of a base, such as trimethylamine or pyridine, followed by reaction of the resulting construct with carrier-protein3. Alternatively, saccharide 10* can be reacted with a suitable dialdehyde, such as glutaraldehyde, under reductive amination condition, and the resulting construct can be subsequently treated with the carrier-protein3 under reductive amination conditions.

Saccharides 10* can be prepared following synthetic methods disclosed in the international patent application WO 2015/040140A1.

DESCRIPTION OF THE FIGURES

FIG. 6 part A & B show results for incubation with serotype 2 (conjugate 1) and part C & D show results for incubation with Serotype 8 (conjugate 41).

FIG. 9 part A & B show results for incubation with serotype 2 (conjugate 1) and part C & D show results for incubation with Serotype 8 (conjugate 41).

Figure 1:
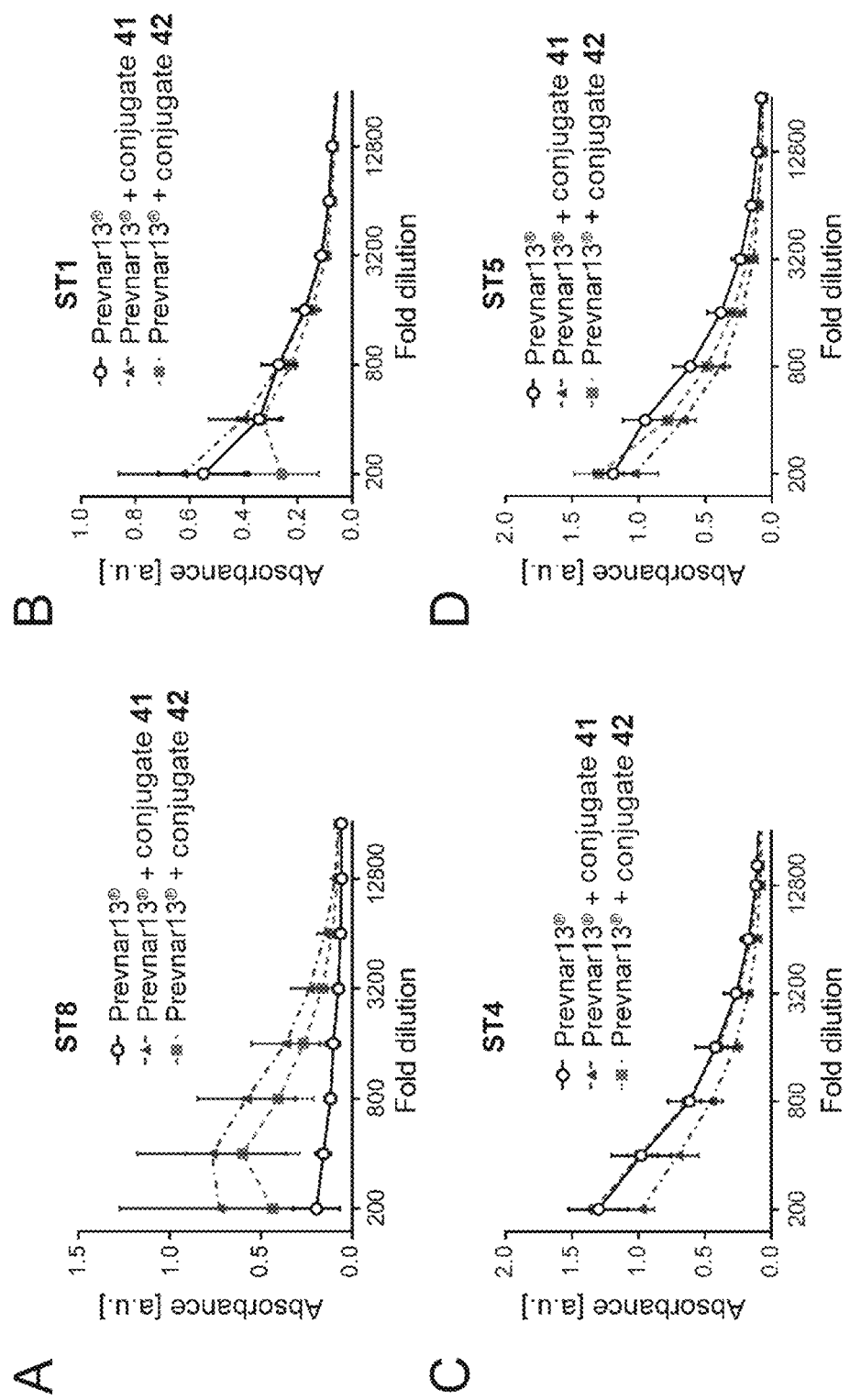
FIG. 1 shows the effect of coformulation of the conjugates 41 and 42 with Prevnar13® on the immune response against several capsular polysaccharides of *S. pneumoniae*, as assessed by polysaccharide ELISA. Sera were pre-adsorbed to pneumococcal cell wall polysaccharides (CWPs) and *S. pneumoniae* serotype 22F CPS before application. Bars depict mean±SD of polysaccharide binding of three rabbits per group. A binding to *S. pneumoniae* serotype 8-CPS; B binding to *S. pneumoniae* serotype 1-CPS; C: binding to *S. pneumoniae* serotype 4-CPS; D: binding to *S. pneumoniae* serotype 5-CPS; E: binding to *S. pneumoniae* serotype 7F-CPS; F: binding to *S. pneumoniae* serotype 9V-CPS; G: binding to *S. pneumoniae* serotype 19A-CPS.
Figure 1:
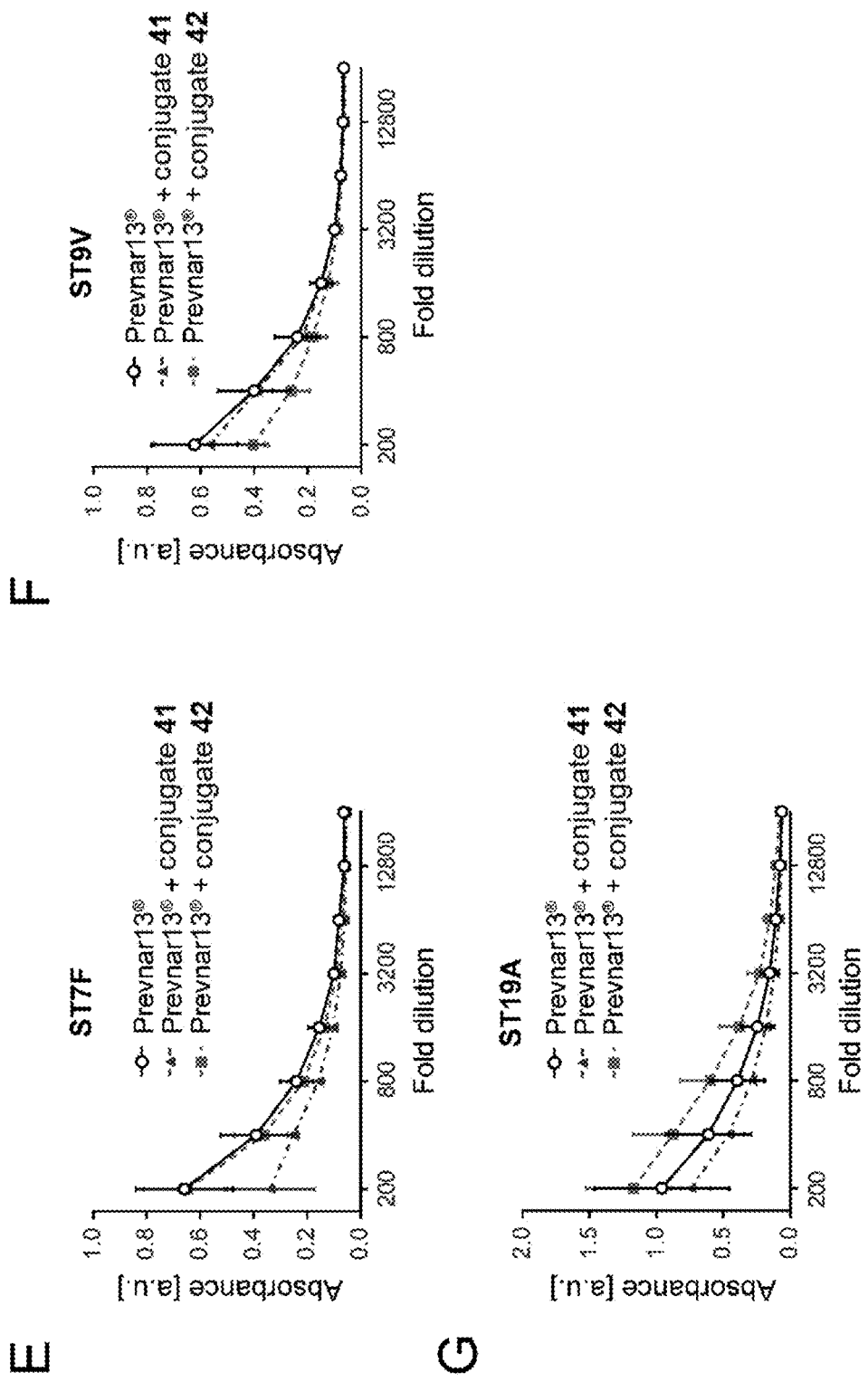

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Examples

Abbreviations
d day(s)
TLC thin layer chromatography
TEMPO 2,2,6,6-tetramethyl-1-piperidinyloxy, free radical
Ac Acetyl
AcOH Acetic acid
Ac$_2$O Acetic anhydride
BAIB Bisacetyliodobenzene
Bn Benzyl
$^t$BuOH t-Butanol
Bz Benzoyl
CAN Cericammonium nitrate
Cbz Benzyloxycarbonyl
Cu(OAc)$_2$ Copper(II) acetate
DBU 1,8-Diazabicyclo[5.4.0]undec-7-ene
DCC N,N'-Dicyclohexylcarbodiimide
DMAP N,N-Dimethylaminopyridine
DMF N,N'-Dimethylformamide
ESI Electrosprayionization
Et$_3$N Triethylamine
Et Ethyl
EtOAc Ethyl acetate
FmocCl 9-Fluorenylmethylchloroformate
g Grams
h Hours
HRMS High resolution mass spectrometry
Lev Levulinyl
min Minute
mL Millilitre
Me Methyl
MeI Methyl iodide
MeOH Methanol
MP p-Methoxy phenyl
MS Molecular sieves
NaHCO$_3$ Sodium bicarbonate
NaOH Sodium hydroxide
NaOMe Sodium methoxide
NIS N-Iodo succinimide
General Information Commercial grade solvents were used unless stated otherwise. Dry solvents were obtained from a Waters Dry Solvent System. Solvents for chromatography were distilled prior to use. Sensitive reactions were carried out in heat-dried glassware and under an argon atmosphere. Analytical thin layer chromatography (TLC) was performed on silica gel 60 F254 glass plates precoated with a 0.25 mm thickness of silica gel. Spots were visualized by staining with vanillin solution (6% (w/v) vanillin and 10% (v/v) sulfuric acid in 95% EtOH) or Hanessian's stain (5% (w/v) ammonium molybdate, 1% (w/v) cerium(II) sulfate and 10% (v/v) sulfuric acid in water). Silica column chromatography was performed on Fluka silica gel 60 (230-400 mesh).

$^1$H, $^{13}$C and two-dimensional NMR spectra were measured with a Varian 400-MR, 600-MR and Bruker Avance 700 spectrometer at 296 K. Chemical shifts ($\delta$) are reported in parts per million (ppm) relative to the respective residual solvent peaks (CDCl$_3$: $\delta$ 7.27 in $^1$H and 77.16 in $^{13}$C NMR; CD$_3$OD: $\delta$ 3.31 in $^1$H and 49.00 in $^{13}$C NMR; D$_2$O: $\delta$ 4.80 in $^1$H NMR; acetone-d$_6$: $\delta$ 2.05 in $^1$H and 29.92 in $^{13}$C NMR). The following abbreviations are used to indicate peak multiplicities: s singlet; d doublet; dd doublet of doublets; t triplet; dt doublet of triplets; q quartet; m multiplet. Coupling constants (J) are reported in Hertz (Hz). Optical rotation (OR) measurements were carried out with a Schmidt & Haensch UniPol L1000 polarimeter at $\lambda$=589 nm and a concentration (c) expressed in g/100 mL in the solvent noted in parentheses. High resolution mass spectrometry (HRMS) was performed at the Free University Berlin, Mass Spectrometry Core Facility, with an Agilent 6210 TOF mass spectrometer. Infrared (IR) spectra were measured with a Perkin Elmer 100 FTIR spectrometer.

Example A. Synthesis of *S. pneumoniae* Serotype 2 Conjugate 1 (CRM$_{197}$—*S. pneumoniae* Serotype 8 hexasaccharide 22)

Example A.1: Synthesis of Disaccharide Acceptor 2

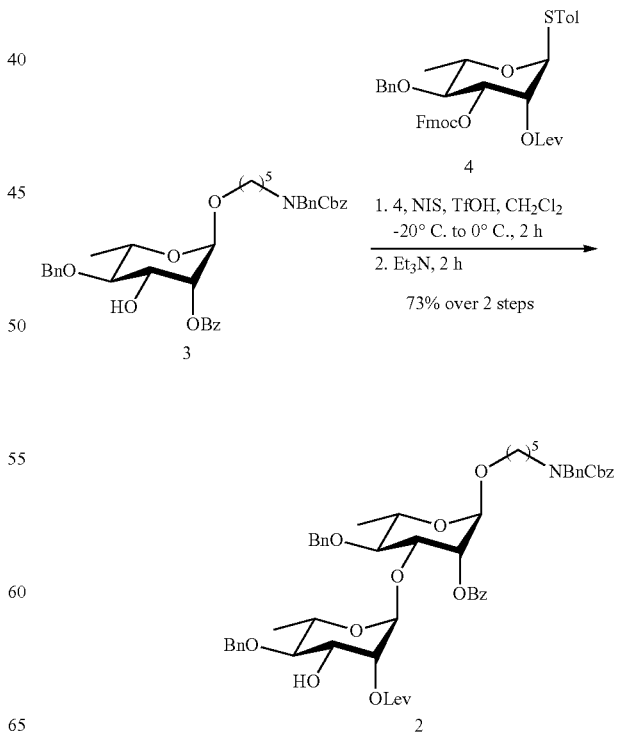

Synthesis of Building Block 15

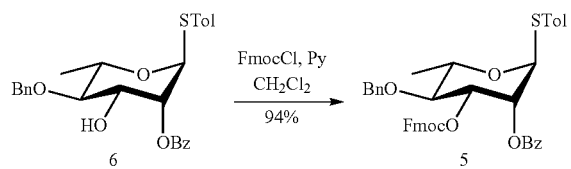

To a clear solution of 6 (Dhénin S. G. Y. et al., Org. Biomol. Chem. 2009, 7, 5184) (6.7 g, 14.4 mmol) in $CH_2Cl_2$ (80 mL) were added FmocCl (5.6 g, 21.62 mmol), and pyridine (2.4 mL, 28.8 mmol) and stirred at room temperature for 12 h. After complete consumption of starting material, the reaction mixture was diluted with $CH_2Cl_2$ (80 mL) and washed successively with 1 M HCl (60 mL), water (60 mL) and aq. sat. $NaHCO_3$ (60 mL). The organic layer was dried over $Na_2SO_4$, filtered and concentrated. The crude was purified by flash chromatography using hexanes and ethyl acetate as eluent (9:1) to afford the desired product 5 as white foam (9.3 g, 94%).

H NMR (400 MHz, $CDCl_3$) δ 8.06 (d, J=7.7 Hz, 2H), 7.78-7.67 (m, 2H), 7.63 (t, J=7.5 Hz, 1H), 7.58-7.52 (m, 2H), 7.49 (t, J=7.6 Hz, 2H), 7.44-7.05 (m, 13H), 5.89 (s, 1H), 5.49 (s, 1H), 5.29 (dd, J=9.5, 3.2 Hz, 1H), 4.87 (d, J=11.1 Hz, 1H), 4.71 (d, J=11.1 Hz, 1H), 4.61-4.48 (m, 1H), 4.41 (dq, J=12.2, 6.5 Hz, 1H), 4.28 (d, J=6.0 Hz, 2H), 3.76 (t, J=9.6 Hz, 1H), 2.32 (s, 3H), 1.42 (d, J=6.1 Hz, 3H); $^{13}C$ NMR (101 MHz, $CDCl_3$) δ 165.6, 154.3, 143.7, 143.2, 141.4, 141.3, 138.2, 137.9, 133.6, 132.7, 130.1, 130.0, 129.7, 129.6, 128.6, 128.5, 128.1, 128.0 (2C), 127.9, 127.3, 127.2, 125.5, 125.2, 120.1 (2C), 86.2, 78.8, 76.8, 75.4, 72.1, 70.4, 69.1, 46.8, 21.3, 18.1;

HRMS (ESI): Calcd for $C_{42}H_{38}O_7S$ $[M+Na]^+$ 709.2236, found: 709.2238.

Synthesis of Building Block 3

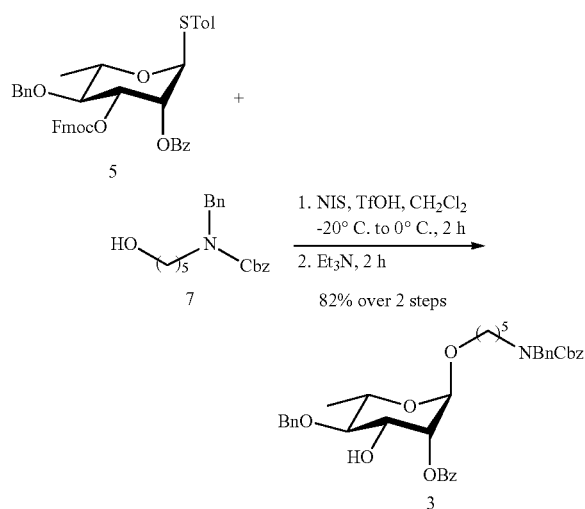

A solution of compound 5 (0.17 g, 0.25 mmol), aminopentyl linker 15 (0.16 g, 0.5 mmol) and 4 Å acid washed molecular sieves (AWMS) (0.3 g) in $CH_2CL_2$ (5 mL) were stirred at room temperature for 30 min. The solution was cooled to −20° C. and NIS (62 mg, 0.28 mmol), and TfOH (2.5 µL, 0.028 mmol) were added. The reaction mixture was gradually brought to room temperature over 2 h. After complete consumption of starting material, $Et_3N$ (2 mL) was added and the reaction mixture was stirred at room temperature for another 2 h. Reaction mixture was diluted with $CH_2Cl_2$ (25 mL) and washed with aq. sat. $Na_2S_2O_3$ (10 mL). Separated organic layer was dried over $Na_2SO_4$, filtered and concentrated. The crude was purified by flash chromatography using hexanes and ethyl acetate as eluent (4:1) to obtain the desired product 3 as colorless oil (0.135 g, 82%).

$^1H$ NMR (400 MHz, $CDCl_3$) δ 8.06 (d, J=7.7 Hz, 2H), 7.59 (q, J=9.3, 8.4 Hz, 1H), 7.47 (t, J=7.6 Hz, 2H), 7.42-7.13 (m, 15H), 5.32 (s, 1H), 5.18 (d, J=12.1 Hz, 2H), 4.86 (d, J=11.1 Hz, 1H), 4.83-4.79 (m, 1H), 4.75 (d, J=11.1 Hz, 1H), 4.51 (d, J=6.4 Hz, 2H), 4.21 (s, 1H), 3.78 (d, J=8.1 Hz, 1H), 3.62 (d, J=16.6 Hz, 1H), 3.46 (t, J=9.4 Hz, 1H), 3.42-3.13 (m, 2H), 2.16 (s, 1H), 1.70-1.42 (m, 6H), 1.39 (d, J=6.2 Hz, 3H);

$^{13}C$ NMR (101 MHz, $CDCl_3$) δ 174.0, 166.4, 133.5, 130.0, 129.8, 128.7, 128.6, 128.2, 128.1, 128.0, 127.4, 125.3, 110.1, 97.4, 81.9, 75.4, 73.5, 70.7, 67.6, 67.3, 50.4, 29.2, 18.3;

HRMS (ESI): Calcd for $C_{40}H_{45}O_8N$ $[M+K]^+$ 706.2782, found: 706.2705.

Synthesis of Building Block 4

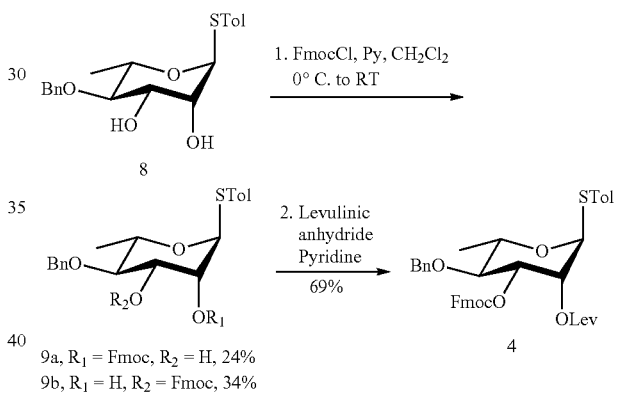

9a, $R_1$ = Fmoc, $R_2$ = H, 24%
9b, $R_1$ = H, $R_2$ = Fmoc, 34%

Pyridine (0.8 mL, 10.0 mmol) was added dropwise at 0° C. to a stirred solution of 8 (Rajput V. K. J. Org. Chem. 2008, 73, 6924) (2.4 g, 6.6 mmol) and FmocCl (1.8 g, 7.0 mmol) in $CH_2Cl_2$ (50 mL). The mixture was gradually heated to room temperature over 2 h, and diluted $CH_2Cl_2$ (100 mL), washed successively with 1 M HCl (50 mL) and water (50 mL). The organic layer was dried over $Na_2SO_4$, filtered and concentrated. The crude was purified by flash chromatography using hexanes and ethyl acetate as eluent (10:1 to 4:1) to obtain 9a (0.92 g, 24%) and 9b (1.3 g, 34%; 20% of 8 was recovered).

$^1H$ NMR (400 MHz, $CDCl_3$) δ 7.78 (d, J=7.5 Hz, 2H), 7.71 (t, J=8.4 Hz, 2H), 7.42 (t, J=8.3 Hz, 4H), 7.38-7.28 (m, 7H), 7.13 (d, J=7.8 Hz, 2H), 5.39 (d, J=3.5 Hz, 1H), 4.86-4.71 (m, 3H), 4.56-4.42 (m, 2H), 4.36 (t, J=7.6 Hz, 1H), 3.88 (dt, J=8.2, 3.6 Hz, 1H), 3.49 (t, J=9.2 Hz, 1H), 3.41 (dd, J=9.5, 5.8 Hz, 1H), 2.34 (s, 3H), 1.46 (d, J=6.0 Hz, 3H);

$^{13}C$ NMR (101 MHz, $CDCl_3$) δ 155.8, 143.5, 141.5, 138.3, 138.2, 132.5, 130.2, 130.0, 128.8, 128.2 (2C), 128.0, 127.4, 127.3, 125.6, 125.5, 120.2, 120.1, 85.7, 80.9, 77.9, 76.2, 75.6, 74.3, 70.7, 46.9, 21.3, 18.4; HRMS (ESI): Calcd for $C_{35}H_{34}O_6S$ $[M+Na]^+$ 605.1974, found: 609.1993.

Levulinic anhydride (1.4 g, 6.69 mmol) and pyridine (0.54 mL, 6.69 mmol) were added to a stirred solution of 9b (1.3 g, 2.23 mmol) in $CH_2Cl_2$ (20 mL). After stirring at room temperature for 2 days, the reaction mixture was diluted with $CH_2Cl_2$ (50 mL) and washed successively with 1 M HCl (50 mL) and aq. sat. $NaHCO_3$ (50 mL). The organic layer was dried over $Na_2SO_4$, filtered and concentrated. The crude was purified by flash chromatography using hexanes and ethyl acetate as eluent (4:1) to obtain 4 as viscous oil (1.04 g, 69%).

$^1H$ NMR (400 MHz, $CDCl_3$) δ 7.77 (d, J=7.6 Hz, 2H), 7.61 (dd, J=15.4, 7.5 Hz, 2H), 7.45-7.27 (m, 11H), 7.12 (d, J=7.8 Hz, 2H), 5.62 (dd, J=3.2, 1.6 Hz, 1H), 5.33 (d, J=1.6 Hz, 1H), 5.16 (dd, J=9.7, 3.3 Hz, 1H), 4.83 (d, J=11.0 Hz, 1H), 4.67 (d, J=11.0 Hz, 1H), 4.51 (dd, J=10.3, 6.7 Hz, 1H), 4.42-4.24 (m, 3H), 3.62 (t, J=9.5 Hz, 1H), 2.80-2.65 (m, 4H), 2.33 (s, 3H), 2.15 (s, 3H), 1.36 (d, J=6.2 Hz, 3H);

$^{13}C$ NMR (101 MHz, $CDCl_3$) δ 206.1, 171.8, 154.1, 143.6, 143.1, 141.3, 141.2, 138.1, 137.8, 132.6, 129.9, 129.5, 128.4, 127.9, 127.8 (2C), 127.2, 127.1, 125.2, 125.1, 120.1, 120.0, 85.8, 78.6, 76.3, 75.3, 71.7, 70.1, 68.9, 46.7, 37.9, 29.8, 28.0, 21.1, 17.8;

HRMS (ESI): Calcd for $C_{40}H_{40}O_8S$ $[M+Na]^+$ 703.2342, found: 703.2359.

Synthesis of Disaccharide Acceptor 2

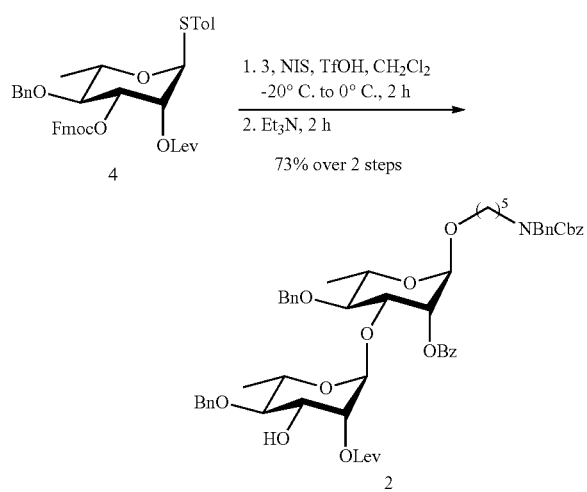

A solution of donor 4 (0.25 g, 0.37 mmol), acceptor 3 (0.165 g, 0.25 mmol) and 4 Å acid washed molecular sieves (AWMS) (0.3 g) in $CH_2Cl_2$ (5 mL) were stirred at room temperature for 30 min. The solution was cooled to −20° C. and NIS (83 mg, 0.37 mmol), TfOH (3.3 µL, 0.037 mmol) were added. The reaction mixture was gradually brought to room temperature over 2 h. After complete consumption of starting material, $Et_3N$ (2 mL) was added and the reaction mixture was stirred at room temperature for another 2 h. Reaction mixture was diluted with $CH_2Cl_2$ and washed with aq. sat. $Na_2S_2O_3$. The organic layer was dried over $Na_2SO_4$, filtered and concentrated. The crude was purified by flash chromatography using hexanes and ethyl acetate as eluent (3:1) to obtain the desired product 2 as colorless oil (0.18 g, 73%).

$^1H$ NMR (400 MHz, $CDCl_3$) δ 8.05 (d, J=7.7 Hz, 2H), 7.60 (t, J=7.4 Hz, 1H), 7.48 (t, J=7.6 Hz, 2H), 7.39-7.18 (m, 20H), 5.32 (s, 1H), 5.24-5.12 (m, 3H), 4.87 (d, J=10.8 Hz, 1H), 4.83-4.76 (m, 2H), 4.76-4.55 (m, 3H), 4.50 (d, J=4.8 Hz, 2H), 4.26-4.15 (m, 1H), 3.97 (dd, J=9.5, 3.4 Hz, 1H), 3.77 (dd, J=9.7, 6.0 Hz, 2H), 3.57 (t, J=9.4 Hz, 2H), 3.24 (dd, J=19.8, 10.2 Hz, 4H), 2.75 (q, J=6.4, 5.8 Hz, 2H), 2.60 (qd, J=16.7, 8.1 Hz, 2H), 2.18 (s, 3H), 1.64-1.43 (m, 6H), 1.31 (d, J=6.2 Hz, 3H), 1.18 (d, J=6.2 Hz, 3H);

$^{13}C$ NMR (101 MHz, $CDCl_3$) δ 207.1, 172.2, 166.0, 138.1, 138.0, 133.4, 129.9, 129.8, 128.6 (2C), 128.5 (2C), 128.51, 128.4, 128.3, 128.0, 127.7 (2C), 127.3, 99.5, 97.0, 81.4, 80.5, 77.9, 77.4, 75.7, 74.1, 73.0, 69.9, 68.3, 67.8, 67.3, 50.6, 50.3, 47.2, 46.3, 38.3, 29.9, 29.2, 28.3, 23.5, 18.2, 17.9;

HRMS (ESI): Calcd for $C_{58}H_{67}O_{14}N$ $[M+Na]^+$ 1024.4459, found: 1024.4321.

Example A.2: Synthesis of Disaccharide Donor 10

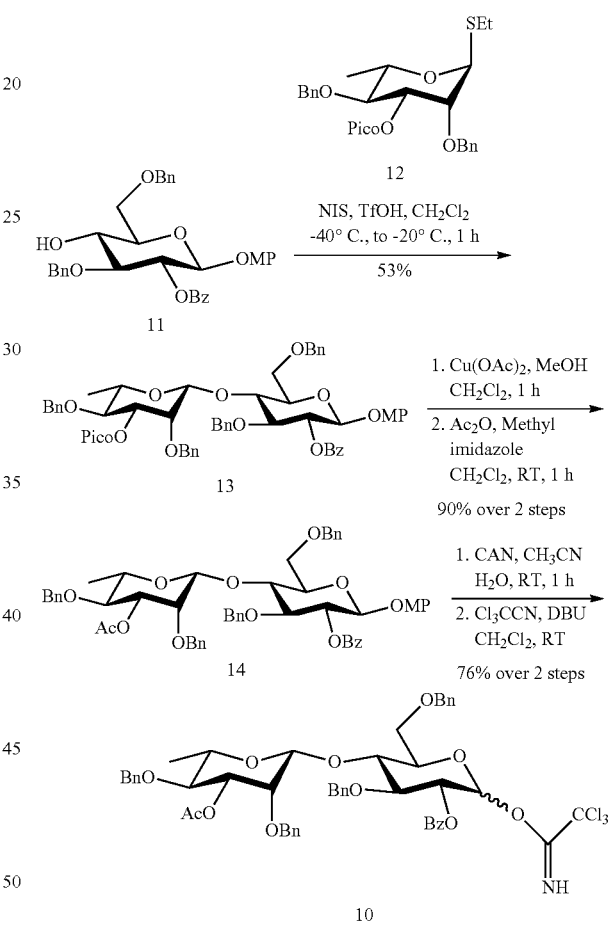

Synthesis of Building Block 12

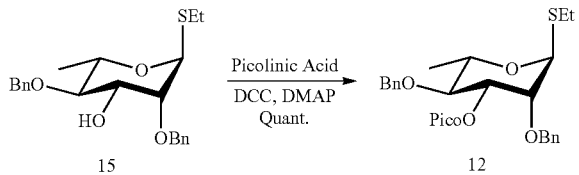

To a stirred solution of compound 15 (Bourke J. *Org. Biomol. Chem.* 2014, 12, 1114) (0.25 g, 0.55 mmol) in $CH_2Cl_2$ (2.5 mL) were added picolinic acid (93 mg, 0.75 mmol), DCC (0.17 g, 0.8 mmol) and DMAP (13.5 mg, 0.11 mmol). After stirring at room temperature for 2.5 h, the reaction mixture was diluted with CH$_2$Cl$_2$ (25 mL) and washed successively with cold water (10 mL) and aq. sat. NaHCO$_3$ (10 mL). The organic layer was dried over Na$_2$SO$_4$ filtered and concentrated. The crude was purified by flash chromatography using hexanes and ethyl acetate as eluent (3:1) to give the desired product 12 as pale yellowish oil (0.307 g, quantitative).

$^1$H NMR (400 MHz, CDCl$_3$) δ 8.80 (ddd, J=4.7, 1.8, 0.9 Hz, 1H), 8.01 (dt, J=7.9, 1.1 Hz, 1H), 7.81 (td, J=7.7, 1.8 Hz, 1H), 7.49 (ddd, J=7.6, 4.7, 1.2 Hz, 1H), 7.32-7.27 (m, 2H), 7.25-7.17 (m, 4H), 7.17-7.09 (m, 4H), 5.43 (dd, J=9.5, 3.4 Hz, 1H), 5.31 (d, J=1.7 Hz, 1H), 4.85 (d, J=11.1 Hz, 1H), 4.74-4.65 (m, 2H), 4.57 (d, J=12.3 Hz, 1H), 4.27-4.14 (m, 1H), 4.11 (dd, J=3.4, 1.7 Hz, 1H), 3.90 (t, J=9.5 Hz, 1H), 2.74-2.51 (m, 2H), 1.38 (d, J=6.2 Hz, 3H), 1.27 (t, J=7.4 Hz, 3H).

Synthesis of Disaccharide 13

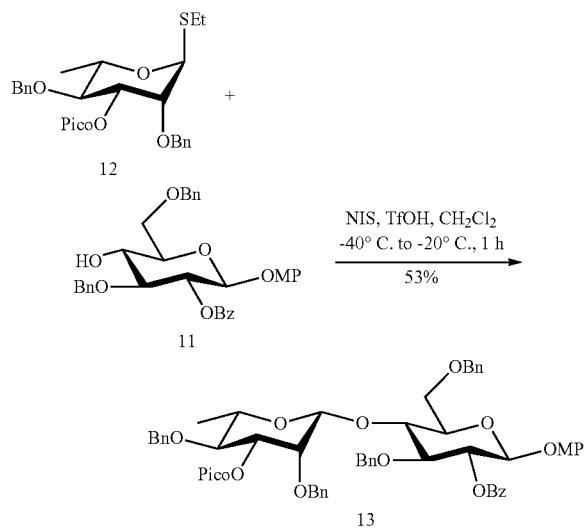

NIS (0.15 g, 0.65 mmol) and TfOH (6.0 μL, 0.065 mmol) were added to a cooled solution of donor 12 (0.32 g, 0.64 mmol), acceptor 11 (Bundle D. R. et al. ACS Chem. Biol. 2012, 7, 1754) (0.25 g, 0.43 mmol) and 4 Å acid washed molecular sieves (AWMS) (2.0 g) in CH$_2$Cl$_2$ (20 mL) at −40° C. Reaction mixture was gradually warmed to −20° C. over 1 h, diluted with CH$_2$Cl$_2$ (30 mL) and washed with aq. sat. Na$_2$S$_2$O$_3$ (15 mL). The organic layer was dried over Na$_2$SO$_4$ filtered and concentrated. The crude was purified by flash chromatography using hexanes and ethyl acetate as eluent (4:1 to 3:1) to obtain the desired product 13 as pale yellowish oil (0.23 g, 53%).

$^1$H NMR (400 MHz, CDCl$_3$) δ 8.88 (d, J=4.7 Hz, 1H), 8.15 (d, J=7.8 Hz, 2H), 8.05 (d, J=8.0 Hz, 1H), 7.87 (t, J=7.9 Hz, 1H), 7.64 (t, J=7.4 Hz, 1H), 7.59-7.44 (m, 3H), 7.42-7.17 (m, 20H), 7.04 (d, J=8.6 Hz, 2H), 6.77 (d, J=8.8 Hz, 2H), 5.59 (t, J=8.3 Hz, 1H), 5.09 (d, J=7.9 Hz, 1H), 5.03 (dd, J=9.8, 3.2 Hz, 1H), 4.88-4.82 (m, 3H), 4.76-4.58 (m, 6H), 4.54 (d, J=10.4 Hz, 1H), 4.27 (d, J=10.4 Hz, 1H), 4.11 (d, J=3.2 Hz, 1H), 4.00-3.79 (m, 4H), 3.77 (s, 3H), 3.39 (dq, J=11.9, 6.2 Hz, 1H), 1.40 (d, J=6.0 Hz, 3H);

$^{13}$C NMR (101 MHz, CDCl$_3$) δ 165.3, 164.0, 155.4, 151.5, 150.2, 147.7, 138.7, 138.4, 138.0, 137.0, 133.4, 129.8 (2C), 128.9, 128.6, 128.4, 128.3 (3C), 128.1, 128.0, 127.8, 127.6, 127.5 (2C), 127.0, 125.2, 118.6, 114.5, 100.8, 100.5, 83.2, 78.6, 75.8, 75.7, 75.3, 74.8, 74.0, 73.5, 71.7, 70.0, 55.6, 17.9;

HRMS (ESI): Calcd for C$_{60}$H$_{59}$O$_{13}$N [M+Na]$^+$ 1024.3884, found: 1024.3896.

Synthesis of Disaccharide Building Block 14

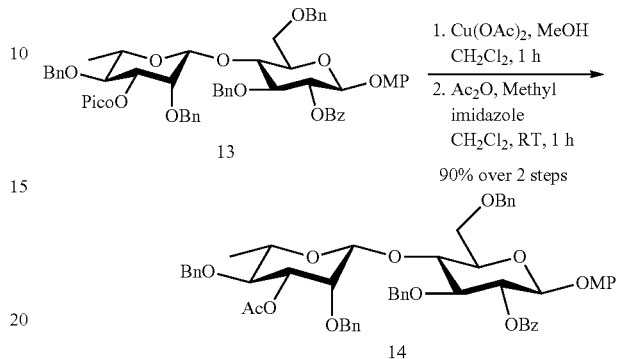

Cu(OAc)$_2$.H$_2$O (70 mg, 0.347 mmol) was added to a solution of 13 (0.23 g, 0.23 mmol) in CH$_2$Cl$_2$ (6 mL) and MeOH (3 mL). After stirring at room temperature for 1 h, reaction mixture was filtered through celite pad and the filtrate was concentrated. The crude product was dissolved in CH$_2$Cl$_2$ (5 mL) and to this Ac$_2$O (1 mL), and methyl imidazole (0.2 mL) was added. After 1 h, the reaction mixture was evaporated and purified by flash chromatography using hexanes and ethyl acetate as eluent (6:1 to 5:1) to obtain the desired product 14 as colorless oil (0.193 g, 90%).

$^1$H NMR (400 MHz, CDCl$_3$) δ 8.01 (d, J=7.7 Hz, 2H), 7.51 (t, J=7.4 Hz, 1H), 7.39 (t, J=7.6 Hz, 2H), 7.33-7.01 (m, 20H), 6.89 (d, J=8.9 Hz, 2H), 6.64 (d, J=8.9 Hz, 2H), 5.42 (t, J=8.3 Hz, 1H), 4.93 (d, J=7.9 Hz, 1H), 4.71 (t, J=6.2 Hz, 2H), 4.65-4.43 (m, 7H), 4.39 (d, J=10.5 Hz, 1H), 4.15-4.07 (m, 1H), 3.83-3.67 (m, 4H), 3.65 (s, 3H), 3.63-3.41 (m, 2H), 3.19 (dq, J=12.1, 6.2 Hz, 1H), 1.87 (s, 3H), 1.23 (d, J=6.1 Hz, 3H);

$^{13}$C NMR (101 MHz, CDCl$_3$) δ 170.2, 165.3, 155.4, 151.6, 138.7, 138.6, 138.2, 137.1, 133.4, 129.9, 129.8, 128.8, 128.7, 128.6, 128.5, 128.4, 128.3 (2C), 128.0, 127.9, 127.8, 127.6, 127.5, 118.7, 114.5, 100.8, 100.6, 83.1, 78.7, 77.4, 76.0, 75.79, 75.76, 75.4 (2C), 75.3, 74.9, 74.0, 73.5, 71.8, 70.1, 55.7, 29.8, 21.1, 17.9; HRMS (ESI): Calcd for C$_{56}$H$_{58}$O$_{13}$ [M+Na]$^+$ 961.3775, found: 961.3841.

Synthesis of Imidate Donor 10

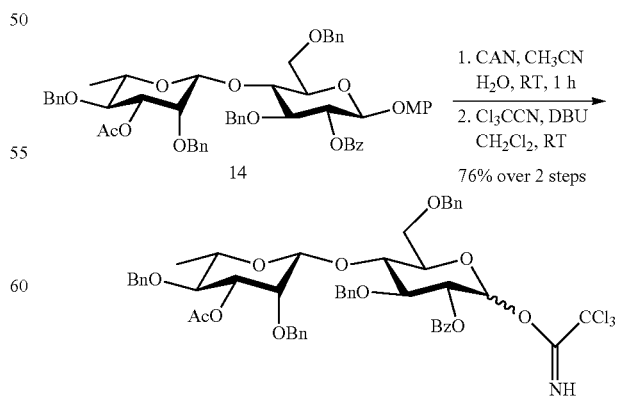

Ceric ammonium nitrate (0.46 g, 0.85 mmol) was added to a solution of 14 (0.16 g, 0.17 mmol) in acetonitrile (5 mL) and H$_2$O (1 mL). After stirring at room temperature for 1 h, Na$_2$SO$_4$ was added to the reaction mixture and filtered through celite pad. The filtrate was concentrated and purified by flash chromatography using hexanes and ethyl acetate as eluent (4:1) to obtain the desired hemiacetal as pale yellowish oil.

The obtained hemiacetal was dissolved in CH$_2$Cl$_2$ (5 mL) and to this Cl$_3$CCN (0.17 mL, 0.17 mmol), DBU (5.2 µL) were added. After 30 min, hexanes (5 mL) was added to the reaction mixture and purified by flash chromatography using hexanes and ethyl acetate as eluent (5:1) to afford the desired product 10 as colorless oil (0.126 g, 76%, α/β=9:1).

$^1$H NMR (400 MHz, CDCl$_3$) δ 8.47 (s, 1H), 7.95 (d, J=7.8 Hz, 2H), 7.50 (t, J=7.5 Hz, 1H), 7.36 (t, J=7.7 Hz, 2H), 7.32-7.01 (m, 20H), 6.56 (d, J=3.5 Hz, 1H), 5.29 (dd, J=9.9, 3.5 Hz, 1H), 4.76 (s, 1H), 4.70-4.49 (m, 7H), 4.43 (dd, J=23.8, 11.2 Hz, 2H), 4.12 (t, J=9.3 Hz, 1H), 4.05-3.90 (m, 2H), 3.90-3.76 (m, 2H), 3.73 (dd, J=11.2, 4.8 Hz, 1H), 3.51 (t, J=9.5 Hz, 1H), 3.19 (dt, J=12.1, 6.2 Hz, 1H), 1.90 (s, 3H), 1.19 (d, J=4.9 Hz, 3H);

$^{13}$C NMR (101 MHz, CDCl$_3$) δ 170.2, 165.5, 160.6, 138.5 (2C), 138.2, 137.2, 133.6, 129.9, 129.3, 128.8, 128.7, 128.6, 128.5, 128.4, 128.3 (2C), 127.9, 127.8 (2C), 127.6, 127.5, 101.2, 94.1, 91.3, 79.6, 78.7, 76.0, 75.9, 75.9, 75.3, 75.0, 74.8, 73.4, 73.3, 72.9, 71.8, 68.6, 29.8, 21.2, 17.9.

Example A.3: Synthesis of Tetrasaccharide Acceptor 16

Synthesis of Tetrasaccharide 17

To a solution of donor 10 (60 mg, 0.06 mmol), acceptor 2 (40 mg, 0.04 mmol) and 4 Å acid washed molecular sieves (AWMS) (100 mg) in CH$_2$Cl$_2$ (2 mL) at −40° C. was added TMSOTf (1.5 µL, 8 µmol). The reaction mixture was gradually warmed to 0° C. over 3 h. After complete consumption of donor, a drop of Et$_3$N was added and the solvents were removed under vacuum. The crude was purified by flash chromatography using hexanes and ethyl acetate as eluent (3:1 to 2:1) to afford the desired product 17 as pale yellowish oil (49 mg, 68%).

$^1$H NMR (400 MHz, CDCl$_3$) δ 8.02 (d, J=7.6 Hz, 2H), 7.82 (d, J=7.7 Hz, 2H), 7.54-7.33 (m, 6H), 7.31-7.14 (m, 36H), 6.98-6.90 (m, 2H), 6.79-6.70 (m, 2H), 5.30 (s, 1H), 5.21 (s, 1H), 5.19-5.05 (m, 3H), 4.95 (s, 1H), 4.80 (d, J=10.5 Hz, 1H), 4.76-4.62 (m, 3H), 4.61-4.45 (m, 5H), 4.43-4.37 (m, 4H), 4.35-4.21 (m, 4H), 4.12-4.09 (m, 2H), 3.80-3.69 (m, 2H), 3.67-3.57 (m, 3H), 3.55-3.37 (m, 5H), 3.30-3.03 (m, 7H), 2.63 (t, J=7.0 Hz, 2H), 2.55-2.45 (m, 2H), 2.06 (s, 3H), 1.85 (s, 3H), 1.62-1.31 (m, 6H), 1.19 (s, 3H), 1.10 (d, J=6.1 Hz, 3H), 0.91 (d, J=6.1 Hz, 3H);

$^{13}$C NMR (101 MHz, CDCl$_3$) δ 206.9, 171.7, 170.1, 166.1, 165.0, 139.1, 138.6, 138.5, 138.2, 138.1, 138.0, 136.7, 133.3, 130.1, 129.9, 129.7, 129.6, 128.7, 128.6 (2C), 128.5 (2C), 128.4, 128.3 (2C), 128.2 (2C), 128.0, 127.9 (2C), 127.8, 127.7, 127.3, 127.2, 127.1, 126.7, 101.1, 100.9, 99.29, 97.0, 83.1, 80.4, 80.1, 78.6, 78.0, 77.4, 76.0, 75.8, 75.6, 75.3, 75.2, 74.8, 74.7, 74.1, 74.0, 73.1, 73.0, 72.4, 71.6, 69.3, 68.3, 67.8, 67.5, 67.2, 62.4, 60.5, 50.6, 50.3, 47.2, 46.2, 38.3, 29.8, 29.2, 28.3, 28.0, 27.6, 25.0, 23.4, 22.8, 22.3, 21.2, 21.1, 18.1, 17.7, 17.6;

HRMS (ESI): Calcd for C$_{107}$H$_{117}$O$_{25}$N [M+Na]$^+$ 1839.7846, found: 1839.7621.

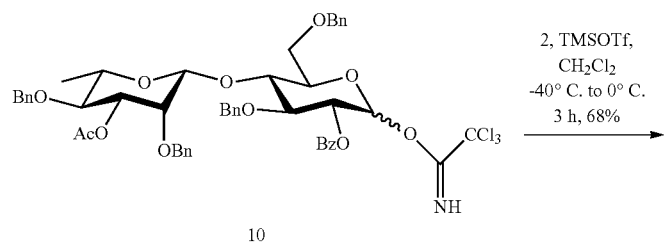

10

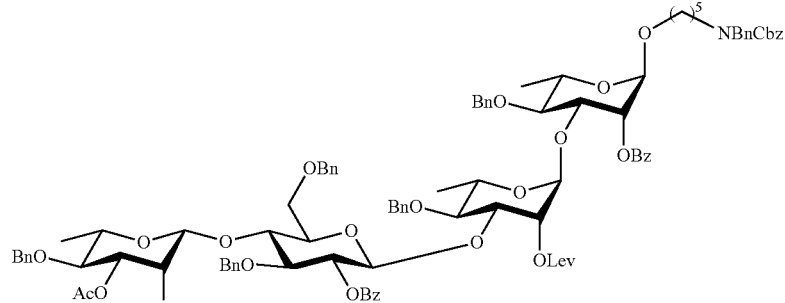

17

Synthesis of Tetrasaccharide Acceptor 16

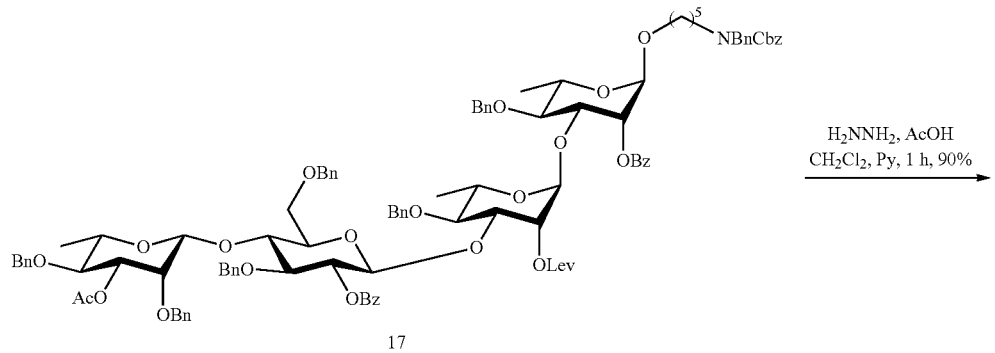

Hydrazine solution [310 μL, a premixed solution of H$_2$NNH$_2$.H$_2$O (50 μL), pyridine (0.6 mL), AcOH (0.4 mL)] was added to a stirred solution of compound 17 (57 mg, 0.03 mmol) in CH$_2$Cl$_2$ (2.0 mL) and pyridine (2 mL) at 0° C. After stirring at 0° C. for 1 h, the reaction mixture was diluted with CH$_2$Cl$_2$ (10 mL) and washed successively with 1 M HCl (5 mL) and aqueous saturated NaHCO$_3$ solution (5 mL). The organic layer was dried over Na$_2$SO$_4$ filtered and concentrated. The crude was purified by flash chromatography using hexanes and ethyl acetate as eluent (3:1 to 2.5:1) to give the desired product 16 as colorless oil (49 mg, 90%).

$^1$H NMR (400 MHz, CDCl$_3$) δ 7.98 (d, J=7.7 Hz, 2H), 7.81 (d, J=7.8 Hz, 2H), 7.52-7.32 (m, 6H), 7.31-7.13 (m, 28H), 7.12-6.94 (m, 10H), 6.77 (d, J=7.3 Hz, 2H), 5.24 (dd, J=14.9, 6.1 Hz, 2H), 5.09 (d, J=9.9 Hz, 2H), 4.90 (s, 1H), 4.81-4.67 (m, 3H), 4.65-4.38 (m, 10H), 4.36-4.21 (m, 3H), 4.20-3.96 (m, 4H), 3.85-3.63 (m, 5H), 3.60-3.39 (m, 6H), 3.35-3.07 (m, 7H), 1.86 (s, 3H), 1.56-1.38 (m, 6H), 1.23 (d, J=6.2 Hz, 3H), 1.19 (d, J=6.2 Hz, 3H), 0.85 (d, J=6.4 Hz, 3H);

$^{13}$C NMR (101 MHz, CDCl$_3$) δ 170.2, 165.9, 165.2, 138.6, 138.5, 138.4, 138.3, 138.1, 138.0, 136.9, 133.3, 133.2, 130.2, 129.9, 129.8, 129.5, 128.8, 128.7, 128.6, 128.5 (3C) 128.4 (3C), 128.3, 128.1, 127.9 (3C), 127.8 (2C), 127.6, 127.4, 127.2, 127.1, 101.2, 100.9, 100.5, 97.1, 83.0, 82.1, 80.2, 79.2, 78.6, 78.3, 77.4, 76.0, 75.7, 75.6, 75.5, 75.3, 74.8, 74.4, 74.3, 73.6, 73.5, 72.9, 71.7, 70.1, 69.5, 68.1, 68.0, 67.6, 67.3, 50.7, 50.3, 47.2, 46.3, 21.1, 18.2, 17.9, 17.7;

HRMS (ESI): Calcd for C$_{102}$H$_{111}$O$_{23}$N [M+Na]$^+$ 1741.7478, found: 1741.7240.

Example A.4: Synthesis of Disaccharide Donor 18

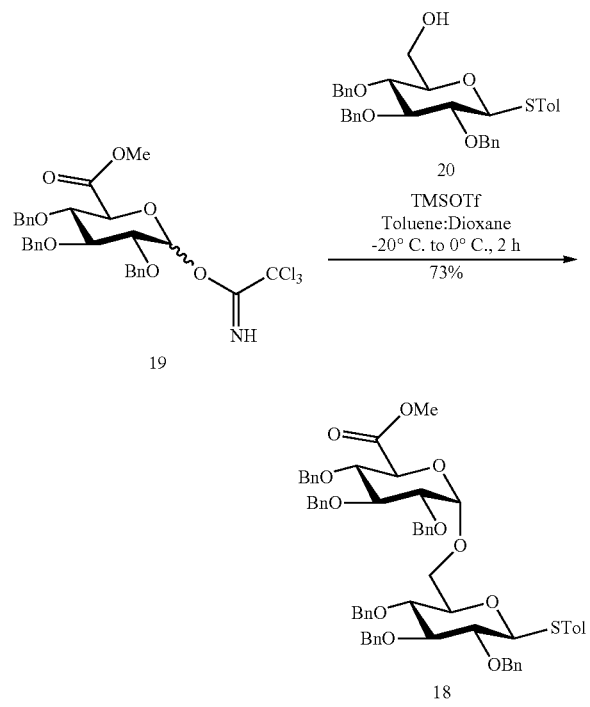

Synthesis of Glucuronic Acid Building Block 21

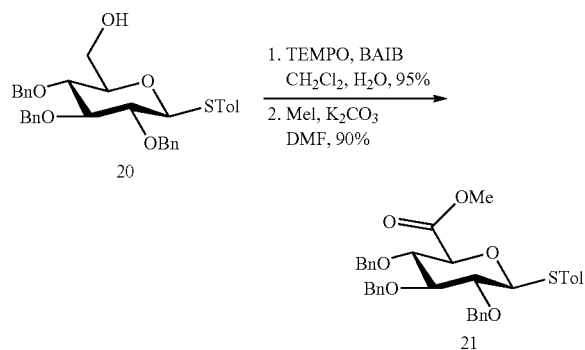

BAIB (4.34 g, 13.47 mmol) and TEMPO (0.17 g, 1.08 mmol) were added to a solution of 20 (Z. Guan et al. *J. Org. Chem.* 2012, 77, 8888) (3 g, 5.39 mmol) in $CH_2Cl_2$ (15 mL) and $H_2O$ (7.5 mL). The reaction mixture was stirred at room temperature for 2 h and quenched using aq. sat. $Na_2S_2O_3$ solution (150 mL). The aqueous phase was extracted with EtOAc (3×100 mL) and dried over $Na_2SO_4$. After concentration, the residue was purified by flash chromatography using cyclohexane and ethyl acetate as eluent (7:1 and 0.5% formic acid in eluent) to afford the acid as a white solid (2.92 g, 95%).

To a stirred solution of the acid (2.92 g, 5.12 mmol) in DMF (25 mL) was added MeI (1.45 g, 10.23 mmol) and $K_2CO_3$ (1.7 g, 12.3 mmol). The solution was stirred at room temperature for 10 h and quenched by the addition of MeOH (20 mL). The reaction mixture was diluted with EtOAc (80 mL) and washed with $H_2O$ (50 mL). The organic layer was dried over $Na_2SO_4$ and concentrated. The crude was purified by flash chromatography using hexanes and ethyl acetate as eluent (9:1 to 6:1) to give the desired product 21 as a white solid (2.7 g, 90%).

$^1$H NMR (400 MHz, $CDCl_3$) δ 7.49-7.42 (m, 2H), 7.40-7.27 (m, 13H), 7.22 (m, 2H), 7.15-7.09 (m, 2H), 4.91-4.67 (m, 5H), 4.61 (m, 2H), 3.90 (m, 1H), 3.81 (t, J=9.3 Hz, 1H), 3.73 (s, 3H), 3.70 (t, J=8.8 Hz, 1H), 3.49 (dd, J=9.7, 8.7 Hz, 1H), 2.34 (s, 3H); $^{13}$C NMR (101 MHz, $CDCl_3$) δ 168.9, 138.2 (2C), 138.0, 137.8, 133.0, 129.9, 129.4, 128.6, 128.5 (3C), 128.3, 128.1, 128.0 (2C), 127.9 (2C), 127.7, 88.7, 86.0, 80.4, 79.4, 78.1, 76.0, 75.6, 75.2, 52.6, 21.3;

HRMS (ESI): Calcd for $C_{35}H_{36}O_6S$ $[M+Na]^+$ 607.2130, found: 607.2140.

Synthesis of Imidate Donor 19

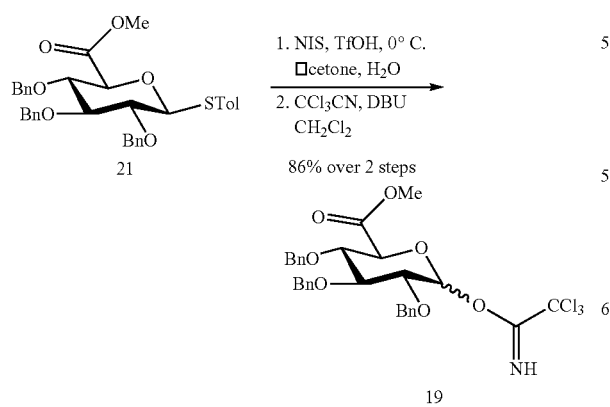

NIS (92 mg, 0.41 mmol) and TfOH (3 μL, 0.34 mmol) were added at 0° C. to a solution of 21 (0.2 g, 0.34 mmol) in acetone (2 mL) and water (1 mL). After stirring at 0° C. for 4 h, the reaction mixture was quenched with $Et_3N$ (0.5 mL). Diluted the reaction mixture with $CH_2Cl_2$ (15 mL). and washed with aq. sat. $Na_2S_2O_3$ (5 mL). Separated organic layer was dried over $Na_2SO_4$ filtered and concentrated. The crude product was purified by flash chromatography using hexanes and ethyl acetate as eluent (4:1 to 3:1) to give the hemiacetal as pale yellowish liquid (0.164 g). DBU (5 μL, 0.034 mmol) and $Cl_3CCN$ (0.34 mL, 3.42 mmol) were added to a cooled solution of hemiacetal (0.164 g, 0.342 mmol) in $CH_2Cl_2$ (2 mL) 0° C. After stirring at 0° C. for 1 h, the reaction mixture was evaporated on rotor and the crude was purified by flash chromatography using hexanes and ethyl acetate as eluent (5:1 to 4:1) to obtain the product 19 as colorless oil (0.183 g, 86%, α/β=2.7/1).

$^1$H NMR (400 MHz, $CDCl_3$) δ 8.60 (s, 1H), 7.33-7.08 (m, 15H), 6.45 (d, J=3.5 Hz, 1H), 5.00-4.50 (m, 5H), 4.36 (d, J=10.1 Hz, 1H), 4.11-3.95 (m, 1H), 3.82-3.66 (m, 3H), 3.65 (s, 3H);

$^{13}$C NMR (101 MHz, $CDCl_3$) δ 169.3, 161.1, 138.4, 138.0, 137.8, 137.7, 129.2, 128.6, 128.5 (3C), 128.4, 128.3, 128.2, 128.1, 128.0 (2C), 127.9, 127.8 (2C), 125.4, 94.0, 91.1, 83.7, 80.8, 78.9, 78.8, 75.9, 75.7, 75.5, 75.2, 73.2, 72.6, 52.7;

HRMS (ESI): Calcd for $C_{30}H_{30}O_7NCl_3$ $[M+Na]^+$ 644.0986, found: 644.1014.

Synthesis of Disaccharide 18

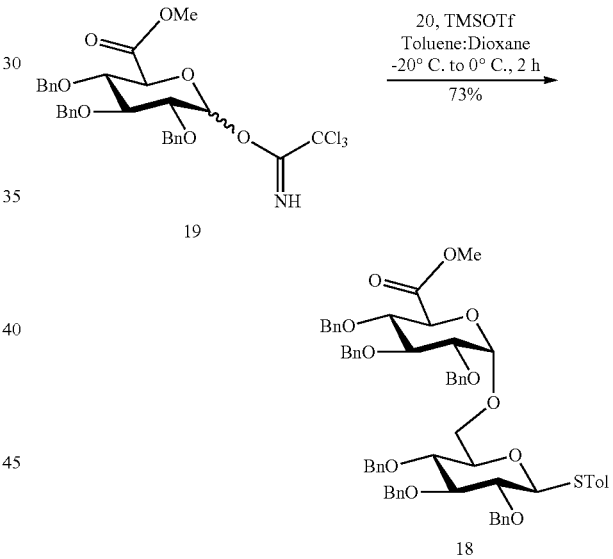

TMSOTf (4 μL, 0.02 μmol) was added to a solution of donor 19 (0.14 g, 0.22 mmol), and acceptor 20 (90 mg, 0.16 mmol) in a mixture of solvents toluene (2 mL) and dioxane (6 mL) at −20° C. The reaction mixture was gradually warmed to 0° C. over 2 h. A drop of $Et_3N$ was added and the solvents were removed under vacuum. The crude was purified by flash chromatography using hexanes and ethyl acetate as eluent (7:1 to 5:1) to afford the desired product 18 as pale yellowish oil (0.12 g, 73%, α/β=3.5:1).

$^1$H NMR (400 MHz, $CDCl_3$, α-anomer) δ 7.43 (d, J=7.8 Hz, 2H), 7.40-7.18 (m, 30H), 7.06 (d, J=7.8 Hz, 2H), 5.08 (d, J=3.5 Hz, 1H), 4.94 (d, J=10.9 Hz, 1H), 4.88-4.60 (m, 9H), 4.58-4.47 (m, 3H), 4.29 (d, J=10.0 Hz, 1H), 3.95 (t, J=9.3 Hz, 1H), 3.86 (dd, J=12.1, 4.3 Hz, 1H), 3.82-3.69 (m, 3H), 3.67 (d, J=4.9 Hz, 3H), 3.64-3.54 (m, 2H), 3.39 (dd, J=9.7, 3.9 Hz, 1H), 3.17 (t, J=9.3 Hz, 1H), 2.21 (s, 3H);

$^{13}$C NMR (101 MHz, $CDCl_3$) δ 170.4, 138.6, 138.3, 138.2, 138.1 (2C), 138.0, 133.2, 129.9, 128.6 (2C), 128.5 (3C), 128.4 (3C), 128.3, 128.1 (2C), 128.0, 127.9, 127.8, 127.7, 127.6 (2C), 98.0, 88.6, 86.7, 81.1, 81.0, 79.8, 79.6, 78.9, 77.3, 75.9, 75.7, 75.6, 75.2, 75.1, 72.6, 70.4, 66.5, 52.5, 21.2;
HRMS (ESI): Calcd for $C_{62}H_{64}O_{11}S$ $[M+Na]^+$ 1039.4067, found: 1039.4091.
Example A.5: Synthesis of *S. pneumoniae* Serotype 2 Hexasaccharide 22
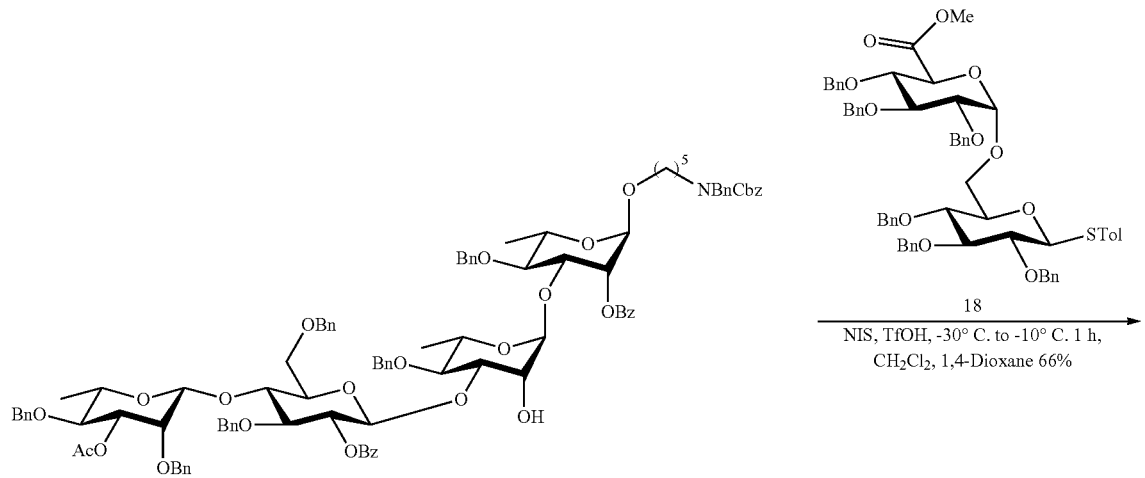
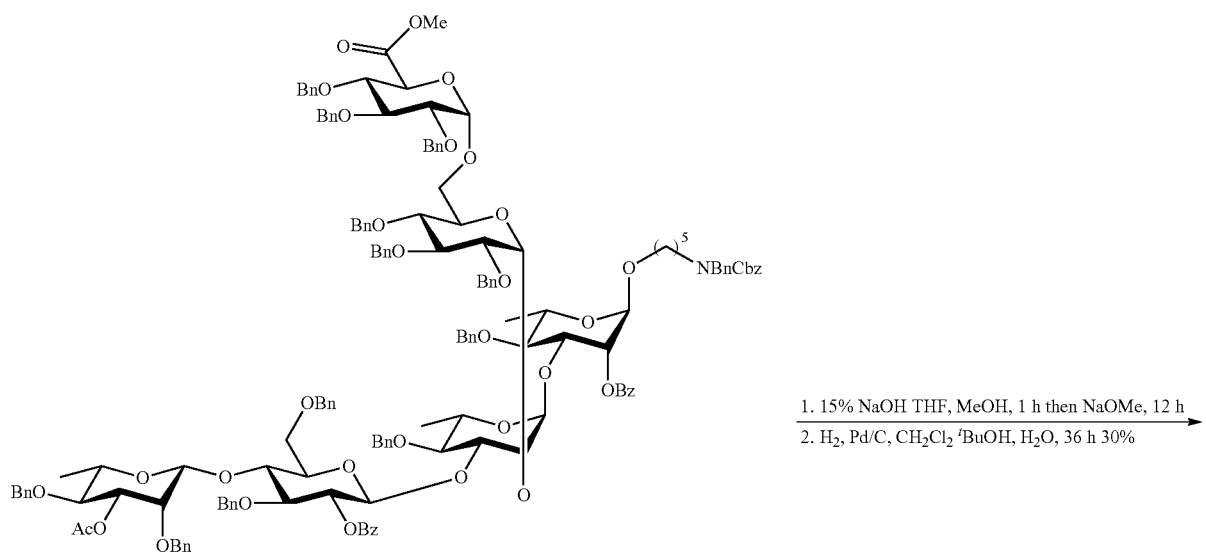

-continued

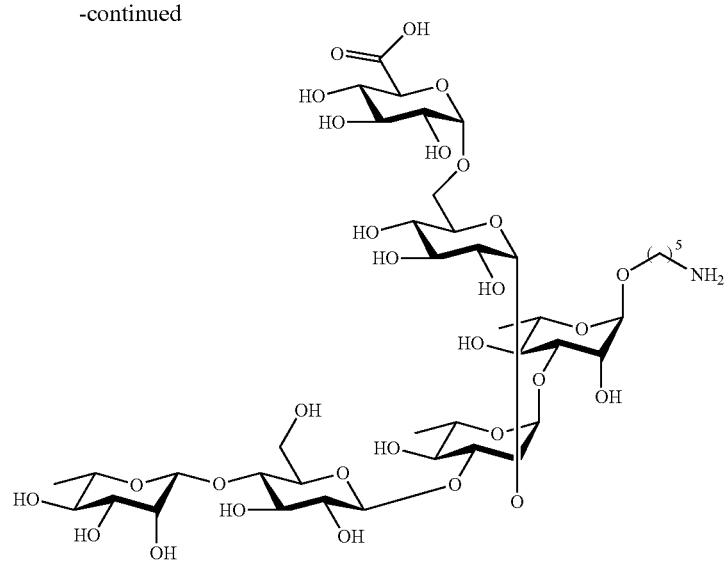

22

Synthesis of Hexasaccharide 23

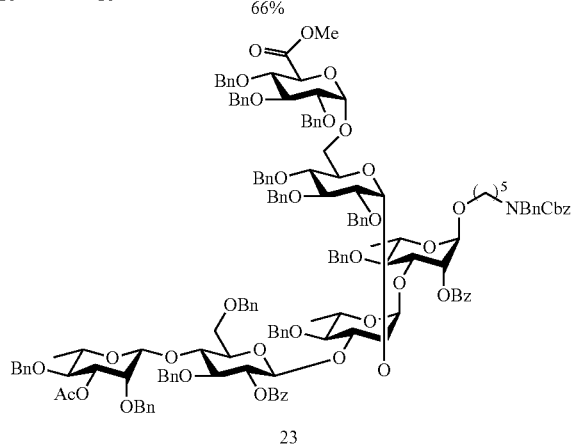

NIS (12 mg, 0.05 mmol) and TfOH (1 μL) were added at −30° C. to a cooled solution of donor 18 (52 mg, 0.05 mmol), acceptor 16 (45 mg, 0.026 mmol) and 4 Å acid washed molecular sieves (AWMS) (0.2 g) in mixture of CH$_2$Cl$_2$ (1 mL) and dioxane (1 mL). Reaction mixture was gradually warmed to −10° C. over 1 h, diluted with CH$_2$Cl$_2$ (10 mL) and washed with aq. sat. Na$_2$S$_2$O$_3$ (5 mL). Separated organic layer was dried over Na$_2$SO$_4$, filtered and concentrated. The crude was purified by flash chromatography using hexanes and ethyl acetate as eluent (4:1 to 3:1) to obtain the desired product 23 as colorless oil (45 mg, 66%).

$^1$H NMR (400 MHz, CDCl$_3$) δ 8.05 (d, J=7.7 Hz, 2H), 7.78 (d, J=7.8 Hz, 2H), 7.50-7.32 (m, 8H), 7.30-7.01 (m, 63H), 6.98-6.89 (m, 3H), 6.86-6.83 (m, 2H), 5.25 (s, 1H), 5.19-5.12 (m, 2H), 5.07 (d, J=4.5 Hz, 2H), 4.90-4.45 (m, 20H), 4.42-4.08 (m, 12H), 4.06-3.52 (m, 16H), 3.50 (d, J=4.1 Hz, 3H), 3.48-2.95 (m, 13H), 1.87 (s, 3H), 1.58-1.36 (m, 6H), 1.14 (d, J=6.2 Hz, 3H), 1.07 (d, J=6.1 Hz, 3H), 0.88 (d, J=6.2 Hz, 3H);

$^{13}$C NMR (101 MHz, CDCl$_3$) δ 170.6, 170.2, 166.2, 164.6, 139.4, 139.3, 138.9 (2C), 138.8, 138.7, 138.5, 138.3, 138.2, 137.0, 133.3, 133.0, 130.2, 130.0, 129.9, 128.8, 128.6 (2C), 128.5 (3C), 128.4 (3C), 128.3, 128.2 (3C), 128.1, 128.0, 127.9 (3C), 127.8, 127.7, 127.6, 127.5, 127.4, 127.3, 127.2, 127.1, 126.6, 101.4, 100.7, 99.3, 98.1, 97.0, 95.9, 83.2, 81.7, 81.0, 80.7, 80.4, 80.2, 79.8, 79.6, 78.7, 77.5, 77.4, 77.3, 77.2, 76.8, 76.1, 75.7, 75.2, 75.1, 75.0, 74.7, 73.8, 73.7, 73.3, 73.1, 72.7, 71.8, 71.5, 71.3, 70.4, 67.6, 67.3, 66.9, 58.6, 53.6, 52.3, 31.1, 29.8, 21.1, 18.6, 18.1, 17.8, 17.6; HRMS (ESI): Calcd for C$_{157}$H$_{167}$O$_{34}$N [M+Na]$^+$ 2634.1301, found: 2634.0912.

Synthesis of 5-amino-pentyl-β-L-rhamnopyranosyl-(1→4)-β-D-glucopyranosyl-(1→3)-α-L-{α-D-glucopyranosyluronate-(1→6)-α-D-glucopyranosyl-(1→2)} rhamnopyranosyl-(1→3)-α-L-rhamnopyranoside (22)

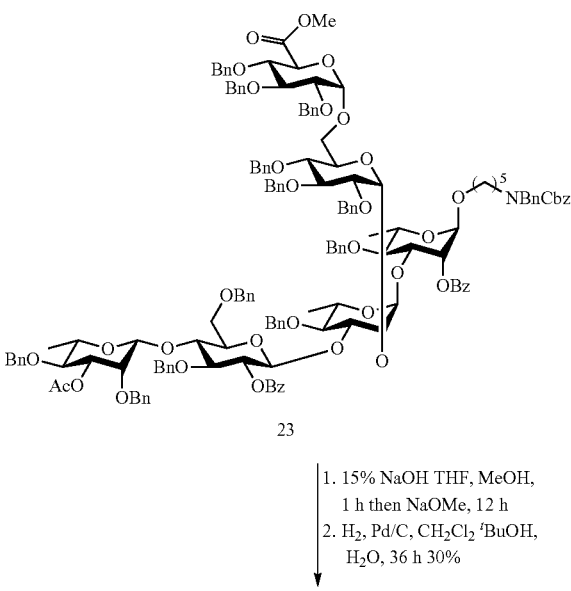

23

1. 15% NaOH THF, MeOH, 1 h then NaOMe, 12 h
2. H$_2$, Pd/C, CH$_2$Cl$_2$ $^t$BuOH, H$_2$O, 36 h 30%

↓

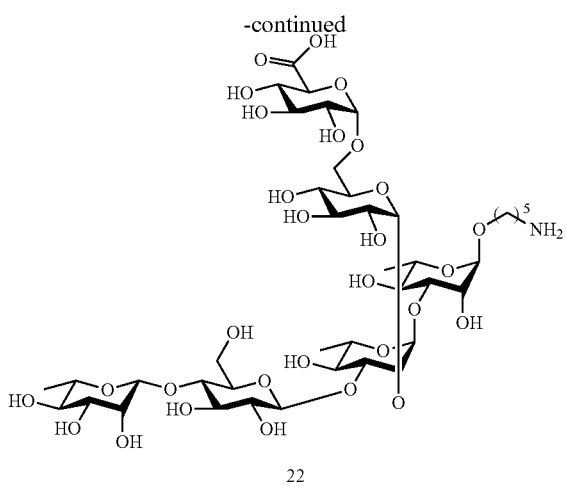

To a stirred solution of hexasaccharide 23 (6 mg, 2.3 μmol) in THF (0.5 mL) and MeOH (0.5 mL), was added aq. NaOH (15%, 100 μL). After stirring at room temperature for 1 h, NaOMe (6 mg) was added and allowed to stir for 12 h. After complete consumption of starting material, the reaction mixture was neutralized with Amberlite 120H$^+$ resin, filtered, and concentrated. The crude material was purified by flash column chromatography using hexanes and ethyl acetate as eluent (1:1 to 1:2) to afford the desired deacylated product as white solid. The obtained deacylated product was dissolved in $CH_2Cl_2$ (0.5 mL), $^tBuOH$ (1 mL) and water (0.5 mL). To this solution a suspension of Pd/C (50 mg) in a mixture of $^tBuOH$ (1 mL) and water (0.5 mL) was added and stirred under hydrogen atmosphere for 36 h. Reaction mixture was then filtered, concentrated and purified by C18 column to afford the desired product 22 (0.7 mg, 30%) as a white solid.

$^1$H NMR (400 MHz, $D_2O$) δ 5.07 (s, 1H), 5.02-4.94 (m, 2H), 4.91 (d, J=3.7 Hz, 1H), 4.73 (d, J=1.5 Hz, 1H), 4.63 (d, J=7.9 Hz, 1H), 4.35-4.18 (m, 3H), 4.05 (m, 4H), 3.96-3.81 (m, 3H), 3.80-3.61 (m, 8H), 3.61-3.40 (m, 8H), 3.38-3.25 (m, 3H), 3.24-3.13 (m, 1H), 2.96 (t, J=7.6 Hz, 2H), 1.66 (dt, J=15.9, 8.0 Hz, 4H), 1.43 (p, J=7.8, 7.3 Hz, 2H), 1.33-1.19 (m, 9H);

HRMS (ESI): Calcd for $C_{41}H_{71}O_{29}N$ [M+Na]$^+$ 1064.4009, found: 1064.4067.

Example A.6: Synthesis and Characterization of *S. pneumoniae* Serotype 2 Conjugate 1

General Procedure Synthesis
Formation of the p-nitro Phenyl (PNP) Amide
To the saccharide 22 (1 equivalent) and diphenyl adipate (7 equivalents) in a glass vial were added a mixture of pyridine and DMSO (1:1) and the mixture let stir for 5 minutes for complete solubilization. Then, triethylamine (0.83 μL, 6 μmol, 10 equivalents) was added and let stir for 20 minutes. TLC indicated complete consumption of the starting material. The solvent was removed in vacuum. The residue was washed with dichloromethane (3×1 mL) to remove PNP ester excess and the white solid obtained was dried in vacuum.

Conjugation of PNP Ester Derivatized Saccharide to $CRM_{197}$ 40 equivalents of lyophilized $CRM_{197}$ was dissolved in 0.4 mL of sterile 0.1M sodium phosphate, pH 8.0 and transfer into upper chamber of 10,000 Da Millipore centrifugal filter (0.5 mL). Rinse glass vial with 3×0.4 mL of sterile 0.1M sodium phosphate, pH 8.0, transfer to the same centrifugal filter. Centrifuge at 10,000 rpm for 6-8 min. If needed, prolong final centrifugation step such that volume in upper chamber is 80-100 μL. The $CRM_{197}$ solution was then transfer into 1.5 mL tube containing lyophilized PNP ester derivatized saccharide and shake slowly (around 180-200 rpm) for 18-24 hrs at room temperature. The conjugate was washed once with 0.1M Sodium phosphate, pH 8.0 and 2-3 times with deionized, autoclaved water using 10,000 Da Millipore centrifugal filters. Take out small sample for MALDI analysis and transfer the conjugate into PBS. If needed, prolong final centrifugation step such that volume in upper chamber is about 250 μL. Transfer content of upper chamber to new 1.5 mL Eppendorf tube, store at 4° C.

Characterization of Glycoconjugate

A. MALDI analysis: The average molecular size of conjugates were determined by Matrix-assisted laser desorption/ionization (MALDI) analysis using $CRM_{197}$ as standard and calculate the average oligosaccharides attachments with per $CRM_{197}$ molecule.

B. SDS-PAGE: The conjugates were resolved by SDS-PAGE (10%) in denaturing condition. The samples were prepared in 6× SDS-PAGE sample loading dye. The electrophoresis was carried out at 120 V and 25 mA for 1 hr 30 min in electrode buffer and gel was stained with Coomassie brilliant blue R250.

Protein Estimation

The protein concentration was estimated using Micro BCA Protein Assay Kit (Thermo-scientific, USA) following the manufacturer's instructions. The sample was prepared in PBS and mixed with equal volume of reagent mixture (B:C:A: 24:1:25). The plate was incubated at 37° C. and the absorbance was measured at 560 nm. The standard curve was plotted with known concentration of BSA provided with the kit.

Synthesis of *S. pneumoniae* Serotype 2 Conjugate 1 ($CRM_{197}$—*S. pneumoniae* Serotype 2 Hexasaccharide 22)

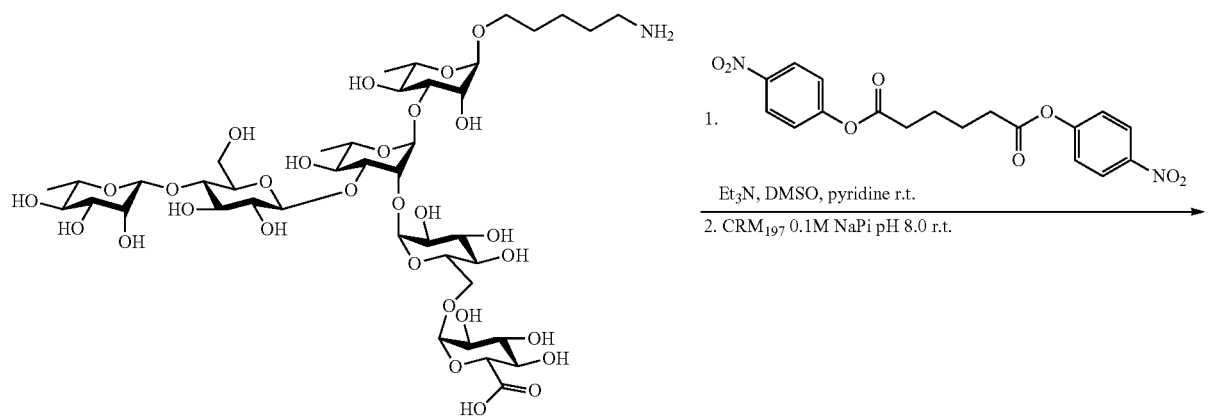

-continued

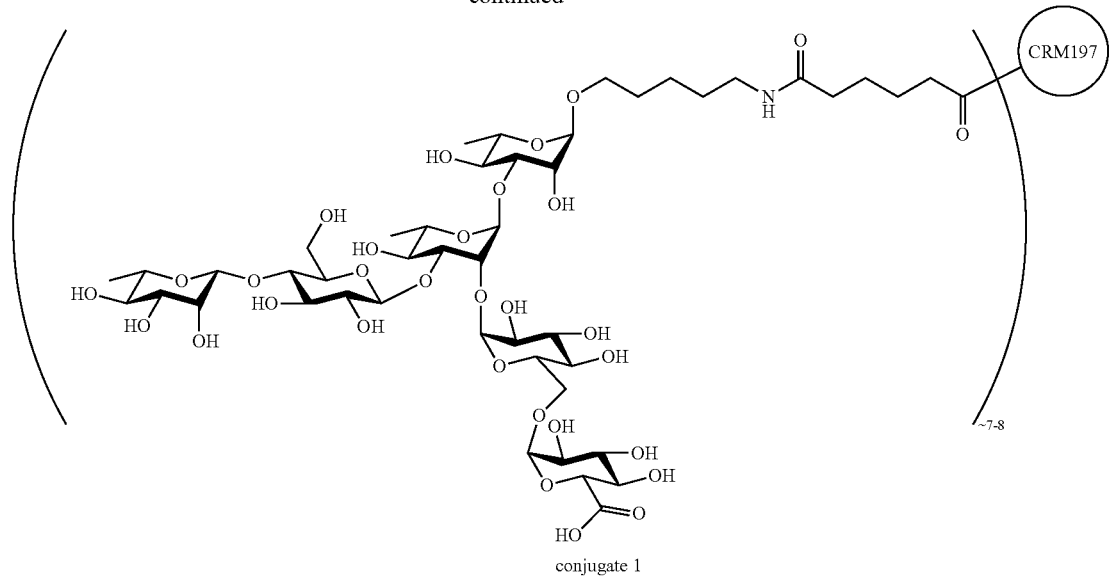

conjugate 1

Figure 3:
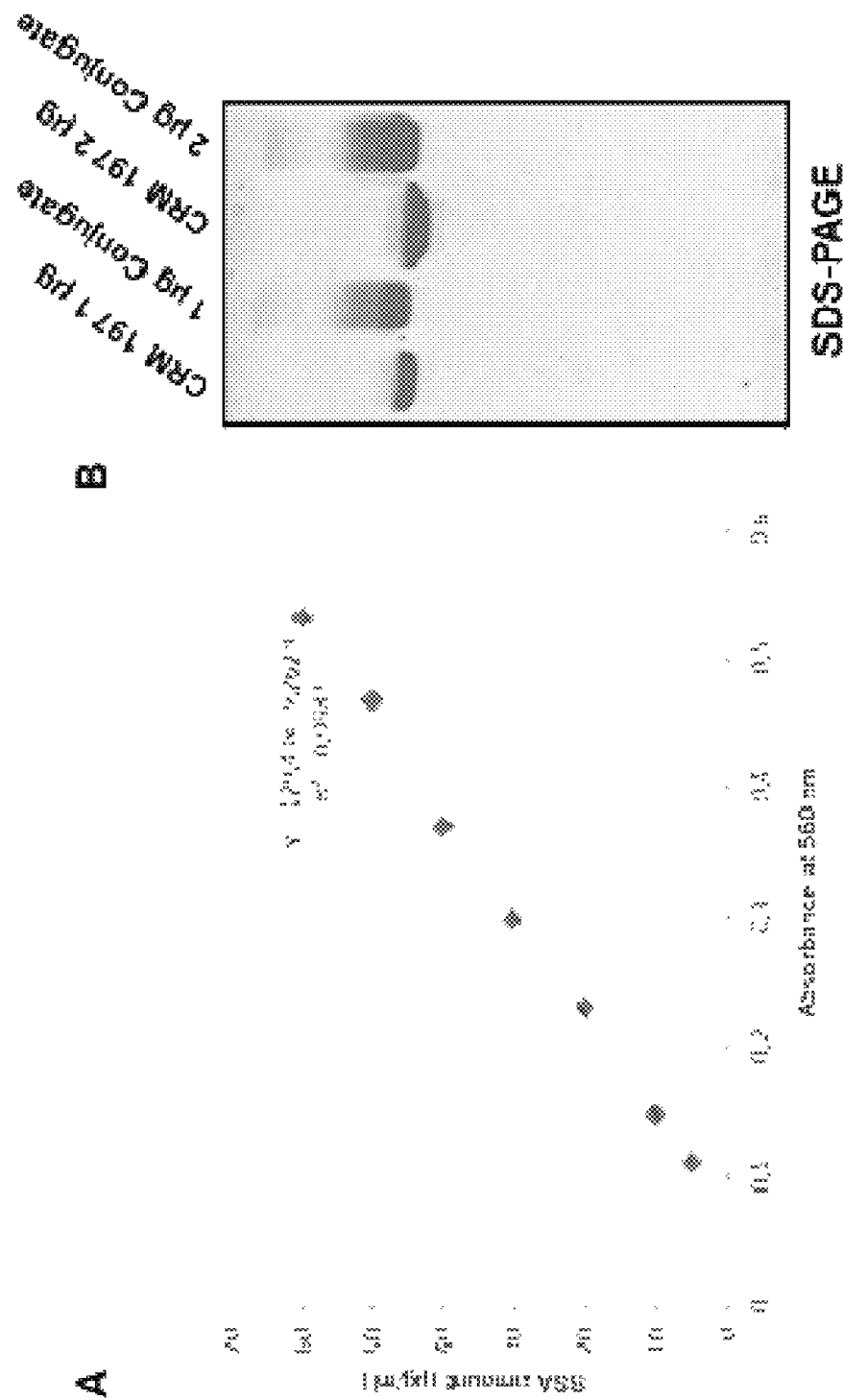
FIG. 3 shows the characterization of *S. pneumoniae* serotype 2 conjugate 1 ($CRM_{197}$—*S. pneumoniae* serotype 2 hexasaccharide 22). (A) The protein amount was estimated using the standard curve plotted with known concentration of BSA. (B) The conjugate 1 ($CRM_{197}$—*S. pneumoniae* serotype 2 hexasaccharide 22) was resolved on 10% SDS-PAGE along with $CRM_{197}$ and stained with Coomassie brilliant blue R250. (C) Matrix-assisted laser desorption/ionization (MALDI) analysis was carried out to measure the average molecular size of the conjugate. $CRM_{197}$ was used as standard.
Figure 3:
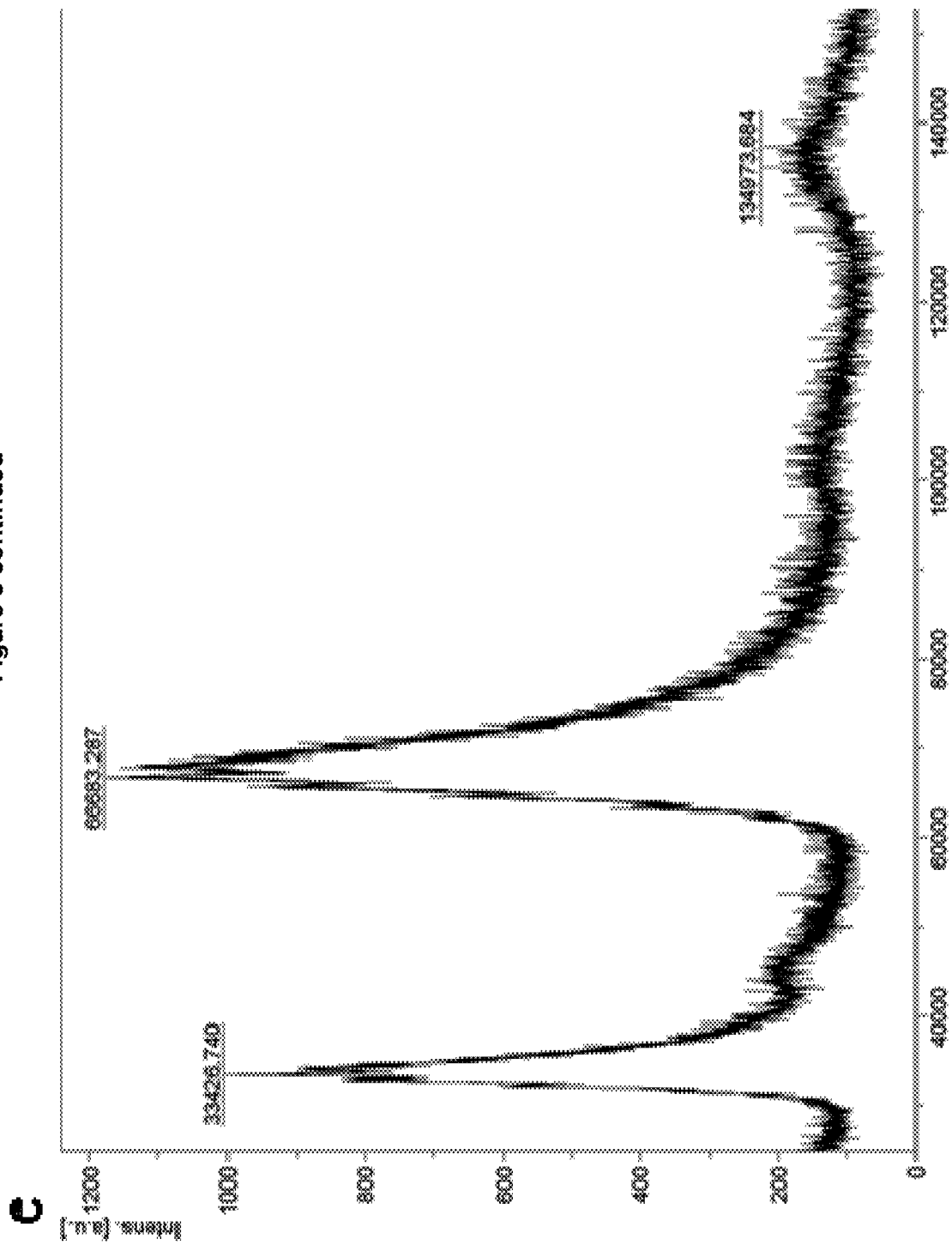

Following the above-described procedure, conjugate CRM$_{197}$—S. pneumoniae serotype 2 hexasaccharide 22 was synthesized. The conjugate 1 was estimated using known amount of BSA as slandered and confirmed by 10% SDS-PAGE, showing a shift toward a higher mass of the glycoconjugates compared with unconjugated CRM$_{197}$ (see FIGS. 3A and 3B). MALDI-TOF mass spectrometry analysis was used to determine the oligosaccharide-to-CRM$_{197}$ molar ratio (see FIG. 3C). Mass analysis of the conjugate CRM$_{197}$—S. pneumoniae serotype 2 hexasaccharide 22 revealed that an average of 7-8 molecules of hexasaccharide 22 was loaded onto one molecule of CRM$_{197}$.

Example B. Synthesis of S. pneumoniae Serotype 3 Conjugate 24 (CRM$_{197}$—S. pneumoniae Serotype 3 Tetrasaccharide 25)

Example B.1. Synthesis of S. pneumoniae Serotype 3 Tetrasaccharide 25

The synthesis of the S. pneumoniae serotype 3 tetrasaccharide 25 is outlined in the figure below.

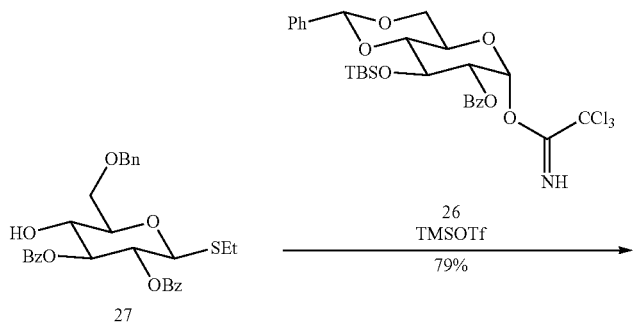

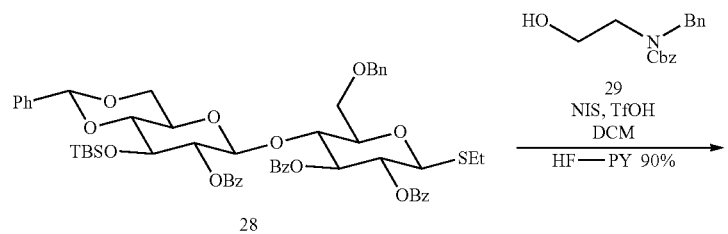

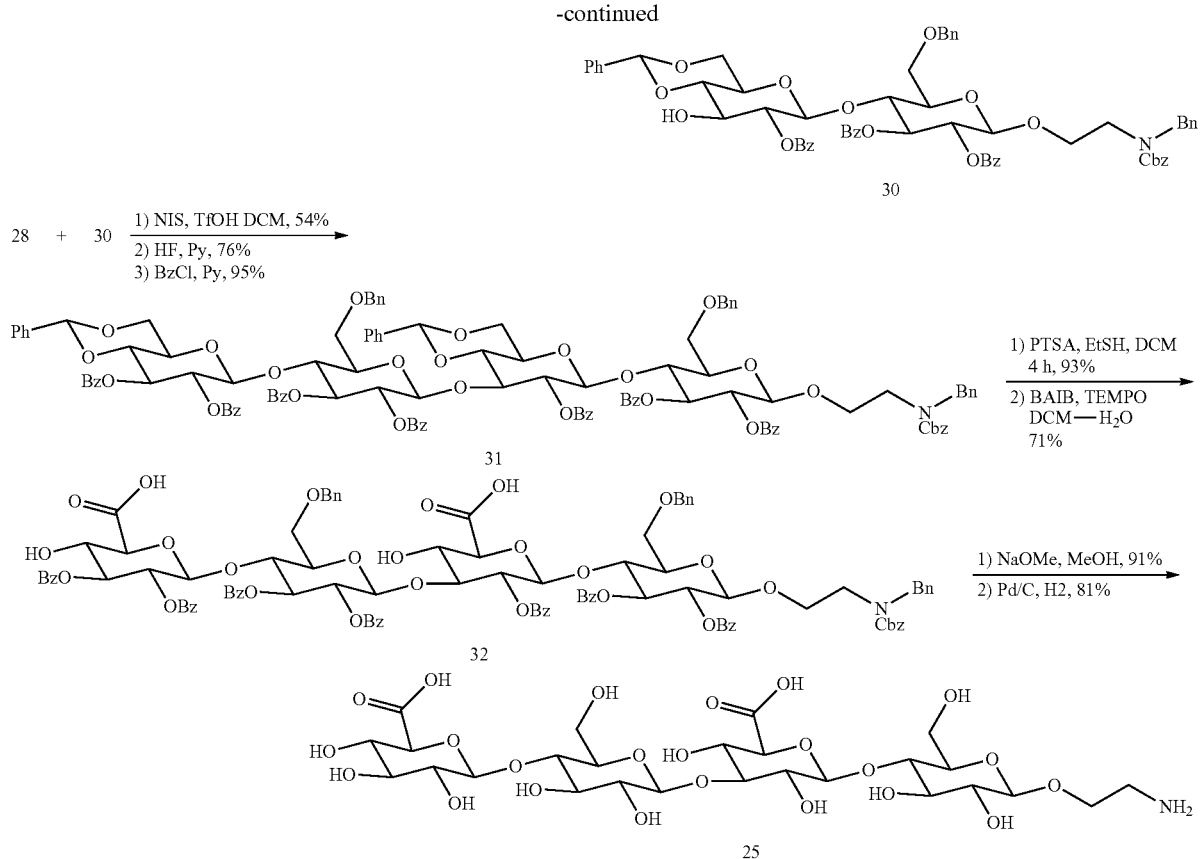

Example B.1.1. Synthesis of Disaccharide 28

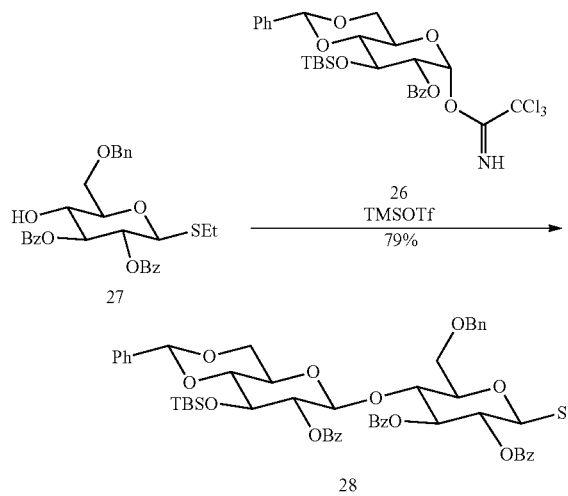

Compounds 26 (Yu, H., and Ensley, H. E. (2003) Tetrahedron Lett. 44, 9363-9366; Mo, K.-F., Li, H., Mague, J. T., and Ensley, H. E. (2009) Carbohydr. Res. 344, 439-447) (4.0 g, 7.65 mmol) and 27 (6.28 g, 9.95 mmol) were taken in DCM (140 mL) and stirred for 30 min. The reaction mixture was cooled to −20° C. and TMSOTf (0.16 mL, 0.88 mmol) was added. After stirring for 45 min at −20° C., the reaction mixture was quenched by the addition of Et$_3$N (1.0 mL), and concentrated under vacuum. Purification by flash chromatography using 25% ethyl acetate in hexanes yielded disaccharide 28 (6 g, 79%) as a colorless solid. $^1$H NMR (400 MHz, CDCl$_3$) δ 7.88-8.03 (m, 6H), 7.29-7.72 (m, 19H), 5.63 (t, J=9.3 Hz, 1H), 5.41 (t, J=9.8 Hz, 1H), 5.21 (s, 1H), 5.12 (dd, J=8.9, 8.2 Hz, 1H), 4.67 (d, J=12.2 Hz, 1H), 4.59 (dd, J=15.1, 9.0 Hz, 2H), 4.57 (d, J=10.0 Hz, 1H), 4.37 (d, J=12.2 Hz, 1H), 4.19 (t, J=9.5 Hz, 1H), 3.79 (t, J=9.0 Hz, 1H), 3.74-3.55 (m, 1H), 3.53-3.37 (m, 1H), 3.28 (t, J=9.2 Hz, 1H), 3.15 (td, J=9.7 Hz, 4.9 Hz, 2H), 2.67 (m, 2H), 1.20 (t, J=7.4 Hz, 3H), 0.63 (s, 9H), −0.11 (s, 3H), −0.19 (s, 3H); $^{13}$C NMR (101 MHz, CDCl$_3$) δ 165.3, 165.1, 164.5, 138.2, 137.0, 133.1, 133.1, 133.0, 130.2, 129.8 (3C), 129.3, 129.0, 128.5, 128.4, 128.3, 128.2, 128.1, 128.0 (2C), 126.2, 101.6, 101.1, 83.4, 81.1, 78.7, 77.4, 77.1, 76.8, 75.4, 74.9, 74.5, 73.5, 72.9, 70.6, 67.9, 67.5, 66.0, 25.4, 24.1, 17.8, 14.9, −4.2, −5.0.

Example B.1.2. Synthesis of Glucose Building Block 33

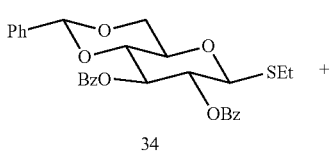

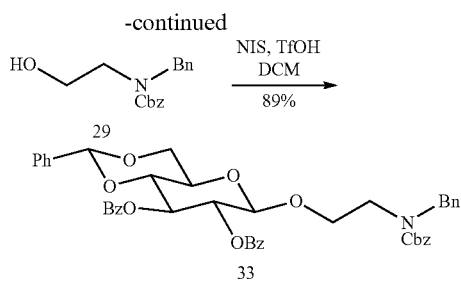

Thioglycoside donor 34 (Yu, H., and Ensley, H. E. (2003) Tetrahedron Lett. 44, 9363-9366) (6.0 g, 11.53 mmol) and amino alcohol acceptor 29 (Beshore, D. C., and Dinsmore, C. J. (2002). Org. Lett. 4, 1201-1204) (3.95 g, 13.83 mmol) were taken in DCM (100 mL). 5 g of microwave (MW) dried 4 Å molecular sieves (MS) were added and the RM stirred at room temperature for 15 min and then cooled to −10° C. NIS (3.89 g, 17.29 mmol) and TfOH (0.15 mL, 1.73 mmol) were added to the reaction mixture and stirred between −10° C. to −5° C. for 1 h. The reaction was then quenched with 10% aq. Na$_2$S$_2$O$_3$ solution (50 mL) and the aqueous was extracted with ethyl acetate (25 mL×3). Combined organic layer was washed with brine (10 mL), dried over anhyd. Na$_2$SO$_4$, filtered and concentrated in vacuum to obtain the crude as a pale yellow oil. Purification by flash column chromatography using 20-30% ethyl acetate in hexanes yielded the desired product 33 as pale yellow colored gummy liquid which under vacuum drying became a fluffy solid (7.60 g, 89%). [α]$_D^{20}$=−0.59° (c=1.0, CH$_2$Cl$_2$); IR (thin film, cm$^{-1}$): ν$_{max}$: 1728, 1699; $^1$H NMR (400 MHz, CDCl$_3$) δ 7.95 (d, J=8.1 Hz, 4H), 7.61-6.79 (m, 21H), 5.90-5.63 (m, 1H), 5.59-5.35 (m, 2H), 5.14 (s, 1H), 5.03 (dd, J=33.7, 12.6 Hz, 1H), 4.78 (d, J=7.7 Hz, 0.5H), 4.65 (d, J=7.6 Hz, 0.5H), 4.48-4.23 (m, 3H), 4.13-3.48 (m, 5H), 3.47-3.23 (m, 2H); $^{13}$C NMR (101 MHz, CDCl$_3$) δ 165.7, 165.4, 156.35, 156.2, 137.9, 136.9, 133.4, 133.2, 129.9, 129.5, 129.3, 129.1, 128.7, 128.5, 128.4, 128.3, 128.1, 127.8, 127.4, 127.2, 126.2, 101.9, 101.6, 78.9, 72.6, 72.1, 69.1, 68.7, 67.4, 67.2, 66.7, 51.7, 46.9, 45.8; HRMS (ESI): calculated for C$_{44}$H$_{41}$NNaO$_{10}$ [M+Na]$^+$, 766.2628, found 766.2657.

Example B.1.3. Synthesis of Glucose Building Block 34

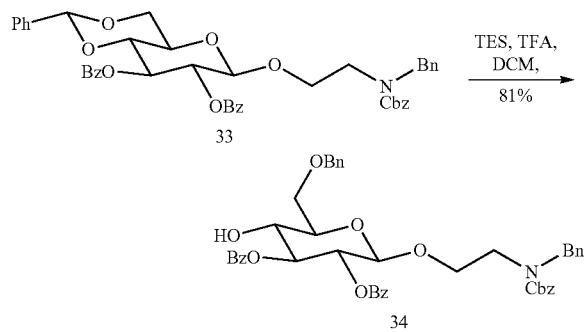

Compound 33 (7.50 g, 10.08 mmol) was stirred in DCM (75 mL) containing activated 3 Å MS for 10 min before cooling to 0° C. Added triethylsilane (12.88 mL, 81.0 mmol) followed by trifluoroacetic acid (4.66 mL, 60.5 mmol) dropwise and stirred the reaction mixture at room temperature for 16 h before quenching with water (100 mL). Extracted the aqueous with DCM (30 mL×3), combined organics were washed thoroughly with water (20 mL×3), brine (20 mL), dried over anhyd. Na$_2$SO$_4$, filtered, and evaporated under vacuum. Purification by flash column chromatography using 30%-100% ethyl acetate in hexanes yielded 34 as colorless oil (6.1 g, 81%). [α]$_D^{20}$=34.17° (c=1.0, CH$_2$Cl$_2$); IR (thin film, cm$^{-1}$): V$_{max}$: 3434, 1727, 1699; $^1$H NMR (600 MHz, CDCl$_3$) δ 7.97 (dd, J=11.4, 8.2 Hz, 4H), 7.69-6.66 (m, 21H), 5.56-5.39 (m, 2H), 5.13 (q, J=12.3 Hz, 1H), 5.04 (dd, J=38.3, 12.5 Hz, 1H), 4.79-4.54 (m, 3H), 4.40 (ddd, J=30.7, 25.4, 12.9 Hz, 2H), 4.16-3.89 (m, 2H), 3.89-3.55 (m, 4H), 3.50-3.21 (m, 3H); $^{13}$C NMR (151 MHz, CDCl$_3$) δ 167.1 (2C), 165.4, 156.4, 156.2, 137.9 (2C), 137.7, 137.6, 136.7, 136.5, 133.3, 133.2, 133.1, 129.9, 129.7, 129.3, 129.2, 129.0 (2C), 128.5, 128.4, 128.3, 128.0, 127.9, 127.8 (2C), 127.7, 127.6, 127.2, 127.0, 101.1, 101.0, 76.4, 74.6 (2C), 73.7, 71.5, 71.4, 70.8 (2C), 69.8, 69.7, 68.8 (2C), 67.2, 67.0, 51.5, 51.4, 46.7, 45.6; HRMS (ESI): calculated for C$_{44}$H$_{43}$NNaO$_{10}$ [M+Na]$^+$, 768.2785, found 768.2815.

Example B.1.4. Synthesis of Disaccharide 35

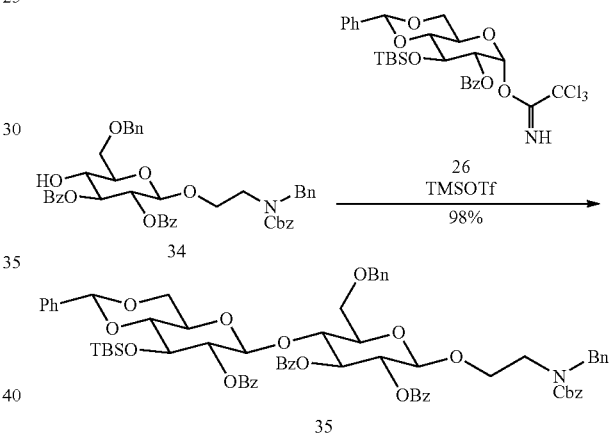

Acceptor 34 (2.0 g, 2.68 mmol) was taken in DCM (30 mL) with activated 4 Å AW MS and stirred at room temperature for 30 min before cooling to 0° C. TMSOTf (0.49 μL, 0.27 mmol) was then added followed by the imidate donor 26 (2.20 g, 3.49 mmol) in DCM (5 mL) over 5 min and the reaction mixture was stirred for 30 min at 0° C. Quenched the reaction mixture with Et$_3$N (1 mL), filtered and the solvents removed under vacuum. Crude product was purified by flash chromatography using 30-50% ethyl acetate in hexanes yielded 35 as a white fluffy solid (3.2 g, 98%). [α]$_D^{20}$=6.20° (c=1.0, CH$_2$Cl$_2$); IR (thin film, cm$^{-1}$): V$_{max}$: 1731; $^1$H NMR (400 MHz, CDCl$_3$) δ 8.06-7.84 (m, 6H), 7.68-6.91 (m, 29H), 5.58 (dt, J=22.8, 9.5 Hz, 1H), 5.47-5.31 (m, 1H), 5.21 (s, 1H), 5.16-4.95 (m, 3H), 4.69 (t, J=12.1 Hz, 1H), 4.59-4.08 (m, 6H), 4.03-3.72 (m, 2H), 3.71-3.19 (m, 8H), 3.14 (td, J=9.7, 4.9 Hz, 1H), 2.64 (t, J=10.1 Hz, 1H), 0.63 (s, 9H), −0.12 (s, 3H), −0.19 (s, 3H); $^{13}$C NMR (101 MHz, CDCl$_3$) δ 165.2, 165.1, 164.4, 156.2, 156.0, 138.0, 137.8 (2C), 136.9, 136.5, 133.2, 133.0, 130.1, 129.8, 129.7, 129.3, 129.0, 128.6, 128.5, 128.4, 128.3, 128.2, 128.1(2C), 128.0, 127.9, 127.7, 127.2, 127.0, 126.2, 101.5, 101.1, 101.0, 81.0, 75.3, 74.8, 74.4, 73.6, 73.2, 72.8, 71.8, 71.7, 68.7, 67.8, 67.2, 67.0, 65.9, 51.5, 46.7, 45.7, 25.4, 17.8, −4.2, −5.0; HRMS (ESI): calculated for C$_{70}$H$_{75}$NNaO$_{16}$Si [M+Na]$^+$, 1236.4753, found 1236.4796.

Example B.1.5. Synthesis of Disaccharide 35

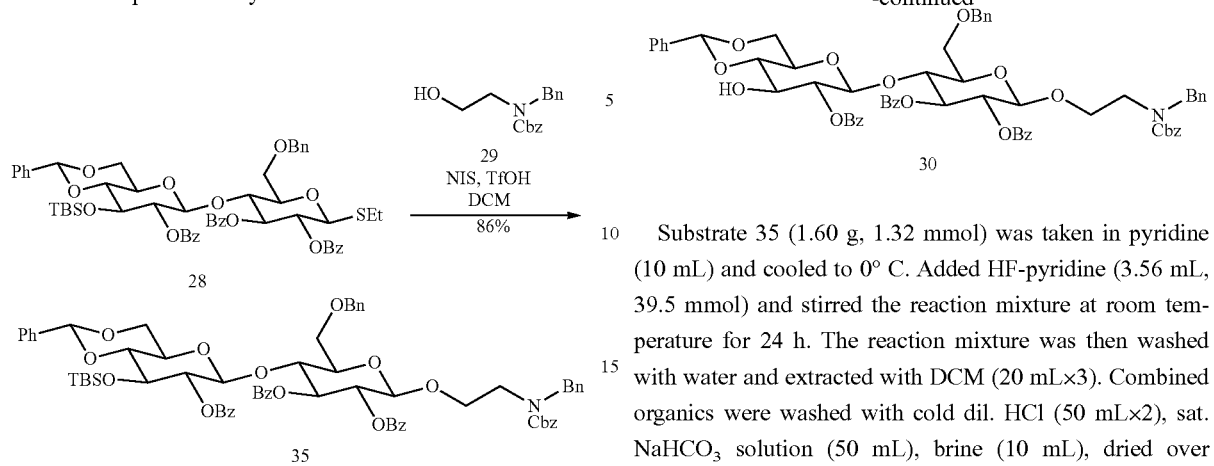

Thioglycoside disaccharide donor 28 (1.0 g, 1.01 mmol) and amino alcohol acceptor 29 (0.37 g, 1.31 mmol) were dried azeotropically using toluene in rotary evaporator. DCM (15 mL) was then added followed by activated 4 Å AW MS and the solution stirred at room temperature for 30 min before cooling to −10° C. NIS (0.238 g, 1.06 mmol) and TfOH (0.02 mL, 0.20 mmol) were added and the reaction mixture stirred between −10° C. to 0° C. for 1 h. The reaction mixture was then quenched with 10% aq. $Na_2S_2O_3$ solution (50 mL) and extracted with DCM (25 mL×3). Combined organic layer was washed with brine (10 mL), dried over anhyd. $Na_2SO_4$, filtered and concentrated under vacuum. Purification was by flash chromatography using 30-50% ethyl acetate in hexanes yielded 35 as a white fluffy solid (1.05 g, 86%).

Example B.1.6. Synthesis of Disaccharide 30

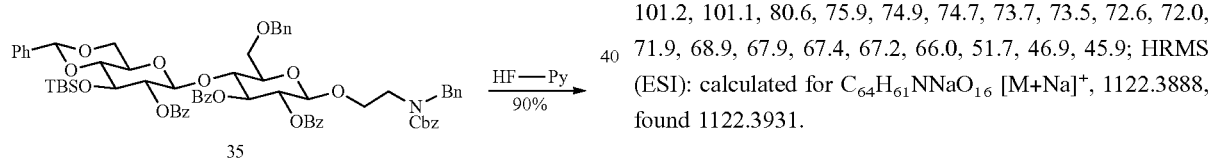

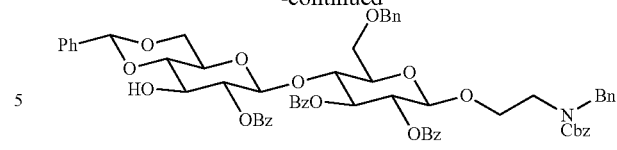

Substrate 35 (1.60 g, 1.32 mmol) was taken in pyridine (10 mL) and cooled to 0° C. Added HF-pyridine (3.56 mL, 39.5 mmol) and stirred the reaction mixture at room temperature for 24 h. The reaction mixture was then washed with water and extracted with DCM (20 mL×3). Combined organics were washed with cold dil. HCl (50 mL×2), sat. $NaHCO_3$ solution (50 mL), brine (10 mL), dried over $Na_2SO_4$, filtered and concentrated under vacuum. Purification using flash column chromatography using 35-50% ethyl acetate in hexanes yielded compound 30 as a white foam (1.30 g, 90%). $[\alpha]_D^{20}$=12.18° (c=1.0, $CH_2Cl_2$); IR (thin film, cm$^{-1}$): $V_{max}$: 3446, 1724, 1691; $^1$H NMR (600 MHz, CDCl$_3$) δ 8.07-7.85 (m, 6H), 7.68-6.81 (m, 29H), 5.59 (dt, J=31.0, 9.5 Hz, 1H), 5.39 (dt, J=36.6, 8.7 Hz, 1H), 5.23 (s, 1H), 5.15-4.93 (m, 3H), 4.73-4.57 (m, 2H), 4.53 (d, J=7.8 Hz, 0.5H), 4.47-4.25 (m, 3.5H), 4.17 (dt, J=27.2, 9.3 Hz, 1H), 4.00-3.75 (m, 2H), 3.72-3.22 (m, 8H), 3.15 (td, J=9.5, 5.0 Hz, 1H), 2.67 (t, J=10.3 Hz, 1H), 2.51 (s, 1H); $^{13}$C NMR (101 MHz, CDCl$_3$) δ 165.4, 165.3, 156.2, 156.2, 138.2, 136.9, 133.6, 133.2, 130.3, 130.0, 129.9, 129.4, 128.7 (2C), 128.5 (2C), 128.4, 128.1 (2C), 127.8, 127.4, 126.4, 101.8, 101.2, 101.1, 80.6, 75.9, 74.9, 74.7, 73.7, 73.5, 72.6, 72.0, 71.9, 68.9, 67.9, 67.4, 67.2, 66.0, 51.7, 46.9, 45.9; HRMS (ESI): calculated for $C_{64}H_{61}NNaO_{16}$ [M+Na]$^+$, 1122.3888, found 1122.3931.

Example B.1.7. Synthesis of Tetrasaccharide 36

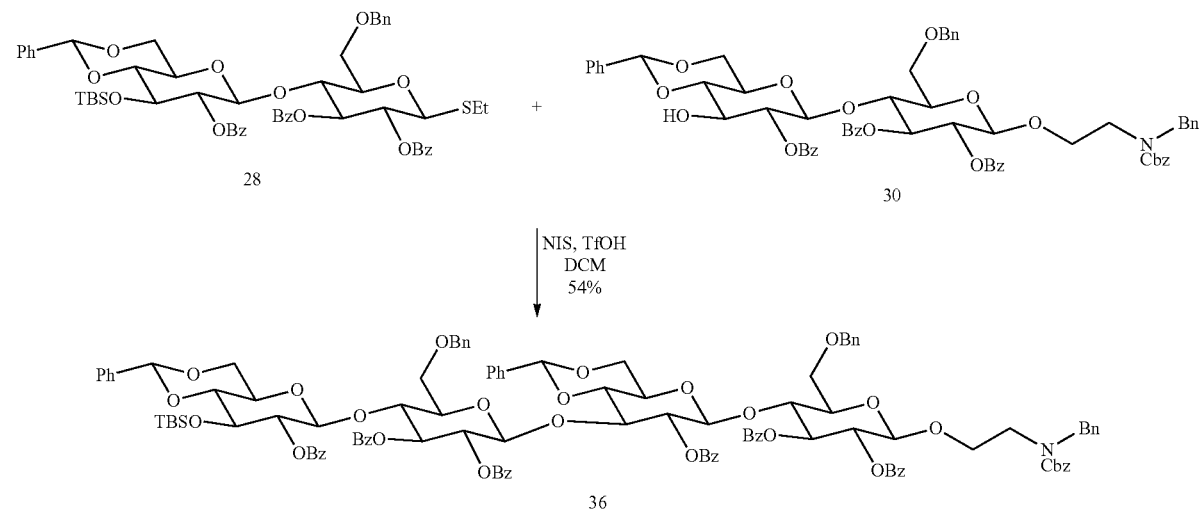

Acceptor disaccharide 30 (1.0 g, 0.91 mmol) and donor substrate 28 (1.08 g, 1.09 mmol) were taken in DCM (30 mL) to which was added 20 g of 4 Å MS and stirred at room temperature for 15 min and then cooled to −10° C. NIS (0.245 g, 1.09 mmol) and TfOH (0.016 mL, 0.18 mmol) were then added to reaction mixture and stirred at −5° C. for 1 h. Donor substrate 28 (0.45 g, 0.45 mmol) and NIS (0.102 mg, 0.45 mmol) were added again to the reaction mixture and stirred at −5° C. for 1 h, and then slowly warmed to 5° C. The reaction mixture was then quenched with 10% $Na_2S_2O_3$ solution (25 mL) and filtered through a Celite® bed and the aqueous extracted with DCM (15 mL×3). Combined organic layer was washed with sat. $NaHCO_3$ solution (15 mL), brine (10 mL), dried over anhyd. $Na_2SO_4$, filtered and concentrated in vacuum. Purification by silica gel flash column chromatography using 30-35% ethyl acetate in hexanes yielded tetrasaccharide 36 as a fluffy white solid (1.0 g, 54%). $[α]_D^{20}$=11.68° (c=1.0, $CH_2Cl_2$); IR (thin film, $cm^{-1}$): $V_{max}$: 1732, 1701; $^1H$ NMR (600 MHz, $CDCl_3$) δ 8.07-6.91 (m, 60H), 5.49 (dt, J=31.2, 9.5 Hz, 1H), 5.32 (dt, J=17.9, 9.5 Hz, 2H), 5.25-4.90 (m, 7H), 4.61 (d, J=7.9 Hz, 1H), 4.58-4.19 (m, 8H), 4.16 (d, J=12.2 Hz, 1H), 4.06 (dt, J=24.7, 9.4 Hz, 1H), 4.00-3.89 (m, 1.5H), 3.85-3.70 (m, 2.5H), 3.69-3.56 (m, 2H), 3.53 (dd, J=10.7, 4.8 Hz, 1H), 3.49-2.99 (m, 12H), 2.64 (t, J=9.8 Hz, 1H), 2.55 (t, J=10.4 Hz, 1H), 0.60 (s, 9H), −0.16 (s, 3H), −0.24 (s, 3H); $^{13}C$ NMR (151 MHz, $CDCl_3$) δ 165.4, 165.1, 164.8, 164.5, 164.0, 156.3, 156.2, 138.4, 138.0, 137.1, 137.0, 136.7, 133.2, 133.1 (2C), 133.0, 132.6, 130.2, 130.1, 130.0, 129.9 (2C), 129.8, 129.7, 129.5, 129.4, 129.2, 129.1, 128.6, 128.5 (2C), 128.4, 128.3 (2C), 128.2, 128.1 (3C), 128.0, 127.8, 127.3, 127.1, 126.4, 126.1, 101.7, 101.4, 101.2 (2C), 101.0, 100.2, 81.1, 79.4, 78.4, 75.8, 75.6, 75.0, 74.5, 74.4, 73.6, 73.5, 73.4, 73.1, 72.3, 72.0, 68.8, 68.0, 67.9, 67.4, 67.2, 67.0, 66.2, 66.0, 51.7, 46.9, 45.8, 25.6, 17.9, −4.1, −4.9; HRMS (ESI): calculated for $C_{117}H_{117}NNaO_{29}Si$ [M+Na]$^+$, 2050.7378, found 2050.7372.

Example B.1.8. Synthesis of Tetrasaccharide 37

Tetrasaccharide substrate 36 (0.60 g, 0.30 mmol) was taken in pyridine (10 mL) at 0° C. and to it was added HF-pyridine (0.80 mL, 8.87 mmol) and stirred at room temperature for 24 to 36 h. The reaction mixture was diluted with water and extracted with DCM (20 mL×3). Combined organics were then washed with cold dil. HCl (50 mL×2), sat. $NaHCO_3$ solution (50 mL), brine (10 mL), dried over $Na_2SO_4$, filtered and concentrated in vacuum. Purification by silica gel column chromatography using 50% ethyl acetate in hexanes yielded 37 as white colored foam (0.55 g, 97%). $[α]_D^{20}$=17.88° (c=1.0, $CH_2Cl_2$); IR (thin film, $cm^{-1}$): $V_{max}$: 3455, 1732; $^1H$ NMR (600 MHz, $CDCl_3$) δ 8.06-6.84 (m, 60H), 5.49 (dt, J=31.0, 9.5 Hz, 1H), 5.32 (dt, J=17.7, 9.5 Hz, 2H), 5.25-4.90 (m, 7H), 4.61 (dd, J=7.9, 1.9 Hz, 2H), 4.54 (dd, J=16.2, 12.5 Hz, 1H), 4.49-4.18 (m, 7H), 4.06 (dt, J=24.6, 9.4 Hz, 1H), 3.98 (t, J=9.4 Hz, 1H), 3.95-3.89 (m, 0.5H), 3.86-3.73 (m, 2.5H), 3.66-3.56 (m, 2H), 3.50 (dd, J=10.7, 4.9 Hz, 1H), 3.48-3.33 (m, 4H), 3.33-2.98 (m, 8H), 2.65 (t, J=10.2 Hz, 1H), 2.56 (t, J=10.4 Hz, 1H), 2.42 (d, J=3.5 Hz, 1H); $^{13}C$ NMR (151 MHz, $CDCl_3$) δ 165.4, 165.37, 165.1, 165.08, 164.8, 164.0, 156.3, 156.2, 138.3, 138.1, 138.0, 137.0, 136.9, 136.7, 133.6, 133.2, 133.1, 132.7, 130.3, 130.2, 130.1, 130.0, 129.9, 129.7, 129.6, 129.4, 129.3, 129.2, 128.6, 128.5 (2C), 128.4 (2C), 128.2 (2C), 128.1 (2C), 128.0, 127.8, 127.3, 127.1, 126.3, 126.1, 101.7, 101.5, 101.2, 101.0 (2C), 100.2, 80.5, 79.5, 78.4, 76.1, 75.6, 74.9, 74.5, 74.4, 73.7, 73.5, 73.4, 73.1, 72.7, 72.3, 72.0, 71.9, 68.9, 68.0, 67.8, 67.4, 67.3, 67.2, 67.0, 66.2, 65.8, 51.7, 46.9, 45.8; HRMS (ESI): calculated for $C_{111}H_{103}NNaO_{29}$ [M+Na]$^+$, 1936.6513, found 1936.6508.

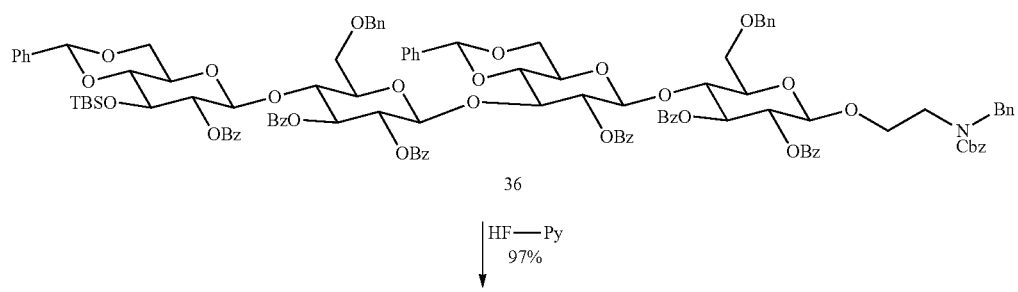

36

HF—Py
97%

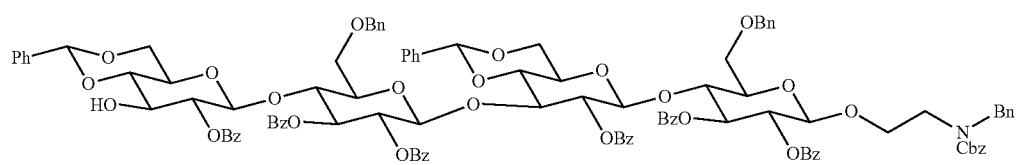

37

Example B.1.9. Synthesis of Tetrasaccharide 31

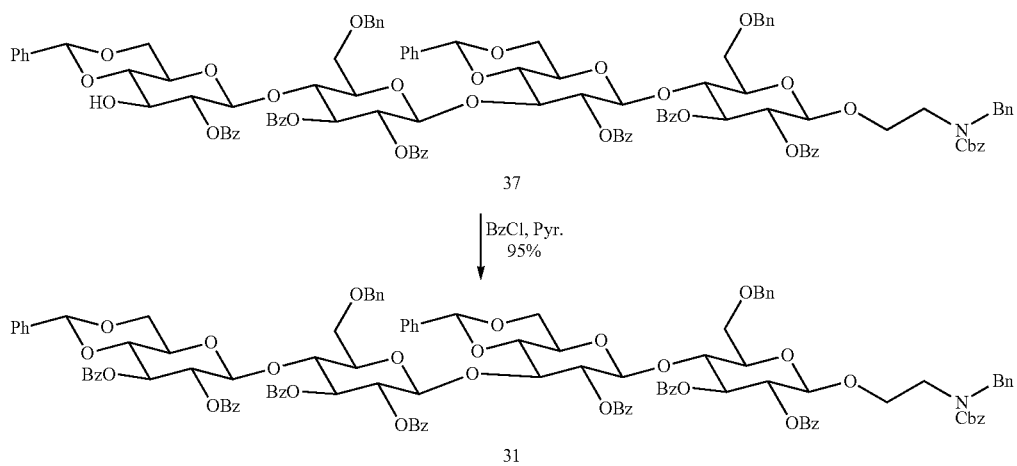

Intermediate 37 (0.65 g, 0.34 mmol) was taken in pyridine (5 mL) and benzoyl chloride (0.08 mL, 0.68 mmol) was added and the reaction mixture stirred at room temperature for 16 h. Diluted the reaction mixture with water and extracted with DCM (20 mL×3). Combined organics were washed with cold dil. HCl (10 mL×2), sat. NaHCO$_3$ solution (10 mL×2), water (10 mL), brine (20 mL), dried over Na$_2$SO$_4$, filtered, and concentrated. Trituration with cold methanol (5 mL×3) yielded 31 as a white solid (0.65 g, 95%). $[\alpha]_D^{20}$=11.05° (c=1.0, CH$_2$Cl$_2$); IR (thin film, cm$^{-1}$): $v_{max}$: 1732; $^1$H NMR (400 MHz, CDCl$_3$) δ 8.18-6.86 (m, 65H), 5.54-5.40 (m, 2H), 5.38-5.14 (m, 4H), 5.12-4.94 (m, 4H), 4.91 (s, 1H), 4.65 (d, J=7.9 Hz, 1H), 4.59 (d, J=7.9 Hz, 1H), 4.55-4.47 (m, 1H), 4.43 (d, J=7.9 Hz, 1H), 4.41-4.13 (m, 6H), 4.09-3.85 (m, 3H), 3.8-3.70 (m, 1H), 3.64-3.3 (m, 6H), 3.33-3.15 (m, 6H), 3.31-2.98 (m, 3H), 2.61 (dd, J=20.1, 9.9 Hz, 2H); $^{13}$C NMR (101 MHz, CDCl$_3$) δ 165.6, 165.4, 165.2, 165.1, 164.8, 164.0, 156.3, 156.2, 138.1 (2C), 138.0, 137.0, 136.8, 133.4, 133.1, 132.7, 130.2, 129.9, 129.9, 129.8, 129.8, 129.7, 129.5, 129.3, 129.3, 129.2, 129.1, 128.6 (3C), 128.5, 128.4 (2C), 128.3, 128.2 (2C), 128.1, 127.8, 127.3, 126.2, 126.1, 125.4, 101.5, 101.3, 101.2, 101.0, 100.1, 79.5, 78.4, 77.4, 76.3, 75.6, 74.3, 73.7, 73.5, 73.4, 73.1, 72.3, 72.3 (2C), 68.8, 68.0, 67.8, 67.1, 66.2 (2C), 51.7, 46.9, 45.8; HRMS (ESI): calculated for C$_{118}$H$_{107}$NNaO$_{30}$ [M+Na]$^+$, 2040.6776, found 2040.6770.

Example B.1.10. Synthesis of Tetrasaccharide 38

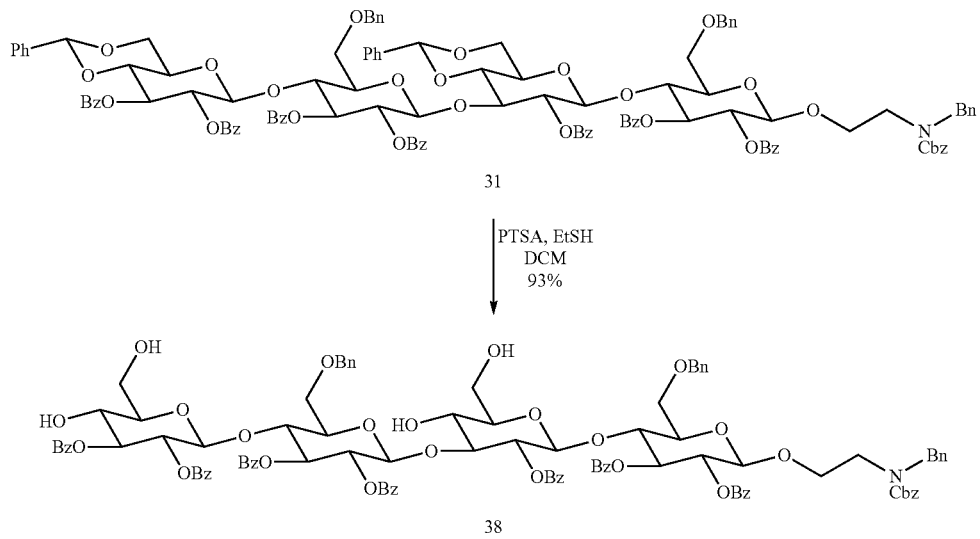

Compound 31 (0.54 g, 0.267 mmol) was taken in DCM (5 mL) at room temperature, added PTSA (10 mg, 0.053 mmol) and EtSH (0.30 mL, 4.01 mmol) and stirred the reaction mixture for 4 h. Reaction mixture was then quenched with Et$_3$N (1 mL) and evaporated under vacuum. Purification by flash chromatography using 60% ethyl acetate in hexanes yielded the tetraol 38 as white solid (0.46 g, 93%). $[\alpha]_D^{20}$=3.83° (c=1.0, CH$_2$Cl$_2$); IR (thin film, cm$^{-1}$): $v_{max}$: 3479, 1732; $^1$H NMR (400 MHz, CDCl$_3$) δ 8.02-7.81 (m, 10H), 7.59-6.91 (m, 45H), 5.52 (t, J=9.2 Hz, 1H), 5.47-5.15 (m, 5H), 5.12-4.90 (m, 3H), 4.62 (d, J=7.6 Hz, 1H), 4.61-4.57 (m, 1H), 4.52 (d, J=7.7 Hz, 1H), 4.47-4.36 (m, 3H), 4.34-4.18 (m, 4H), 4.13-3.99 (m, 2H), 3.95-3.73 (m, 2H), 3.69 (td, J=9.1, 4.3 Hz, 1H), 3.61-3.50 (m, 3H), 3.45-3.13 (m, 10H), 3.11-2.95 (m, 3H), 2.89 (d, J=4.3 Hz, 1H); $^{13}$C NMR (101 MHz, CDCl$_3$) δ 167.4 (2C), 165.2 (2C), 164.9, 163.8, 156.3, 156.2, 138.1, 137.3, 133.7, 133.6, 133.3, 133.0, 132.7, 130.1, 130.0, 129.9, 129.8, 129.7, 129.6, 129.5

(2C), 129.2, 129.0, 128.9, 128.8, 128.7 (2C), 128.6, 128.5, 128.4, 128.3, 128.1 (2C), 127.8, 127.3, 127.2, 101.3, 101.1, 100.8, 100.3, 85.1, 77.4, 77.0, 76.0, 75.8, 74.8, 74.7, 74.4, 73.8, 73.6, 73.3, 72.2, 71.7 (2C), 69.4, 69.3, 68.9, 67.6, 67.1, 62.5, 61.6, 51.7, 46.9, 45.9; HRMS (ESI): calculated for $C_{104}H_{99}NNaO_{30}$ [M+Na]$^+$, 1864.6150, found 1864.6144.

Example B.1.11. Synthesis of Tetrasaccharide 32

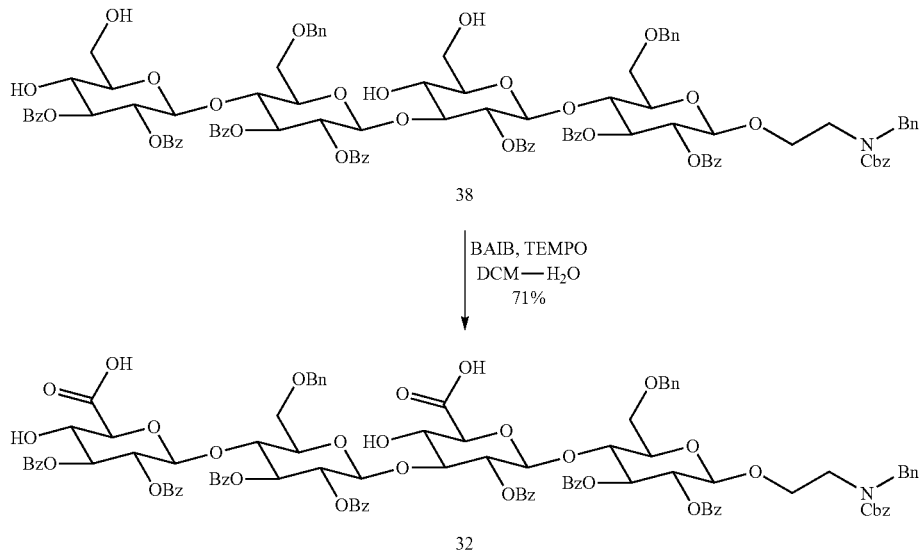

Tetraol 38 (125 mg, 0.07 mmol) was taken in a mixture of DCM (5 mL)—water (2 mL) and cooled to 0° C. TEMPO (2.1 mg, 0.014 mmol) and BAIB (0.11 g, 0.34 mmol) were added and stirred at 0° C. for 20 min and slowly warmed to room temperature and stirred at room temperature for 2 to 3 h. Reaction mixture was then diluted with DCM (5 mL) and water (5 mL) and the aqueous layer was extracted with DCM (5 mL×4). Combined organics were dried over Na$_2$SO$_4$, filtered, and concentrated. Purification by flash chromatography using 10-15% acetone in DCM+1-2% AcOH yielded the diacid 32 as a pale yellowish solid (0.09 g, 71%). $^1$H NMR (400 MHz, CD$_3$OD) δ 8.00-6.52 (m, 55H), 5.61-5.29 (m, 3H), 5.27-5.05 (m, 3H), 4.99 (d, J=9.8 Hz, 1H), 4.94 (d, J=8.0 Hz, 1H), 4.88-4.83 (m, 2H), 4.76 (d, J=7.9 Hz, 1H), 4.53 (d, J=8.0 Hz, 1.5H), 4.43 (dd, J=12.1, 4.8 Hz, 1H), 4.37 (d, J=7.8 Hz, 0.5H), 4.33-4.02 (m, 7H), 3.87-3.39 (m, 11H), 3.26-3.03 (m, 4H); $^{13}$C NMR (101 MHz, CD$_3$OD) δ 170.4 (2C), 167.2 (2C), 166.9, 166.7, 166.5, 166.4, 165.7, 158.0, 157.7, 139.2, 138.8, 138.6, 134.8, 134.5, 134.4, 134.1, 134.0, 131.4, 130.8 (2C), 130.7, 130.6, 130.5, 130.3, 130.1, 129.8, 129.7, 129.5 (2C), 129.4, 129.3, 129.2, 129.1, 128.8, 128.6, 128.2, 102.2, 101.9, 101.8, 101.7, 84.2, 77.6, 76.7, 76.4, 75.4, 74.6, 74.4, 73.7, 73.5, 73.3, 71.5, 71.1, 69.5, 69.4, 68.5, 68.3 (2C), 52.6, 52.5, 47.1; HRMS (ESI): calculated for $C_{104}H_{95}NNaO_{32}$ [M+Na]$^+$, 1892.5735, found 1892.5703.

Example B.1.12. Synthesis of Tetrasaccharide 39

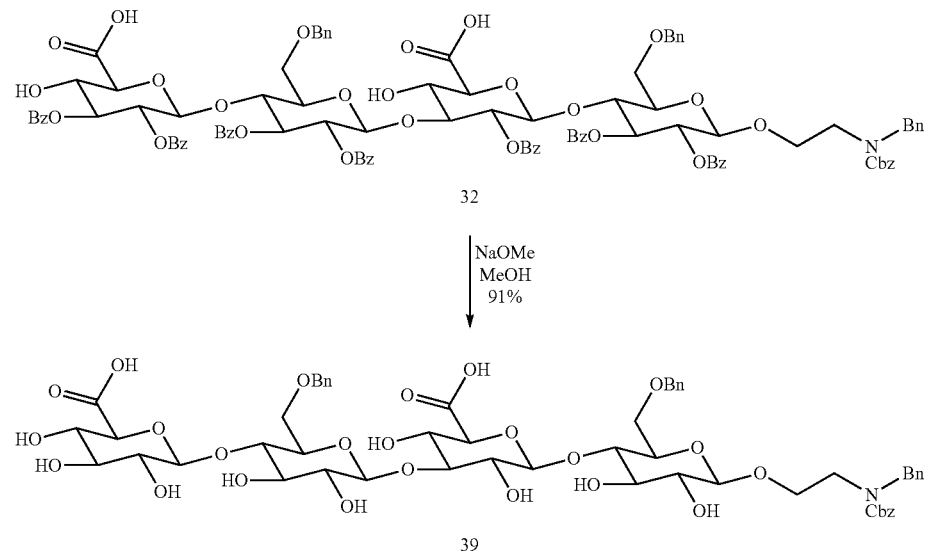

Diacid 32 (0.09 g, 0.05 mmol) was taken in methanol (5 mL) and to it was added 0.5 M solution of NaOMe in methanol (4.81 mL, 2.41 mmol) and stirred at room temperature for 24 to 36 h. The reaction mixture was neutralized with Amberlite® 120H+ resin and stirred for 10 min. The clear solution was filtered through a cotton plug and washed thoroughly with methanol and evaporated under vacuum. Diethyl ether (5 mL) was then added and triturated to get a pale yellowish solid which was then decanted. DCM (5 mL) was then added to the crude solid and triturated to get a off-white solid on decanting, which was then dried under vacuum to obtain 39 (0.05 g, 91%) as a white powder. $^1$H NMR (400 MHz, CD$_3$OD) δ 7.48-7.11 (m, 20H), 5.14 (d, J=9.1 Hz, 2H), 4.69-4.31 (m, 9H), 4.28-4.18 (m, 1H), 3.99-3.40 (m, 20H), 3.41-3.33 (m, 2H), 3.30-3.17 (m, 2H); $^{13}$C NMR (101 MHz, CD$_3$OD) δ 172.2, 171.9, 158.2, 139.6, 139.4, 138.0, 129.6, 129.5, 129.3, 129.2, 129.2, 129.04, 129.0, 128.8, 128.4, 104.8, 104.5, 104.1, 88.2, 86.9, 80.8, 77.7, 77.3, 76.9, 76.0, 75.97, 75.5, 75.0, 74.7, 74.5, 74.4, 74.1, 73.8, 73.0, 71.7, 71.5, 69.8, 69.6, 69.2, 69.0, 68.5, 62.4, 52.4, 47.5. LCMS (ESI): calculated for C$_{55}$H$_{66}$NO$_{25}$ [M-H]+, 1140.39, found 1140.2.

Example B.1.13. Synthesis of Tetrasaccharide 25

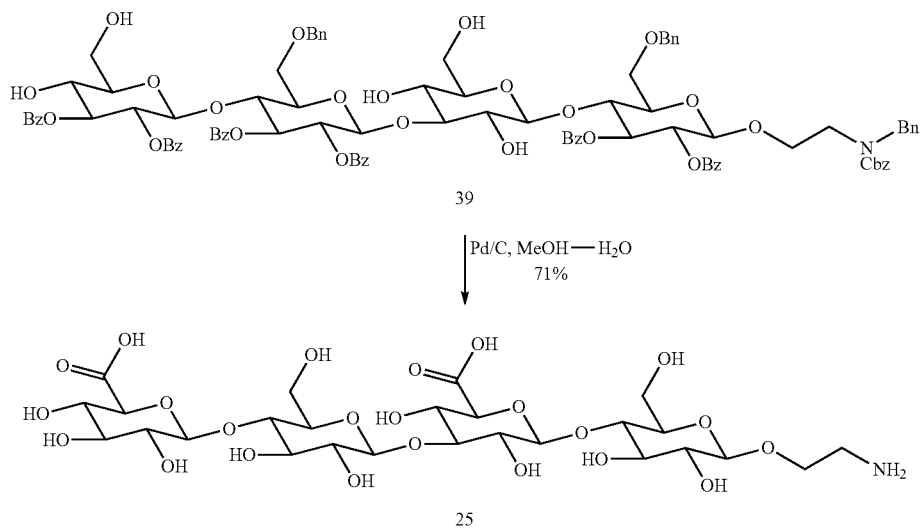

Substrate 39 (50 mg) was taken in methanol (2 mL) and 10% Pd/C (100 mg) was added. Hydrogenated the reaction mixture at room temperature using balloon for 18 h. Reaction mixture was then filtered through a PTFE hydrophobic filter and the filter washed thoroughly with methanol (3 mL×5), water-methanol (3 mL×5), and finally with NH$_4$OH in methanol (3 mL in 15 mL). After evaporation of the filtrate and drying under vacuum, target molecule 25 (23 mg, 71%) was obtained as an off-white glassy material. $^1$H NMR (400 MHz, D$_2$O) δ 4.84 (d, J=8.0 Hz, 1H), 4.56 (d, J=8.0 Hz, 2H), 4.53 (d, J=7.9 Hz, 1H), 4.14 (dt, J=11.5, 4.9 Hz, 1H), 4.04-3.92 (m, 3H), 3.89-3.75 (m, 5H), 3.72-3.49 (m, 10H), 3.43-3.34 (m, 3H), 3.29 (t, J=5.1 Hz, 2H); $^{13}$C NMR (101 MHz, d$_2$o) δ 175.4, 175.2, 102.3, 102.2, 102.0, 101.8, 82.7, 78.9, 78.6, 75.7, 75.2, 74.8, 74.7, 74.1, 73.1, 72.9, 72.7, 71.6, 70.1, 65.7, 60.0 39.3; HRMS (ESI): calculated for C$_{26}$H$_{43}$NNaO$_{23}$ [M+Na]+, 760.2124, found 760.2134.

Example B.2. Preparation of *S. pneumoniae* Serotype 3 Conjugate 2 (CRM$_{197}$—*S. pneumoniae* Serotype 3 Tetrasaccharide 25)

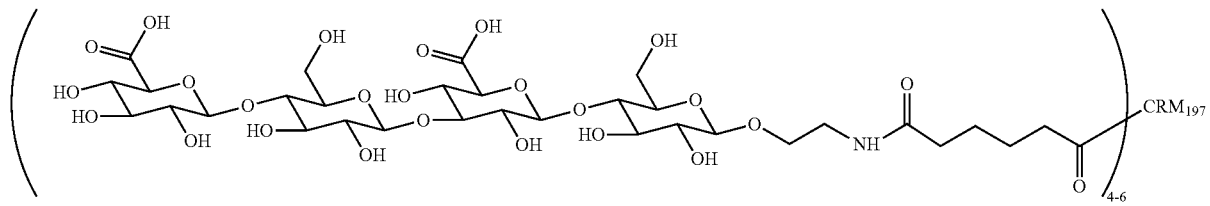

Figure 4:
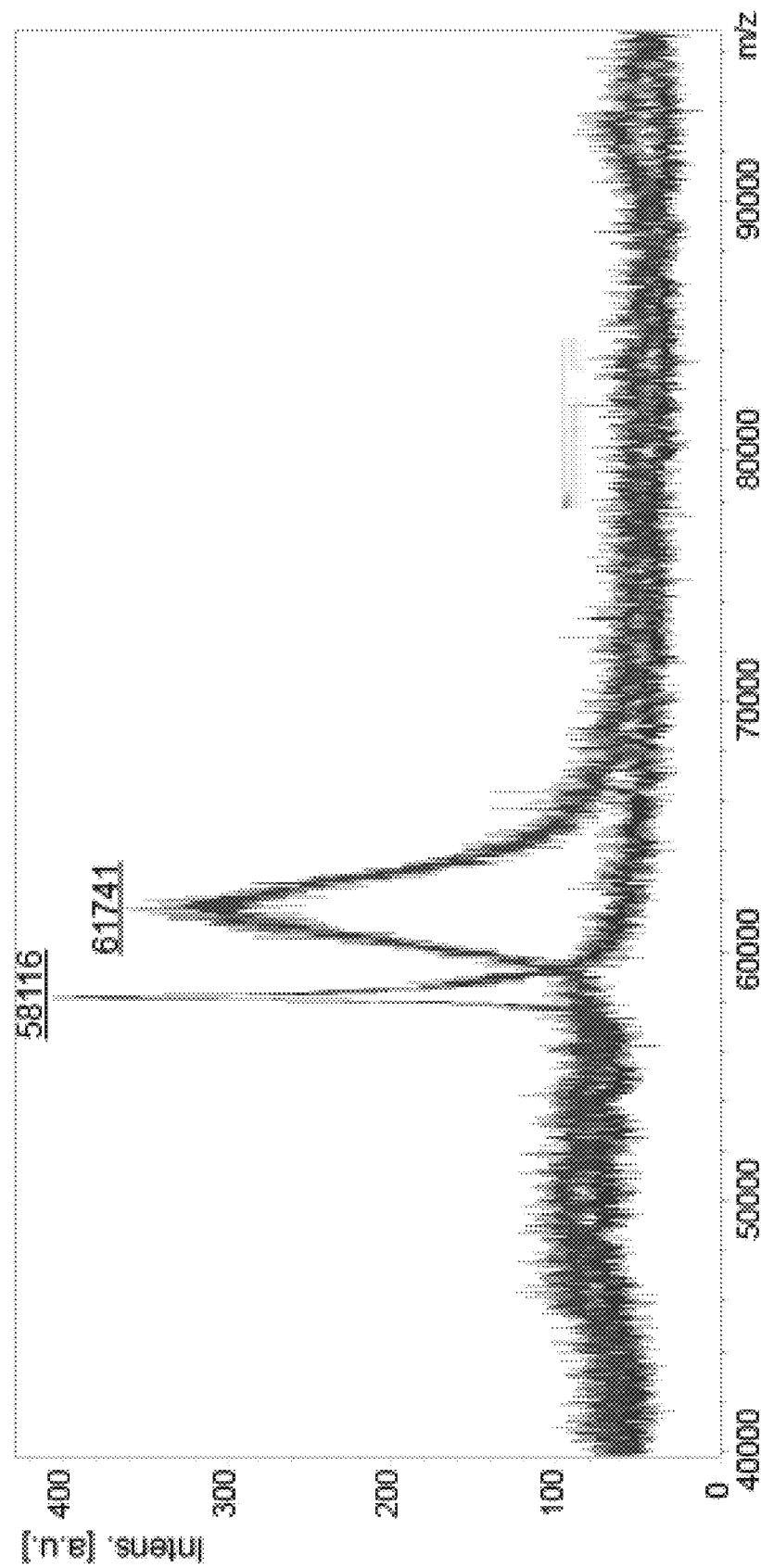
FIG. 4 shows the characterization of *S. pneumoniae* serotype 3 conjugate 2 ($CRM_{197}$—*S. pneumoniae* serotype 3 tetrasaccharide 25) by MALDI-TOF. The mass shift (3625 Da) compared to unmodified $CRM_{197}$ (peak at m/z 61741) for this conjugate batch indicates an average loading of 4-5 oligosaccharides per $CRM_{197}$ molecule. An increase in molecular weight is also visible as band shift in the SDS-PAGE.

The CRM$_{197}$-tetrasaccharide 25 conjugate was prepared as described previously (Anish et al., Angew. Chem. Int. Ed. 2013, 52, 9524-9528; Anish et al. ACS Chem. Biol. 2013, 8, 2412-2422). Tetrasaccharide 25 was reacted with di-(N-succinimidyl) adipate in DMSO catalyzed by triethylamine for 2 h at RT. Addition of coupling buffer (100 mM sodium phosphate buffer, pH 7.5) and extraction of unreacted linker with chloroform was followed by reaction of linker appended tetrasaccharide with recombinant CRM$_{197}$ (Pfenex Inc,) overnight in coupling buffer. After desalting with 10 kDa Amicon ultrafiltration devices (Millipore), The CRM$_{197}$-tetrasaccharide 25 conjugate was characterized by SDS-PAGE and MALDI-TOF MS. Coupling was confirmed by SDS-PAGE. Matrix-assisted laser desorption/ionization time-of-flight mass spectrometry (MALDI-TOF MS) allowed the calculation that on average four to six oligosaccharide haptens were loaded on each CRM$_{197}$ molecule (see FIG. 4).

Example C. Synthesis of *S. pneumoniae* Serotype 8 Conjugates 40 (CRM$_{197}$—*S. pneumoniae* Serotype 8 Tetrasaccharide 44), 41 (CRM$_{197}$—*S. pneumoniae* Serotype 8 Tetrasaccharide 45), 42 (CRM$_{197}$—*S. pneumoniae* Serotype 8 Tetrasaccharide 46) and 43 (CRM$_{197}$—*S. pneumoniae* Serotype 8 Hexasaccharide 66)

Example C.1. Synthesis of *S. pneumoniae* Serotype 8 Tetrasaccharides 44, 45 and 46

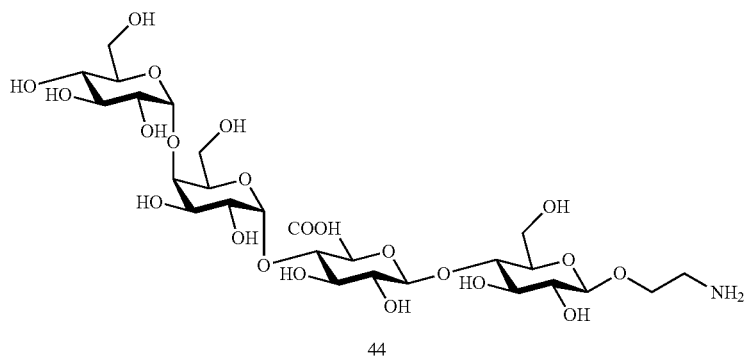

44

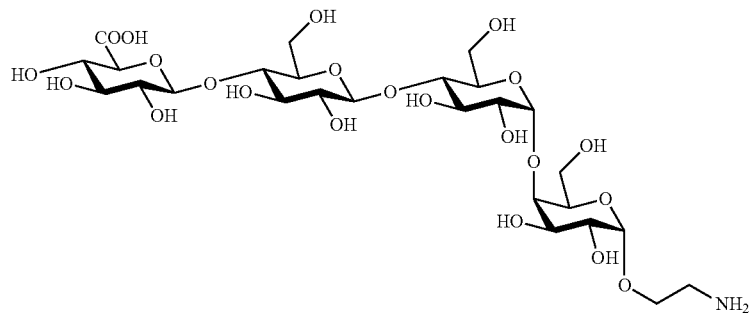

45

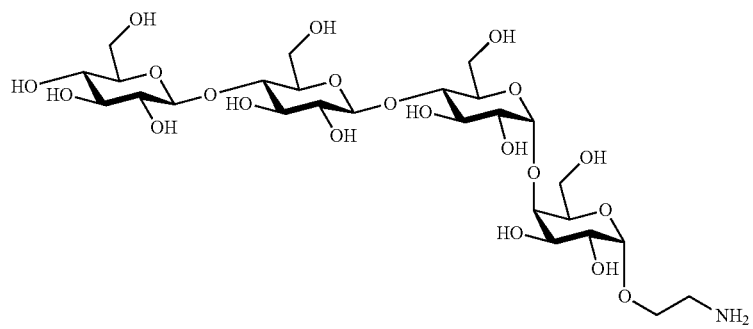

46

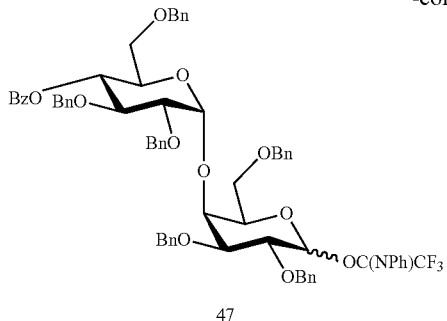

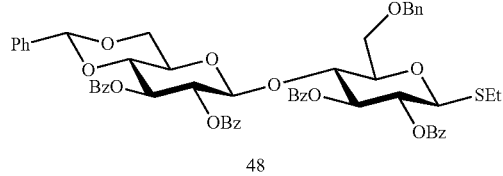

Example C.1.1. Synthesis of Compound 48

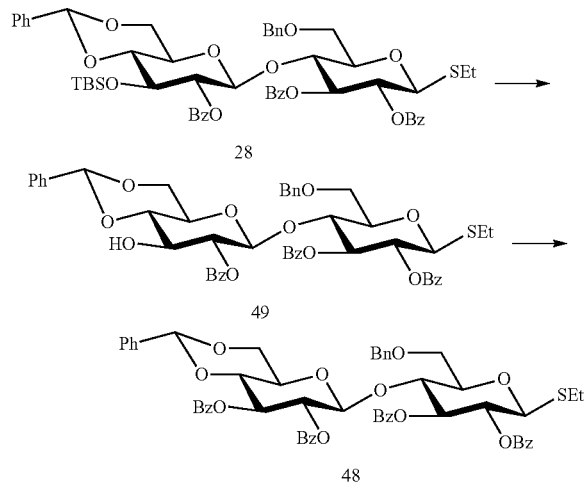

TBS substrate 28 (2.0 g, 2.018 mmol, 1 equiv.) obtained from Example B.1. was taken in pyridine (10 mL) at 0° C. and added 70% HF-pyridine (5.45 mL, 60.5 mmol, 30 equiv.) to it and stirred at rt for 36 h.

RM was washed with water (50 mL) and extracted with DCM (50 mL×3). Combined organics were then washed with sat. NaHCO$_3$ solution (50 mL), brine (20 mL), dried over Na$_2$SO$_4$, filtered and concentrated in vacuum to get crude product which on purification using silica column chromatography using 35-40% EtOAc/Hexanes to yield white colored foam 49 (1.7 g, 96%).

$^1$H NMR (400 MHz, CDCl$_3$) δ=8.08-7.85 (m, 6H), 7.69-7.28 (m, 19H), 5.62 (t, J=9.3 Hz, 1H), 5.41 (t, J=9.8 Hz, 1H), 5.22 (s, 1H), 5.08 (dd, J=9.2, 7.9 Hz, 1H), 4.70 (d, J=7.8 Hz, 1H), 4.63 (d, J=12.1 Hz, 1H), 4.58 (d, J=10.0 Hz, 1H), 4.40 (d, J=12.1 Hz, 1H), 4.19 (t, J=9.5 Hz, 1H), 3.82 (td, J=9.2, 3.6 Hz, 1H), 3.70 (dd, J=11.2, 3.4 Hz, 1H), 3.63 (dd, J=10.6, 5.0 Hz, 1H), 3.59-3.55 (m, 1H), 3.54-3.48 (m, 1H), 3.32 (t, J=9.3 Hz, 1H), 3.15 (td, J=9.7, 5.0 Hz, 1H), 2.78-2.60 (m, 3H), 2.50 (d, J=3.6 Hz, 1H), 1.22 (t, J=7.5 Hz, 3H). $^{13}$C NMR (101 MHz, CDCl$_3$) δ=165.38, 165.29, 165.13, 138.02, 136.70, 133.43, 133.14, 133.09, 130.08, 129.87, 129.81, 129.71, 129.30, 129.28, 129.23, 128.50, 128.48, 128.29, 127.95, 127.86, 126.19, 101.59, 100.88, 83.42, 80.42, 78.71, 75.71, 74.67, 74.51, 73.46, 72.42, 70.48, 67.70, 67.51, 65.76, 24.11, 14.85.

Substrate 49 (1.6 g, 1.824 mmol, 1 equiv.) was taken in anhydrous DCM (10 mL) at 0° C. and added pyridine (10 mL) and BzCl (0.635 mL, 5.47 mmol, 3 equiv.) to it dropwise and RM was stirred for 16 h.

RM was then evaporated in vacuum to remove solvents and then taken again in DCM (25 mL) and washed with aq.NaHCO$_3$ solution (5 mL×2). Organic layer was then dried on Na$_2$SO$_4$, filtered and evaporated in vacuum which was then triturated using methanol to get off-white solid (48), filtered, dried in vacuum (1.5 g, 84%).

$^1$H NMR (400 MHz, CDCl$_3$) δ 7.95 (ddd, J=16.9, 12.1, 7.3 Hz, 8H), 7.60-7.12 (m, 22H), 5.66 (t, J=9.3 Hz, 1H), 5.58 (t, J=9.6 Hz, 1H), 5.43 (t, J=9.8 Hz, 1H), 5.36 (dd, J=9.5, 7.9 Hz, 1H), 5.20 (s, 1H), 4.77 (d, J=7.9 Hz, 1H), 4.60 (t, J=10.3 Hz, 2H), 4.39 (d, J=12.1 Hz, 1H), 4.23 (t, J=9.5 Hz, 1H), 3.74-3.43 (m, 5H), 3.29 (td, J=9.7, 4.9 Hz, 1H), 2.83-2.55 (m, 3H), 1.22 (t, J=7.4 Hz, 3H). $^{13}$C NMR (101 MHz, CDCl$_3$) δ 165.46, 165.25, 165.16, 164.72, 137.82, 136.62, 133.31, 133.12, 133.02, 130.05, 129.80, 129.73, 129.70, 129.27, 129.24, 128.99, 128.97, 128.63, 128.43, 128.29, 128.22, 128.17, 128.10, 127.98, 126.03, 101.12, 83.39, 78.65, 78.29, 75.85, 74.44, 73.44, 72.43, 71.96, 70.47, 67.71, 67.31, 66.16, 24.04, 14.84.

Example C.1.2. Synthesis of 2,3-di-O-benzoyl-β-D-glucopyranosyl-(1→4)-2,3-di-O-benzoyl-6-O-benzyl-β-D-glucoyranosyl-(1→1)-(2-N-benzyl-N-benzyloxycarbonylamino)ethanol (50)

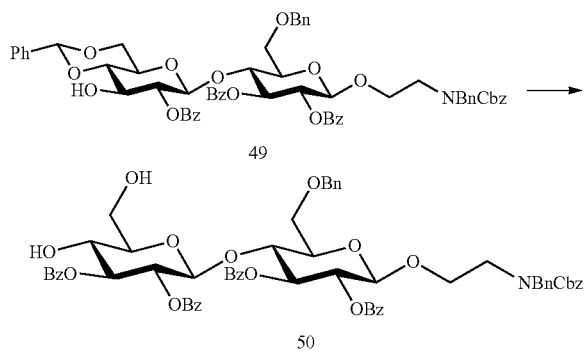

To a stirred solution of alcohol 49 (400 mg, 0.36 mmol) in pyridine (5.0 mL) was added at 0° C. benzoyl chloride (63 μL, 0.55 mmol). The reaction was slowly warmed to room temperature and stirred for 16 h at that temperature. An additional 0.5 equiv. BzCl were added to drive the reaction to completion. The mixture was stirred for 2 h at room temperature, quenched with water (30 ml) and diluted with EtOAc (50 mL). After separation, the organic fraction was washed with 0.1 M HCl (20 mL) and the aqueous fraction was re-extracted with EtOAc (30 mL). The combined organic fractions were washed with sat. aq. NaHCO$_3$ (20 mL) and brine (10 mL), dried over Na$_2$SO$_4$ and concentrated to give the intermediate tetrabenzoate as a yellow oil.

To a stirred solution of the intermediate tetrabenzoate in CH$_2$Cl$_2$ (6.5 mL) were added at room temperature ethanethiol (0.36 mL, 4.9 mmol) and p-toluenesulfonic acid (12 mg, 0.06 mmol). The mixture was stirred for 2 h at that temperature, quenched with Et$_3$N (50 μL) and concentrated. The residue was purified by flash chromatography (EtOAc/hexanes 0:1 to 1:10 to 1:8) to give diol 50 (389 mg, 0.349 mmol) as a white foam. HRMS (ESI) calcd. for C$_{64}$H$_{61}$NO$_{17}$ (M+Na)$^+$ 1138.3837 found 1138.3850 m/z.

Example C.1.3. Synthesis of methyl(2,3-di-O-benzoyl-β-D-glucopyranosyl)uronate-(1→4)-2,3-di-O-benzoyl-6-O-benzyl-β-D-glucoyranosyl-(1→1)-(2-N-benzyl-N-benzyloxycarbonylamino)ethanol (51)

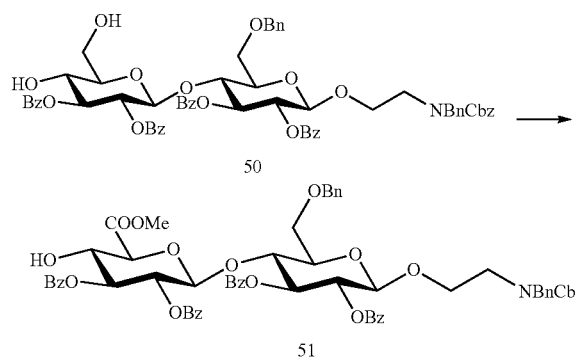

To a stirred solution of alcohol 50 (90 mg, 0.081 mmol) in CH$_2$Cl$_2$ (2.0 mL) and water (0.8 mL) were added at 0° C. TEMPO (2.5 mg, 0.016 mmol) and BAIB (55 mg, 0.170 mmol). The reaction was stirred for 20 min at that temperature and warmed to room temperature. The mixture was stirred for 2 h at that temperature and diluted with EtOAc (20 mL) and water (10 mL). After separation, the aqueous fraction was extracted with EtOAc (2×10 mL), the combined organic fractions were dried over Na$_2$SO$_4$ and concentrated. The residue was purified by flash chromatography (EtOAc/hexanes 1:2 to 1:1, then 1:1+5% AcOH) to give the intermediate carboxylic acid as a white foam.

To a stirred solution of the intermediate carboxylic acid in toluene (1.6 mL) and MeOH (0.8 mL) was added at room temperature TMS-diazomethane (0.04 mL, 0.081 mmol). The reaction was stirred for 2 h at that temperature. An additional 0.25 equiv. TMS-diazomethane was added to drive the reaction to completion. The mixture was stirred for 1 h at that temperature, quenched with AcOH (0.1 mL) and concentrated. The residue was purified by flash chromatography (EtOAc/hexanes 0:1 to 1:1) to give methyl ester 51 (73 mg, 0.064 mmol, 79% over two steps) as a clear oil. HRMS (ESI) calcd. for C$_{65}$H$_{61}$NO$_{18}$ (M+Na)$^+$ 1166.3786 found 1166.3762 m/z.

Example C.1.4. Synthesis of t-hexyl 2,3,6-tri-O-benzyl-β-D-galactopyranoside (52)

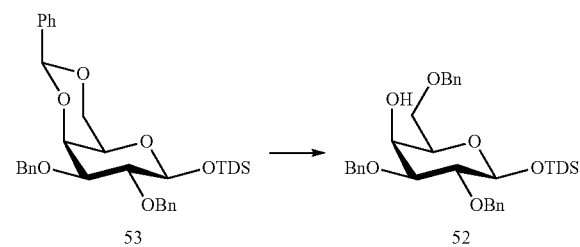

To a stirred solution of benzylidene acetal 53 (*J Carbohyd Chem* 1996, 15 (2), 241) (1.68 g, 2.84 mmol) in CH$_2$Cl$_2$ (60 mL) over activated MS (3 Å-AW) were added at 0° C. triethyl silane (2.72 mL, 17.06 mmol) and trifluoroacetic acid (1.81 mL, 17.06 mmol). The reaction was slowly warmed to room temperature and stirred for 16 h at that temperature. The reaction was quenched with Et$_3$N (2 mL), filtered through Celite and concentrated. The residue was purified by flash chromatography (EtOAc/hexanes 1:20 to 1:7) to give alcohol 52 (1.46 g, 2.46 mmol, 87%) as a clear oil. HRMS (ESI) calcd. for C$_{35}$H$_{48}$O$_6$Si (M+Na)$^+$ 615.3117 found 615.3104 m/z.

Example C.1.5. Synthesis of tHexyl 4-O-benzoyl-2,3,6-tri-O-benzyl-α-D-glucopyranosyl-(1→4)-2,3,6-tri-O-benzyl-β-D-galactopyranoside (54)

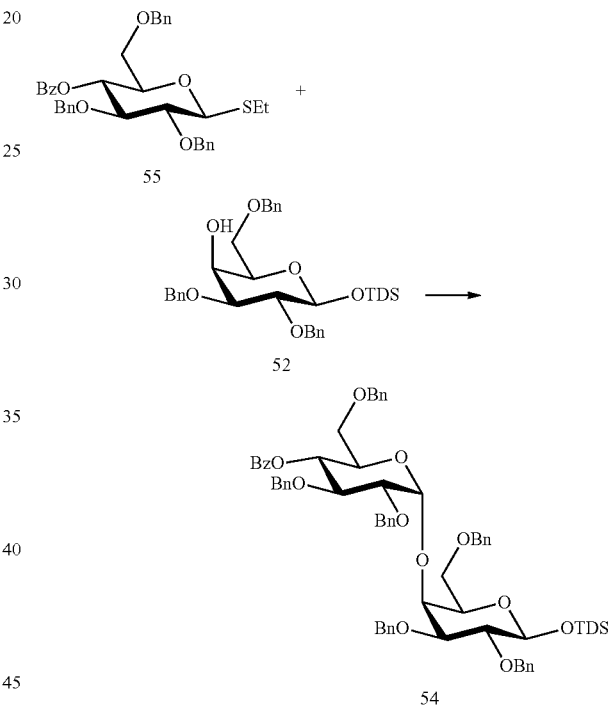

Thioglycoside 55 (*J. Org. Chem.* 2012, 77 (1), 291). (667 mg, 1.11 mmol) and alcohol 52 (550 mg, 0.93 mmol) were co-evaporated with dry toluene (3×10 mL) and kept under high vacuum for 30 min. The mixture was dissolved in Et$_2$O (14 mL) and CH$_2$Cl$_2$ (2.8 mL) and stirred over activated molecular sieves (3 Å-AW) for 30 min at room temperature. The solution was cooled to −20° C. and treated with NIS (250 mg, 1.11 mmol) and triflic acid (16 μL, 0.19 mmol). The mixture was stirred for 1 h and slowly warmed to −10° C. The reaction was quenched with Et$_3$N (0.05 mL), diluted with CH$_2$Cl$_2$ (20 mL), filtered through Celite and concentrated. The residue was purified by flash chromatography (EtOAc/hexanes 0:1 to 1:8 to 1:6) to give disaccharide 54 (553 mg, 0.490 mmol, 53%) along with the corresponding β-anomer (231 mg, 0.205 mmol, 22%). Analytical data for 54: Clear oil. HRMS (ESI) calcd. for C$_{69}$H$_{80}$O$_{12}$Si (M+Na)$^+$ 1151.5316 found 1151.5293 m/z.

Example C.1.6. Synthesis of 4-O-benzoyl-2,3,6-tri-O-benzyl-α-D-glucopyranosyl-(1→4)-2,3,6-tri-O-benzyl-αβ-D-galactopyranosyl trifluoro-(N-phenyl)acetimidate (47)

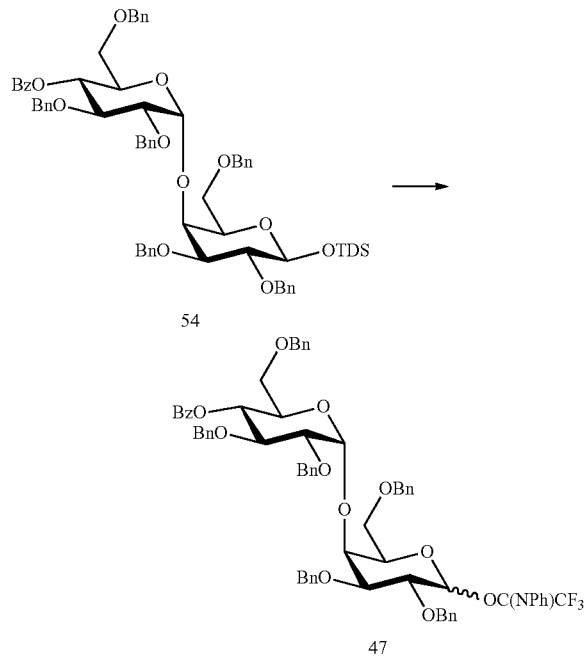

To a stirred solution of silyl ether 54 (470 mg, 0.416 mmol) in THF (8.3 mL) was added at 0° C. acetic acid (0.24 mL, 4.19 mmol) and TBAF (1.0 M solution in THF, 4.2 mL, 4.20 mmol). The reaction was slowly warmed to room temperature and stirred for 2 h at that temperature. Acetic acid (0.24 mL, 4.19 mmol) and TBAF (1.0 M solution in THF, 4.2 mL, 4.20 mmol) were added and the reaction was stirred for 16 h at room temperature. The mixture was diluted with Et$_2$O (50 mL), washed with water (3×30 mL) and the aqueous phase was re-extracted with Et$_2$O (2×20 mL). The combined organic fractions were dried over Na$_2$SO$_4$ and concentrated. The residue was filtered through a short plug of silica gel (EtOAc/hexanes 1:3 to 1:1) to give the intermediate lactol mixture as a clear oil.

To a stirred solution of the lactol mixture in CH$_2$Cl$_2$ (7.8 mL) were added at room temperature cesium carbonate (318 mg, 0.975 mmol) and F$_3$CC(NPh)Cl (202 mg, 0.975 mmol). The mixture was stirred for 2.5 h at that temperature, diluted with hexanes (0.5% (v/v) Et$_3$N, (10 mL) and filtered through Celite. The residue was purified by flash chromatography (EtOAc/hexanes 0:1+0.5% Et$_3$N to 1:3+0.5% Et$_3$N) to give imidate mixture 47 (404 mg, 0.349 mmol, 84% over two steps) as a clear oil. HRMS (ESI) calcd. for C$_{69}$H$_{66}$F$_3$NO$_{12}$ (M+Na)$^+$ 1180.4434 found 1180.4458 m/z.

Example C.1.7: Synthesis of 4-O-benzoyl-2,3,6-tri-O-benzyl-α-D-glucopyranosyl-(1→4)-2,3,6-tri-O-benzyl-α-D-galactopyranosyl-(1→4)-methyl [2,3-Di-O-benzoyl-β-D-glucopyranosyl]uronate-(1→4)-2,3-di-O-benzoyl-6-O-benzyl-β-D-glucoyranosyl-(1→1)-(2-N-benzyl-N-benzyloxycarbonylamino)ethanol (56)

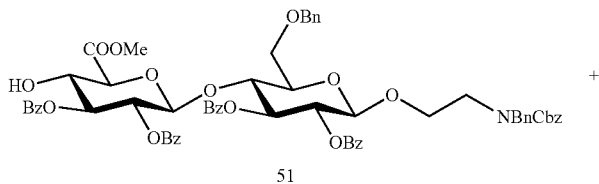

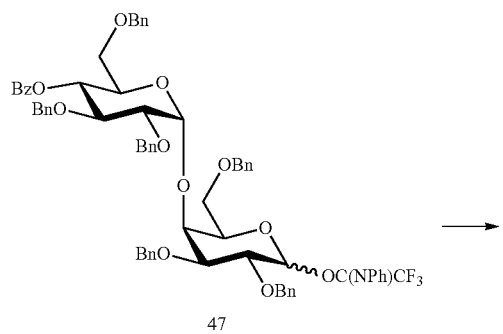

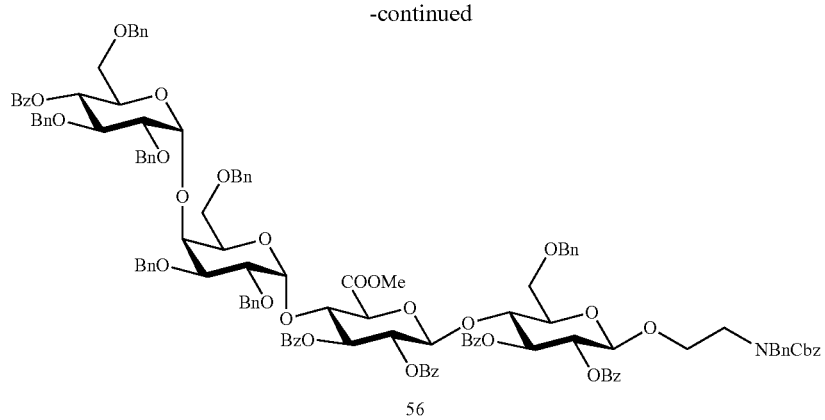

56

Alcohol 51 (100 mg, 87 μmol) and imidate 47 (121 mg, 105 μmol) were co-evaporated with dry toluene (3×10 mL) and kept under high vacuum for 30 min.

The mixture was dissolved in Et$_2$O (3.3 mL) and CH$_2$Cl$_2$ (1.1 mL) and stirred over activated molecular sieves (3 Å-AW) for 30 min at room temperature. The solution was cooled to −20° C. and treated with TMSOTf (3.2 μL, 17 μmol). The mixture was stirred for 1 h and slowly warmed to 0° C. The reaction was quenched with sat. aq. NaHCO$_3$ (10 mL), extracted with CH$_2$Cl$_2$ (3×20 mL) and the combined organic fractions were dried over Na$_2$SO$_4$ and concentrated. The residue was purified by flash chromatography (EtOAc/hexanes/toluene 1:3:3 to 1:2:2) to give tetrasaccharide 56 (130 mg, 62 μmol, 71%) as a clear oil. HRMS (ESI) calcd. for C$_{126}$H$_{121}$NO$_{29}$ (M+Na)$^+$ 2134.7921 found 2134.7879 m/z.

Example C.1.8 Synthesis of α-D-glucopyranosyl-(1→4)-α-D-galactopyranosyl-(1→4)-β-D-glucopyranosyluronic acid-(1→4)-β-D-glucopyranosyl-(1→1)-(2-amino)ethanol (44)

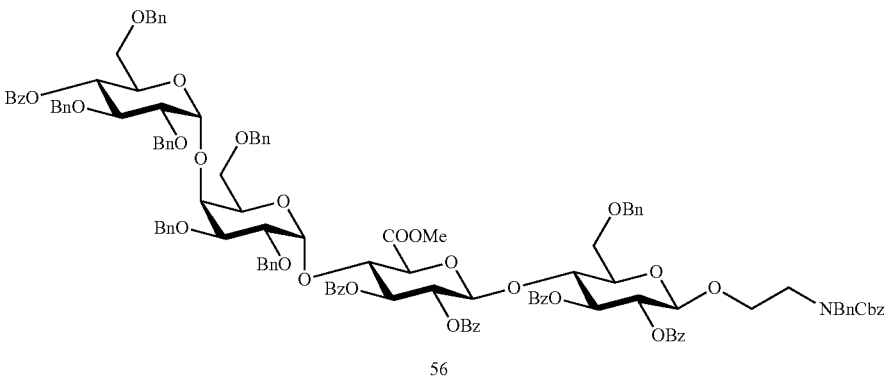

56

↓

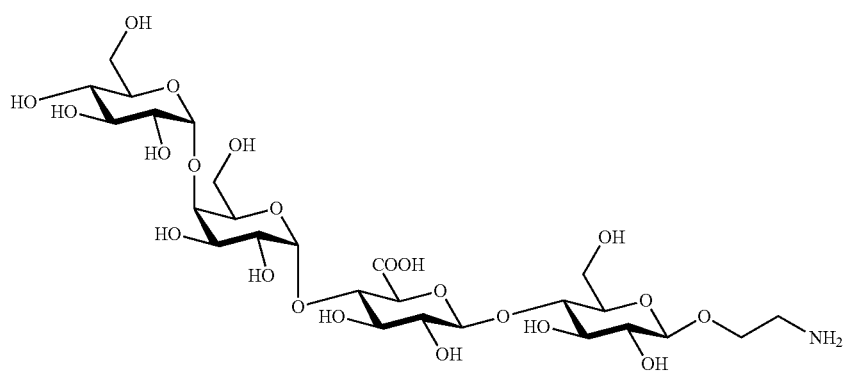

44

To a stirred solution of ester 56 (56 mg, 26 μmol) in THF (5 mL) and MeOH (1 mL) were added at 0° C. hydrogen peroxide (6% aq. solution, 265 μL, 530 μmol) and LiOH (1 M aq. solution, 265 μL, 132 mol). The reaction was stirred for 1 h and warmed to room temperature. The reaction was kept at that temperature and treated after 2 h with hydrogen peroxide (6% aq. solution, 265 μL, 530 μmol) and LiOH (1 M aq. solution, 265 μL, 132 mol). After 2 h, NaOH (15% aq. solution, 1 mL) was added and the mixture was stirred for 72 h at room temperature. The solvents were evaporated under reduced pressure, the residue was co-evaporated with toluene (2×5 mL) and dissolved in MeOH (5 mL). The solution was treated at room temperature with sodium methoxide (143 mg, 2.65 mmol) and stirred for 96 h at that temperature. The solvent was evaporated and the residue was dissolved in water (5 mL). The solution was neutralized at 0° C. with 0.5 M aq. NaHSO$_4$ and extracted with EtOAc (5×5 mL). The combined organic fractions were dried over Na$_2$SO$_4$ and concentrated to give the intermediate acid as a white foam.

The intermediate acid in MeOH (2 mL) was added at room temperature to a suspension of Pd/C (50 mg) in MeOH (1 mL), water (0.1 mL) and AcOH (5 drops). The reaction was stirred under an atmosphere of H$_2$ for 48 h, filtered and concentrated. The residue was purified by solid phase extraction (Chromabond C18, Macherey-Nagel) and lyophilized to give tetrasaccharide 44 (acetate salt, 13.6 mg, 18 μmol, 69% over 3 steps) as a white solid. HRMS (MALDI) calcd. for C$_{26}$H$_{45}$NO$_{22}$ (M+Na)$^+$ 746.2330 found 746.2323 m/z.

Example C.1.9. Synthesis of 4-O-Benzoyl-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (57)

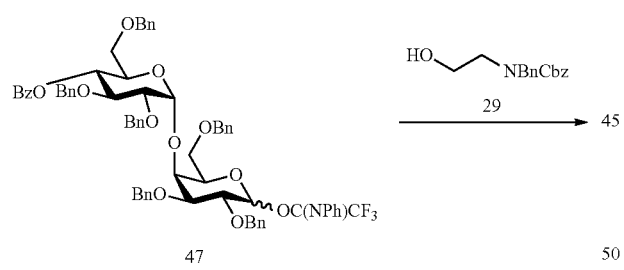

Imidate 47 (200 mg, 0.173 mmol) and alcohol 29 (74 mg, 0.259 mmol) were co-evaporated with dry toluene (2×5 mL) and kept under high vacuum for 30 min. The mixture was dissolved in Et$_2$O (2.8 mL) and CH$_2$Cl$_2$ (0.7 mL) and stirred over activated molecular sieves (3 Å-AW) for 30 min at room temperature. The solution was cooled to −40° C. and treated with TMSOTf (6.2 μL, 35 μmol). The mixture was stirred for 10 min at that temperature and then slowly warmed to −10° C. The reaction was quenched with sat. aq. NaHCO$_3$ (5 mL), extracted with CH$_2$Cl$_2$ (3×20 mL) and the combined organic fractions were dried over Na$_2$SO$_4$ and concentrated. The residue was purified by flash chromatography (EtOAc/hexanes 0:1 to 1:6 to 1:4) to give carbamate 57 (160 mg, 0.128 mmol, 74%) along with the corresponding β-anomer (32 mg, 0.026 mmol, 15%). Analytical data for 57: Clear oil. HRMS (ESI) calcd. for C$_{78}$H$_{79}$NO$_{14}$ (M+Na)$^+$ 1276.5398 found 1276.5405 m/z.

Example C.1.10. Synthesis of 2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (58)

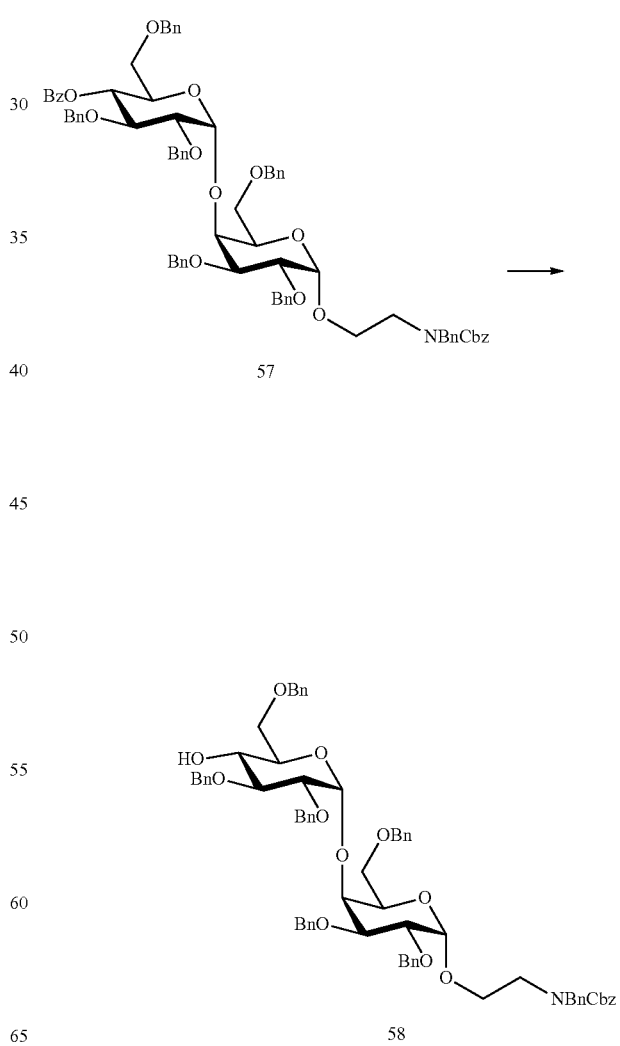

To a stirred solution of ester 57 (126 mg, 0.100 mmol) in THF (5 mL) and MeOH (5 mL) was added at 0° C. sodium methoxide (0.5 M in MeOH, 1 mL, 0.500 mmol). The reaction was slowly warmed to room temperature and kept at that temperature for 24 h. Sodium methoxide (0.5 M in MeOH, 1 mL, 0.500 mmol) was added and the reaction was warmed to 37° C. The mixture was stirred for 7 h at that temperature, neutralized with Amberlite IR120 (H$^+$ form), filtered and concentrated. The residue was purified by flash chromatography (EtOAc/hexanes 0:1 to 1:6 to 1:4) to give alcohol 58 (98 mg, 85 μmol, 85%) as a clear oil. HRMS (ESI) calcd. for $C_{71}H_{75}NO_{13}$ (M+Na)$^+$ 1172.5136 found 1172.5103 m/z.

Example C.1.11. Synthesis of α-D-glucopyranosyl-(1→4)-α-D-galactopyranosyl-(1→1)-(2-amino)ethanol (59)

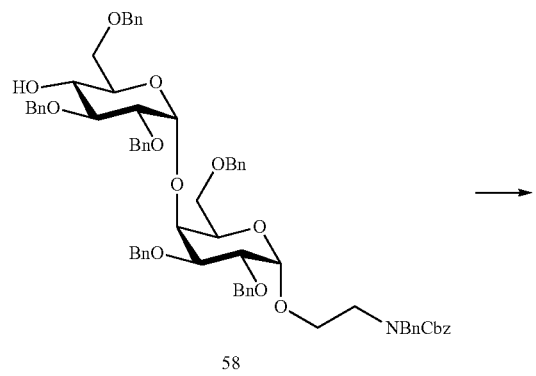

58

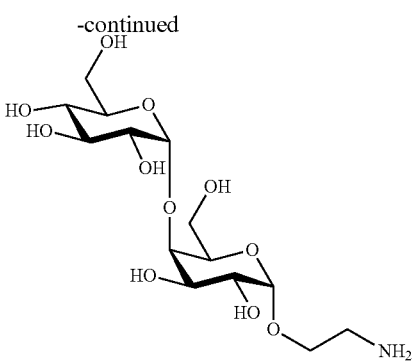

59

Benzyl ether 58 in EtOAc (1 mL) was added at room temperature to a suspension of Pd/C (30 mg) in MeOH (3 mL), water (0.5 mL) and AcOH (3 drops). The reaction was stirred under an atmosphere of H$_2$ for 24 h, filtered and concentrated to give disaccharide 59 (2.9 mg, 18 μmol, 87%) as a white solid. HRMS (ESI) calcd. for $C_{14}H_{27}NO_{11}$ (M+Na)$^+$ 408.1481 found 408.1499 m/z.

Example C.1.12. Synthesis of 2,3-di-O-benzoyl-β-D-glucopyranosyl-(1→4)-2,3-di-O-benzoyl-6-O-benzyl-β-D-glucoyranosyl-(1→4)-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (60)

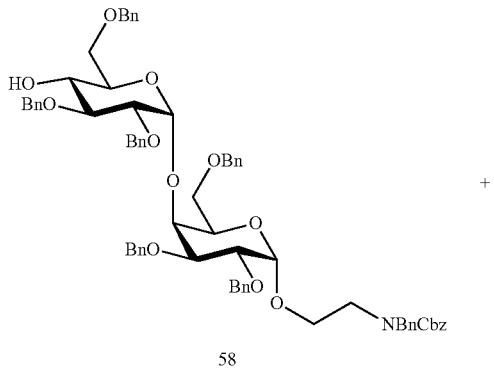

58

+

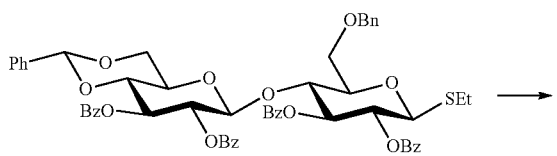

48

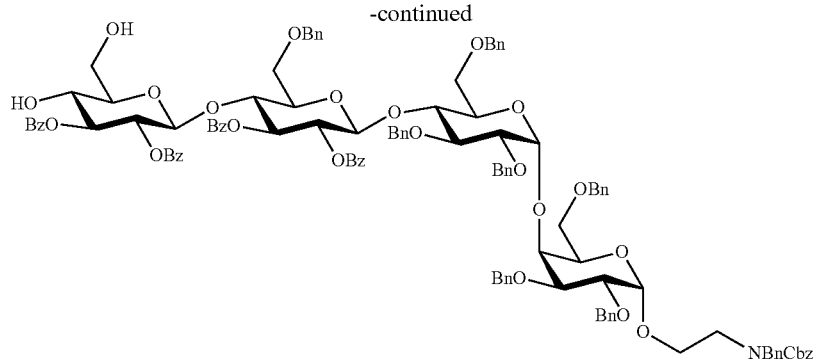

60

Alcohol 58 (47 mg, 41 μmol) and thioglycoside 48 (60 mg, 61 μmol) were co-evaporated with dry toluene (2×5 mL) and kept under high vacuum for 30 min. The mixture was dissolved in CH$_2$Cl$_2$ (2 mL) and stirred over activated molecular sieves (3 Å-AW) for 30 min at room temperature. The solution was cooled to −10° C. and treated with NIS (13.8 mg, 61 μmol) and triflic acid (1 μL, 11 μmol). The mixture was kept for 1 h at that temperature and slowly warmed to 0° C. The reaction was quenched with Et$_3$N (50 μL), filtered and concentrated to give the intermediate benzylidene acetal as a yellow oil.

To a stirred solution of the intermediate benzylidene acetal in CH$_2$Cl$_2$ (2 mL) were added at room temperature ethanethiol (0.3 mL, 4.06 mmol) and p-toluenesulfonic acid (10 mg, 0.053 mmol). The mixture was stirred for 1 h at that temperature, quenched with Et$_3$N (20 μL) and concentrated. The residue was purified by flash chromatography (EtOAc/hexanes 0:1 to 1:3 to 1:2) to give diol 60 (78 mg, 39 μmol, 96%) as a clear oil. HRMS (ESI) calcd. for C$_{118}$H$_{117}$NO$_{27}$ (M+Na)$^+$ 2002.7710 found 2002.7731 m/z.

Example C.1.13. Synthesis of 2,3-d-O-benzoyl-β-D-glucopyranosyluronate-(1→4)-2,3-di-O-benzoyl-6-O-benzyl-β-D-glucoyranosyl-(1→4)-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (61)

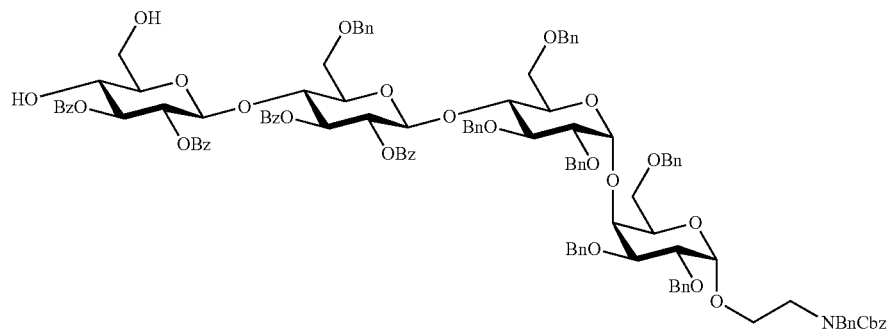

60

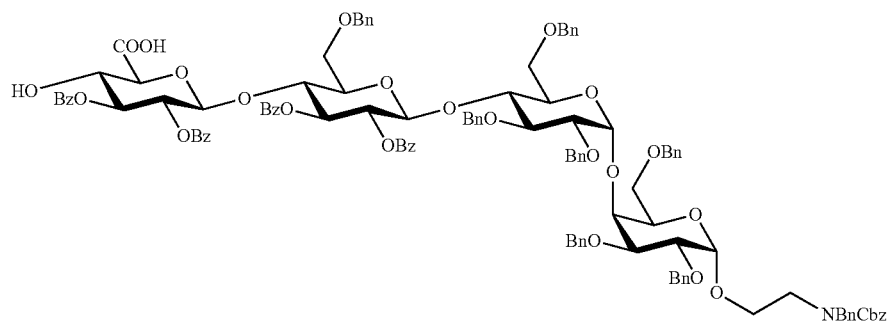

61

To a vigorously stirred solution of alcohol 60 (45 mg, 23 μmol, 73%) in CH$_2$Cl$_2$ (2 mL) and water (0.8 mL) were added at 0° C. TEMPO (3 crystals) and BAIB (15.4 mg, 48 μmol). The reaction was stirred for 20 min at that temperature and slowly warmed to room temperature. After 1 h, TEMPO (2 crystals) and BAIB (10 mg, 31 μmol) were added and the mixture was stirred for 2 h at room temperature. The reaction was diluted with CH$_2$Cl$_2$ (5 mL) and quenched with 10% aq. Na$_2$S$_2$O$_3$ (5 mL). Following separation, the aqueous phase was extracted with EtOAc (2×10 mL), the combined organic fractions were dried over Na$_2$SO$_4$ and concentrated. The residue was purified by flash chromatography twice (EtOAc/hexanes 0:1 to 1:2 to 8:1, then EtOAc/hexanes 1:1+1% AcOH) and co-evaporated with heptane repeatedly to give acid 61 (33 mg, 17 μmol, 74%) as a clear oil. HRMS (ESI) calcd. for C$_{118}$H$_{115}$NO$_{28}$ (M+Na)$^+$ 2016.7503 found 2016.7558 m/z.

Example C.1.14. Synthesis of β-D-Glucopyranosyluronic acid-(1→4)-β-D-glucoyranosyl-(1→4)-α-D-glucopyranosyl-(1→4)-α-D-galactopyranosyl-(1→1)-(2-amino)ethanol (45)

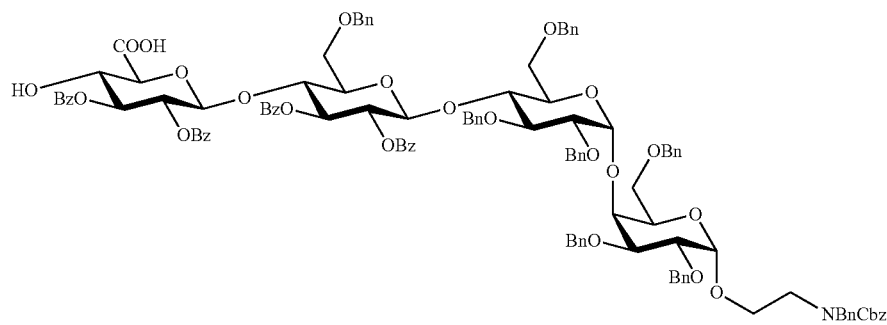

61

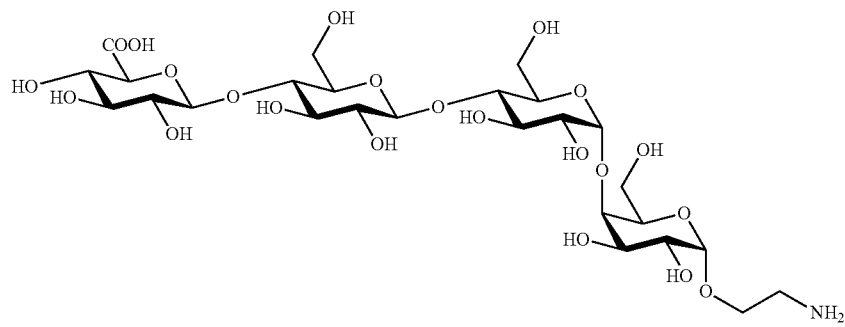

45

To a stirred solution of ester 61 (45 mg, 23 µmol) in THF (4 mL) and MeOH (0.5 mL) were added at 0° C. NaOH (1 M aq. solution, 1 mL). The reaction was slowly warmed to room temperature and stirred for 16 h at that temperature. The solution was neutralized at 0° C. with 0.5 M aq. NaHSO$_4$ and extracted with EtOAc (5×5 mL). The combined organic fractions were dried over Na$_2$SO$_4$ and concentrated to give the intermediate alcohol as a white foam.

The intermediate alcohol in MeOH (3 mL) was added at room temperature to a suspension of Pd/C (20 mg) in MeOH (6 mL), water (6 drops) and AcOH (3 drops). The reaction was stirred under an atmosphere of H$_2$ for 96 h, filtered and concentrated. Since the reaction had not proceeded to completion, the residue was subjected to the same conditions again and stirred for 72 h at room temperature. The reaction was filtered and concentrated, the residue was purified by solid phase extraction (Chromabond C18, Macherey-Nagel) and lyophilized to give tetrasaccharide 45 (11.3 mg, 16 µmol, 68% over 2 steps) as a white solid. HRMS (MALDI) calcd. for C$_{26}$H$_{45}$NO$_{22}$ (M+Na)$^+$ 746.2330 found 746.2416 m/z.

Example C.1.15. 2-Amino-ethyl β-D-glucopyranosyl-(1→4)-β-D-glucopyranosyl-(1→4)-α-D-glucopyranosyl-(1→4)-α-D-galactopyranoside (46)

To a stirred solution of ester 60 (20 mg, 10.1 µmol) in THF (1 mL) and MeOH (0.33 mL) was added at room temperature NaOMe (0.5 M solution in MeOH, 0.5 mL). The reaction was warmed to 40° C. and stirred for 5 h at that temperature. The mixture was cooled to room temperature and stirred for 16 h at that temperature. The reaction was neutralized with Amberlite IR-120 (H+ form), filtered and concentrated. The residue was purified by size exclusion chromatography (Sephadex LH-20, CH$_2$Cl$_2$/MeOH 2:1) to give the intermediate hexanol as a white foam.

The intermediate hexaol in CH$_2$Cl$_2$/tBuOH/water (1:16:8, 1 mL) was purged with argon and treated at 0° C. with a suspension of Pd(OH)$_2$ on carbon (20% (w/w) loading, 20 mg) in the same solvent mixture (1 mL). The suspension was purged with hydrogen, stirred under a hydrogen atmosphere for 18 h, filtered and concentrated. The residue was purified by solid phase extraction (Chromabond C18, Macherey-Nagel) and lyophilized to give tetrasaccharide 46 (6.8 mg, 9.0 µmol, 89% over two steps) as a white solid. 1H NMR (600 MHz, D2O) δ 5.15 (d, J=3.5 Hz, 1H, H-1b), 5.02 (d, J=3.7 Hz, 1H, H-1a), 4.66 (d, J=7.9 Hz, 1H, H-1c or H-1d), 4.61 (d, J=7.9 Hz, 1H, H-1c or H-1d), 4.33 (d, J=10.1 Hz, 1H), 4.18 (d, J=2.2 Hz, 1H), 4.14-4.06 (m, 4H), 4.05-3.97 (m, 4H), 3.96-3.89 (m, 4H), 3.87-3.67 (m, 7H), 3.64-3.56

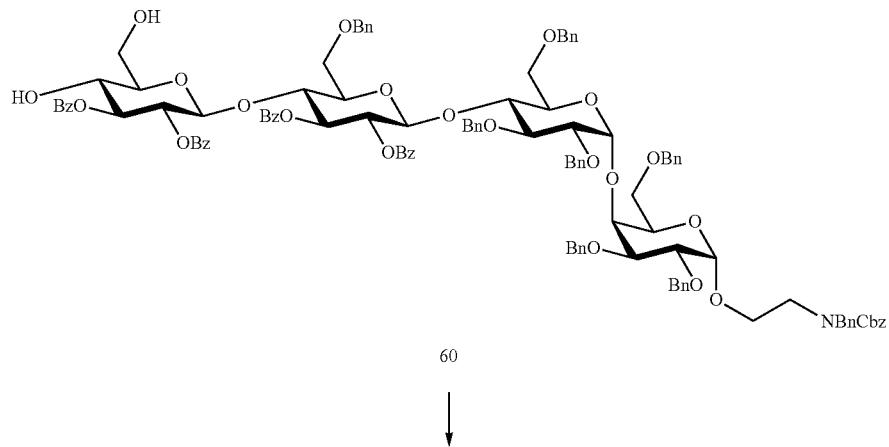

60

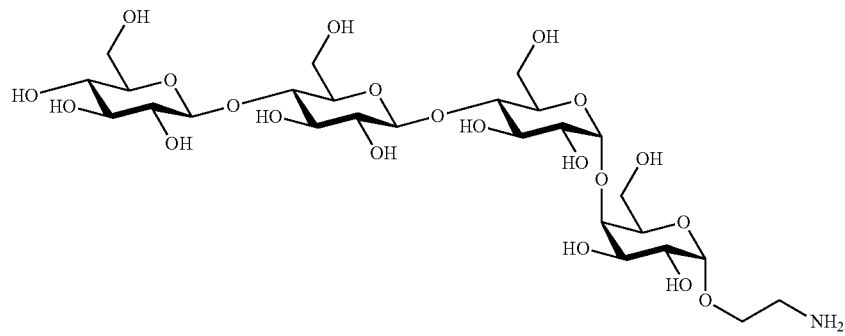

46

(m, 2H), 3.55-3.49 (m, 1H), 3.46 (t, J=8.4 Hz, 1H), 3.45-3.34 (m, 3H); 13C NMR (150 MHz, D2O) δ 105.2 (C-1c or C-1d), 104.9 (C-1c or C-1d), 102.5 (C-1a), 101.2 (C-1b), 81.2, 81.0, 80.9, 78.6, 78.1, 77.4, 76.7, 75.7, 75.6, 74.2, 74.1, 73.8, 73.3, 72.1, 71.4, 70.9, 66.6, 63.2, 63.1, 62.5, 62.1, 41.9; HRMS (ESI) calcd. for C26H47NO21 (M+Na)+ 732.2538 found 732.2504 m/z.
Example C.2. Synthesis of *S. pneumoniae* Serotype 8 Pentasaccharide 62
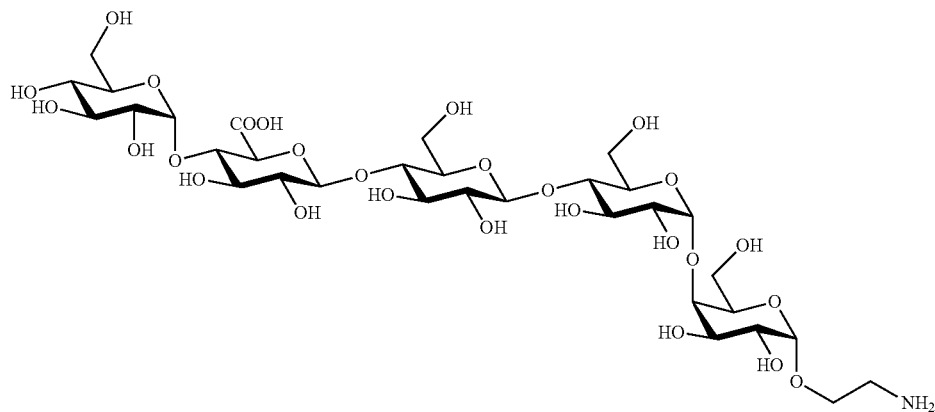
62
Example C.2.1. N-Benzyl-N-benzyloxycarbonyl-2-amino-ethyl methyl[2,3-di-O-benzoyl-β-D-glucopyranosyl]uronate-(1→4)-2,3-di-O-benzoyl-6-O-benzyl-β-D-glucopyranosyl-(1→4)-2,3,6-tri-O-benzyl-α-D-glucopyranosyl-(1→4)-2,3,6-tri-O-benzyl-α-D-galactopyranoside (63)
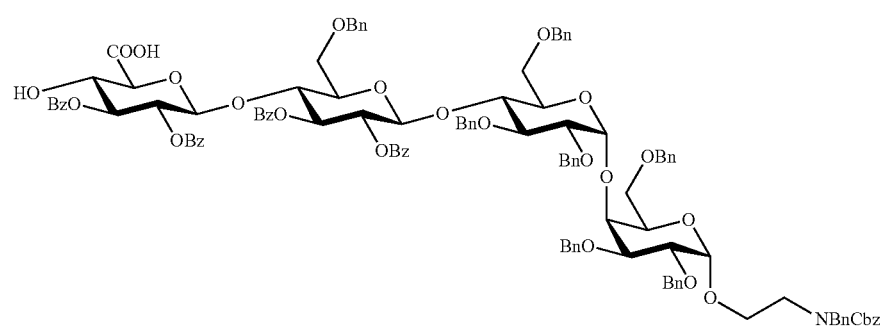
61
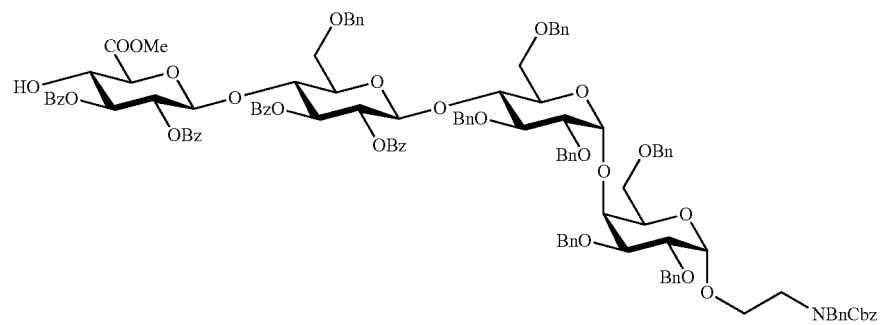
63

To a stirred solution of carboxylic acid 61 (100 mg, 50 µmol) in DMF (2.5 mL) were added at room temperature Cs$_2$CO$_3$ (24.5 mg, 75 µmol) and methyl iodide (10.7 mg, 75 µmol) and the reaction was stirred at that temperature. After 2 h, methyl iodide (10.7 mg, 75 µmol) was added and the mixture was stirred for another 2 h at room temperature. The reaction was quenched with sat. aq. NH$_4$Cl (5 mL), extracted with EtOAc (4×10 mL), the combined organic extracts were dried over Na$_2$SO$_4$ and concentrated. The residue was purified by flash chromatography (EtOAc/hexanes 0:1 to 2:3) to give methyl ester 63 (81 mg, 40 µmol, 80%) as a white foam. R$_f$ (EtOAc/hexanes 1:1)=0.83; $[\alpha]_D^{20}$=+33.1° (c=0.25, CH$_2$Cl$_2$); 1H NMR (600 MHz, CDCl$_3$) δ 8.07-7.91 (m, 6H), 7.76 (d, J=7.4 Hz, 2H), 7.66 (t, J=7.4 Hz, 1H), 7.62-7.03 (m, 56H), 5.39 (m, 3H), 5.30 (t, J=9.5 Hz, 1H), 5.25 (t, J=9.5 Hz, 1H), 5.21-5.14 (m, 2H), 5.00 (s, 1H), 4.81 (d, J=11.9 Hz, 1H), 4.77 (d, J=11.4 Hz, 1H), 4.71 (d, J=8.0 Hz, 1H), 4.68-4.62 (m, 3H), 4.60-4.47 (m, 5H), 4.32 (m, 4H), 4.22 (d, J=9.2 Hz, 2H), 4.12 (d, J=12.1 Hz, 2H), 4.08-3.87 (m, 6H), 3.83-3.64 (m, 5H), 3.62-3.47 (m, 6H), 3.45 (s, 3H), 3.42-3.29 (m, 2H), 3.17 (d, J=2.6 Hz, 1H), 3.05 (d, J=9.4 Hz, 2H); 13C NMR (150 MHz, CDCl3) δ 168.4, 166.7, 165.6, 164.83, 164.79, 156.6, 156.3, 140.1, 138.80, 138.76, 138.6, 138.4, 138.34, 138.29, 138.1, 138.0, 137.9, 137.6, 136.83, 136.76, 133.6, 133.5, 133.1, 132.6, 130.4, 130.0, 129.84, 129.80, 129.7, 129.3, 129.18, 129.15, 129.1, 129.0, 128.9, 128.8, 128.7, 128.6, 128.51, 128.46, 128.44, 128.35, 128.3, 128.2, 128.1, 128.0, 127.94, 127.87, 127.7, 127.6, 127.5, 127.43, 127.40, 127.0, 100.3 (C-1c), 100.2 (C-1d), 99.8 (C-1a), 98.5 (C-1b), 80.7, 79.2, 76.7, 76.6, 75.2, 75.12, 75.07, 75.0, 74.8, 74.6, 74.40, 74.36, 74.1, 73.7, 73.62, 73.59, 73.4, 73.1, 72.5, 72.1, 71.4, 70.5, 69.6, 69.5, 67.8, 67.3, 67.0, 66.8, 52.6, 51.4, 46.5, 45.5; IR (thin film) 2928, 1734, 1602, 1453, 1364, 1272, 1094, 1070, 740, 710 cm$^{-1}$; HRMS (MALDI) calcd. for C$_{119}$H$_{117}$NO$_{28}$ (M+Na)+ 2030.7659 found 2030.7660 m/z.

Example C.2.2. N-Benzyl-N-benzyloxycarbonyl-2-amino-ethyl 2,3,4,6-tetra-O-benzyl-α-D-galactopyranosyl-(1→4)-methyl[2,3-di-O-benzoyl-β-D-glucopyranosyl]uronate-(1→4)-2,3-di-O-benzoyl-6-O-benzyl-β-D-glucoyranosyl-(1→4)-2,3,6-tri-O-benzyl-α-D-glucopyranosyl-(1→4)-2,3,6-tri-O-benzyl-α-D-galactopyranoside (64)

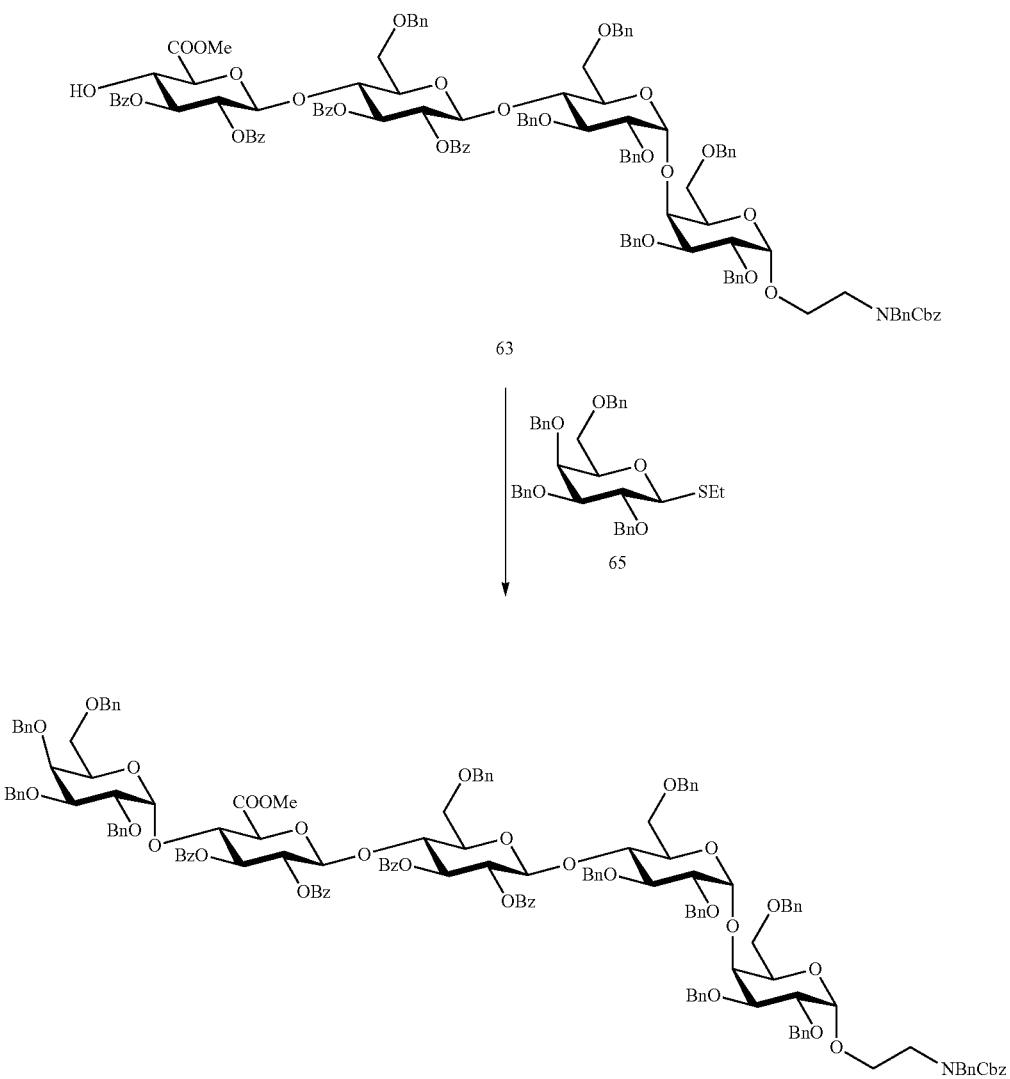

Alcohol 63 (14 mg, 7 μmol) and thioglycoside 65 (16 mg, 28 μmol) were co-evaporated with anhydrous toluene (3×10 mL) and kept under high vacuum for 30 min. The mixture was dissolved in Et$_2$O (1.05 mL) and CH$_2$Cl$_2$ (0.35 mL) and stirred over activated molecular sieves (3 Å-AW) for 30 min at room temperature. The solution was cooled to −20° C. and treated with NIS (6.3 mg, 28 μmol) and TMSOTf (1 μL, 5.5 μmol). The mixture was stirred for 1 h at that temperature and slowly warmed to 0° C. The reaction was quenched with a 1:1 (v/v) mixture of sat. aq. NaHCO$_3$ (10 mL) and 10% (w/v) Na$_2$SO$_3$ (5 mL) and extracted with CH$_2$Cl$_2$ (4×10 mL). The combined organic fractions were dried over Na$_2$SO$_4$ and concentrated. The residue was purified by flash chromatography (EtOAc/hexanes 0:1 to 1:4 to 1:3) to give pentasaccharide 64 (12.5 mg, 4.9 μmol, 70%) along with the corresponding β-anomer (3.4 mg, 1.3 μmol, 19%). Analytical data for 64: Clear oil. $R_f$ (EtOAc/hexanes 2:3)=0.63; $[\alpha]_D^{20}$=+20.4° (c=0.33, CH$_2$Cl$_2$); $_1$H NMR (600 MHz, CDCl$_3$) δ 7.97-7.82 (m, 5H), 7.67 (d, J=7.3 Hz, 2H), 7.57 (t, J=7.4 Hz, 1H), 7.48-6.98 (m, 77H), 5.52 (t, J=9.6 Hz, 1H), 5.37 (dd, J=9.9, 8.2 Hz, 1H), 5.27 (t, J=9.1 Hz, 2H), 5.17 (t, J=9.5 Hz, 1H), 5.11 (t, J=9.9 Hz, 2H), 4.92 (s, 1H), 4.82 (d, J=11.3 Hz, 1H), 4.77-4.53 (m, 9H), 4.52-4.37 (m, 7H), 4.32-4.07 (m, 9H), 4.03 (d, J=6.9 Hz, 1H), 3.96 (d, J=12.0 Hz, 2H), 3.91-3.78 (m, 6H), 3.76-3.56 (m, 7H), 3.54-3.39 (m, 7H), 3.38-3.21 (m, 4H), 3.07 (s, 3H), 3.05-2.91 (m, 2H); $^{13}$C NMR (150 MHz, CDCl$_3$) δ 166.8, 165.49, 165.46, 164.84, 164.79, 156.6, 156.3, 140.0, 139.1, 138.9, 138.8, 138.6, 138.5, 138.4, 138.3, 138.2, 138.1, 138.0, 137.5, 136.8, 133.5, 133.0, 132.5, 130.2, 129.9, 129.8, 129.7, 129.4, 129.2, 129.1, 129.03, 128.95, 128.8, 128.7, 128.6, 128.5, 128.43, 128.41, 128.35, 128.28, 128.26, 128.22, 128.15, 128.03, 127.98, 127.93, 127.91, 127.8, 127.6, 127.52, 127.49, 127.45, 127.2, 127.0, 100.5 (C-1c), 100.2 (C-1d), 99.8 (C-1b), 99.47 (C-1a), 98.46 (C-1b), 80.7, 79.2, 78.4, 76.8, 76.61, 76.55, 75.34, 75.30, 75.26, 75.1, 75.0, 74.9, 74.8, 74.5, 74.2, 73.7, 73.6, 73.5, 73.4, 73.3, 73.1, 72.6, 72.1, 71.6, 70.5, 70.0, 69.6, 67.9, 67.5, 67.3, 67.0, 66.9, 52.2, 51.4, 46.5, 45.5; IR (thin film) 2928, 1737, 1498, 1454, 1271, 1094, 1047, 1028, 738, 699 cm$_{-1}$; HRMS (MALDI) calcd. for C$_{153}$H$_{151}$NO$_{33}$ (M+Na)$_+$ 2553.0066 found 2553.0066 m/z.

Example C.2.3. 2-Amino-ethyl α-D-galactopyranosyl-(1→4)-β-D-glucopyranosyluronate-(1→4)-β-D-glucoyranosyl-α-D-glucopyranosyl-(1→4)-α-D-galactopyranoside (62)

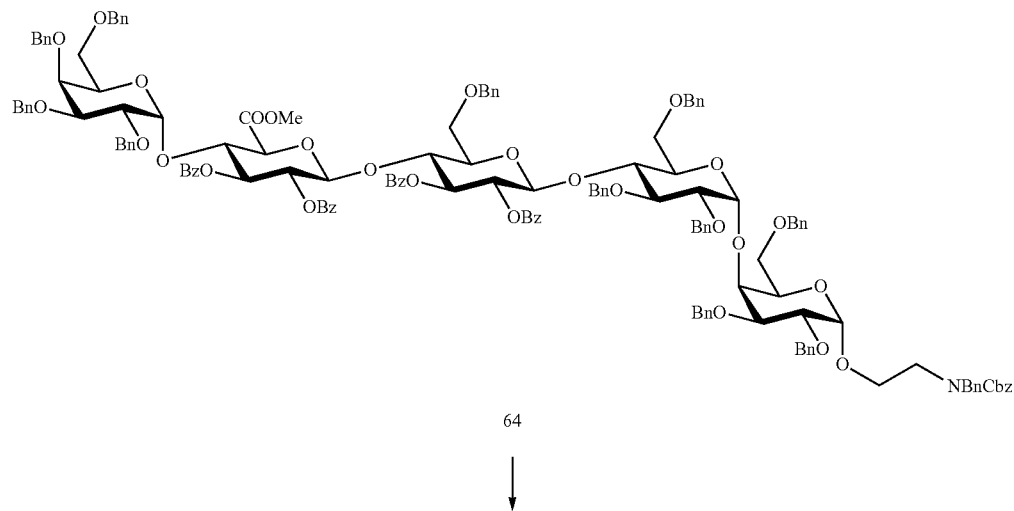

64

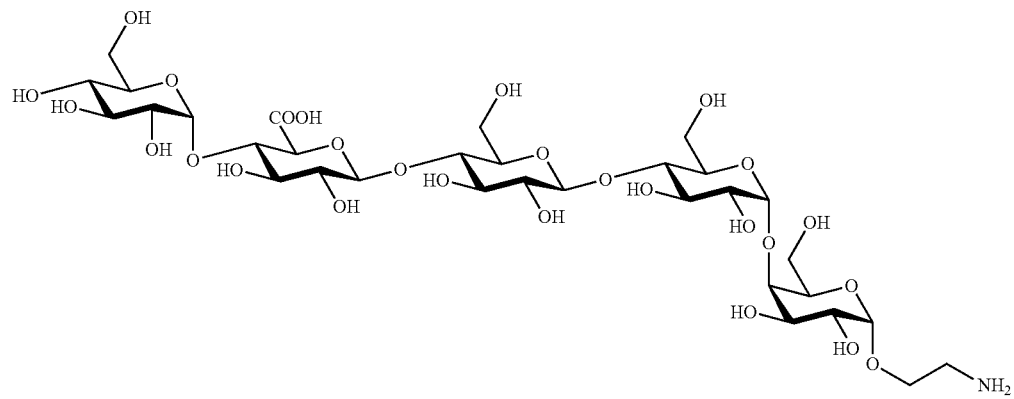

62

To a stirred solution of ester 64 (26 mg, 10.3 µmol) in THF (1 mL) and MeOH (1 mL) was added at 0° C. a 1:1 (v/v) mixture (450 µL) of hydrogen peroxide (6% (v/v) aq. solution, 397 µmol) and LiOH (0.5 M aq. solution, 113 µmol). The reaction was warmed to room temperature and stirred for 1 h at that temperature. The reaction was treated with NaOH (0.5 M aq. solution, 1 mL) and stirred for 16 h at room temperature. The solvents were evaporated under reduced pressure, the residue was co-evaporated with toluene (2×5 mL) and dissolved in MeOH (1 mL). The solution was treated at room temperature with NaOMe (0.5 M in MeOH, 1 mL) and stirred for 16 h at that temperature. The reaction was diluted with water (0.5 mL) and $CH_2Cl_2$ (0.5 mL), neutralized at 0° C. with Amberlite IR-120 ($H^+$ form), filtered and concentrated. The residue was purified by flash chromatography (EtOAc/hexanes 0:1 to 1:4 to 1:2 to 1:2+1% (v/v) AcOH to 1:1+1% (v/v) AcOH) to give the intermediate carboxylic acid as a clear oil.

The intermediate carboxylic acid in $CH_2Cl_2$/tBuOH/water (1:16:8, 1 mL) was purged with argon and treated at 0° C. with a suspension of $Pd(OH)_2$ on carbon (20% (w/w) loading, 20 mg) in the same solvent mixture (0.5 mL). The suspension was purged with hydrogen, stirred under a hydrogen atmosphere for 16 h, filtered and concentrated. Since the reaction had not proceeded to completion, the residue was subjected to the same conditions again and stirred for 24 h at room temperature. The mixture was filtered and concentrated, the residue was purified by solid phase extraction (Chromabond C18, Macherey-Nagel) and lyophilized to give pentasaccharide 62 (8.1 mg, 9.1 µmol, 88% over three steps) as a white solid. $^1$H NMR (600 MHz, $D_2O$) δ 5.52 (d, J=3.5 Hz, 1H, H-1b), 5.07 (d, J=3.7 Hz, 1H, H-1b), 4.93 (d, J=3.8 Hz, 1H, H-1a), 4.56 (2xd, J=8.4 and 8.4 Hz, 2H, H-1c and H-1d), 4.24 (d, J=10.0 Hz, 1H), 4.09 (d, J=2.6 Hz, 1H), 4.07-3.78 (m, 19H), 3.77-3.58 (m, 8H), 3.39 (dt, J=24.4, 8.5 Hz, 2H), 3.34-3.26 (m, 2H); 13C NMR (150 MHz, D2O) δ 104.86 (C-1c and C-1d), 104.85 (C-1a), 102.5 (C-1b), 101.2 (C-1b), 101.0, 81.2, 81.0, 80.9, 78.7, 78.6, 77.4, 76.6, 75.7, 75.5, 74.2, 74.1, 73.8, 73.31, 73.29, 71.8, 71.6, 71.5, 71.0, 70.9, 66.5, 63.3, 63.1, 62.5, 62.1, 41.9; HRMS (MALDI) calcd. for $C_{32}H_{55}NO_{27}$ (M+Na)+ 884.2883 found 884.2942 m/z.

Example C.3. Synthesis of *S. pneumoniae* Serotype 8 Hexasaccharide 66

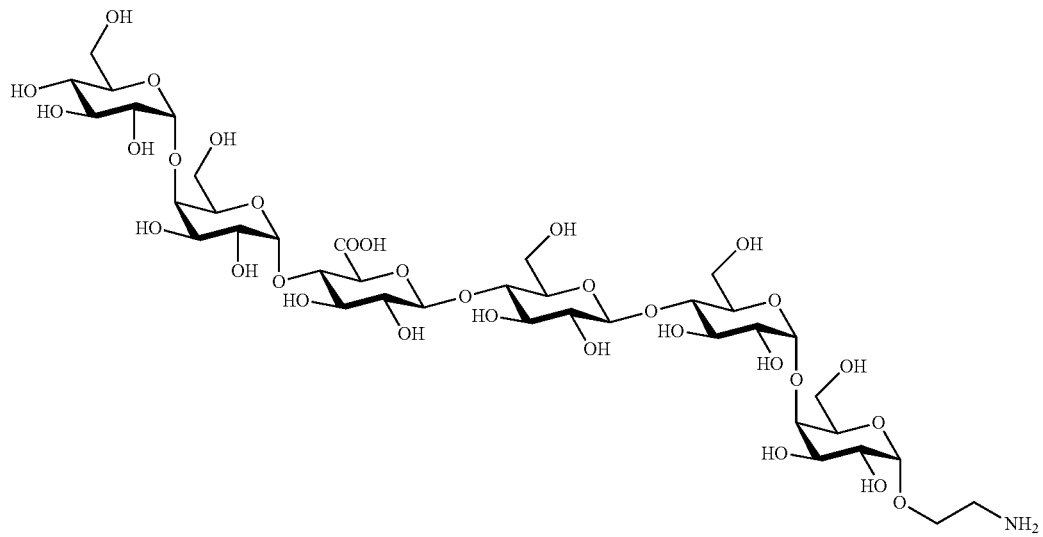

Example C.3.1. N-Benzyl-N-benzyloxycarbonyl-2-amino-ethyl 4-O-benzoyl-2,3,6-tri-O-benzyl-α-D-glucopyranosyl-(1→4)-2,3,6-tri-O-benzyl-α-D-galacto-pyranosyl-(1→4)-methyl[2,3-di-O-benzoyl-β-D-glucopyranosyl]uronate-(1→4)-2,3-di-O-benzoyl-6-O-benzyl-β-D-glucopyranosyl-(1→4)-2,3,6-tri-O-benzyl-α-D-glucopyranosyl-(1→4)-2,3,6-tri-O-benzyl-α-D-galactopyranoside (67)

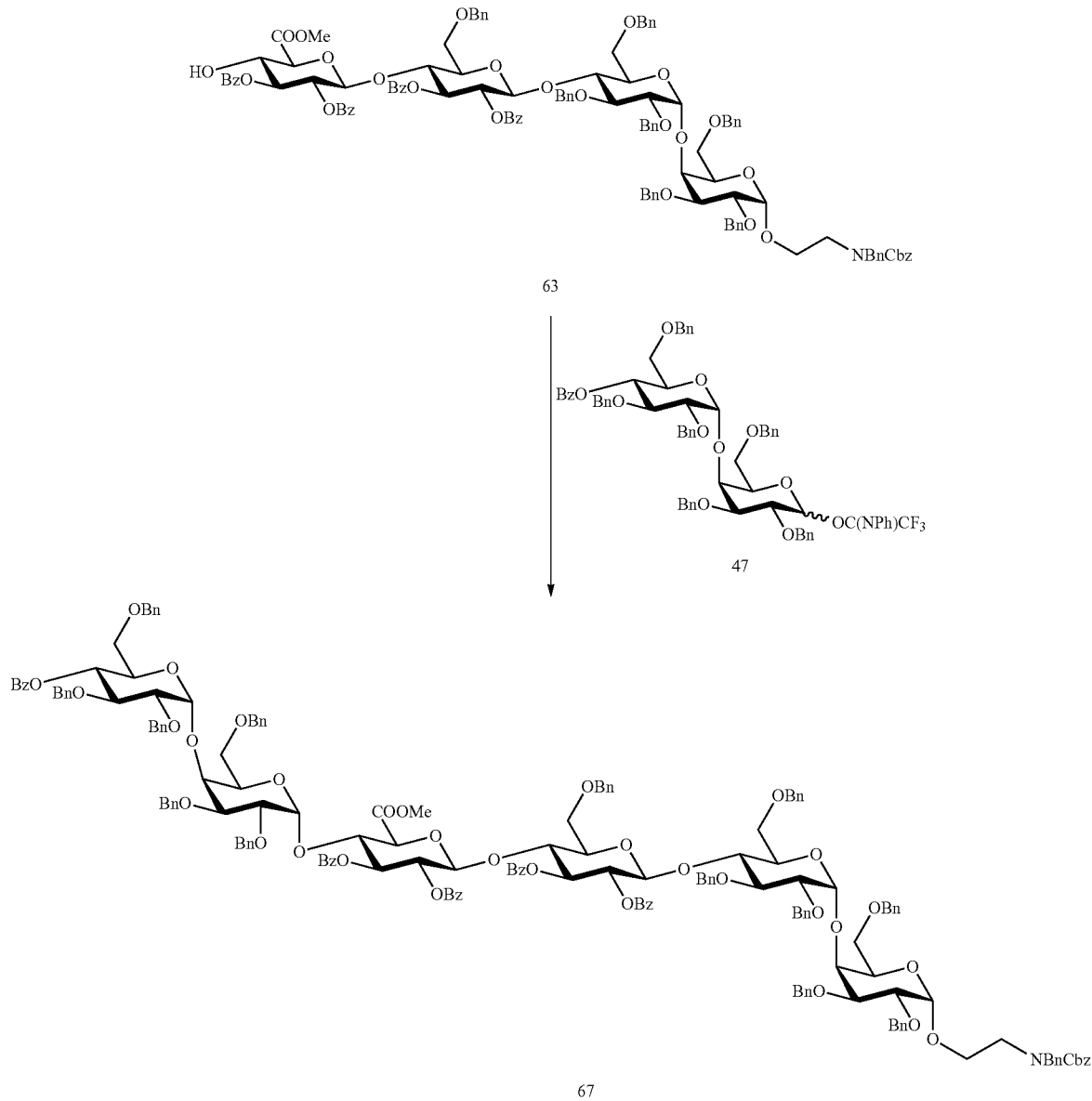

Alcohol 63 (50 mg, 25 μmol) and imidate 47 (72.1 mg, 62 μmol) were co-evaporated with anhydrous toluene (3×10 mL) and kept under high vacuum for 30 min. The mixture was dissolved in Et$_2$O (2 mL) and CH$_2$Cl$_2$ (0.67 mL) and stirred over activated molecular sieves (3 Å-AW) for 30 min at room temperature. The solution was cooled to −20° C. and treated with TMSOTf (2 μL, 11 μmol). The mixture was stirred for 1 h at that temperature and slowly warmed to 0° C. The reaction was quenched with sat. aq. NaHCO$_3$ (10 mL) and extracted with CH$_2$Cl$_2$ (4×10 mL). The combined organic fractions were dried over Na$_2$SO$_4$ and concentrated. The residue was purified by flash chromatography (EtOAc/hexanes 0:1 to 1:3 to 3:7 to 1:2) to give hexasaccharide 67 (51 mg, 17 μmol, 68%) as a clear oil. $R_f$ (EtOAc/hexanes 2:3)=0.63; $[\alpha]_D^{20}$=+36.6° (c=0.21, CH$_2$Cl$_2$); $^1$H NMR (600 MHz, CDCl$_3$) δ 7.95 (d, J=7.3 Hz, 2H), 7.89 (d, J≤7.7 Hz, 4H), 7.84 (d, J=7.3 Hz, 2H), 7.67 (d, J=7.4 Hz, 2H), 7.55 (dt, J=26.6, 7.4 Hz, 2H), 7.48-6.98 (m, 88H), 5.49 (dt, J=19.5, 9.8 Hz, 2H), 5.39 (dd, J=9.9, 8.2 Hz, 1H), 5.28 (m, 2H), 5.16 (t, J=9.5 Hz, 1H), 5.09 (m, 3H), 4.92 (s, 1H), 4.74 (dd, J=11.7, 9.1 Hz, 2H), 4.71-4.66 (m, 3H), 4.60 (m, 7H), 4.53-4.41 (m, 6H), 4.35-4.28 (m, 3H), 4.28-4.20 (m, 5H), 4.18-4.01 (m, 8H), 4.00-3.78 (m, 9H), 3.77-3.59 (m, 8H), 3.55 (d, J=9.6 Hz, 1H), 3.53-3.20 (m, 8H), 3.17 (dd, J=8.8, 4.9 Hz, 1H), 3.06 (s, 3H), 2.97 (m, 3H); $^{13}$C NMR (150 MHz, CDCl$_3$) δ 167.0, 165.54, 165.50, 165.2, 164.8, 156.6, 156.3, 140.1, 138.9, 138.79, 138.76, 138.6, 138.41, 138.36, 138.3, 138.2, 138.1, 138.0, 137.6, 136.84, 136.77, 133.5, 133.1, 133.0, 132.5, 130.4, 130.2, 130.1, 129.9, 129.8, 129.7, 129.3, 129.2, 129.1, 129.04, 128.95, 128.8, 128.7, 128.6, 128.44, 128.41, 128.37, 128.35, 128.33, 128.30, 128.25, 128.18, 128.15, 128.1, 128.03, 127.99, 127.96, 127.94, 127.85, 127.8, 127.7, 127.64, 127.61, 127.55, 127.4, 127.3, 127.2, 127.0, 100.4 (J$_{1,2}$=165.6 Hz, C-1c), 100.2 (J$_{1,2}$=165.6 Hz, C-1d), 100.0 (J$_{1,2}$=171.3 Hz, C-1a), 99.8 (J$_{1,2}$=171.0 Hz, C-1b), 99.3 (J$_{1,2}$=172.8 Hz, C-1a), 98.5 (J$_{1,2}$=174.0 Hz, C-1b), 80.7, 80.1, 79.7, 79.2, 77.6, 76.64, 76.56, 75.9, 75.3, 75.2, 74.9, 74.43, 74.41, 74.2, 73.9, 73.62, 73.57, 73.4, 73.3, 73.2, 73.1, 73.0, 72.6, 72.4, 72.1, 71.6, 71.1, 70.5, 70.1, 69.6, 69.5, 69.2, 67.9, 67.8, 67.6, 67.3, 67.0, 66.9, 66.8, 66.3, 52.2, 51.40, 51.37, 46.5, 45.5; IR (thin film) 2926, 1736, 1454, 1271, 1095, 1045, 737, 699 cm-1; HRMS (MALDI) calcd. for C$_{180}$H$_{177}$NO$_{39}$ (M+2Na)$^{2+}$ 1511.0847 found 1511.0576 m/z.

Example C.3.2. 2-Amino-ethyl α-D-glucopyranosyl-(1→4)-α-D-galactopyranosyl-(1→4)-β-D-glucopyranosyluronate-(1→4)-β-D-glucopyranosyl-(1→4)-α-D-glucopyranosyl-(1→4)-α-D-galactopyranoside (66)

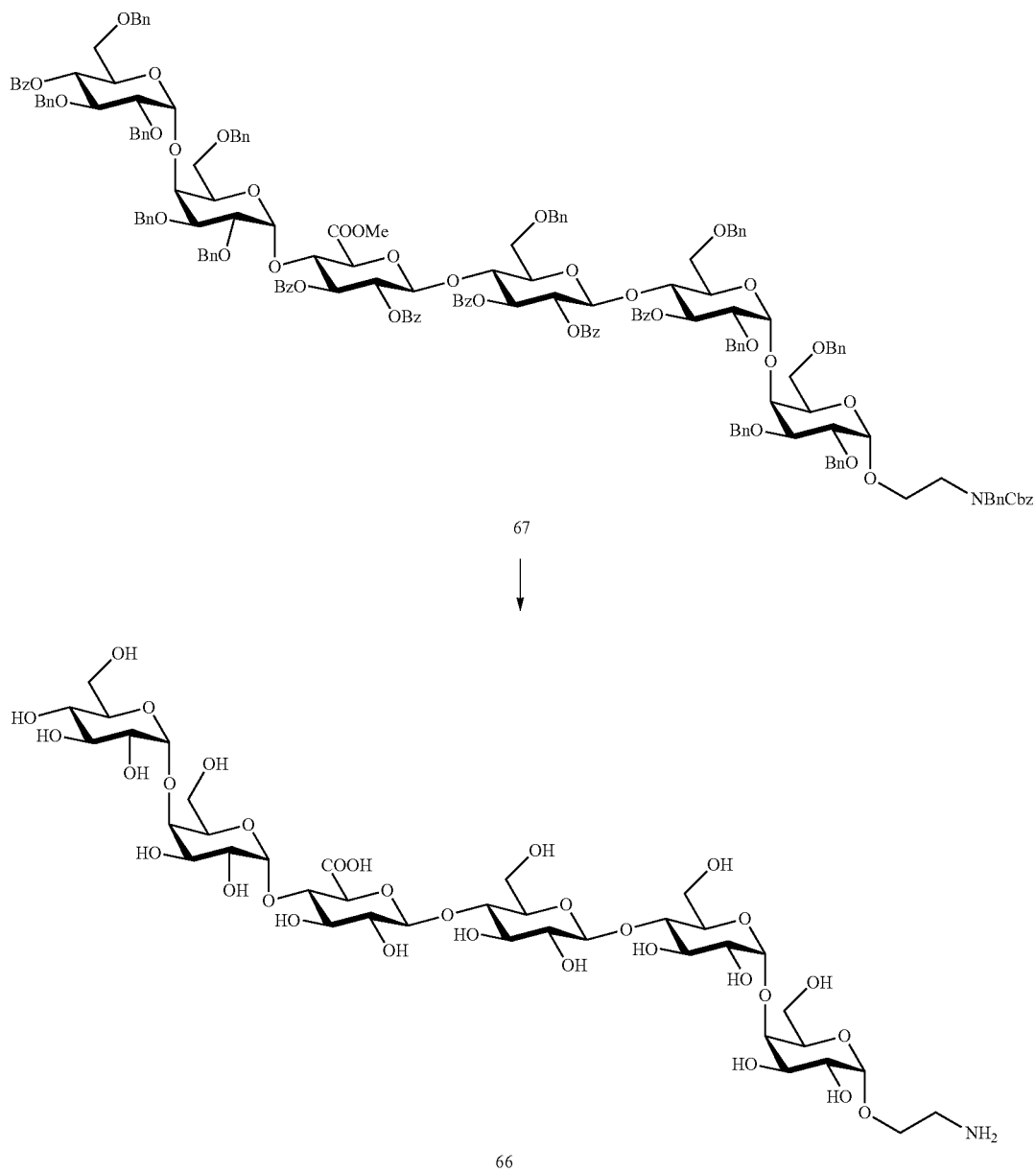

To a stirred solution of ester 67 (22 mg, 7.4 μmol) in THF (1 mL) and MeOH (1 mL) was added at 0° C. a 1:1 (v/v) mixture (296 μL) of hydrogen peroxide (6% (v/v) aq. solution, 295 μmol) and LiOH (0.5 M aq. solution, 74 μmol). The reaction was warmed to room temperature and treated after 2 h and 4 h with another 294 μL of the same lithium peroxide solution, respectively. The mixture was stirred for 16 h at room temperature and treated with NaOH (1 M aq. solution, 0.5 mL) and MeOH (0.5 mL). The reaction was stirred for 20 h at that temperature, quenched with 10% aq. $Na_2SO_3$ (0.8 mL) and concentrated under reduced pressure. The residue was dissolved in water (4 mL), acidified at 0° C. with 0.5 M aq. $NaHSO_4$ to approx. pH 4 and extracted with EtOAc (4×10 mL). The combined organic fractions were dried over $Na_2SO_4$ and concentrated. The residue was treated with NaOMe (0.5 M solution in MeOH, 1 mL), warmed to 40° C. and stirred for 5 h at that temperature. The reaction was cooled to room temperature, stirred for another 16 h at that temperature and treated with water (0.5 mL). The mixture was neutralized with Amberlite IR-120 (H+ form), filtered and concentrated. The residue was purified by flash chromatography (EtOAc/hexanes 0:1:0 to 1:4+2% (v/v) AcOH to 1:1+2% (v/v) AcOH) to give the intermediate carboxylic acid as a clear oil. The intermediate carboxylic acid in $CH_2Cl_2$/tBuOH/water (1.5:16:8, 3 mL) was purged with argon and treated at 0° C. with a suspension of $Pd(OH)_2$ on carbon (20% (w/w) loading, 30 mg) in the same solvent mixture (1 mL). The suspension was purged with hydrogen, warmed to room temperature, stirred under a hydrogen atmosphere for 18 h, filtered and concentrated. The residue was purified by solid phase extraction (Chromabond C18, Macherey-Nagel) and lyophilized to give hexasaccharide 66 (7 mg, 6.7 μmol, 86% over three steps) as a white solid. $^1$H NMR (600 MHz, $D_2O$) δ 5.57 (d, J=3.2 Hz, 1H, H-1b), 5.07 (d, J=2.9 Hz, 1H, H-1b), 4.97 (d, J=3.0 Hz, 1H, H-1a), 4.94 (d, J=3.0 Hz, 1H, H-1a), 4.56 (2xd, J=8.0 and 7.9 Hz, 2H, H-1c and H-1d), 4.24 (d, J=9.8 Hz, 1H), 4.15-4.07 (m, 3H), 4.01 (m, 4H), 3.89 (m, 16H), 3.77-3.60 (m, 8H), 3.56 (dd, J=9.9, 3.1 Hz, 1H), 3.47 (t, J=9.6 Hz, 1H), 3.43-3.28 (m, 4H); $^{13}$C NMR (150 MHz, $D_2O$) δ 104.9 (C-1c or C-1d), 104.82 (C-1c or C-1d), 102.80 (C-1a), 102.5 (C-1a), 101.2 (C-1b), 101.0 (C-1b), 81.2, 81.01, 80.98, 80.9, 78.68, 78.67, 77.4, 76.6, 75.7, 75.5, 75.4, 74.5, 74.4, 74.2, 74.1, 73.8, 73.6, 73.3, 71.9, 71.5, 71.3, 71.1, 70.9, 66.5, 63.1, 62.7, 62.5, 62.4, 62.1, 41.9; HRMS (ESI) calcd. for $C_{38}H_{65}NO_{32}$ $(M+Na)^+$ 1070.3387 found 1070.3391 m/z.

Example C.4. Conjugation of *S. pneumoniae* Serotype 8 Saccharides 44, 45, 46 and 66 to $CRM_{197}$

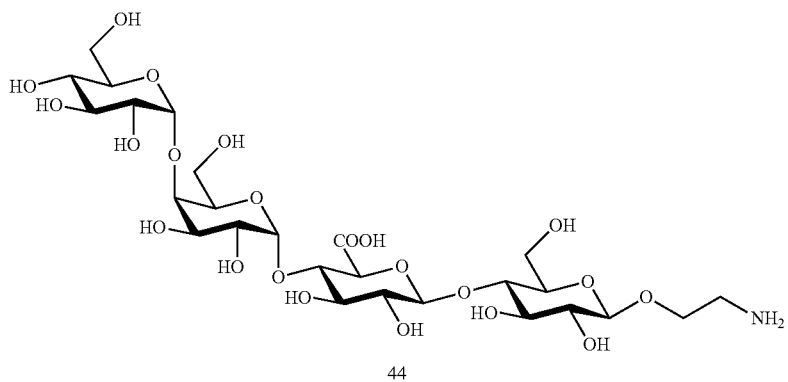

44

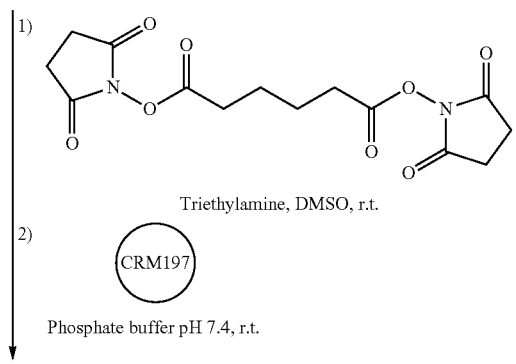

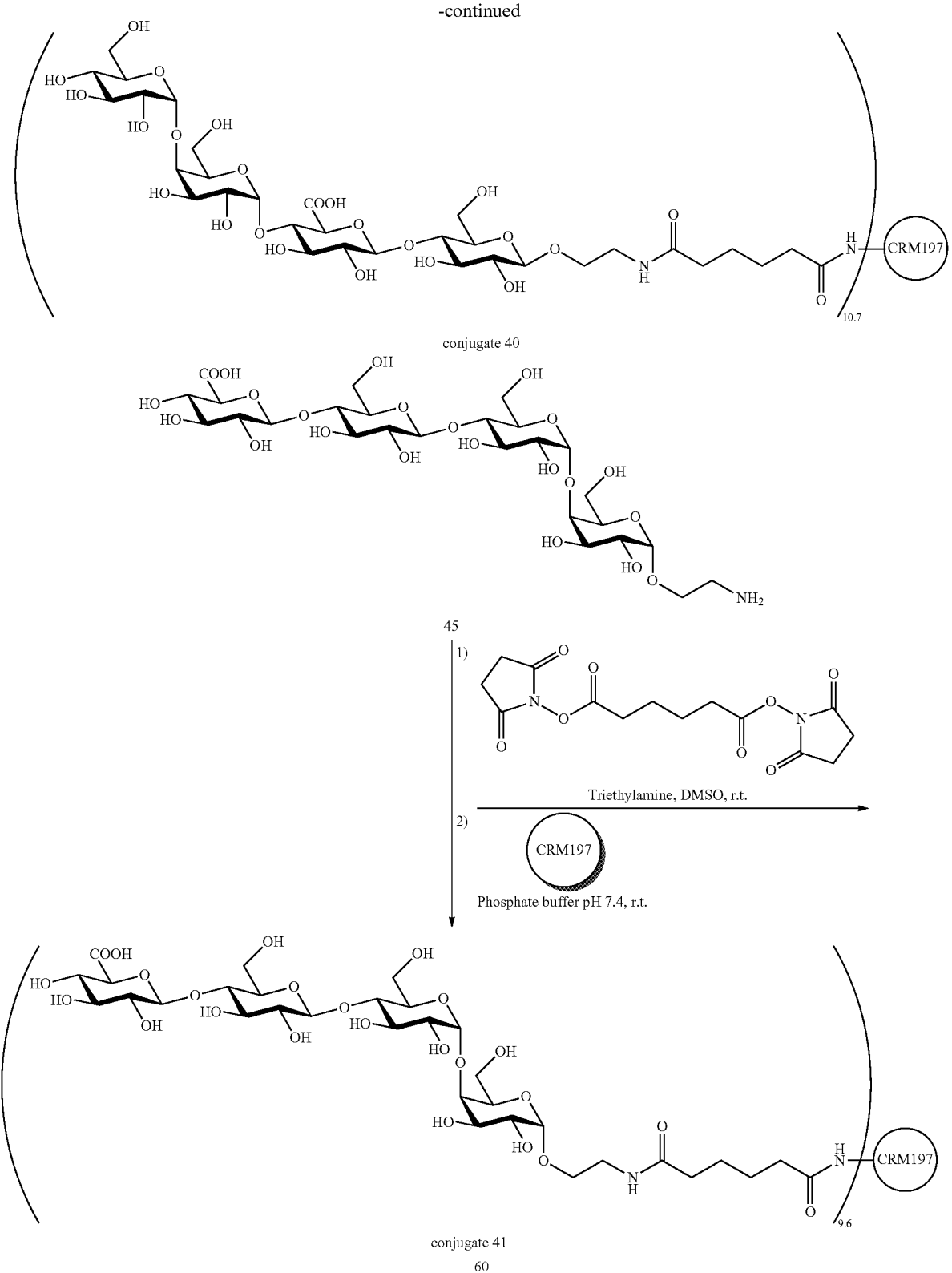

Method A:

To a stirred solution of disuccinimidyl adipate (10 mg, 29 μmol) and triethylamine (10 μL, 72 μmol) in anhydrous DMSO (150 μL) was added at room temperature dropwise a suspension of tetrasaccharide 44 or 45 (approx. 2 mg, 2.8 μmol) in anhydrous DMSO (150 μL). The reaction was stirred for 2 h at that temperature under an Argon atmosphere and treated with a 100 mM sodium phosphate buffer pH 7.4 (NaPi, 200 μL). The mixture was extracted with chloroform (10 mL) and the phases separated by centrifugation (2 min, 1800 g, room temperature). The organic phase was discarded and the extraction step was repeated two times. The aqueous layer was clarified by centrifugation in a 1.5 mL reaction tube (1 min, 14500 g, room temperature) and added to a stirring solution of CRM$_{197}$ (1 mg, 17.3 nmol) in NaPi (1 mL). The mixture was stirred for 16 h at room temperature and dialyzed using a centrifugal filter (10 kDa MWCO, Millipore, Darmstadt, Germany). The conjugate was characterized by MALDI-MS:

Conjugate 40 (CRM$_{197}$-44): ca. 67000 m/z (incorporation of 10.7 tetrasaccharide molecules on average)

Conjugate 41 (CRM$_{197}$-45): ca. 66000 m/z (incorporation of 9.6 tetrasaccharide molecules on average)

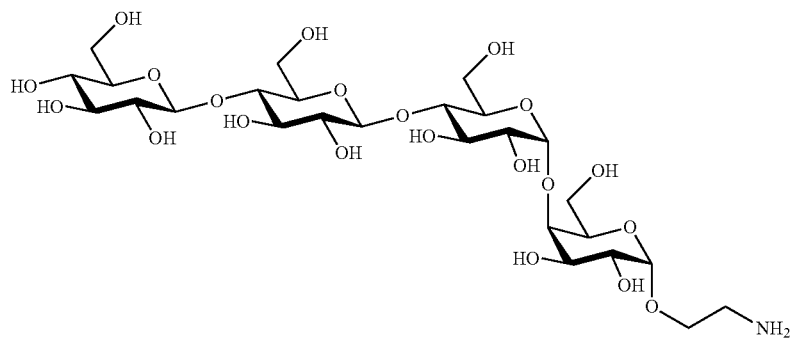

46

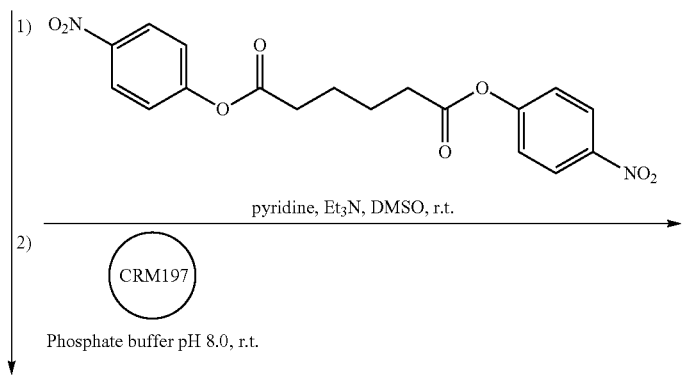

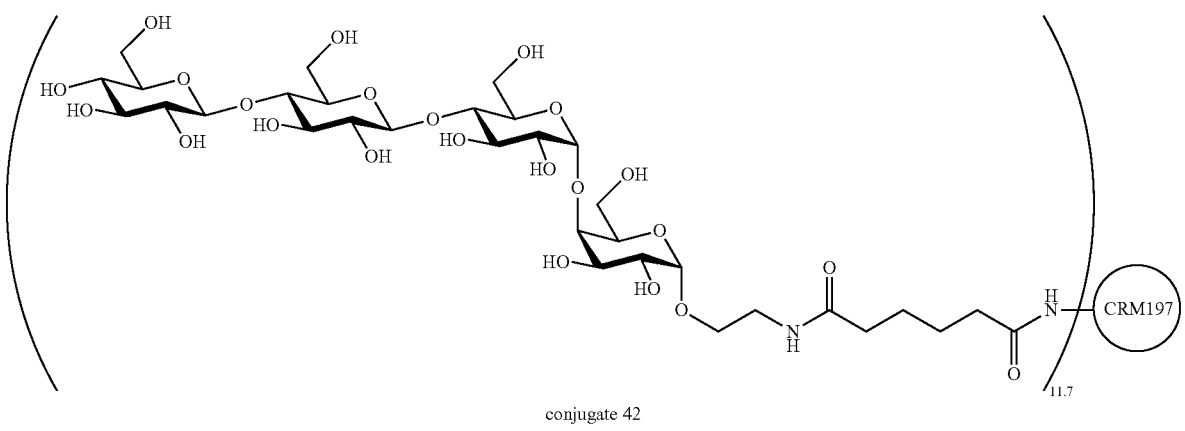

conjugate 42

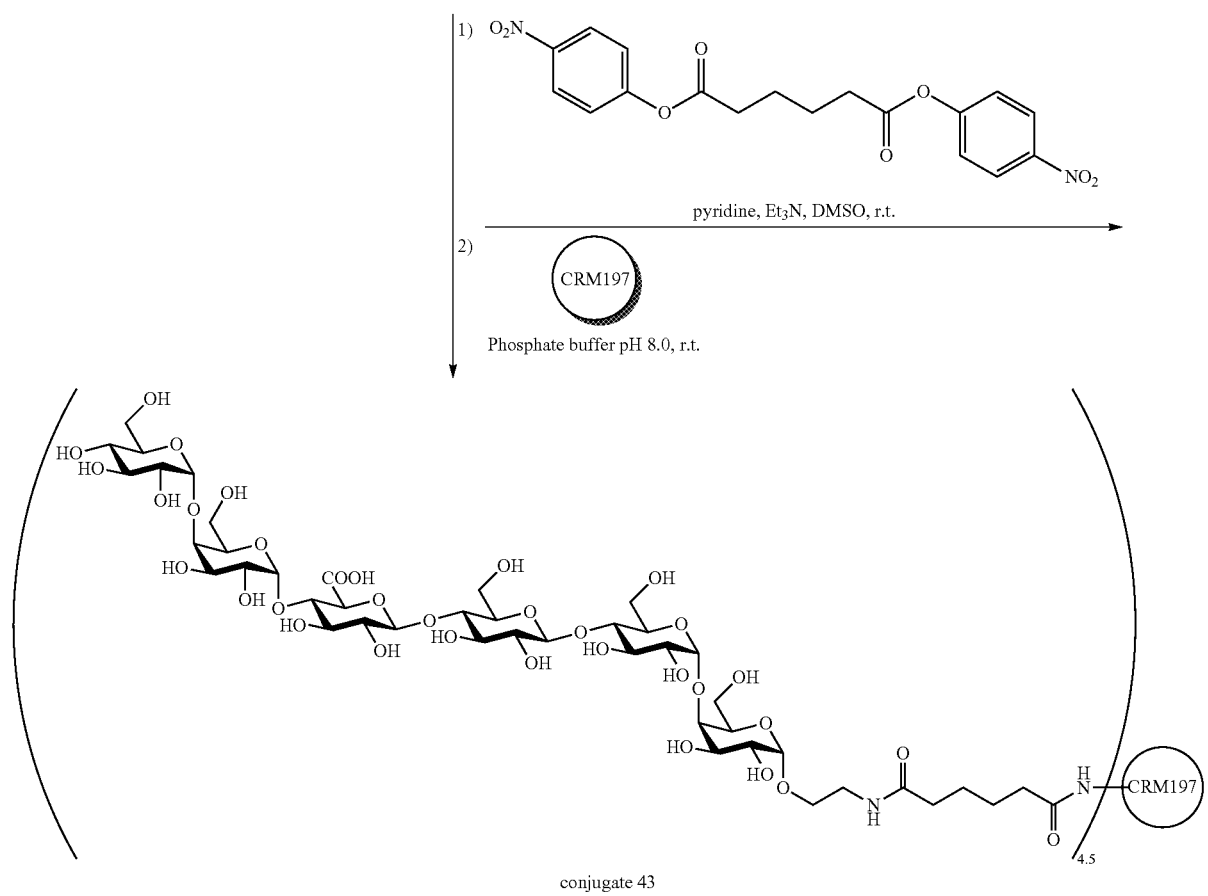

conjugate 43

Method B:

To a stirred solution of the oligosaccharide 46 or 66 (2 μmol) in a 1:3 (v/v) mixture of anhydrous DMSO and anhydrous pyridine (100-200 μL) were added bis(4-nitrophenyl)adipate (DNAP, 9.3 mg, 24 μmol) and triethylamine (10 μL). The reaction was stirred for 2 h at room temperature under argon atmosphere. The mixture was shock-frozen and lyophilized. The residue was triturated with chloroform (4×0.5 mL) and dichloromethane (4×0.5 mL), transferred to a new reaction tube using DMSO as a solvent and lyophilized again. $CRM_{197}$ (3 mg, 52 nmol) was dialyzed twice against 0.1 M sodium phosphate buffer pH 8.0 using a centrifugal filter (10 kDa MWCO), concentrated to approx. 300 μL and added to the activated oligosaccharide. The mixture was stirred at room temperature for 16 h and dialyzed against water four times. An aliquot was taken for characterization and the mixture was dialyzed three times against phosphate-buffered saline. The glycoconjugates were characterized by MALDI-TOF MS, SDS-PAGE and Immunoblot. Conjugates were stable for at least two months at 4° C. (if handled under sterile conditions) or −20° C.

Conjugate 42 ($CRM_{197}$-46): ca. 68281 m/z (incorporation of 12.9 tetrasaccharide molecules on average).

Conjugate 43 ($CRM_{197}$-66): ca. 63535 m/z (incorporation of 4.6 hexasaccharide molecules on average)

Example C.5: Synthesis of Building Blocks BB2, BB4 and BB5 Synthesis of Building Block BB2

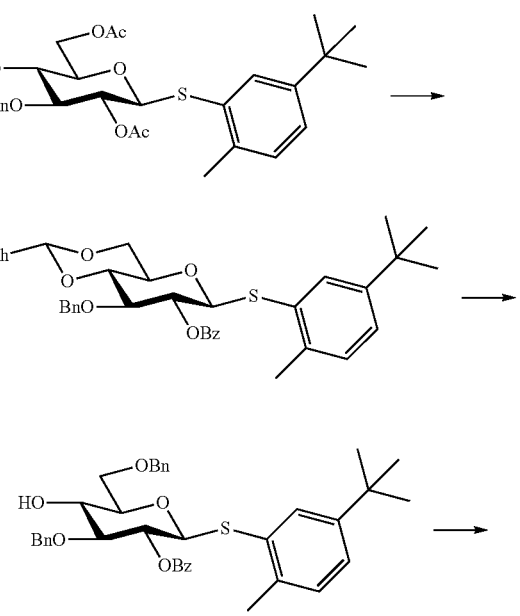

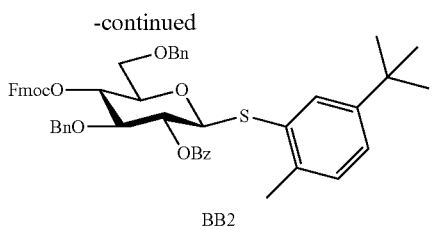

BB2

Step 1: Synthesis of (2-methyl-5-tert-butylphenyl) 2-O-benzoyl-3-O-benzyl-4,6-O-benzylidene-1-thio-β-D-glucopyranose (2- Methyl-5-tert-butylphenyl) 2,4,6-tri-O-acetyl-3-O-benzyl-1-thio-β-D-gluco-pyranose (*Chem. Eur. J.* 2013, 19, 12497-12503) was dissolved in MeOH, NaOMe (1.0 eq) was added and the reaction mixture was stirred overnight. The mixture was neutralized with IR-120-H+ amberlite resin, filtered off, concentrated and co-evaporated with toluene. The crude triol was dissolved in DMF. Benzaldehyde dimethyl acetal (2.0 eq) and a catalytic amount of para-toluene sulfonic acid were added and the mixture was stirred at 80° C. for 2 h. After the mixture was cooled to room temperature, saturated aqueous $NaHCO_3$ was added. After phase separation, the organic phase was extracted three times with ethyl acetate. The combined organic layers were washed with brine, dried over $MgSO_4$, filtered and concentrated. The crude was dissolved in DCM, cooled to 0° C. and $Bz_2O$ (2.0 eq), DMAP (0.5 eq) and triethylamine (4.0 eq) were added. After complete conversion, the reaction was quenched with saturated aqueous $NaHCO_3$ and the combined organic layers were washed with brine, dried over $MgSO_4$, filtered and concentrated. The residue was purified by flash column chromatography on silica gel to provide compound (88% over three steps). $R_f$: 0.25 (Hexane:EtOAc=9:1). $[α]_D$=68.96 (c=3.18, $CHCl_3$). IR (thin film, chloroform): u=2962, 1729, 1265, 1093 cm$^{-1}$; $^1$HNMR (400 MHz, $CDCl_3$) δ=8.01 (ddd, J=5.8, 5.3, 0.8 Hz, 2H, H Ar), 7.60 (ddd, J=7.1, 2.6, 1.3 Hz, 1H, H Ar), 7.51 (ddd, J=6.0, 5.6, 2.3 Hz, 3H, H Ar), 7.49-7.43 (m, 2H, H Ar), 7.43-7.35 (m, 3H, H Ar), 7.19 (dt, J=6.3, 3.1 Hz, 1H, H Ar), 7.13 (dd, J=6.7, 4.0 Hz, 3H, H Ar), 7.10-7.04 (m, 3H, H Ar), 5.63 (s, 1H $CHO_2Ph$), 5.42-5.32 (m, 1H, H-2), 4.82 (d, J=11.9 Hz, 1H, CHHPh), 4.81 (d, J=10.2 Hz, 1H, H-1), 4.69 (d, J=12.0 Hz, 1H, CHHPh), 4.39 (dd, J=10.5, 5.0 Hz, 1H, H-6'), 3.94-3.86 (m, 3H, H-3, H-4, H-6), 3.56 (dt, J=14.6, 4.9 Hz, 1H, H-5), 2.19 (s, 3H), 1.27 (s, 9H). $^{13}$C NMR (100 MHz, $CDCl_3$) δ 165.23 (C=O), 149.66, 137.84, 137.28, 137.03, 133.34, 132.37, 130.07, 130.04, 129.93, 129.90, 129.19, 128.51, 128.43, 128.29, 128.22, 127.71, 126.13, 125.38 (Ar), 101.44 ($CHO_2Ph$), 88.03 (C-1), 81.64 (C-3), 79.43 (C-4), 74.36 ($CH_2Ph$), 72.25 (C-2), 70.66 (C-5), 68.81 (C-6), 34.56 (Cq tBu thio), 31.36 (tBu), 20.36 ($CH_3$ thio); MS ESI+-HRMS m/z [M+Na]+ calcd for $C_{38}H_{40}O_6SNa$ 647.2462, found 647.

Step 2: Synthesis of (2-methyl-5-tert-butylphenyl) 2-O-benzoyl-3,6-di-O-benzyl-1-thio-β-D-glucopyranose A solution of the compound of step 1 was co-evaporated with toluene, and dissolved in DCM (6.5 mL) under an argon atmosphere. Triethylsilane (0.62 mL, 3.88 mmol) and trifluoroacetic anhydride (0.27 mL, 1.94 mmol) were added and the solution was cooled to 0° C. Trifluoroacetic acid (0.30 mL, 3.88 mmol) were added dropwise, and the reaction was stirred and allowed to warm to room temperature. After complete conversion of the starting material, the solution was diluted with DCM, and quenched with saturated aqueous $NaHCO_3$. The combined organic layer was dried over $MgSO_4$ and the solvent was removed in vacuo. The residue was purified by column chromatography on silica gel (hexane/ethyl acetate, 9:1 to 7:3) to give a white foam (92%). MS ESI+-HRMS m/z [M+Na]+ calcd for $C_{38}H_{42}O_6SNa$ 649.2600 found 649.2585.

Step 3: Synthesis of (2-methyl-5-tert-butylphenyl) 2-O-benzoyl-3,6-di-O-benzyl-4-O-fluorenylmethoxycarbonyl-1-thio-β-D-glucopyranoside The compound obtained at step 2 was dissolved in DCM (6.5 mL) under an argon atmosphere. 9-fluorenylmethyl chloroformate (8.3 g, 31.9 mmol) and pyridine (3.44 mL, 42.5 mmol) were added into the solution at 0° C. After complete conversion of the starting material, the solution was diluted with DCM, extracted with 1 M aqueous HCl and saturated aqueous $NaHCO_3$. The combined organic phase was dried over $MgSO_4$ and the solvent was removed in vacuo. The crude product was purified by silica gel flash column chromatography affording the title compound. MS ESI+-HRMS m/z [M+Na]+ calcd for $C_{53}H_{52}O_8SNa$ 871.3281 found 871.3311.

Synthesis of Building Block BB5

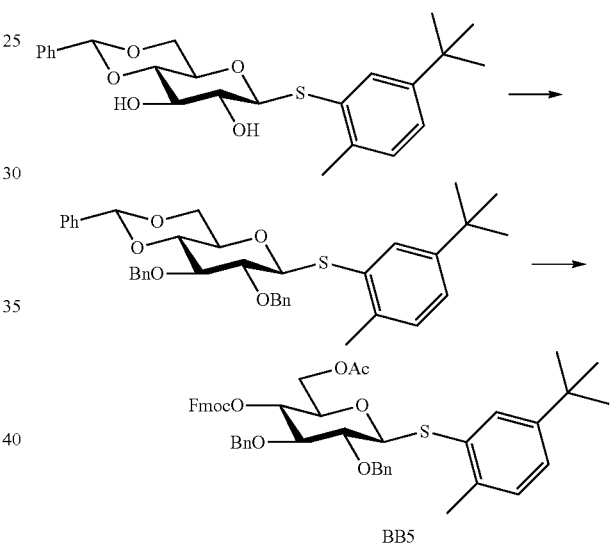

BB5

Step 1: Synthesis of (2-methyl-5-tert-butylphenyl) 2,3-di-O-benzyl-4,6-O-benzylidene-1-thio-β-D-glucopyranoside (2-Methyl-5-tert-butyl phenyl) 4,6-O-benzylidene-1-thio-β-D-glucopyranoside (*Chem. Eur. J.* 2013, 19, 12497-12503) was dissolved in DCM (6.5 mL) under an argon atmosphere. Benzyl bromide and NaH were added into the solution at 0° C. After complete conversion of the starting material, the reaction mixture was quenched with methanol, and diluted with ether, extracted with saturated $NH_4Cl$. The combined organic phase was dried over $MgSO_4$ and the solvent was removed in vacuo. The crude product was purified by silica gel flash column chromatography affording the title compound.

MS ESI+-HRMS m/z [M+Na]+ calcd for $C_{38}H_{42}O_5SNa$ 633.2651 found 633.2644.

Step 2: Synthesis of (2-Methyl-5-tert-butylphenyl) 6-O-acetyl-2,3-di-O-benzyl-4-O-fluorenylmethoxycarbonyl-1-thio-β-D-galactopyranoside To the solution of (2-methyl-5-tert-butylphenyl) 2,3-di-O-benzyl-4,6-O-benzylidene-1-thio-β-D-glucopyranoside in DCM (6.5 mL) were added TFA and water. After completion, the crude was decanted with hexane to remove byproduct. The crude was used to the next reaction. To the solution of the crude was added acetic acid, 2-chloro-1-methylpyridium iodide, and DABCO at −15° C. After complete conversion of the starting material, the solution was diluted with DCM, extracted with 1 M aqueous HCl and saturated aqueous NaHCO$_3$. The combined organic phase was dried over MgSO$_4$ and the solvent was removed in vacuo. The crude product was purified by silica gel flash column chromatography affording the title compound. The crude was dissolved in DCM (6.5 mL) under an argon atmosphere. 9-fluorenylmethyl chloroformate (8.3 g, 31.9 mmol) and pyridine (3.44 mL, 42.5 mmol) were added into the solution at 0° C. After complete conversion of the starting material, the solution was diluted with DCM, extracted with 1 M aqueous HCl and saturated aqueous NaHCO$_3$. The combined organic phase was dried over MgSO$_4$ and the solvent was removed in vacuo. The crude product was purified by silica gel flash column chromatography affording the title compound.

MS ESI$^+$-HRMS m/z [M+Na]$^+$ calcd for C$_{48}$H$_{53}$O$_8$SNa 809.3124 found 809.3137.

Synthesis of Building Block BB4

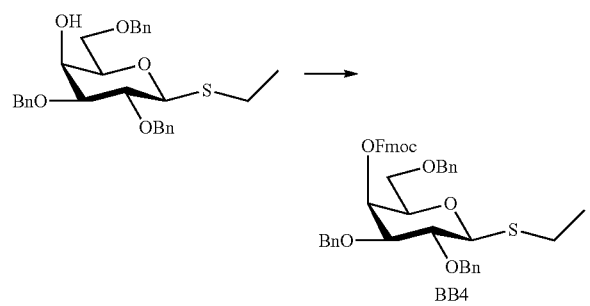

To a solution of 2,3,6-tri-O-benzyl-1-thio-β-D-galactopyranoside (*Chem. Commun.*, 2011, 47, 10260-10262) were added 9-fluorenylmethyl chloroformate (8.3 g, 31.9 mmol) and pyridine (3.44 mL, 42.5 mmol) at 0° C. After complete conversion of the starting material, the solution was diluted with DCM, extracted with 1 M aqueous HCl and saturated aqueous NaHCO$_3$. The combined organic phase was dried over MgSO$_4$ and the solvent was removed in vacuo. The crude product was purified by silica gel flash column chromatography affording the title compound ethyl 2,3,6-tri-O-benzyl-4-O-fluorenylmethoxycarbonyl-1-thio-β-D-galactopyranoside.

MS ESI$^+$-HRMS m/z [M+Na]$^+$ calcd for C$_{44}$H$_{44}$O$_7$SNa 739.2705 found 739.2673.

Example D. Coformulation

Example D.1. Coformulation of Prevnar13® and Conjugate 41 or 42

Conjugate 41 or conjugate 42 (2.2 μg glycan per dose) in 20 μL PBS was admixed to a full dose Prevnar13® for each immunization dose and incubated overnight at 4° C.

Example D.2. Characterization of Conjugate Adsorption to Prevnar13®

Figure 5:
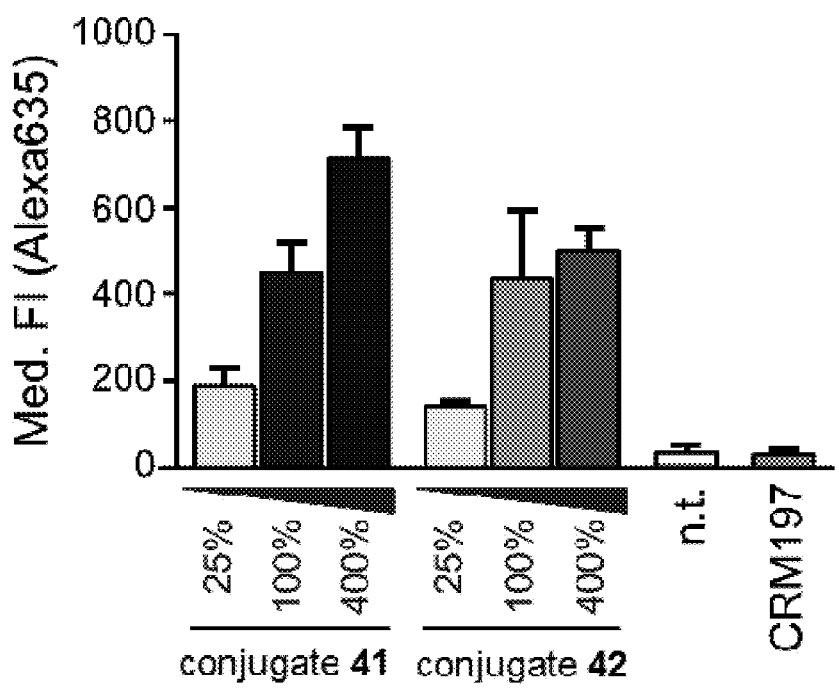
FIG. 5 shows the characterization of the absorption of the *S. pneumoniae* serotype 8 conjugates 41 and 42 to Prevnar®13: bars depict mean±SD of the median fluorescence intensity of three independent experiments. Gates were set by omitting primary antibodies. Pooled murine sera against Prevnar13® were used as a positive control for mouse antibody binding.
Figure 6:
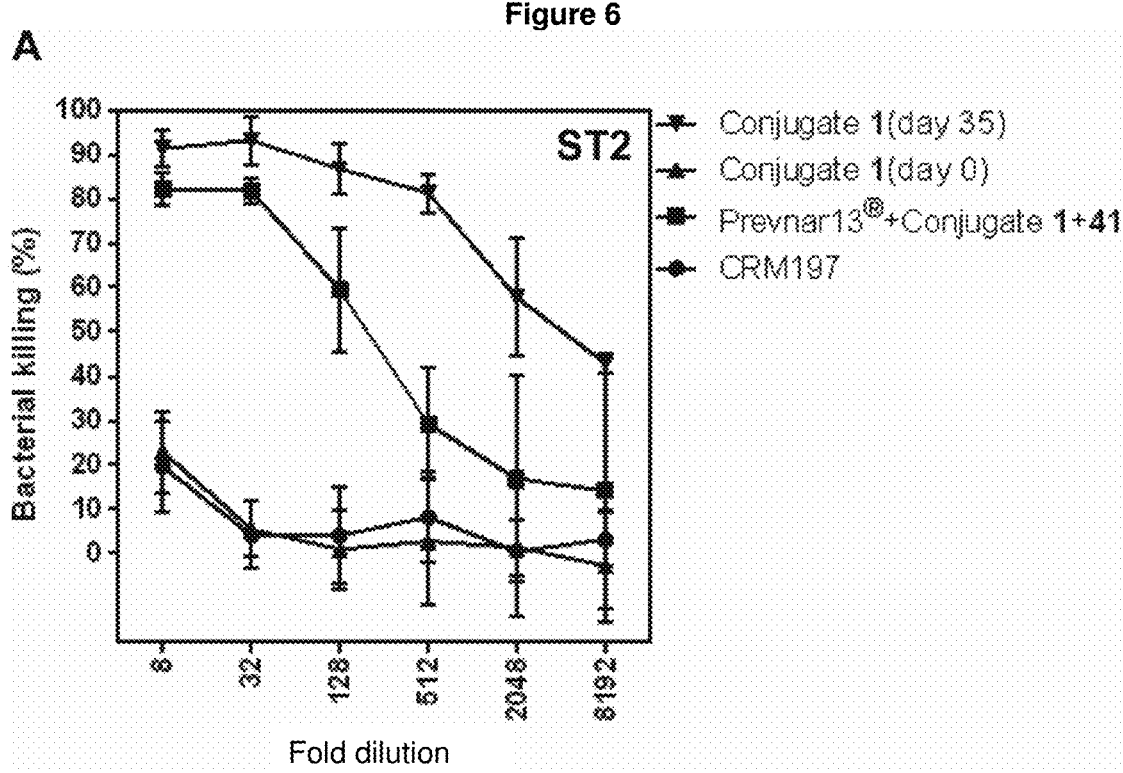
FIG. 6 shows opsonophagocytic activity of antibodies elicited by coformulation of Prevnar13® with conjugate 1 and conjugate 41 and coformulation of Synflorix® with conjugate 1, conjugate 2 and conjugate 41. N,N-dimethyl-formamide differentiated HL-60 cells were incubated with pneumococcal bacteria pre-opsonized with pooled sera in multiple dilutions (4 fold), and incubated for 45 min with shaking. The phagocytic reaction was stopped keeping the mixture on ice for 20 min. The viable extracellular pneumococci were determined by plating on blood agar plates. Percent killing of pneumococci was calculated based on viable pneumococcal colonies obtained relative to "no sera" control. These are the representative values from one out of two independent experiments performed in triplicates.
Figure 6:
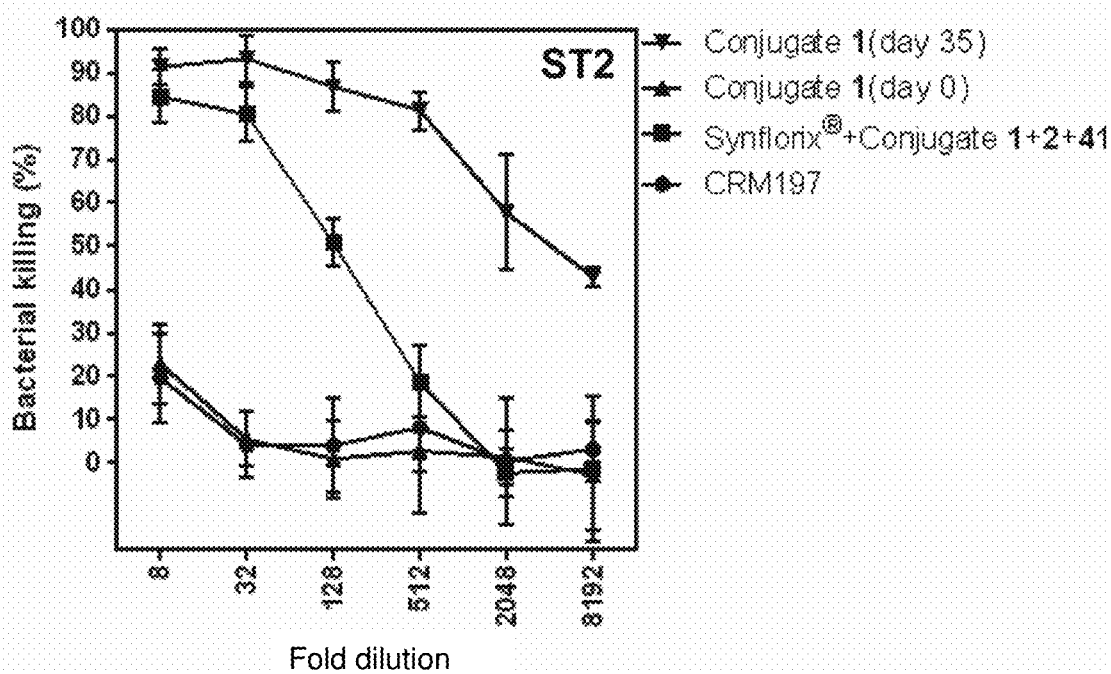
Figure 6:
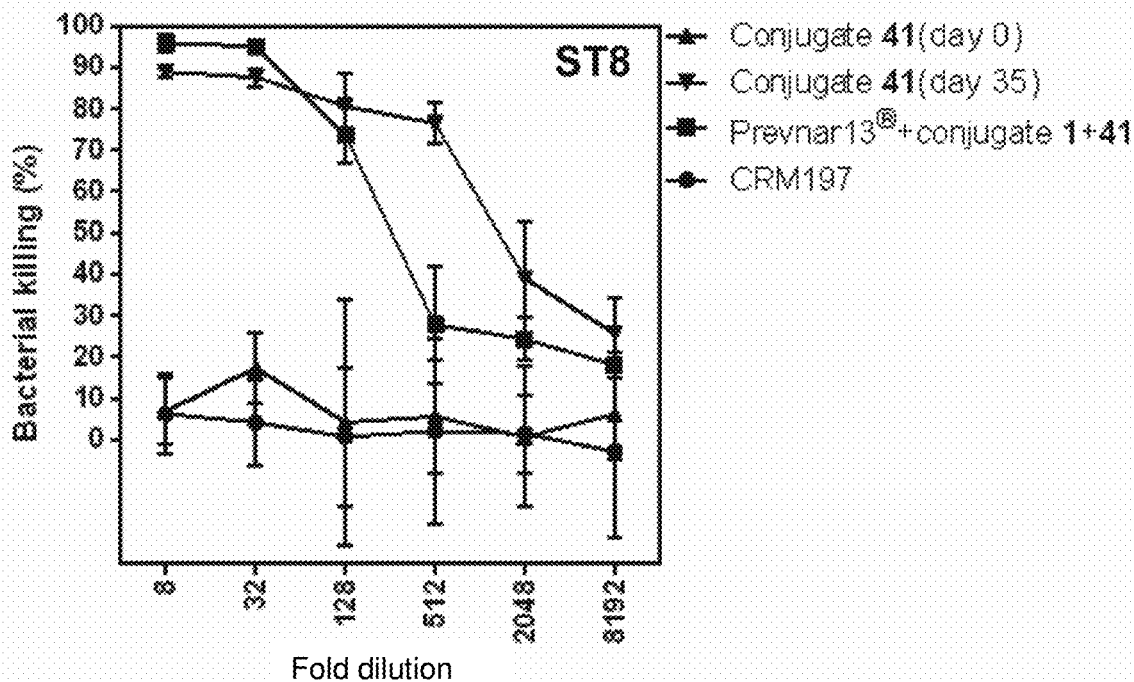
Figure 6:
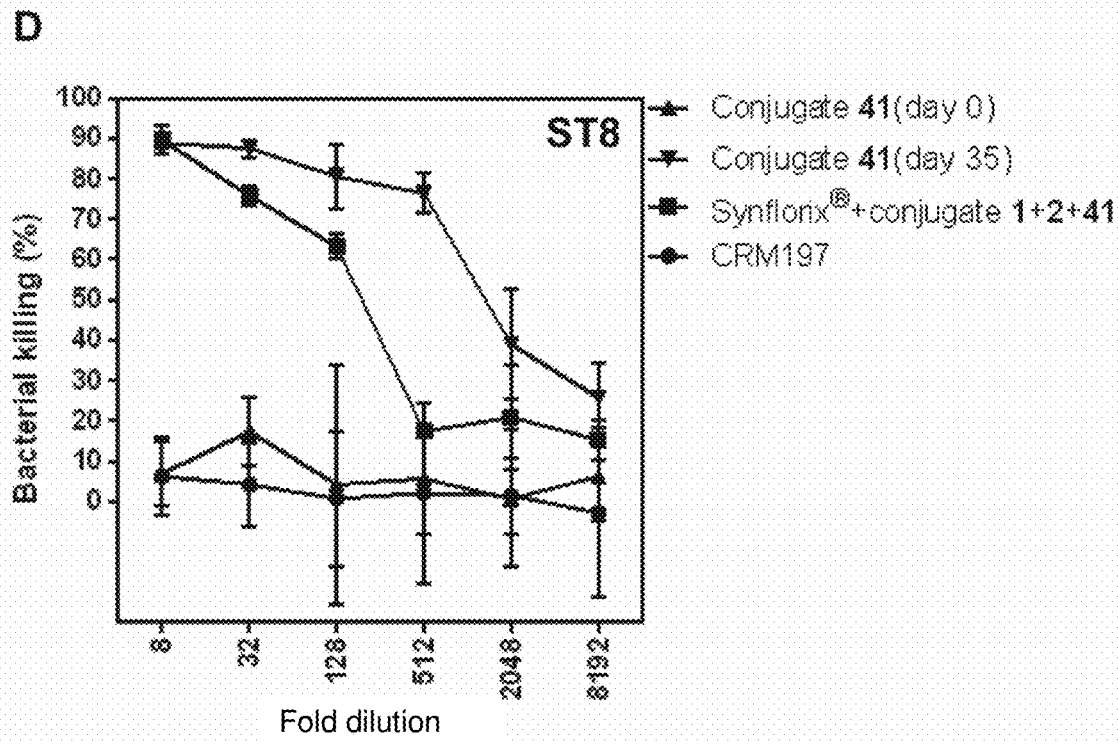

A flow cytometry-based assay was used to assess adsorption of conjugates 41 and 42 to Prevnar13®. Aliquots of 10% (50 μL) of a dose of Prevnar13® were mixed with different amounts of conjugate 41 or 42, equivalent to 25%, 100% or 400% of the normal glycan content (2.2 μg glycan/dose) of CPSs of other serotypes in the vaccine. Suspensions were incubated overnight at 4° C., particles were harvested (3000 g, 5 min, room temperature) and blocked with 10% (w/v) BSA in PBS (50 μL) for 30 min at room temperature. Particles were harvested and incubated with primary antibody samples (1:100 dilutions of ST1 typing serum and 10 μg/mL mAb 1H8 in 1% (w/v) BSA in PBS) for 30 min at room temperature. Particles were harvested, washed once with PBS (100 μL) and incubated with fluorescently labeled secondary antibodies (1:100 dilutions in 1% (w/v) BSA in PBS, 100 μL) for 20 min at room temperature. Particles were washed, suspended in PBS and analyzed by flow cytometry. Control samples included non-treated or CRM$_{197}$-treated (9.2 μg CRM$_{197}$/aliquot, corresponding to the CRM$_{197}$ dose of the highest conjugate concentration) Prevnar13® particles (see FIG. 5). Co-adsorbed conjugates 41 and 42 were stable for at least one week after adsorption.

Example D.3. Coformulation of Prevnar13® with Conjugate 1 and Conjugate 41

Conjugate 1 and conjugate 41 (2.2 μg glycan per dose) in 30 μL PBS were admixed to a full dose Prevnar13® for each immunization dose and incubated overnight at 4° C.

Example D.4. Coformulation of Synflorix® with Conjugate 1

Conjugate 1 (2.2 μg glycan per dose) in 40 μL PBS was admixed to a full dose Synflorix® for each immunization dose and incubated overnight at 4° C.

Example D.5. Coformulation of Synflorix® with Conjugate 41

Conjugate 41 (2.2 μg glycan per dose) in 40 μL PBS was admixed to a full dose Synflorix® for each immunization dose and incubated overnight at 4° C.

Example D.6. Coformulation of Synflorix® with Conjugate 1, 2 and 41

Conjugate 1, 2 and 41 (2.2 μg glycan per dose) in 40 μL PBS were admixed to a full dose Synflorix® for each immunization dose and incubated overnight at 4° C.

Example E. Immunogenicity Studies

Antisera, Polysaccharides and Carrier Protein

Human pooled pneumococcal antiserum (WHO 1st International Standard for Human Anti-pneumococcal capsule Reference Serum, prod. no. 007sp) was obtained from NIBSC (South Mimms, UK). Rabbit ST8 typing serum (Type 8 Neufeld antiserum), pneumococcal capsular polysaccharides and pneumococcal cell wall polysaccharide (CWPS) were purchased from SSI Diagnostica (Hillerød, Denmark).

Antibodies

Fluorescent antibodies were used from commercial sources: Goat anti-Rabbit IgG H+L FITC conjugate (abcam, Cambridge, UK), Goat anti-Human IgG H+L Alexa Fluor® 647 conjugate (life Technologies), Goat anti-Mouse IgG H+L FITC conjugate (Sigma-Aldrich), Goat anti-Mouse IgG H+L Alexa Fluor® 635 conjugate (life Technologies), Goat anti-Mouse IgM H chain Alexa Fluor® 680 conjugate (life Technologies), Donkey anti-Mouse IgM H chain Alexa Fluor® 594 conjugate (dianova, Hamburg, Germany).

Secondary antibodies used for ELISA and immunoblot were horseradish peroxidase (HRP)-labeled: goat anti-mouse IgG HRP conjugate (cat. no. 115-035-062, dianova, Hamburg, Germany), goat anti-mouse IgM H chain HRP conjugate (cat. no. 62-6820, Life Technologies) or goat anti-rabbit IgG (whole molecule)-peroxidase conjugate (cat. no. A6154, Sigma-Aldrich) and used according to the manufacturers' specifications.

Example E.1 Immunization in Rabbits

Rabbit immunization experiments were performed by Biogenes GmbH. Rabbits were housed and handled according to international animal regulations (EU Directive 2010/63/EU) and sanctioned by governmental authorities (Landesamt für Landwirtschaft, Lebensmittelsicherheit and Fischerei Mecklenburg-Vorpommern). Rabbits (female Zika rabbits, 10-12 weeks, 2.5-3 kg, n=3 per group) were immunized subcutaneously at four different sites. The rabbits (n=3 per group) were s.c. immunized three times with Prevnar13®, with Prevnar13® coformulated with conjugate 41 or with Prevnar13® coformulated with conjugate 42. Booster doses were given at days 14 and 28 using the same strategy. Sera were collected at days 0, 14, 21 and 35. Prevnar13® without any additive was used for control immunizations. Sera of Prevnar13®-immunized rabbits were pre-adsorbed to 5 µg pneumococcal CWPS and 5 µg/mL *S. pneumoniae* 22F CPS prior to evaluation by glycan microarray or ELISA. Serum was collected at day 35 and analyzed by ELISA and OPKA.

Example E.2 Enzyme-Linked Immunosorbent Assay (ELISA)

ELISA was performed using Costar™ high-binding polystyrene 96-well plates (cat. no. 3361, Corning, Corning, US). Plates were coated using native pneumococcal polysaccharides (SSI Diagnostica, Copenhagen) at a concentration of 10 µg/mL in PBS for 20 h at 4° C. Plates were blocked with 10% (v/v) fetal calf serum in PBS for 2 h at 37° C. and washed once with PBS-T. After applying cell culture supernatants or mAb dilutions (30-50 µL), plates were incubated for 1 h at 37° C., washed with PBS-T three times and treated with a horseradish peroxidase (HRP)-labeled secondary antibody. Plates were washed with PBS-T three times and HRP activity was measured with TMB substrate (BD Biosciences, San Jose, US) according to the manufacturer's instructions. Endpoint titers were determined as the reciprocal of the highest dilution resulting in an absorbance above a value of 0.1. The anti-polysaccharide IgG endpoint titers of rabbits immunized with Prevnar13® alone or coformulated with conjugate 41 or 42, as determined by polysaccharide ELISA are shown in the table below.

TABLE 1

Anti-polysaccharide IgG endpoint titers of rabbits immunized with Prevnar13® alone or coformulated with conjugate 41 or 42, as determined by polysaccharide ELISA.

| | Prevnar13® | | | Prevnar13® + conjugate 41 | | | Prevnar13® + conjugate 42 | | |
|---|---|---|---|---|---|---|---|---|---|
| | Rabbit 1 | Rabbit 2 | Rabbit 3 | Rabbit 1 | Rabbit 2 | Rabbit 3 | Rabbit 1 | Rabbit 2 | Rabbit 3 |
| ST8 | 400 | 1600 | 1600 | 12800 | 12800 | 6400 | 6400 | 3200 | 3200 |
| ST1 | 1600 | 1600 | 3200 | 6400 | 3200 | 1600 | 1600 | 1600 | 3200 |
| ST4 | 6400 | 25600 | 12800 | 6400 | 6400 | 3200 | 12800 | 12800 | 12800 |
| ST5 | 6400 | 12800 | 12800 | 6400 | 3200 | 3200 | 6400 | 3200 | 6400 |
| ST7F | 1600 | 6400 | 1600 | 800 | 1600 | 1600 | 1600 | 800 | 1600 |
| ST9V | 1600 | 3200 | 1600 | 3200 | 3200 | 1600 | 1600 | 800 | 3200 |
| ST19A | 1600 | 6400 | 6400 | 1600 | 6400 | 3200 | 12800 | 12800 | 3200 |

Example E.3 Opsonophagocytic Killing Assay (OPKA)

HL-60 cells were differentiated for one week with N,N-dimethylformamide as reported, washed twice with Hank's balanced sterile saline supplemented with 0.1% (w/v) gelatin (OPKA buffer) and diluted to a density of 107 cells/mL in the same buffer directly before use. Bacteria were grown in growth medium at 37° C./5% $CO_2$ to log phase (OD600 approx. 0.2-0.3), diluted in freezing medium to a density of 106 cfu/mL and frozen in 0.5 mL aliquots at −80° C. Bacteria were diluted with OPKA buffer and aliquoted (1000 cfu in 20 µL each) in a 96 well-plate. Bacterial suspensions were treated with mAb solutions or antiserum dilutions and incubated for 15 min at 37° C. Complement source (10% (v/v) of the total volume, rabbit complement, CedarLane, Ontario, Canada) and differentiated HL-60 cell suspension (40 µL, phagocyte/bacteria ratio 400:1) were added and the suspensions were incubated for 45 min at 37° C. with shaking. Opsonophagocytosis was performed in triplicates. An aliquot of the contents of each well was plated on Columbia Agar plates with 5% (v/v) sheep blood, and cfu were counted after incubation at 37° C./5% $CO_2$ overnight. Control wells lacked either antibody or complement sources. Killing was calculated relative to wells lacking antiserum. Antibody concentration in graphs relates to the initial opsonization stage (mAbs) or dilution after addition of all assay components (antisera).

Figure 2:
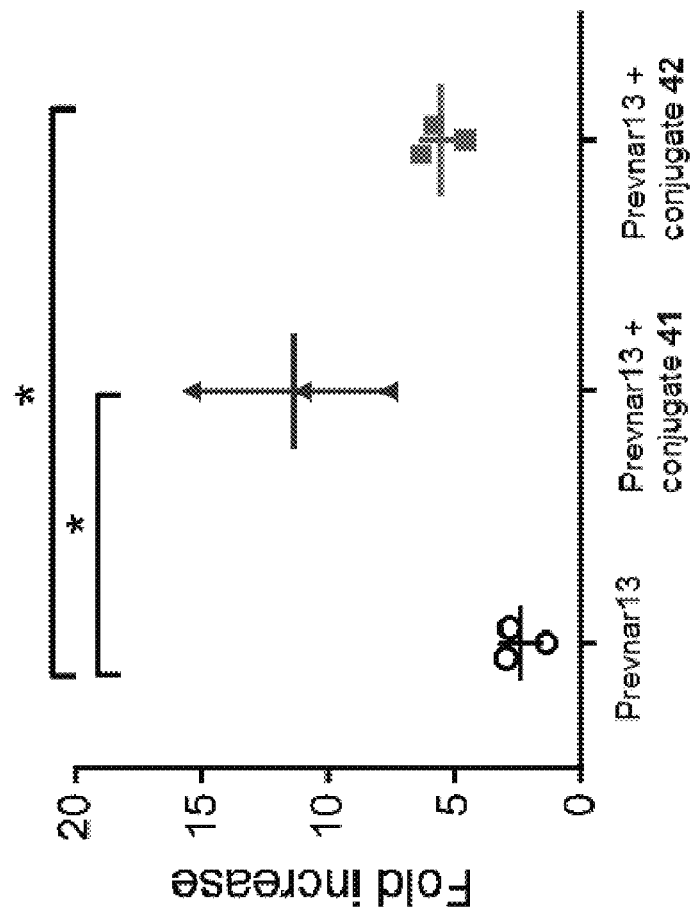
FIG. 2 (A) shows the evaluation of polysaccharide binding by rabbit sera at day 35 (1:200 dilution). Statistical analysis (two-tailed, unpaired t test) was performed and asterisk indicates P value: * P<0.05. Bars depict mean±SD of three rabbits per group. (B) shows a comparison of opsonophagocytic killing of *S. pneumoniae* serotype 8 pneumococci of pooled rabbit sera or human serum standard 007sp at different dilutions. Bars depict mean±SD of triplicate wells of one out of three independent experiments.

The coformulations containing Prevnar13® and conjugate 41 or 42 induced a pronounced immune response against *Streptococcus pneumoniae* serotype 8 CPS (see FIG. 1A and FIG. 2A) that induced opsonophagocytic killing of *Streptococcus pneumoniae* serotype 8 pneumococci (FIG. 2B). Thereby, 50% killing was achieved at serum dilutions between 1:32 and 1:128, well above the criteria of 1:8 for protective immunity against pneumococci and similar to the opsonophagocytic killing efficacy of 007sp, the reference serum established by the World Health Organization to evaluate new pneumococcal conjugate vaccines. Rabbits immunized with Prevnar13® alone developed a significantly lower immune response against *Streptococcus pneumoniae* serotype 8 with no detectable opsonophagocytic killing of *Streptococcus pneumoniae* serotype 8 bacteria (FIG. 1A). Coformulations with conjugate 41 or conjugate 42 did not impair the immunogenicity of other Prevnar13®-specific conjugates, as the binding capacity of rabbit sera towards six Prevnar13®-specific CPSs was unchanged (FIG. 1B-G). Thus, conjugate 41 and conjugate 42 induce a robust, antibacterial immune response when coformulated with a multivalent, polysaccharide conjugate vaccine.

Example F. Synthesis of Capsular Polysaccharides-$CRM_{197}$ Conjugates

Example F.1: Preparation of Serotype 1 *S. pneumoniae* Capsular Polysaccharide—$CRM_{197}$ Conjugate Preparation of Master and Working Cell Banks

*S. pneumoniae* serotype 1 was obtained from the American Type Culture Collection, ATCC, strain 6301. Several generations of seed stocks were created in order to expand the strain and remove components of animal origin (generations F1, F2, and F3). Two additional generations of seed stocks were produced. The first additional generation was made from an F3 vial, and the subsequent generation was made from a vial of the first additional generation. Seed vials were stored frozen (<−70° C.) with synthetic glycerol as a cryopreservative. In addition to frozen vials, lyophilized vials were prepared for the F4 generation. For cell bank preparation, all cultures were grown in a soy-based medium. Prior to freezing, cells were concentrated by centrifugation, spent medium was removed, and cell pellets were re-suspended in fresh medium containing a cryopreservative, such as synthetic glycerol.

Fermentation and Harvesting

Cultures from the working cell bank were used to inoculate seed bottles containing a soy-based medium. The bottles were incubated at 36° C.±2° C. without agitation until growth requirements were met. A seed bottle was used to inoculate a seed fermentor containing soy-based medium. A pH of about 7.0 was maintained with sterile sodium carbonate solution. After the target optical density was reached, the seed fermentor was used to inoculate the production fermentor containing soy-based medium. The pH was maintained with sterile sodium carbonate solution. The fermentation was terminated after cessation of growth or when the working volume of the fermentor was reached. An appropriate amount of sterile 12% deoxycholate sodium was added to the culture to lyse the bacterial cells and release cell-associated polysaccharide. After lysing, the fermentor contents were cooled. The pH of the lysed culture broth was adjusted to approximately pH 6.6 with acetic acid. The lysate was clarified by continuous flow centrifugation followed by depth filtration and 0.45 μm microfiltration.

In an alternate process, the fermentation pH of about 7.0 was maintained with 3N NaOH. After the target optical density was reached, the seed fermentor was used to inoculate the production fermentor containing soy-based medium. The pH was maintained with 3N NaOH. The fermentation was terminated after cessation of growth or when the working volume of the fermentor was reached. An appropriate amount of sterile 12% deoxycholate sodium was added to the culture to obtain a 0.12% concentration in the broth, to lyse the bacterial cells and release cell-associated polysaccharide. After lysing, the fermentor contents were held, with agitation, for a time interval between 8 and 24 hours at a temperature between 7° C. and 13° C., to assure that complete cellular lysis and polysaccharide release had occurred. Agitation during this hold period prevented lysate sediment from settling on the fermentor walls and pH probe, thereby allowing the pH probe integrity to be maintained. Next, the pH of the lysed culture broth was adjusted to approximately pH 5.0 with 50% acetic acid. After a hold time without agitation, for a time interval between 12 and 24 hours at a temperature between 15° C. and 25° C., a significant portion of the previously soluble proteins dropped out of solution as a solid precipitate with little loss or degradation of the polysaccharide, which remained in solution. The solution with the precipitate was then clarified by continuous flow centrifugation followed by depth filtration and 0.45 μm microfiltration.

Purification

The purification of the pneumococcal polysaccharide consisted of several concentration/diafiltration operations, precipitation/elution, column chromatography, and depth filtration steps. All procedures were performed at room temperature unless otherwise specified.

Clarified broth from the fermentor cultures of *S. pneumoniae* serotype 1 was concentrated and diafiltered using a 100 kDa MWCO (kilodalton molecular weight cutoff) filter. Diafiltration was accomplished using sodium phosphate buffer at neutral pH. Diafiltration removed the low molecular weight medium components from the higher molecular weight biopolymers such as nucleic acid, protein and polysaccharide.

The polysaccharide was precipitated from the concentrated and diafiltered solution by adding hexadecyltrimethyl ammonium bromide (HB) from a stock solution to give a final concentration of 1% HB (w/v). The polysaccharide/HB precipitate was captured on a depth filter and the filtrate was discarded. The polysaccharide precipitate was resolubilized and eluted by recirculating a sodium chloride solution through the precipitate-containing depth filter. The filters were then rinsed with additional sodium chloride solution.

Sodium iodide (NaI) was added to the polysaccharide solution from a stock NaI solution to achieve a final concentration of 0.5% to precipitate HB. The precipitate was removed by depth filtration. The filtrate contains the target polysaccharide. The precipitation vessel and the filter were rinsed with a NaCl/NaI solution and the rinse was combined with the partially purified polysaccharide solution. The filter was discarded. The polysaccharide was then filtered through a 0.2 μm filter.

The polysaccharide solution was concentrated on a 30 kDa MWCO ultrafilter and diafiltered with a sodium chloride solution.

The partially purified polysaccharide solution was further purified by filtration through a depth filter impregnated with activated carbon. After filtration, the carbon filter was rinsed with a sodium chloride solution. The rinse is combined with the polysaccharide solution, which is then filtered through a 0.2 μm filter.

The polysaccharide solution was concentrated on a 30 kDa MWCO ultrafilter and adjusted with a 1 M sodium phosphate buffer to achieve a final concentration of 0.025 M sodium phosphate. The pH was checked and adjusted to 7.0±0.2. The ceramic hydroxyapatite (HA) column was equilibrated with sodium phosphate buffer containing sodium chloride to obtain the appropriate conductivity (<15 μS). The polysaccharide solution was then loaded onto the column. Under these conditions, impurities bound to the resin and the polysaccharide was recovered in the flow-through from the column. The polysaccharide solution was filtered through 0.2 μm inline filters located before and after the column.

The polysaccharide solution was concentrated using a 30 kDa MWCO filter. The concentrate was then diafiltered with Water for Injection (WFI). The diafiltered polysaccharide solution was filtered through a 0.2 μm membrane filter into polypropylene bottles. Samples were removed for release testing and the purified polysaccharide was stored frozen at −25°±5° C.

Characterization

The $^1$H-NMR data of the purified polysaccharide can be compared to the $^1$H-NMR data of the polysaccharide molecule. The $^1$H-NMR spectrum showed a series of well-resolved signals (protons from the methyl group) for the quantitation of the O-acetyl functional group in the polysaccharide.

The identity of the monovalent polysaccharide was confirmed by countercurrent immunoelectrophoresis using specific antisera.

High performance gel filtration chromatography coupled with refractive index and multiangle laser light scattering (MALLS) detectors was used in conjunction with the sample concentration to calculate the molecular weight.

Size exclusion chromatography media (CL-4B) was used to profile the relative molecular size distribution of the polysaccharide.

Activation and Conjugation

Containers of purified polysaccharide were thawed and combined in a reaction vessel. To the vessel, 0.2 M sodium carbonate, pH 9.0 was added for partial deacetylation (hydrolysis) for 3 hours at 50° C. The reaction was cooled to 20° C. and neutralization was performed by 0.2 M acetic acid. Oxidation in the presence of sodium periodate was performed by incubation at 2-8° C., and the mixture was stirred for 15-21 hours.

The activation reaction mixture was concentrated and diafiltered 10× with 0.9% NaCl using a 30K MWCO membrane. The retentate was 0.2 μm filtered. The activated saccharide was filled into 100 mL glass lyophilization bottles and shell-frozen at −75° C. and lyophilized. "Shell-freezing" is a method for preparing samples for lyophilization (freeze-drying). Flasks are automatically rotated by motor driven rollers in a refrigerated bath containing alcohol or any other appropriate fluid. A thin coating of product is evenly frozen around the inside "shell" of a flask, permitting a greater volume of material to be safely processed during each freeze-drying run. These automatic, refrigerated units provide a simple and efficient means of pre-freezing many flasks at a time, producing the desired coatings inside, and providing sufficient surface area for efficient freeze-drying.

Bottles of lyophilized material were brought to room temperature and resuspended in CRM$_{197}$ solution at a saccharide/protein ratio of 2:1. To the saccharide/protein mixture 1M sodium phosphate buffer was added to a final 0.2M ionic strength and a pH of 7.5, then sodium cyanoborohydride was added. The reaction was incubated at 23° C. for 18 hours, followed by a second incubation at 37° C. for 72 hours. Following the cyanoborohydride incubations, the reaction mixture was diluted with cold saline followed by the addition of 1M sodium carbonate to adjust the reaction mixture to pH 9.0. Unreacted aldehydes were quenched by addition of sodium borohydride by incubation at 23° C. for 3-6 hours.

The reaction mixture was diluted 2-fold with saline and transferred through a 0.45-5 μm prefilter into a retentate vessel. The reaction mixture is diafiltered 30× with 0.15 M phosphate buffer, pH 6, and 20× with saline. The retentate was filtered through a 0.2 μm filter.

The conjugate solution was diluted to a target of 0.5 mg/mL in 0.9% saline, and then sterile filtered into final bulk concentrate (FBC) containers in a Class 100 hood. The conjugate was stored at 2-8° C.

Characterization

Size exclusion chromatography media (CL-4B) was used to profile the relative molecular size distribution of the conjugate.

The identity of the conjugate was confirmed by the slot-blot assay using specific antisera.

The saccharide and protein concentrations were determined by the uronic acid and Lowry assays, respectively. The ratio of saccharide to protein in the covalently bonded conjugate complex was obtained by the calculation:

Ratio=(μg/mL saccharide)/(μg/mL protein)

O-acetyl content was measured by the Hestrin method (Hestrin et. al., *J. Biol. Chem.* 1949, 180, p. 249). The ratio of O-acetyl concentration to total saccharide concentration gave μmoles of O-acetyl per mg of saccharide.

Example F.2: Preparation of Serotype 3 *S. pneumoniae* Capsular Polysaccharide—CRM$_{197}$ Conjugate Preparation of Master and Working Cell Banks

*S. pneumoniae* serotype 3 was obtained from American Type Culture Collection, ATCC, strain 6303. For preparation of the cell bank system, see Example F.1.

Fermentation and Harvesting

Cultures from the working cell bank were used to inoculate seed bottles containing soy-based medium. The bottles were incubated at 36° C.±2° C. without agitation until growth requirements were met. A seed bottle was used to inoculate a seed fermentor containing soy-based medium. A pH of about 7.0 was maintained with sterile sodium carbonate solution. After the target optical density was reached, the seed fermentor was used to inoculate an intermediate seed fermentor. After the target optical density was reached, the intermediate seed fermentor was used to inoculate the production fermentor. The pH was maintained with sterile sodium carbonate solution. The fermentation was terminated after the working volume of the fermentor was reached. An appropriate amount of sterile 12% sodium deoxycholate was added to the culture to lyse the bacterial cells and release cell-associated polysaccharide. After lysing, the fermentor contents were cooled. The pH of the lysed culture broth was adjusted to approximately pH 6.6 with acetic acid. The lysate was clarified by continuous flow centrifugation followed by depth filtration and 0.45 μm microfiltration.

Purification

The purification of the pneumococcal polysaccharide consisted of several concentration/diafiltration operations, precipitation/elution, column chromatography, and depth filtration steps. All procedures were performed at room temperature unless otherwise specified.

Clarified broth from the fermentor cultures of *S. pneumoniae* serotype 3 were concentrated and diafiltered using a 100 kDa MWCO filter. Diafiltration was accomplished using sodium phosphate buffer at neutral pH. Diafiltration removed the low molecular weight medium components from the higher molecular weight biopolymers such as nucleic acid, protein and polysaccharide.

Prior to the addition of hexadecyltrimethyl ammonium bromide (HB), a calculated volume of a NaCl stock solution was added to the concentrated and diafiltered polysaccharide solution to give a final concentration of 0.25 M NaCl. The polysaccharide was then precipitated by adding HB from a stock solution to give a final concentration of 1% HB (w/v). The polysaccharide/HB precipitate was captured on a depth filter and the filtrate was discarded. The polysaccharide precipitate was resolubilized and eluted by recirculating a sodium chloride solution through the precipitate-containing depth filter. The filters were then rinsed with additional sodium chloride solution.

Sodium iodide (NaI) was added to the polysaccharide solution from a stock NaI solution to achieve a final concentration of 0.5% to precipitate HB. The precipitate was removed by depth filtration. The filtrate contained the target polysaccharide. The precipitation vessel and the filter were rinsed with a NaCl/NaI solution and the rinse was combined with the partially purified polysaccharide solution. The filter was discarded. The polysaccharide was then filtered through a 0.2 μm filter. The polysaccharide solution was concentrated on a 30 kDa MWCO ultrafilter and diafiltered with a sodium chloride solution.

The partially purified polysaccharide solution was further purified by filtration through a depth filter impregnated with activated carbon. After filtration, the carbon filter was rinsed with a sodium chloride solution. The rinse was combined with the polysaccharide solution, which was then filtered through a 0.2 μm filter.

The polysaccharide solution was concentrated on a 30 kDa MWCO ultrafilter and adjusted with a 1 M sodium phosphate buffer to achieve a final concentration of 0.025 M sodium phosphate. The pH was checked and adjusted to 7.0±0.2.

The ceramic hydroxyapatite (HA) column was equilibrated with sodium phosphate buffer containing sodium chloride to obtain the appropriate conductivity (15 μS). The polysaccharide solution was then loaded onto the column. Under these conditions, impurities bound to the resin and the polysaccharide was recovered in the flow-through from the column. The polysaccharide was flushed through the column with buffer and was filtered through a 0.2 μm filter.

The polysaccharide solution was concentrated using a 30 kDa MWCO filter. The concentrate was then diafiltered with WFI.

The diafiltered polysaccharide solution was filtered through a 0.2 μm membrane filter into stainless steel containers. Samples were removed for release testing and the purified polysaccharide was stored frozen at −25°±5° C.

Activation and Conjugation

Containers of purified serotype 3 saccharide were thawed and combined in a reaction vessel. To the vessel, WFI and 2M acetic acid were added to a final concentration of 0.2 M and 2 mg/mL saccharide. The temperature of the solution was raised to 85° C. for one hour to hydrolyze the polysaccharide. The reaction was cooled to <25° C. and 1 M magnesium chloride was added to a final concentration of 0.1 M. Oxidation in the presence of sodium periodate was performed by incubation for 16-24 hours at 23° C.

The activation reaction mixture was concentrated and diafiltered 10× with WFI using a 100K MWCO membrane. The retentate was filtered through a 0.2-μm filter.

For compounding, 0.2M sodium phosphate, pH 7.0, was added to the activated saccharide to a final concentration of 1 OmM and a pH of 6.0-6.5. $CRM_{197}$ carrier protein was mixed with the saccharide solution to a ratio of 2 g of saccharide per 1 g of $CRM_{197}$. The combined saccharide/protein solution was filled into 100 mL glass lyophilization bottles with a 5 OmL target fill, shell-frozen at −75° C., and lyophilized.

Bottles of co-lyophilized saccharide/protein material were brought to room temperature and resuspended in 0.1M sodium phosphate buffer, pH 7.0, to a final saccharide concentration of 20 mg/mL The pH was adjusted to 6.5 and then a 0.5 molar equivalent of sodium cyanoborohydride was added. The reaction was incubated at 37° C. for 48 hours. Following the cyanoborohydride incubation, the reaction mixture was diluted with cold 5 mM succinate/0.9% saline buffer. Unreacted aldehydes were quenched by the addition of sodium borohydride and incubation at 23° C. for 3-6 hours. The reaction mixture was transferred through a 0.45-5 μm prefilter into a retentate vessel.

The reaction mixture was diafiltered 30× with 0.1M phosphate buffer (pH 9), 20× with 0.15M phosphate butter (pH 6), and 20× with 5 mM succinate/0.9% saline. The retentate was filtered through a 0.2-μm filter.

The conjugate solution was diluted to a saccharide target of 0.5 mg/mL, and then sterile filtered into FBC containers in a Class 100 hood. The conjugate was stored at 2-8° C.

Characterization

Size exclusion chromatography media (CL-4B) was used to profile the relative molecular size distribution of the conjugate.

The identity of the conjugate was confirmed by the slot-blot assay using specific antisera.

The saccharide and protein concentrations were determined by the Anthrone and Lowry assays, respectively. The ratio of saccharide to protein in the covalently bonded conjugate complex was obtained by the calculation:

$$\text{Ratio} = (\mu g/mL \text{ saccharide})/(\mu g/mL \text{ protein})$$

Example F.3: Preparation of Serotype 5 S. pneumoniae Capsular Polysaccharide—$CRM_{197}$ Conjugate S. pneumoniae serotype 5 was obtained from American Type Culture Collection, ATCC, strain 6305. For preparation of the cell bank system, see Example F.1. For fermentation, harvesting, purification and characterization of the polysaccharide, see Example F.1.

Alternate Fermentation Process

Cultures from the working cell bank were used to inoculate seed bottles containing a soy-based medium and a 10 mM sterile $NaHCO_3$ solution. The bottles were incubated at 36° C.±2° C. without agitation until growth requirements were met. A seed bottle was used to inoculate a seed fermentor containing soy-based medium and a 10 mM sterile $NaHCO_3$ solution. A pH of about 7.0 was maintained with 3N NaOH. After the target optical density was reached, the seed fermentor was used to inoculate the production fermentor containing soy-based medium with a 10 mM $NaHCO_3$ concentration. The pH was maintained with 3N NaOH. The fermentation was terminated after cessation of growth or when the working volume of the fermentor was reached. An appropriate amount of sterile 12% sodium deoxycholate was added to the culture to obtain a 0.12% concentration in the broth, to lyse the bacterial cells and release cell-associated polysaccharide. After lysing, the fermentor contents were held, with agitation, for a time interval between 8 and 24 hours at a temperature between 7° C. and 13° C. to assure that complete cellular lysis and polysaccharide release had occurred. Agitation during this hold period prevented lysate sediment from settling on the fermentor walls and pH probe, thereby allowing the pH probe integrity to be maintained. Next, the pH of the lysed culture broth was adjusted to approximately pH 4.5 with 50% acetic acid. After a hold time without agitation, for a time interval between 12 and 24 hours at a temperature between 15° C. and 25° C., a significant portion of the previously soluble proteins dropped out of solution as a solid precipitate with little loss or degradation of the polysaccharide, which remained in solution. The solution with the precipitate was then clarified by continuous flow centrifugation followed by depth filtration and 0.45 µm microfiltration.

Activation and Conjugation

Containers of serotype 5 saccharide were thawed and combined in a reaction vessel. To the vessel, 0.1 M sodium acetate, pH 4.7, was added followed by oxidation in the presence of sodium periodate by incubation for 16-22 hours at 23° C. The activation reaction mixture was concentrated and diafiltered 10× with WFI using a 100K MWCO membrane. The retentate was filtered through a 0.2 µm filter.

The serotype 5 activated saccharide was combined with $CRM_{97}$ at a ratio of 0.8:1. The combined saccharide/protein solution was filled into 100 mL glass lyophilization bottles (50 mL target fill), shell-frozen at −75° C., and co-lyophilized. Bottles of co-lyophilized material were brought to room temperature and resuspended in 0.1M sodium phosphate, pH 7.5, and sodium cyanoborohydride was added. The reaction was incubated at 30° C. for 72 hours, followed by a second addition of cyanoborohydride and incubated at 30° C. for 20-28 hours.

Following the cyanoborohydride incubations, the reaction mixture was diluted 2-fold with saline and transferred through a 0.45-5 µm prefilter into a retentate vessel.

The reaction mixture was diafiltered 30× with 0.01M phosphate buffer, pH 8, 20× with 0.15M phosphate buffer, pH 6, and 20× with saline. The retentate was filtered through a 0.2 µm filter.

The conjugate solution was diluted to a saccharide target of 0.5 mg/mL, and then sterile filtered into FBC containers in a Class 100 hood. The conjugate was stored at 2-8° C.

For the characterization of the conjugate, see Example F.1.

Example F.4: Preparation of Serotype 6A *S. pneumoniae* Capsular Polysaccharide—$CRM_{197}$ Conjugate

*S. pneumoniae* serotype 6A was obtained from American Type Culture Collection, ATCC, strain 6306. For preparation of the cell bank system, see Example F.1. For fermentation, harvesting and purification of the polysaccharide, see Example F.1, except that during purification, the 30 kDa MWCO concentration step, prior to the chromatography step, is omitted.

Activation and Conjugation

Serotype 6A polysaccharide is a high molecular weight polymer that had to be reduced in size prior to oxidation. Containers of serotype 6A saccharide were thawed and combined in a reaction vessel. To the vessel, 2M acetic acid was added to a final concentration of 0.1M for hydrolysis for 1.5 hours at 60° C. The reaction was cooled to 23° C. and neutralization was performed by adjusting the reaction mixture with 1M NaOH to pH 6. Oxidation in the presence of sodium periodate was performed by incubation at 23° C. for 14-22 hours. The activation reaction mixture was concentrated and diafiltered 10× with WFI using a 100K MWCO membrane. The retentate was filtered through a 0.2 µm filter.

Serotype 6A was compounded with sucrose and filled into 100 mL glass lyophilization bottles (5 OmL target fill) and shell-frozen at −75° C. and lyophilized.

Bottles of lyophilized material were brought to room temperature and resuspended in dimethylsulfoxide (DMSO) at a saccharide/protein ratio of 1:1. After addition of sodium cyanoborohydride, the reaction mixture was incubated at 23° C. for 18 hours. Following the cyanoborohydride incubation, the reaction mixture was diluted with cold saline. Unreacted aldehydes were quenched by addition of sodium borohydride by incubation at 23° C. for 3-20 hours.

The diluted reaction mixture was transferred through a 5 µm prefilter into a retentate vessel. The reaction mixture was diafiltered 10× with 0.9% NaCl and 30× with succinate-buffered NaCl. The retentate was filtered through a 0.2 µm filter. The conjugate solution was diluted to a saccharide target of 0.5 mg/mL, and then sterile filtered into FBC containers in a Class 100 hood. The conjugate was stored at 2-8° C. For the characterization of the conjugate, see Example F.1.

Example F.5: Preparation of Serotype 7F *S. pneumoniae* Capsular Polysaccharide $CRM_{197}$ Conjugate

*S. pneumoniae* serotype 7F was obtained from American Type Culture Collection, ATCC, strain 10351. For preparation of the cell bank system, and for fermentation and harvesting of the polysaccharide, see Example F.2. For an alternate fermentation and harvesting process, see the alternate process described in Example F.1.

Purification

The purification of the pneumococcal polysaccharide consisted of several concentration/diafiltration operations, precipitation/elution, column chromatography, and depth filtration steps. All procedures were performed at room temperature unless otherwise specified.

Clarified broth from fermentor cultures of *S. pneumoniae* serotype 7F were concentrated and diafiltered using a 100 kDa MWCO filter. Diafiltration was accomplished using sodium phosphate buffer at neutral pH. Diafiltration removed the low molecular weight medium components from the higher molecular weight biopolymers such as nucleic acid, protein and polysaccharide.

Serotype 7F does not form a precipitate with HB. Instead, impurities were precipitated from the concentrated and diafiltered solution by adding the HB from a stock solution to a final concentration of 1% HB. The precipitate was captured on a depth filter and the filter was discarded. The polysaccharide was contained in the filtrate.

Sodium iodide (NaI) was added to the polysaccharide solution from a stock NaI solution to achieve a final concentration of 0.5% to precipitate HB. The precipitate was removed by depth filtration. The filtrate contained the target polysaccharide. The precipitation vessel and the filter were rinsed with a NaCl/NaI solution and the rinses were combined with the partially purified polysaccharide solution. The filter was discarded. The polysaccharide was then filtered through a 0.2 µm filter.

The polysaccharide solution was concentrated on a 30 kDa MWCO ultrafilter and diafiltered with a sodium chloride solution. The partially purified polysaccharide solution was further purified by filtration through a depth filter impregnated with activated carbon. After filtration, the carbon filter was rinsed with a sodium chloride solution. The rinse was combined with the polysaccharide solution, which was then filtered through a 0.2 µm filter.

The polysaccharide solution was concentrated on a 30 kDa MWCO ultrafilter and adjusted with a 1M sodium phosphate buffer to achieve a final concentration of 0.025M sodium phosphate. The pH was checked and adjusted to 7.0±0.2.

The ceramic hydroxyapatite (HA) column was equilibrated with sodium phosphate buffer containing sodium chloride to obtain the appropriate conductivity (15 µS). The polysaccharide solution was then loaded onto the column. Under these conditions, impurities bound to the resin and the polysaccharide was recovered in the flow-through from the column. The polysaccharide was flushed through the column with buffer and was filtered through a 0.2 µm filter.

The polysaccharide solution was concentrated using a 30 kDa MWCO filter. The concentrate was then diafiltered with WFI. The diafiltered polysaccharide solution was filtered through a 0.2 µm membrane filter into stainless steel containers. Samples were removed for release testing and the purified polysaccharide was stored at 2°-8° C.

Activation and Conjugation

Oxidation in the presence of sodium periodate was performed by incubation for 16-24 hrs at 23° C.

The activation reaction mixture was concentrated and diafiltered 10× with 10 mM NaOAc, pH 4.5, using a 100K MWCO membrane. The retentate was filtered through a 0.2 µm filter. Serotype 7F was filled into 100 mL glass lyophilization bottles (50 ml. target fill) and shell-frozen at −75° C. and lyophilized.

Bottles of lyophilized serotype 7F and CRM$_{197}$ were brought to room temperature and resuspended in DMSO at a saccharide/protein ratio of 1.5:1. After the addition of sodium cyanoborohydride, the reaction was incubated at 23° C. for 8-10 hours. Unreacted aldehydes were quenched by the addition of sodium borohydride by incubation at 23° C. for 16 hours.

The reaction mixture was diluted 10-fold with cold saline and transferred through a 5 µm prefilter into a retentate vessel. The reaction mixture was diafiltered 10× with 0.9% saline and 30× with succinate-buffered saline. The retentate was filtered through a 0.2 µm filter.

The conjugate solution was diluted to a saccharide target of 0.5 mg/mL 0.9% saline, and then sterile filtered into FBC containers in a Class 100 hood. The conjugate was stored at 2-8° C.

Example F.6: Preparation of Serotype 19A *S. pneumoniae* Capsular Polysaccharide—CRM$_{197}$ Conjugate

*S. pneumoniae* serotype 19A was obtained from American Type Culture Collection, ATCC, strain 10357. For preparation of the cell bank system, see Example F.1. For fermentation, harvesting and purification of the polysaccharide, see Example F.4.

Activation and Conjugation

Containers of serotype 19A saccharide were thawed and combined in a reaction vessel. Sodium acetate was added to 10 mM (pH 5.0) and oxidation was carried out in the presence of sodium periodate by incubation for 16-24 hrs at 23° C.

The activation reaction mixture was concentrated and diafiltered 10× with 10 mM acetate, pH 5.0, using a 100K MWCO membrane. The retentate was filtered through a 0.2 µm filter.

The activated saccharide was compounded with sucrose followed by the addition of CRM$_{197}$. The serotype 19A activated saccharide and CRM$_{197}$ mixture (0.8:1 ratio) was filled into 100 mL glass lyophilization bottles (50 mL target fill) and shell-frozen at −75° C. and lyophilized.

Bottles of lyophilized material were brought to room temperature and resuspended in DMSO. To the saccharide/protein mixture, sodium cyanoborohydride (100 mg/ml) was added. The reaction was incubated at 23° C. for 15 hours. Following the cyanoborohydride incubation, unreacted aldehydes were quenched by the addition of sodium borohydride by incubation at 23° C. for 3-20 hours.

The reaction mixture was diluted 10-fold with cold saline and transferred through a 5 µm prefilter into a retentate vessel. The reaction mixture was diafiltered 10× with 0.9% NaCl, 0.45-µm filtered, and 30× with diafiltration using 5 mM succinate/0.9% NaCl buffer, pH 6. The retentate was filtered through a 0.2 µm filter.

The conjugate solution was diluted to a target of 0.5 mg/mL using 5 mM succinate/0.9% saline, and then sterile filtered into FBC containers in a Class 100 hood. The conjugate was stored at 2-8° C.

For characterization of the conjugate, see Example F.2.

Example F.7: Preparation of Serotype 4, 6B, 9V, 14, 18C, 19F and 23F *S. pneumoniae* Capsular Polysaccharide—CRM$_{197}$ Conjugates Preparation of the *S. pneumoniae* Seed Culture

*S. pneumoniae* serotypes 4, 6B, 9V, 14, 18C, 19F and 23F were obtained from American Type Culture Collection, ATCC, strain 6304, strain 6326, strain 10368, strain 6314, strain 10356, strain 6319 and strain 6323.

Separately, one vial of each of the desired serotypes of *Streptococcus pneumoniae* was used to start a fermentation batch. Two bottles containing a soy-based medium and phenol red were adjusted to a pH range of 7.4±0.2 using sodium carbonate, and the required volume of 50% dextrose/1% magnesium sulfate solution was then added to the bottles. The two bottles were inoculated with different amounts of seed. The bottles were incubated at 36°±2° C. until the medium turned yellow. Following incubation, samples were removed from each bottle and tested for optical density (OD) (0.3 to 0.9) and pH (4.6 to 5.5). One of the two bottles was selected for inoculation of the seed fermentor.

Soy-based medium was transferred to the seed fermentor and sterilized. Then a volume of 50% dextrose/1% magnesium sulfate solution was added to the fermentor. The pH and agitation of the seed fermentor were monitored and controlled (pH 6.7 to 7.4). The temperature was maintained at 36°±2° C. The seed inoculum (bottle) was aseptically connected to the seed fermentor and the inoculum was transferred. The fermentor was maintained in pH control and samples were periodically removed and tested for OD and pH. When the desired OD of 0.5 at 600 nm was reached, the intermediate fermentor was inoculated with the fermentation broth from the seed fermentor.

Soy-based medium was transferred to the intermediate fermentor and sterilized. Then a volume of 50% dextrose/1% magnesium sulfate solution was added to the fermentor. The pH and agitation of the intermediate fermentor were monitored and controlled (pH 6.7 to 7.4). The temperature was maintained at 36°±2° C. The contents of the seed fermentor were transferred to the intermediate fermentor. The fermentor was maintained in pH control and samples were periodically removed and tested for OD and pH. When the desired OD of 0.5 at 600 nm was reached, the production fermentor was inoculated with the fermentation broth from the intermediate fermentor.

Soy-based medium was transferred to the production fermentor and sterilized. Then a volume of 50% dextrose/

1% magnesium sulfate solution was added to the fermentor. The pH and agitation of the production fermentor were monitored and controlled (pH 6.7 to 7.4). The temperature was maintained at 36°±2° C. The fermentor was maintained in pH control and samples were periodically removed and tested for OD and pH, until the fermentation was complete.

Deoxycholate sodium was added to the fermentor to a final concentration of approximately 0.12% w/v. The culture was mixed for a minimum of thirty minutes and the temperature set point was reduced to 10° C. The culture was incubated overnight and following confirmation of inactivation, the pH of the culture was adjusted to between 6.4 and 6.8, as necessary, with 50% acetic acid. The temperature of the fermentor was increased to 20°±5° C. and the contents were transferred to the clarification hold tank.

The contents of the clarification hold tank (including the cellular debris) were processed through a centrifuge at a flow rate between 25 and 600 liters per hour (except serotype 4, wherein the cell debris was discarded and the flow rate tightened to between 25 and 250 liters per hour). Samples of the supernatant were removed and tested for OD. The desired OD during the centrifugation was <0.15. Initially, the supernatant was recirculated through a depth filter assembly until an OD of 0.05±0.03 was achieved. Then the supernatant was passed through the depth filter assembly and through a 0.45 µm membrane filter to the filtrate hold tank.

Subsequently, the product was transferred through closed pipes to the purification area for processing.

All of the above operations (centrifugation, filtration and transfer) were performed between 10° C. to 30° C.

For an alternate fermentation and harvesting process for serotypes 4 and 6B, see the alternate process described in Example F.1.

Purification

The purification of each pneumococcal polysaccharide consisted of several concentration/diafiltration operations, precipitation/elution, column chromatography, and depth filtration steps. All procedures were performed at room temperature unless otherwise specified.

Clarified broth from the fermentor cultures of the desired *S. pneumoniae* serotype was concentrated and diafiltered using a 100 kDa MWCO filter. Diafiltration was accomplished using sodium phosphate buffer at pH<9.0. Diafiltration removed the low molecular weight medium components from the higher molecular weight biopolymers such as nucleic acid, protein and polysaccharide.

The polysaccharide was precipitated from the concentrated and diafiltered solution by adding HB from a stock solution to give a final concentration of 1% HB (w/v) (except serotype 23F, which had a final concentration of 2.5%). The polysaccharide/HB precipitate was captured on a depth filter and the filtrate was discarded. (Note: serotype 14 does not precipitate; therefore the filtrate was retained.) The polysaccharide precipitate was resolubilized and eluted by recirculating a sodium chloride solution through the precipitate-containing depth filter. The filters were then rinsed with additional sodium chloride solution.

Sodium iodide (NaI) was added to the polysaccharide solution from a stock NaI solution to achieve a final concentration of 0.5% to precipitate HB (except for Serotype 6B, which had a final concentration of 0.25%). The precipitate was removed by depth filtration. The filtrate contained the target polysaccharide. The filter was discarded. The polysaccharide was then filtered through a 0.2 µm filter.

The polysaccharide solution was concentrated on a 30 kDa MWCO ultrafilter and diafiltered with a sodium chloride solution.

The partially purified polysaccharide solution was further purified by filtration through a depth filter impregnated with activated carbon. After filtration, the carbon filter was rinsed with a sodium chloride solution. The rinse was combined with the polysaccharide solution, which was then filtered through a 0.2 µm filter.

The polysaccharide solution was concentrated on a 30 kDa MWCO ultrafilter and the filter was rinsed with a sodium chloride solution. The pH was checked and adjusted to 7.0±0.3.

The ceramic hydroxyapatite (HA) column was equilibrated with sodium phosphate buffer containing sodium chloride until the pH is 7.0±0.3 and the conductivity was 26+4 µS. The polysaccharide solution was then loaded onto the column. Under these conditions, impurities bound to the resin and the polysaccharide was recovered in the flow through from the column. The polysaccharide solution was filtered through a 0.2 µm filter. The polysaccharide solution was concentrated using a 30 kDa MWCO filter.

The concentrate was then diafiltered with WFI until the conductivity was <15 µS.

The diafiltered polysaccharide solution was filtered through a 0.2 µm membrane filter into bulk containers and stored at 2-8° C.

Activation Process

The different serotype saccharides follow different pathways for activation (hydrolysis or no hydrolysis prior to activation) and conjugation (aqueous or DMSO reactions) as described in this example.

Polysaccharide was transferred from the bulk containers to the reactor vessel. The polysaccharide was then diluted in WFI and sodium phosphate to a final concentration range of 1.6-2.4 mg/mL Step 1

For serotypes 6B, 9V, 14, 19F and 23F, pH was adjusted to pH 6.0±0.3.

For serotype 4, hydrochloric acid (0.01M final acid concentration) was added and the solution was incubated for 25-35 minutes at 45°±2° C. Hydrolysis was stopped by cooling to 21-25° C. and adding 1M sodium phosphate to a target of pH 6.7±0.2. An in-process test was done to confirm an appropriate level of depyruvylation.

For serotype 18C, glacial acetic acid (0.2 M final acid concentration) was added and the solution was incubated for 205-215 minutes at 94°±2° C. Temperature was then decreased to 21-25° C. and 1-2 M sodium phosphate was added to a target of pH 6.8±0.2.

Step 2: Periodate Reaction

The required sodium periodate molar equivalents for pneumococcal saccharide activation was determined using total saccharide content (except for serotype 4). For serotype 4, a ratio of 0.8-1.2 moles of sodium periodate per mole of saccharide was used. With thorough mixing, the oxidation reaction was allowed to proceed between 16 to 20 hours at 21-25° C. for all serotypes except 19F for which the temperature was ≤15° C.

Step 3: Ultrafiltration

The oxidized saccharide was concentrated and diafiltered with WFI (0.01 M sodium phosphate buffer pH 6.0 for serotype 19F) on a 100 kDa MWCO ultrafilter (5 kDa ultrafilter for 18C). The permeate was discarded and the retentate was filtered through a 0.22 µm filter.

Step 4: Lyophilization

For serotypes 4, 9V, and 14 the concentrated saccharide was mixed with $CRM_{197}$ carrier protein, filled into glass bottles, shell-frozen and stored at <−65° C. The frozen concentrated saccharide-$CRM_{197}$ was lyophilized and then stored at −25°±5° C. For serotypes 6B, 19F, and 23F a specified amount of sucrose was added which was calculated to achieve a 5%±3% sucrose concentration in the conjugation reaction mixture. Serotype 18C did not require sucrose addition. The concentrated saccharide was then filled into glass bottles, shell-frozen and stored at <−65° C. The frozen concentrated saccharide was lyophilized and then stored at −25°±5° C.

Conjugation Process

Two conjugation processes were used: aqueous conjugation for serotypes 4, 9V, 14 and 18C, and DMSO conjugation for serotypes 6B, 19F and 23F.

Aqueous Conjugation

Step 1: Dissolution

For serotypes 4, 9V and 14, the lyophilized activated saccharide-$CRM_{197}$ mixture was thawed and equilibrated at room temperature. The lyophilized activated saccharide-$CRM_{197}$ was then reconstituted in 0.1M sodium phosphate buffer at a typical ratio of:

1 L of buffer per 16-24 g of saccharide for serotype 4 and 9V;

1 L of buffer per 6-10 g of saccharide for serotype 14;

The reaction mixture was incubated at 37°±2° C. until total dissolution for the serotype 9V and at 23°±2° C. for serotypes 4 and 14.

For serotype 18C, the lyophilized saccharide was reconstituted in a solution of $CRM_{197}$ in 1M dibasic sodium phosphate at a typical ratio of 0.11 L of sodium phosphate per 1 L of $CRM_{197}$ solution. The reaction mixture (8-12 g/L saccharide concentration) was incubated at 23°+2° C. until total dissolution.

The pH was tested as an in-process control at this stage.

Step 2: Conjugation Reaction

For serotypes 4 and 9V, the conjugation reaction was initiated by adding the sodium cyanoborohydride solution (100 mg/mL) to achieve 1.0-1.4 moles sodium cyanoborohydride per mole of saccharide. The reaction mixture was incubated for 44-52 hours at 37°±2° C. The temperature was then reduced to 23°±2° C. and sodium chloride 0.9% was added to the reactor. Sodium borohydride solution (100 mg/mL) was added to achieve 1.8-2.2 molar equivalents of sodium borohydride per mole saccharide. The mixture was incubated for 3-6 hours at 23°±2° C. The mixture was diluted with sodium chloride 0.9% and the reactor was rinsed. The diluted conjugation mixture was filtered using a 1.2 µm pre-filter into a holding vessel.

For serotypes 14 and 18C, the conjugation reaction was initiated by adding the cyanoborohydride solution (100 mg/mL) to achieve 1.0-1.4 moles of sodium cyanoborohydride per mole of saccharide. The reaction mixture was incubated for 12-24 hours at 23°±2° C. The temperature was increased to 37°±2° C. and the reaction was incubated for 72-96 hours. The temperature was then reduced to 23°±2° C. and 0.9% sodium chloride was added to the reactor. Sodium borohydride solution (100 mg/mL) was added to achieve 1.8-2.2 molar equivalents of sodium borohydride per mole of saccharide. The mixture was incubated for 3-6 hours at 23°±2° C. The mixture was diluted with 0.9% sodium chloride and the reactor was rinsed. The diluted conjugation mixture was then filtered using a 1.2 µm pre-filter into a holding vessel.

Step 3: Ultrafiltration 100 kDa

The diluted conjugation mixture was concentrated and diafiltrated on a 100 kDa MWCO ultrafilter with either a minimum of 15 volumes (serotype 4) or 40 volumes (serotypes 9V, 14, and 18C) of 0.9% sodium chloride. The permeate was discarded.

For serotype 4, the retentate was filtered through a 0.45 µm filter. An in-process control (saccharide content) was performed at this step.

Step 4: HA Column Purification

This step was only performed for the serotype 4 conjugate. The HA column was first neutralized using 0.5M sodium phosphate buffer (pH 7.0+0.3) and then equilibrated with 0.9% sodium chloride. The filtered retentate (serotype 4) was loaded onto the column at a flow rate of 1.0 L/min. The column was washed with 0.9% sodium chloride at a flow rate of <2.0 L/min. The product was then eluted with 0.5 M sodium phosphate buffer at a flow rate of <2.0 L/min.

The HA fraction was then concentrated and diafiltered on a 100 kDa MWCO membrane with a minimum of 20 volumes of 0.9% sodium chloride. The permeate was discarded.

Step 5: Sterile Filtration

The retentate after the 100 kDa MWCO diafiltration was filtered through a 0.22 µm filter. In-process controls (saccharide content, free protein, free saccharide and cyanide) were performed on the filtered product. In-process controls on filtered retentate were performed to determine whether additional concentration, diafiltration, and/or dilution were needed to meet FBC targets. These and additional tests were repeated in FBC samples.

As necessary, the filtered conjugate was diluted with 0.9% sodium chloride in order to achieve a final concentration of less than 0.55 g/L. Release tests for saccharide content, protein content and saccharide:protein ratio were performed at this stage. Finally, the conjugate was filtered (0.22 µm) and filled into 10 L stainless steel canisters at a typical quantity of 2.64 g/canister. At this stage, yield, saccharide content, protein content, pH, saccharide:protein ratio and lysine content were performed as in-process controls. Release testing (appearance, free protein, free saccharide, endotoxin, molecular size determination, residual cyanide, saccharide identity, $CRM_{197}$ identity) was performed at this stage.

DMSO Conjugation

Step I: Dissolution

The lyophilized activated saccharide serotypes 6B, 19F, 23F and the lyophilized $CRM_{197}$ carrier protein were equilibrated at room temperature and reconstituted in DMSO. The dissolution concentration typically ranged from 2-3 grams of saccharide (2-2.5 g protein) per liter of DMSO.

Step II: Conjugation Reaction

The activated saccharide and $CRM_{197}$ carrier protein were mixed for 60-75 minutes at 23°±2° C. at a ratio range of 0.6 g-1.0 g saccharide/g $CRM_{197}$ for serotypes 6B and 19F or 1.2 to 1.8 g saccharide/g $CRM_{197}$ for serotype 23F.

The conjugation reaction was initiated by adding the sodium cyanoborohydride solution (100 mg/mL) at a ratio of 0.8-1.2 molar equivalents of sodium cyanoborohydride to one mole activated saccharide. WFI was added to the reaction mixture to a target of 1% (v/v) and the mixture was incubated for over 40 hours at 23°±2° C.

Sodium borohydride solution, 100 mg/mL (typical 1.8-2.2 molar equivalents sodium borohydride per mole activated saccharide) and WFI (target 5% v/v) were added to the reaction and the mixture was incubated for 3-6 hours at 23°±2° C. This procedure reduced any unreacted aldehydes present on the saccharides. Then the reaction mixture was transferred to a dilution tank containing 0.9% sodium chloride at <15° C.

Step III: 100 kDa Ultrafiltration

The diluted conjugate mixture was filtered through a 1.2 µm filter and concentrated and diafiltered on a 100 kDa MWCO membrane with a minimum of 15 volumes of 0.9% sodium chloride (0.01 M sodium phosphate/0.05M NaCl buffer was used for serotype 23F). The permeate was discarded. The retentate was filtered through a 0.45 µm filter. An in-process saccharide content sample was taken at this stage.

Step IV: DEAE Column Purification

This step was only performed for serotype 23F.

The DEAE column was equilibrated with 0.01 M sodium phosphate/0.05M sodium chloride buffer. The filtered retentate (serotype 23F) was loaded onto the column and washed with 0.01M sodium phosphate/0.05M sodium chloride buffer. The column was then washed with 0.01M sodium phosphate/0.9% NaCl buffer. The product was then eluted with 0.01M sodium phosphate/0.5M sodium chloride buffer.

Step V: 100 kDa Ultrafiltration

The retentate from 6B and 19F was concentrated and diafiltered with at least 30 volumes of 0.9% sodium chloride. The permeate was discarded. The eluate from serotype 23F was concentrated and diafiltered with a minimum of 20 volumes of 0.9% sodium chloride. The permeate was discarded.

Step VI: Sterile Filtration

The retentate after the 100 kDa MWCO dialfiltration was filtered through 0.22 µm filter. In-process controls (saccharide content, free protein, free saccharide, residual DMSO and residual cyanide) were performed on the filtered product. In-process controls on filtered retentate were performed to determine whether additional concentration, diafiltration, and/or dilution were needed to meet FBC targets. These and additional tests were repeated in FBC samples. As necessary, the filtered conjugate was diluted with 0.9% sodium chloride to achieve a final concentration of less than 0.55 g/L. Release tests for saccharide content, protein content and saccharide:protein ratio were performed at this stage.

Finally, the conjugate was filtered (0.22 µm) and filled into 10 L stainless steel canisters at a quantity of 2.64 g/canister. At this stage, yield, saccharide content, protein content, pH, saccharide: protein ratio and lysine content were performed as in-process controls. Release testing (appearance, free protein, free saccharide, endotoxin, molecular size determination, residual cyanide, residual DMSO, saccharide identity and $CRM_{197}$ identity) was performed at this stage.

Example G. Preparation of *Streptococcus pneumoniae* Capsular Polysaccharides Conjugated to Protein D/Tetanus Toxoid/Diphtheria Toxoid Capsular polysaccharides of different *S. pneumoniae* serotypes were isolated from the corresponding *S. pneumoniae* strain producing said polysaccharides by extraction from fermented cultures according to EP0072513 or similar methods.

Example G.1. *S. pneumoniae* Serotype 1 Polysaccharide-Protein D-Conjugate

Fermentation

A sample of a strain of *Streptococcus pneumoniae* producing capsular polysaccharide of serotype 1 stored at −70° C. in Tryptic Soy Broth supplemented with 10% glycerol is rapidly thawed. The organisms are collected using a platinum loop and transferred to a Petri dish containing 15 ml of culture medium consisting of 40 g of blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 1168 g of sodium chloride are dissolved, which corresponds to an addition of 0.25 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 1 which can be separated by filtration.

Purification of Polysaccharide

Alternatively and preferably, a purification of the polysaccharide solution is carried out. To this end, 34 g of sodium acetate trihydrate is dissolved to obtain a saline solution (called solution C) whose concentration (said concentration C) in sodium acetate is 0.05 N, the pH is adjusted to 5.2 (±0.1) with 1 N hydrochloric acid and the medium is clarified by successive filtrations on 3 membranes whose porosity is 3, 1 and 0.45 micron, respectively.

The polysaccharide is precipitated onto 250 g of filter medium (Celite 512) whith stirring and by adding 500 ml (said volume D) of cetrimide aqueous solution of 5% (w/v), stirring being maintained for 15 minutes after addition of cetrimide.

The mixture is then filtered over a Celite 512 precoat.

The precipitate is purified chromatographically with 10 L of an aqueous solution of sodium acetate trihydrate (concentration C) with additionally 100 ml (said volume E) of aqueous cetrimide solution of 5% (w/v).

The cake is resuspended in 2 liters of an 0.3 N aqueous solution (said eluent F) of sodium acetate. After 15 minutes stirring, the suspension is filtered and the cake is purified chromatographically with 2 liters of eluent F.

Both eluates are filtered through a glass fiber prefilter followed by two membrane filters respectively having a porosity of 0.8 and 0.45 micron. sodium acetate trihydrate is added to obtain a concentration of 8% and the solution is refiltered through a membrane filter with a porosity of 0.2 micron.

The purified serotype 1 polysaccharide is precipitated from the solution by adding 3 volumes of ethanol.

After settling, the supernatant solution is separated and the precipitate is triturated in ethanol until a homogeneous powder is obtained which is filtered and dried under reduced pressure at room temperature.

The resulting product is purified pneumococcal serotype 1 polysaccharide.

Sizing

Purified polysaccharide of *S. pneumoniae* serotype 1 was dissolved in water to a concentration of 2-3 mg/ml. The dissolved polysaccharide was passed through a mechanical homogenizer with pressure preset from 0-1000 bar. Subsequently, the saccharide was concentrated and diafiltered with sterile water on a 10 kDa MWCO ultrafilter. The permeate was discarded and the retentate was transferred to dialysis tubing (12,000 MW cutoff; 45 mm) and dialyzed vs. distilled $H_2O$ for 27 hours with 2 additional changes of distilled $H_2O$. Then the dialyzed sample was transferred to lyophilization flasks, shell-frozen in a dry ice-methanol bath and lyophilized for 2-1/2 days Conjugation with Protein D A 2.5 mg/ml solution of sized polysaccharide of *S. pneumoniae* serotype 1 in water for injection was prepared. To that solution a 100 mg/ml solution of CDAP in acetonitrile/water (1:1 v/v) was added until a ratio of CDAP to polysaccharide of 0.5 (w/w) was reached. 1 minute later the pH was adjusted to 9.0 by adding 0.25 M sodium hydroxide solution under stirring at 25° C. After 3 minutes a 10 mg/ml solution of protein D in 0.2 M aqueous sodium chloride was added until a ratio of protein D/polysaccharide of 1.5:1 was reached. The reaction mixture was stirred for two hours while the pH was maintained at 9.0. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The *S. pneumoniae* serotype 1/PD-conjugate was purified by gel filtration using a Sehacryl S400HR gel filtration column equilibrated with 0.15 sodium chloride (S500HR for 18C) to remove small molecules, salts and unconjugated polysaccharide and protein D. The conjugate eluted first, followed by the polysaccharide and free protein D. Fractions containing the conjugate were detected by UV spectroscopy at 280 mm, combined, sterile filtered (22 μm) and stored between 2-8° C.

Characterization of *S. pneumoniae* Serotype 1/PD-conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example G.2. *S. pneumoniae* Serotype 4 Polysaccharide-Protein D-Conjugate

The purified pneumococcal serotype 4 polysaccharide is obtained by the same method as the pneumococcal serotype 1 polysaccharide using a strain of *Streptococcus pneumoniae* producing capsular polysaccharide of serotype 4.

Fermentation

A sample of a strain of *Streptococcus pneumoniae* producing capsular polysaccharide of serotype 4 stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 4 which can be separated by filtration.

Purification of Polysaccharide

Alternatively and preferably, a purification of the polysaccharide solution is carried out. To this end, 17 g of sodium acetate trihydrate is dissolved to obtain a saline solution (called solution C) whose concentration (said concentration C) in sodium acetate is 0.025 N, the pH is adjusted to 5.2 (±0.1) with 1 N hydrochloric acid and the medium is clarified by successive filtrations on 3 membranes whose porosity is 3, 1 and 0.45 micron, respectively.

The polysaccharide is precipitated onto 250 g of filter medium (Celite 512) whith stirring and by adding 500 ml (said volume D) of cetrimide aqueous solution of 5% (w/v), stirring being maintained for 15 minutes after addition of cetrimide.

The mixture is then filtered over a Celite 512 precoat.

The precipitate is purified chromatographically with 10 L of an aqueous solution of sodium acetate trihydrate (concentration C) with additionally 100 ml (said volume E) of aqueous cetrimide solution of 5% (w/v).

The cake is resuspended in 2 liters of a 0.15 N aqueous solution (said eluent F) of sodium acetate. After 15 minutes stirring, the suspension is filtered and the cake is purified chromatographically with 2 liters of eluent F.

Both eluates are filtered through a glass fiber prefilter followed by two membrane filters respectively having a porosity of 0.8 and 0.45 micron. sodium acetate trihydrate is added to obtain a concentration of 8% and the solution is refiltered through a membrane filter with a porosity of 0.2 micron.

The purified serotype 4 polysaccharide is precipitated from the solution by adding 4 volumes of ethanol.

After settling, the supernatant solution is separated and the precipitate is triturated in ethanol until a homogeneous powder is obtained which is filtered and dried under reduced pressure at room temperature.

The resulting product is purified pneumococcal serotype 4 polysaccharide.

Sizing

Purified polysaccharide of *S. pneumoniae* serotype 4 was dissolved in water to a concentration of 2-3 mg/ml. The dissolved polysaccharide was passed through a mechanical homogenizer with pressure preset from 0-1000 bar. Subsequently, the saccharide was concentrated and diafiltered with sterile water on a 10 kDa MWCO ultrafilter. The permeate was discarded and the retentate was adjusted to a pH of 5.0 with a sodium acetate buffer with a final concentration of 100 mM. The solution was incubated at 50°±2° C. Hydrolysis was stopped by cooling to 20-24° C. The solution was transferred to dialysis tubing (12,000 MW cutoff; 45 mm) and dialyzed vs. distilled $H_2O$ for 27 hours with 2 additional changes of distilled $H_2O$. Then the dialyzed sample was transferred to lyophilization flasks, shell-frozen in a dry ice-methanol bath and lyophilized for 2½ days Conjugation with Protein D A 2.5 mg/ml solution of sized polysaccharide of *S. pneumoniae* serotype 4 in water for injection was prepared. To that solution a 100 mg/ml solution of CDAP in acetonitrile/water (1:1 v/v) was added until a ratio of CDAP to polysaccharide of 0.5 (w/w) was reached. 1 minute later the pH was adjusted to 9.5 by adding 0.25 M sodium hydroxide solution under stirring at 25° C. After 3 minutes a 10 mg/ml solution of protein D in 0.2 M aqueous sodium chloride was added until a ratio of protein D/polysaccharide of 1.5:1 was reached. The reaction mixture was stirred for two hours while the pH was maintained at 9.5. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The *S. pneumoniae* serotype 4/PD-conjugate was purified by gel filtration using a Sehacryl S400HR gel filtration column equilibrated with 0.15 sodium chloride (S500HR for 18C) to remove small molecules, salts and unconjugated polysaccharide and protein D. The conjugate eluted first, followed by the polysaccharide and free protein D. Fractions containing the conjugate were detected by UV spectroscopy at 280 mm, combined, sterile filtered (22 μm) and stored between 2-8° C.

Characterization of *S. pneumoniae* Serotype 4/PD-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example G.3. *S. pneumoniae* Serotype 5 Polysaccharide-Protein D-Conjugate

The purified pneumococcal serotype 5 polysaccharide is obtained by the same method as the pneumococcal serotype 4 polysaccharide using a strain of *Streptococcus pneumoniae* producing capsular polysaccharide of serotype 5.

Fermentation

A sample of a strain of *Streptococcus pneumoniae* producing capsular polysaccharide of serotype 5 stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 5 which can be separated by filtration.

Purification of Polysaccharide

Alternatively and preferably, a purification of the polysaccharide solution is carried out. To this end, 17 g of sodium acetate trihydrate is dissolved to obtain a saline solution (called solution C) whose concentration (said concentration C) in sodium acetate is 0.025 N, the pH is adjusted to 5.0 (±0.1) with 1 N hydrochloric acid and the medium is clarified by successive filtrations on 3 membranes whose porosity is 3, 1 and 0.45 micron, respectively.

The polysaccharide is precipitated onto 250 g of filter medium (Celite 512) whith stirring and by adding 500 ml (said volume D) of cetrimide aqueous solution of 5% (w/v), stirring being maintained for 15 minutes after addition of cetrimide.

The mixture is then filtered over a Celite 512 precoat.

The precipitate is purified chromatographically with 10 L of an aqueous solution of sodium acetate trihydrate (concentration C) with additionally 100 ml (said volume E) of aqueous cetrimide solution of 5% (w/v).

The cake is resuspended in 2 liters of a 0.15 N aqueous solution (said eluent F) of sodium chloride. After 15 minutes stirring, the suspension is filtered and the cake is purified chromatographically with 2 liters of eluent F.

Both eluates are filtered through a glass fiber prefilter followed by two membrane filters respectively having a porosity of 0.8 and 0.45 micron. sodium acetate trihydrate is added to obtain a concentration of 8% and the solution is refiltered through a membrane filter with a porosity of 0.2 micron.

The purified serotype 5 polysaccharide is precipitated from the solution by adding 3 volumes of n-propanol.

After settling, the supernatant solution is separated and the precipitate is triturated in ethanol until a homogeneous powder is obtained which is filtered and dried under reduced pressure at room temperature.

The resulting product is purified pneumococcal serotype 5 polysaccharide.

Conjugation with Protein D

A 7.1 mg/ml solution of polysaccharide of S. pneumoniae serotype 5 in water for injection was prepared. To that solution a 100 mg/ml solution of CDAP in acetonitrile/water (1:1 v/v) was added until a ratio of CDAP to polysaccharide of 0.79 (w/w) was reached. 1 minute later the pH was adjusted to 9.0 by adding 0.25 M sodium hydroxide solution under stirring at 25° C. After 3 minutes a 5.0 mg/ml solution of protein D in 0.2 M aqueous sodium chloride was added until a ratio of protein D/polysaccharide of 1:1 was reached. The reaction mixture was stirred for two hours while the pH was maintained at 9.0. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The S. pneumoniae serotype 5/PD-conjugate was purified by gel filtration using a Sehacryl S400HR gel filtration column equilibrated with 0.15 sodium chloride (S500HR for 18C) to remove small molecules, salts and unconjugated polysaccharide and protein D. The conjugate eluted first, followed by the polysaccharide and free protein D. Fractions containing the conjugate were detected by UV spectroscopy at 280 mm, combined, sterile filtered (22 μm) and stored between 2-8° C.

Characterization of S. pneumoniae Serotype 5/PD-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example G.4. *S. pneumoniae* Serotype 6B Polysaccharide-Protein D-Conjugate

The purified pneumococcal serotype 6B polysaccharide is obtained by the same method as the pneumococcal serotype 4 polysaccharide using a strain of *Streptococcus pneumoniae* producing capsular polysaccharide of serotype 6B.

Fermentation

A sample of a strain of *Streptococcus pneumoniae* producing capsular polysaccharide of serotype 6B stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 6B which can be separated by filtration.

Purification of Polysaccharide

Alternatively and preferably, a purification of the polysaccharide solution is carried out. To this end, 34 g of sodium acetate trihydrate is dissolved to obtain a saline solution (called solution C) whose concentration (said concentration C) in sodium acetate is 0.05 N, the pH is adjusted to 5.2 (±0.1) with 1 N hydrochloric acid and the medium is clarified by successive filtrations on 3 membranes whose porosity is 3, 1 and 0.45 micron, respectively.

The polysaccharide is precipitated onto 250 g of filter medium (Celite 512) whith stirring and by adding 1000 ml (said volume D) of cetrimide aqueous solution of 5% (w/v), stirring being maintained for 15 minutes after addition of cetrimide.

The mixture is then filtered over a Celite 512 precoat.

The precipitate is purified chromatographically with 10 L of an aqueous solution of sodium acetate trihydrate (concentration C) with additionally 1000 ml (said volume E) of aqueous cetrimide solution of 5% (w/v).

The cake is resuspended in 2 liters of a 0.25 N aqueous solution (said eluent F) of sodium acetate. After 15 minutes stirring, the suspension is filtered and the cake is purified chromatographically with 2 liters of eluent F.

Both eluates are filtered through a glass fiber prefilter followed by two membrane filters respectively having a porosity of 0.8 and 0.45 micron. sodium acetate trihydrate is added to obtain a concentration of 8% and the solution is refiltered through a membrane filter with a porosity of 0.2 micron.

The purified serotype 6B polysaccharide is precipitated from the solution by adding 3 volumes of ethanol.

After settling, the supernatant solution is separated and the precipitate is triturated in ethanol until a homogeneous powder is obtained which is filtered and dried under reduced pressure at room temperature.

The resulting product is purified pneumococcal serotype 6B polysaccharide.

Conjugation with Protein D

A 5.0 mg/ml solution of polysaccharide of *S. pneumoniae* serotype 6B and 2 M aqueous sodium chloride solution was prepared. To that solution a 100 mg/ml solution of CDAP in acetonitrile/water (1:1 v/v) was added until a ratio of CDAP to polysaccharide of 0.83 (w/w) was reached. 1 minute later the pH was adjusted to 9.5 by adding 0.25 M sodium hydroxide solution under stirring at 25° C. After 3 minutes a 5 mg/ml solution of protein D in 0.2 M aqueous sodium chloride was added until a ratio of protein D/polysaccharide of 1.1:1 was reached. The reaction mixture was stirred for two hours while the pH was maintained at 9.5. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The *S. pneumoniae* serotype 6B/PD-conjugate was purified by gel filtration using a Sehacryl S400HR gel filtration column equilibrated with 0.15 sodium chloride (S500HR for 18C) to remove small molecules, salts and unconjugated polysaccharide and protein D. The conjugate eluted first, followed by the polysaccharide and free protein D. Fractions containing the conjugate were detected by UV spectroscopy at 280 mm, combined, sterile filtered (22 µm) and stored between 2-8° C.

Characterization of *S. pneumoniae* Serotype 6B/PD-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example G.5. *S. pneumoniae* Serotype 7F Polysaccharide-Protein D-Conjugate

The crude pneumococcal serotype 7F polysaccharide is obtained by the same method as the pneumococcal serotype 4 polysaccharide using a strain of *Streptococcus pneumoniae* producing capsular polysaccharide of serotype 7F.

Fermentation

A sample of a strain of *Streptococcus pneumoniae* producing capsular polysaccharide of serotype 7F stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 7F which can be separated by filtration.

Purification of Polysaccharide

This precipitate is redissolved in an amount of 4 g/L in a 0.005 N trometamol/hydrochloric acid buffer solution at pH 7.1. The solution was clarified by centrifugation for 10 minutes at 3000 tours par minute.

Under stirring, for each liter of the solution 20 g of diethylaminoethyl cellulose (DEAE cellulose) treated with the same buffer solution are added. The pH is adjusted to 7.1 with 1 N hydrochloric acid and stirring is continued for one hour after the addition of DEAE cellulose which is then separated by filtration and washed with 240 ml of the same buffer solution per liter of filtrate.

The Treatment of the filtrate with DEAE cellulose is repeated.

The combined filtrates are passed through two membrane filters having a porosity of 0.8 micron and 0.45 micron, respectively. Sodium acetate trihydrate is added (so that the final concentration is 8% w/v) and the solution is passed through a membrane filter having a porosity of 0.2 micron.

The purified polysaccharide is precipitated by adding 3 volumes of ethanol under stirring.

Precipitates of the purified pneumococcal serotype 7F polysaccharide are isolated by decantation followed by filtration and further washed with ethanol and finally dried at room temperature under reduced pressure.

Sizing

The purified pneumococcal serotype 7F polysaccharide powder was solubilized in distilled $H_2O$ with stirring at room temperature for about 4 hours and then stored at 4° C. overnight. The solution was added to DE52 (Whatman, diethylaminoethyl cellulose) which had been pre-swollen for ca. 15 hours in distilled $H_2O$ at pH of ca. 5-6. The slurry was gently shaken on a platform shaker at room temperature for ca. 15 hrs, after which it was centrifuged at 5,000 rpm for 15 min. at 20° C. The supernatant fluid was further clarified through a sinter glass funnel (150 ml, medium porosity) and collected into a 2 L side arm flask.

The DE52-treated pneumococcal serotype 7F polysaccharide was sonicated in a plastic beaker on an ice bath with a Branson Sonifier (one-half inch probe, setting 8) for 2 min. The sample was allowed to cool for ca. 15 min. while the viscosity was determined and then was sonicated for additional 1 min. intervals. A viscosity end point of 1.096 centistokes was reached after the last sonic treatment. The hydrolyzed sample was brought to room temperature and sodium acetate reagent was added to a final concentration of 1% (w/v).

The hydrolyzed sample was brought to 39.3% isopropanol by the addition of isopropanol (added dropwise with stirring at room temperature). The sample was allowed to stir for 15-30 minutes and then centrifuged at 11,000×g for 30 minutes (Beckman JA-10 rotor; 8,000 rpm; 20° C.) and the supernatant fluid decanted. The waste pellet was triturated with absolute EtOH in a 250-mL Omnimix jar, then collected on a 60-mL sinter glass funnel. The precipitate was washed directly on the funnel with absolute EtOH, then acetone, and dried in vacuo over $CaCl_2$ at room temperature in preparation for analysis.

The supernatant fluid was brought to 41.8% isopropanol by adding further isopropanol dropwise while stirring at room temperature. The sample was aged and centrifuged as described above. The pellet was triturated, collected, washed and dried as described above. The pellet was solubilized in distilled $H_2O$ at room temperature for 2-3 hours. The solution (2.5 mg/mL) was transferred to dialysis tubing (12,000 MW cutoff; 45 mm) and dialyzed vs. distilled $H_2O$ for 27 hours with 2 additional changes of distilled $H_2O$. Then the dialyzed sample was transferred to lyophilization flasks, shell-frozen in a dry ice-methanol bath and lyophilized for 2½ days.

Conjugation with Protein D

A 5.0 mg/ml solution of sized polysaccharide of S. pneumoniae serotype 7F and 2 M aqueous sodium chloride solution was prepared. To that solution a 100 mg/ml solution of CDAP in acetonitrile/water (1:1 v/v) was added until a ratio of CDAP to polysaccharide of 0.75 (w/w) was reached. 1 minute later the pH was adjusted to 9.5 by adding 0.25 M sodium hydroxide solution under stirring at 25° C. After 3 minutes a 10 mg/ml solution of protein D in 0.2 M aqueous sodium chloride was added until a ratio of protein D/polysaccharide of 1.2:1 was reached. The reaction mixture was stirred for two hours while the pH was maintained at 9.5. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The S. pneumoniae serotype 7F/PD-conjugate was purified by gel filtration using a Sehacryl S400HR gel filtration column equilibrated with 0.15 sodium chloride (S500HR for 18C) to remove small molecules, salts and unconjugated polysaccharide and protein D. The conjugate eluted first, followed by the polysaccharide and free protein D. Fractions containing the conjugate were detected by UV spectroscopy at 280 mm, combined, sterile filtered (22 µm) and stored between 2-8° C.

Characterization of S. pneumoniae Serotype 7F/PD-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel.

Example G.6. S. pneumoniae Serotype 9V Polysaccharide-Protein D-Conjugate

The purified pneumococcal serotype 9V polysaccharide is obtained by the same method as the pneumococcal serotype 4 polysaccharide using a strain of Streptococcus pneumoniae producing capsular polysaccharide of serotype 9V.

Fermentation

A sample of a strain of Streptococcus pneumoniae producing capsular polysaccharide of serotype 4 stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 9V which can be separated by filtration.

Purification of Polysaccharide

Alternatively and preferably, a purification of the polysaccharide solution is carried out. To this end, 17 g of sodium acetate trihydrate is dissolved to obtain a saline solution (called solution C) whose concentration (said concentration C) in sodium acetate is 0.025 N, the pH is adjusted to 5.2 (±0.1) with 1 N hydrochloric acid and the medium is clarified by successive filtrations on 3 membranes whose porosity is 3, 1 and 0.45 micron, respectively.

The polysaccharide is precipitated onto 250 g of filter medium (Celite 512) whith stirring and by adding 500 ml (said volume D) of cetrimide aqueous solution of 5% (w/v), stirring being maintained for 15 minutes after addition of cetrimide.

The mixture is then filtered over a Celite 512 precoat.

The precipitate is purified chromatographically with 10 L of an aqueous solution of sodium acetate trihydrate (concentration C) with additionally 100 ml (said volume E) of aqueous cetrimide solution of 5% (w/v).

The cake is resuspended in 2 liters of a 0.15 N aqueous solution (said eluent F) of sodium acetate. After 15 minutes stirring, the suspension is filtered and the cake is purified chromatographically with 2 liters of eluent F.

Both eluates are filtered through a glass fiber prefilter followed by two membrane filters respectively having a porosity of 0.8 and 0.45 micron. sodium acetate trihydrate is added to obtain a concentration of 8% and the solution is refiltered through a membrane filter with a porosity of 0.2 micron.

The purified serotype 9V polysaccharide is precipitated from the solution by adding 3 volumes of ethanol.

After settling, the supernatant solution is separated and the precipitate is triturated in ethanol until a homogeneous powder is obtained which is filtered and dried under reduced pressure at room temperature.

The resulting product is purified pneumococcal serotype 9V polysaccharide.

Sizing

Purified polysaccharide of S. pneumoniae serotype 9V was dissolved in water to a concentration of 2-3 mg/ml. The dissolved polysaccharide was passed through a mechanical homogenizer with pressure preset from 0-1000 bar. Subsequently, the saccharide was concentrated and diafiltered with sterile water on a 10 kDa MWCO ultrafilter. The permeate was discarded and the retentate was transferred to dialysis tubing (12,000 MW cutoff; 45 mm) and dialyzed vs. distilled $H_2O$ for 27 hours with 2 additional changes of distilled $H_2O$. Then the dialyzed sample was transferred to lyophilization flasks, shell-frozen in a dry ice-methanol bath and lyophilized for 2½ days.

Conjugation with Protein D

A 5.0 mg/ml solution of sized polysaccharide of S. pneumoniae serotype 9V and 2 M aqueous sodium chloride solution was prepared. To that solution a 100 mg/ml solution of CDAP in acetonitrile/water (1:1 v/v) was added until a ratio of CDAP to polysaccharide of 0.50 (w/w) was reached. 1 minute later the pH was adjusted to 9.5 by adding 0.25 M sodium hydroxide solution under stirring at 25° C. After 3 minutes a 10 mg/ml solution of protein D in 0.2 M aqueous sodium chloride was added until a ratio of protein D/polysaccharide of 1.2:1 was reached. The reaction mixture was stirred for two hours while the pH was maintained at 9.5. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The S. pneumoniae serotype 9V/PD-conjugate was purified by gel filtration using a Sehacryl S400HR gel filtration column equilibrated with 0.15 sodium chloride (S500HR for 18C) to remove small molecules, salts and unconjugated polysaccharide and protein D. The conjugate eluted first, followed by the polysaccharide and free protein D. Fractions containing the conjugate were detected by UV spectroscopy at 280 mm, combined, sterile filtered (22 µm) and stored between 2-8° C.

Characterization of S. pneumoniae Serotype 9V/PD-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example G.7. S. pneumoniae Serotype 14 Polysaccharide-Protein D-Conjugate

The crude pneumococcal serotype 14 polysaccharide is obtained by the same method as the pneumococcal serotype 7F polysaccharide using a strain of Streptococcus pneumoniae producing capsular polysaccharide of serotype 14.

Fermentation

A sample of a strain of Streptococcus pneumoniae producing capsular polysaccharide of serotype 14 stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 14 which can be separated by filtration.

Purification of Polysaccharide

This precipitate is redissolved in an amount of 4 g/L in a 0.005 N trometamol/hydrochloric acid buffer solution at pH 7.1. The solution was clarified by centrifugation for 10 minutes at 3000 tours par minute.

Under stirring, for each liter of the solution 20 g of diethylaminoethyl cellulose (DEAE cellulose) treated with the same buffer solution are added. The pH is adjusted to 7.1 with 1 N hydrochloric acid and stirring is continued for one hour after the addition of DEAE cellulose which is then separated by filtration and washed with 240 ml of the same buffer solution per liter of filtrate.

The Treatment of the filtrate with DEAE cellulose is repeated.

The combined filtrates are passed through two membrane filters having a porosity of 0.8 micron and 0.45 micron, respectively. Sodium acetate trihydrate is added (so that the final concentration is 8% w/v) and the solution is passed through a membrane filter having a porosity of 0.2 micron.

The purified polysaccharide is precipitated by adding 3 volumes of ethanol under stirring.

Precipitates of the purified pneumococcal serotype 14 polysaccharide are isolated by decantation followed by filtration and further washed with ethanol and finally dried at room temperature under reduced pressure.

Sizing

The purified pneumococcal serotype 14 polysaccharide powder was solubilized in distilled $H_2O$ with stirring at room temperature for about 4 hours and then stored at 4° C. overnight. The solution was added to DE52 (Whatman, diethylamino-ethyl cellulose) which had been pre-swollen for ca. 15 hours in distilled $H_2O$ at pH of ca. 5-6. The slurry was gently shaken on a platform shaker at room temperature for ca. 15 hrs, after which it was centrifuged at 5,000 rpm for 15 min. at 20° C. The supernatant fluid was further clarified through a sinter glass funnel (150 ml, medium porosity) and collected into a 2L side arm flask.

The DE52-treated pneumococcal serotype 14 polysaccharide was sonicated in a plastic beaker on an ice bath with a Branson Sonifier (one-half inch probe, setting 8) for 2 min. The sample was allowed to cool for ca. 15 min. while the viscosity was determined and then was sonicated for additional 1 min. intervals. A viscosity end point of 1.096 centistokes was reached after the last sonic treatment. The hydrolyzed sample was brought to room temperature and sodium acetate reagent was added to a final concentration of 1% (w/v).

The hydrolyzed sample was brought to 39.3% isopropanol by the addition of isopropanol (added dropwise with stirring at room temperature). The sample was allowed to stir for 15-30 minutes and then centrifuged at 11,000×g for 30 minutes (Beckman JA-10 rotor; 8,000 rpm; 20° C.) and the supernatant fluid decanted. The waste pellet was triturated with absolute EtOH in a 250-mL Omnimix jar, then collected on a 60-mL sinter glass funnel. The precipitate was washed directly on the funnel with absolute EtOH, then acetone, and dried in vacuo over $CaCl_2$ at room temperature in preparation for analysis.

The supernatant fluid was brought to 41.8% isopropanol by adding further isopropanol dropwise while stirring at room temperature. The sample was aged and centrifuged as described above. The pellet was triturated, collected, washed and dried as described above. The pellet was solubilized in distilled $H_2O$ at room temperature for 2-3 hours. The solution (2.5 mg/mL) was transferred to dialysis tubing (12,000 MW cutoff; 45 mm) and dialyzed vs. distilled $H_2O$ for 27 hours with 2 additional changes of distilled $H_2O$. Then the dialyzed sample was transferred to lyophilization flasks, shell-frozen in a dry ice-methanol bath and lyophilized for 2½ days.

Conjugation with Protein D

A 5.0 mg/ml solution of sized polysaccharide of S. pneumoniae serotype 14 and 2 M aqueous sodium chloride solution was prepared. To that solution a 100 mg/ml solution of CDAP in acetonitrile/water (1:1 v/v) was added until a ratio of CDAP to polysaccharide of 0.75 (w/w) was reached. 1 minute later the pH was adjusted to 9.5 by adding 0.25 M sodium hydroxide solution under stirring at 25° C. After 3 minutes a 10 mg/ml solution of protein D in 0.2 M aqueous sodium chloride was added until a ratio of protein D/polysaccharide of 1.2:1 was reached. The reaction mixture was stirred for two hours while the pH was maintained at 9.5. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The S. pneumoniae serotype 14/PD-conjugate was purified by gel filtration using a Sehacryl S400HR gel filtration column equilibrated with 0.15 sodium chloride (S500HR for 18C) to remove small molecules, salts and unconjugated polysaccharide and protein D. The conjugate eluted first, followed by the polysaccharide and free protein D. Fractions containing the conjugate were detected by UV spectroscopy at 280 mm, combined, sterile filtered (22 µm) and stored between 2-8° C.

Characterization of S. pneumoniae Serotype 14/PD-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example G.8. S. pneumoniae Serotype 18C Polysaccharide-TT-Conjugate

The purified pneumococcal serotype 18C polysaccharide is obtained by the same method as the pneumococcal serotype 4 polysaccharide using a strain of Streptococcus pneumoniae producing capsular polysaccharide of serotype 18C.

Fermentation

A sample of a strain of Streptococcus pneumoniae producing capsular polysaccharide of serotype 18C stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 18C which can be separated by filtration.

Purification of Polysaccharide

Alternatively and preferably, a purification of the polysaccharide solution is carried out. To this end, 20.4 g of sodium acetate trihydrate is dissolved to obtain a saline solution (called solution C) whose concentration (said concentration C) in sodium acetate is 0.03 N, the pH is adjusted to 5.2 (±0.1) with 1 N hydrochloric acid and the medium is clarified by successive filtrations on 3 membranes whose porosity is 3, 1 and 0.45 micron, respectively.

The polysaccharide is precipitated onto 250 g of filter medium (Celite 512) whith stirring and by adding 500 ml (said volume D) of cetrimide aqueous solution of 5% (w/v), stirring being maintained for 15 minutes after addition of cetrimide.

The mixture is then filtered over a Celite 512 precoat.

The precipitate is purified chromatographically with 10 L of an aqueous solution of sodium acetate trihydrate (concentration C) with additionally 100 ml (said volume E) of aqueous cetrimide solution of 5% (w/v).

The cake is resuspended in 2 liters of a 0.15 N aqueous solution (said eluent F) of sodium acetate. After 15 minutes stirring, the suspension is filtered and the cake is purified chromatographically with 2 liters of eluent F.

Both eluates are filtered through a glass fiber prefilter followed by two membrane filters respectively having a porosity of 0.8 and 0.45 micron. Sodium acetate trihydrate is added to obtain a concentration of 8% and the solution is refiltered through a membrane filter with a porosity of 0.2 micron.

The purified serotype 18C polysaccharide is precipitated from the solution by adding 3 volumes of ethanol.

After settling, the supernatant solution is separated and the precipitate is triturated in ethanol until a homogeneous powder is obtained which is filtered and dried under reduced pressure at room temperature.

The resulting product is purified pneumococcal serotype 18C polysaccharide.

Sizing

Purified polysaccharide of *S. pneumoniae* serotype 18C was dissolved in water to a concentration of 2-3 mg/ml. The dissolved polysaccharide was passed through a mechanical homogenizer with pressure preset from 0-1000 bar. Subsequently, the saccharide was concentrated and diafiltered with sterile water on a 10 kDa MWCO ultrafilter. The permeate was discarded and the retentate was transferred to dialysis tubing (12,000 MW cutoff; 45 mm) and dialyzed vs. distilled $H_2O$ for 27 hours with 2 additional changes of distilled $H_2O$. Then the dialyzed sample was transferred to lyophilization flasks, shell-frozen in a dry ice-methanol bath and lyophilized for 2½ days Conjugation with TT To a 25 mg/mL solution of purified tetanus toxoid in 2 M aqueous sodium chloride was added adipic acid dihydrazide (ADH) until an ADH concentration of 0.2 M was reached. The pH was adjusted to 6.2. EDAC was added to reach a concentration of 0.02 M and the mixture was stirred for 1 hour while maintaining the pH at 6.2. The reaction was quenched by adjusting the pH to 9.0 for at least 30 minutes at 25° C. The modified tetanus toxoid was diafiltrated (10 kDa CO membrane), sterile filtered and stored at −70° C.

A 4.5 mg/ml solution of sized polysaccharide of *S. pneumoniae* serotype 18C and 2 M aqueous sodium chloride solution was prepared. To that solution a 100 mg/ml solution of CDAP in acetonitrile/water (1:1 v/v) was added until a ratio of CDAP to polysaccharide of 0.75 (w/w) was reached. 1 minute later the pH was adjusted to 9.0 by adding 0.30 M sodium hydroxide solution under stirring at 25° C. After 3 minutes a 20 mg/ml solution of modified tetanus toxoid (see above) in 0.2 M aqueous sodium chloride was added until a ratio of modified TT/polysaccharide of 2:1 was reached. The reaction mixture was stirred for two hours while the pH was maintained at 9.0. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The *S. pneumoniae* serotype 18C/TT-conjugate was purified by gel filtration using a Sehacryl S400HR gel filtration column equilibrated with 0.15 sodium chloride (S500HR for 18C) to remove small molecules, salts and unconjugated polysaccharide and TT. The conjugate eluted first, followed by the polysaccharide and free TT. Fractions containing the conjugate were detected by UV spectroscopy at 280 mm, combined, sterile filtered (22 µm) and stored between 2-8° C.

Characterization of *S. pneumoniae* Serotype 18C/TT-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example G.9. *S. pneumoniae* Serotype 19F Polysaccharide-DT-Conjugate

The purified pneumococcal serotype 19F polysaccharide is obtained by the same method as the pneumococcal serotype 4 polysaccharide using a strain of *Streptococcus pneumoniae* producing capsular polysaccharide of serotype 19F.

Fermentation

A sample of a strain of *Streptococcus pneumoniae* producing capsular polysaccharide of serotype 19F stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 19F which can be separated by filtration.

Purification of Polysaccharide

Alternatively and preferably, a purification of the polysaccharide solution is carried out. To this end, 17 g of sodium acetate trihydrate is dissolved to obtain a saline solution (called solution C) whose concentration (said concentration C) in sodium acetate is 0.025 N, the pH is adjusted to 5.2 (±0.1) with 1 N hydrochloric acid and the medium is clarified by successive filtrations on 3 membranes whose porosity is 3, 1 and 0.45 micron, respectively.

The polysaccharide is precipitated onto 250 g of filter medium (Celite 512) whith stirring and by adding 500 ml (said volume D) of cetrimide aqueous solution of 5% (w/v), stirring being maintained for 15 minutes after addition of cetrimide.

The mixture is then filtered over a Celite 512 precoat.

The precipitate is purified chromatographically with 10 L of an aqueous solution of sodium acetate trihydrate (concentration C) with additionally 100 ml (said volume E) of aqueous cetrimide solution of 5% (w/v).

The cake is resuspended in 2 liters of a 0.3 N aqueous solution (said eluent F) of sodium acetate. After 15 minutes stirring, the suspension is filtered and the cake is purified chromatographically with 2 liters of eluent F.

Both eluates are filtered through a glass fiber prefilter followed by two membrane filters respectively having a porosity of 0.8 and 0.45 micron. Sodium acetate trihydrate is added to obtain a concentration of 8% and the solution is refiltered through a membrane filter with a porosity of 0.2 micron.

The purified serotype 19F polysaccharide is precipitated from the solution by adding 3 volumes of ethanol.

After settling, the supernatant solution is separated and the precipitate is triturated in ethanol until a homogeneous powder is obtained which is filtered and dried under reduced pressure at room temperature.

The resulting product is purified pneumococcal serotype 19F polysaccharide.

Sizing

Purified polysaccharide of S. pneumoniae serotype 1 was dissolved in water to a concentration of 2-3 mg/ml. The dissolved polysaccharide was passed through a mechanical homogenizer with pressure preset from 0-1000 bar. Subsequently, the saccharide was concentrated and diafiltered with sterile water on a 10 kDa MWCO ultrafilter. The permeate was discarded and the retentate was transferred to dialysis tubing (12,000 MW cutoff; 45 mm) and dialyzed vs. distilled $H_2O$ for 27 hours with 2 additional changes of distilled $H_2O$. Then the dialyzed sample was transferred to lyophilization flasks, shell-frozen in a dry ice-methanol bath and lyophilized for 2½ days Conjugation with DT A 9.0 mg/ml solution of sized polysaccharide of S. pneumoniae serotype 19F and 2 M aqueous sodium chloride solution was prepared. To that solution a 100 mg/ml solution of CDAP in acetonitrile/water (1:1 v/v) was added until a ratio of CDAP to polysaccharide of 1.5 (w/w) was reached. 1 minute later the pH was adjusted to 9.0 by adding 0.25 M sodium hydroxide solution under stirring at 25° C. After 3 minutes a 20 mg/ml solution of diphtheria toxoid (DT) in 0.2 M aqueous sodium chloride was added until a ratio of DT/polysaccharide of 1.5:1 was reached. The reaction mixture was stirred for two hours while the pH was maintained at 9.0. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The S. pneumoniae serotype 19F/DT-conjugate was purified by gel filtration using a Sehacryl S400HR gel filtration column equilibrated with 0.15 sodium chloride (S500HR for 18C) to remove small molecules, salts and unconjugated polysaccharide and DT. The conjugate eluted first, followed by the polysaccharide and free DT. Fractions containing the conjugate were detected by UV spectroscopy at 280 mm, combined, sterile filtered (22 μm) and stored between 2-8° C.

Characterization of S. pneumoniae Serotype 19F/DT-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example G.10. S. pneumoniae Serotype 23F Polysaccharide-Protein D-Conjugate

The purified pneumococcal serotype 23F polysaccharide is obtained by the same method as the pneumococcal serotype 4 polysaccharide using a strain of Streptococcus pneumoniae producing capsular polysaccharide of serotype 23F.

Fermentation

A sample of a strain of Streptococcus pneumoniae producing capsular polysaccharide of serotype 23F stored at −70° C. in Tryptic Soy Broth supplemented with 10% glycerol is rapidly thawed. The organisms are collected using a platinum loop and transferred to a Petri dish containing 15 ml of culture medium consisting of 40 g of Blood agar base per liter of water, sterilized at 121° C. for 20 minutes and then cooled to 50° C. and supplemented with 5% of fresh defibrinated sheep blood and the microorganism is then incubated at 37° C. for 16 hours in atmosphere enriched with $CO_2$ (5% w/v).

The produced bacteria are collected and a second run is performed in a Roux culture bottle containing 100 ml of synthetic medium according Hoeprich (Paul D. Hoeprich J. Bact. 1955, 69, p. 682-688, and J. Bact. 1957, 74, p. 587-590), solidified by adding agar (20 g/l). After an incubation period of 6 to 9 hours in anaerobic atmosphere, the produced organism is harvested and suspended in 5 ml of aqueous sodium chloride solution (8.5 g per liter). The harvest is used to inoculate a culture vessel containing 8 liters of liquid semi-synthetic medium according to Hoeprich. The medium is maintained without agitation or aeration for 16 hours at 37° C. to form the inoculum for the production culture.

For the production culture, a 100 liter fermenter is used containing 72 liters of semi-synthetic medium following Hoeprich. The medium is inoculated with the above-referenced culture and the incubation is maintained without aeration but gentle stirring at 35.5° C. (±1), the pH being continuously adjusted to 7.2 using a 25% sodium hydroxide solution. The development of the culture is regularly monitored by sampling and measuring the optical density of the medium at 620 nm. When the optical density reaches 0.15 a solution of one kilogram of dextrose in 2 liters of autoclaved deionized water is added over 20 minutes at 121° C. The culture is stopped at the beginning of stationary phase, which corresponds to an optical density of 0.8.

Extraction of Polysaccharide

The fermentation medium (80 l) is transferred into a storage tank and inactivated by adding one liter of 90% phenol; the pH is adjusted to 7.2 with 25% sodium hydroxide solution. After standing overnight at 5-10° C., 702 g of sodium chloride are dissolved, which corresponds to an addition of 0.15 mol of sodium chloride per liter of medium (so-called concentration A).

While stirring, 4 kg of inert porous support (Celite 545) are then added and to the suspension, 800 ml (said volume B) of an aqueous solution of cetrimide (5% w/v) which is previously stored at a temperature of 25° C. is added and the stirring is continued for 10 minutes after the addition of cetrimide.

The medium is then filtered and the cake is washed with 4 L of an aqueous solution of sodium chloride of concentration A, with additional 40 ml of an aqueous solution of cetrimide (5% w/v).

The filtrate is concentrated to a volume of 5 liters by ultrafiltration in an AMICON DC unit 30 provided with cartridges with a cut-off of molecular weight of 100 kDa. The retentate is diafiltrated first with 40 L of sodium chloride solution of concentration A and then with 40 L of water keeping the volume between 10 and 5 liters. Finally, the volume of the solution is reduced to about 3 liters by ultrafiltration and the apparatus is rinsed with water to obtain approximately 5 liters of crude polysaccharide solution still containing substance C.

This polysaccharide can be isolated by dissolving 40 g of sodium acetate trihydrate in the solution and then adding with stirring 3.5 volumes of ethanol, causing the precipitation of the polysaccharide of serotype 23F which can be separated by filtration.

Purification of Polysaccharide

Alternatively and preferably, a purification of the polysaccharide solution is carried out. To this end, ammonium chloride is dissolved to obtain a saline solution (called solution C) whose concentration (said concentration C) in ammonium chloride is 0.08 N, the pH is adjusted to 5.2 (±0.1) with 1 N hydrochloric acid and the medium is clarified by successive filtrations on 3 membranes whose porosity is 3, 1 and 0.45 micron, respectively.

The polysaccharide is precipitated onto 250 g of filter medium (Celite 512) whith stirring and by adding 1500 ml (said volume D) of cetrimide aqueous solution of 5% (w/v), stirring being maintained for 15 minutes after addition of cetrimide.

The mixture is then filtered over a Celite 512 precoat.

The precipitate is purified chromatographically with 10 L of an aqueous solution of ammonium chloride (concentration C) with additionally 3000 ml (said volume E) of aqueous cetrimide solution of 5% (w/v).

The cake is resuspended in 2 liters of a 0.12 N aqueous solution (said eluent F) of ammonium chloride. After 15 minutes stirring, the suspension is filtered and the cake is purified chromatographically with 2 liters of eluent F.

Both eluates are filtered through a glass fiber prefilter followed by two membrane filters respectively having a porosity of 0.8 and 0.45 micron. Sodium acetate trihydrate is added to obtain a concentration of 8% and the solution is refiltered through a membrane filter with a porosity of 0.2 micron.

The purified serotype 23F polysaccharide is precipitated from the solution by adding 3 volumes of ethanol.

After settling, the supernatant solution is separated and the precipitate is triturated in ethanol until a homogeneous powder is obtained which is filtered and dried under reduced pressure at room temperature.

The resulting product is purified pneumococcal serotype 23F polysaccharide.

Conjugation with Protein D

A 2.38 mg/ml solution of polysaccharide of *S. pneumoniae* serotype 23F and 2 M aqueous sodium chloride solution was prepared. To that solution a 100 mg/ml solution of CDAP in acetonitrile/water (1:1 v/v) was added until a ratio of CDAP to polysaccharide of 0.79 (w/w) was reached. 1 minute later the pH was adjusted to 9.5 by adding 0.25 M sodium hydroxide solution under stirring at 25° C. After 3 minutes a 5 mg/ml solution of protein D in 0.2 M aqueous sodium chloride was added until a ratio of protein D/polysaccharide of 1:1 was reached. The reaction mixture was stirred for two hours while the pH was maintained at 9.5. Excess amount of 2 M glycine solution in water for injection was added to quench unreacted cyanate ester groups. The pH was readjusted to 9.0 and the solution was stirred for 30 minutes at 25° C. and afterwards overnight at 2-8° C.

The *S. pneumoniae* serotype 23F/PD-conjugate was purified by gel filtration using a Sehacryl S400HR gel filtration column equilibrated with 0.15 sodium chloride (S500HR for 18C) to remove small molecules, salts and unconjugated polysaccharide and protein D. The conjugate eluted first, followed by the polysaccharide and free protein D. Fractions containing the conjugate were detected by UV spectroscopy at 280 mm, combined, sterile filtered (22 μm) and stored between 2-8° C.

Characterization of *S. pneumoniae* Serotype 23F/PD-Conjugate

The polysaccharide content was measured by the Resorcinol test and the protein content of the conjugate by the Lowry test. Consequently the polysaccharide-protein-ratio was determined from the ratio of the protein content and the polysaccharide content. The molecular weight distribution was measured on a HPLC-SEC gel filtration.

Example H Characterization of Immunogenicity of Inventive Composition Containing a Conjugate of a Saccharide from *Streptococcus pneumoniae* Serotype 2 and a Carrier Protein Rabbit immunization: Ten to twelve week old New Zealand white rabbits (weight around 2.5-3.0 kg) were immunized subcutaneously with conjugate 1, 2 and 41 (2.2 μg sugar per dose) formulated with alum (aluminum hydroxide) containing 125 μg aluminum in different formulation. On day 14 and 28 rabbit received the booster immunization with the same formulation. The polyclonal sera before and after immunization were collected and analyzed.

In vitro opsonophagocytic killing assay: Opsonophagocytic killing assay was performed as described previously (Romero-Steiner et al., 1997). Briefly, the effector cell HL-60 a human origin leukemia cell line was used as phagocytic host cells. For differentiation, the cells were harvested from tissue culture growing in complete medium with antibiotics (90% RPMI 1640, 10% FCS, 1 mM L-glutamine and 1× penicillin-streptomycin solution) at 37° C. in presence of 5% $CO_2$. Approximately $4 \times 10^5$ cells/ml (100 ml volume) was seeded in tissue culture flasks (T-175) in complete medium containing 0.8% N,N-dimethylformamide (tissue culture grade) for 5-6 days at 37° C. in presence of 5% $CO_2$ before performing the assay. After differentiation the cells were harvested by centrifugation (300×g, 5 min)

and viable cells were counted by using 1% trypan blue exclusion and resuspended in opsonophagocytic buffer (HBSS with $Ca^{2+}$ and $Mg^{2+}$ and 0.1% gelatin) at a density of $1\times10^7$ cells/ml.

For opsonophagocytic killing assay we used 400:1 ratio of effector and target cells. The frozen stock of pneumococcal cells (mid-log phage cells; $OD_{600}$=0.3-0.4) were diluted in opsonophagocytic buffer in such a way that 20 µl of bacterial suspension contains approximately 1000 cfu. For final assay, 10 µl pooled rabbit sera samples were aliquoted in round bottom 96 microtiter well plates in triplicates in 4× dilutions (starting from 1:8 to 1:1024). 20 µl of bacterial suspension was added in each well and bacteria were preopsonized for 15 min at 37° C. After preopsonization, 10 µl of baby rabbit complement as complement source and followed by 40 µl differentiated HL-60 cells ($4\times10^5$ cells) were added in each well. Finally the plats were incubated for 45 min at 37° C. and 5% $CO_2$ with intermittent shaking for phagocytosis. The phagocytic reaction was stopped keeping the mixture on ice for 20 min. Each sample was used in triplicates. Preimmune sera (day 0) and day 35 anti-$CRM_{197}$ were used as negative controls, while day 35 sera of anti-Prevnar13® and Synflorix® were used as positive controls, respectively. The viable extracellular pneumococci were determined by plating 5 µl aliquots from each well on blood agar plates. The whole assay repeated 2 times independently and percent killing was analyzed to the reciprocal of control group where 'no sera'.

Result: Antibodies against semisynthetic inventive conjugate vaccine promote killing of pneumococci by phagocytosis. The antibodies against capsular polysaccharides from pathogenic microorganism are reported protective. Here, we interested to check whether the antibodies raised against semisynthetic conjugates facilitate the clearance of pneumococci by phagocytosis. To analyze antibody mediated protection, we performed opsonophagocytic killing assay (OPKA) with the antibodies induced in response to immunization with conjugate 1 (serotype 2), conjugate 2 (serotype 3) and conjugate 41 (serotype 8) in different formulation. The HL-60 a human promyelocytic leukemia cell line was cultured in RPMI 1640 medium containing 10% fetal calf serum at 37° C. in presence of 5% $CO_2$. For OPKA, the HL-60 cells were differentiated into granulocytes using 0.8% dimethylformamide (DMF) in culture medium. After 5 days the differentiated cells were harvested and incubated with pneumococci of different serotypes (ST2 or ST8) that were pre-opsonized with pre and post immunized sera in multiple dilutions (4 fold) and the plate was incubated at 37° C. in 5% $CO_2$ for 45 min with intermittent shaking. The live bacteria were enumerated by plating 5 µl mixtures from each well on blood agar plates by gravity flow and the relative percent killing of pneumococci were calculated. The OPKA results suggest that the antibodies against conjugate 1 (serotype 2) induce significant killing of pneumococci as we tested in individual arm and co-formulation with licensed vaccines (FIGS. 7A&B). Similarly, the conjugate 41 (serotype 8) also promotes the killing of pneumococci in similar fashion (FIGS. 7C&D). In the assay we used anti-Prevnar 13® sera as positive control while anti-$CRM_{197}$ sera as negative control. This result suggested that semisynthetic conjugates generate functional antibodies which promote the killing of pneumococci.

Example I: Glycan Microarray Analysis

For preparation of microarray slides synthetic oligosaccharides (0.2 mM solutions in printing buffer (50 mM sodium phosphate (NaPi) pH 8.5)) and polysaccharides (0.02 or 0.04 µg/mL in printing buffer) were spotted onto "CodeLink" N-hydroxysuccinimide-activated glass slides (SurModics Inc., Eden Prairie, USA) using an automated piezoelectric arraying robot (Scienion, Berlin, Germany) at 0.4 nL per spot and incubated for 24 h at room temperature in a humified chamber. Slides were quenched for 1 h at room temperature using 100 mM ethanolamine in 0.1 M NaPi pH 9, washed with water and stored in a dry chamber until use.

Slides were blocked for 1 h at room temperature with 1% (w/v) bovine serum albumin (BSA) in phosphate buffered saline (PBS, 10 mM $Na_2HPO_4$, 1.8 mM $K_2HPO_4$, 137 mM NaCl, 2.7 mM KCl) and anti-*S. pneumoniae* antibody dilutions were applied using a 64 well gasket (FlexWell 64, Grace Bio-Labs, Bend, US). The slides were incubated for 16 h at 4° C. in a humified chamber, washed three times with 0.1% (v/v) Tween® 20 in PBS (PBS-T) and treated with a fluorescence-labeled goat anti-mouse secondary antibodies (Life Technologies) diluted in 1% BSA in PBS (w/v) in a humid chamber for 1 h at room temperature. The slides were incubated for 1.5 h at room temperature in a dark, humified chamber, washed three times with washing buffer and with water. Fluorescence read-out was performed using an Axon GenePix 4300A microarray scanner and GenePix Pro 7 software (both MDS, Sunnyvale, US). Negative fluorescence intensities were arbitrarily set to 0. All statistical analyses were performed using Prism 6 (Graphpad Software Inc., La Jolla, USA). Brightness and contrast of related images (e.g. all sera of the same mouse) were adjusted equally using Photoshop CS5 (Adobe Systems).

Figure 7:
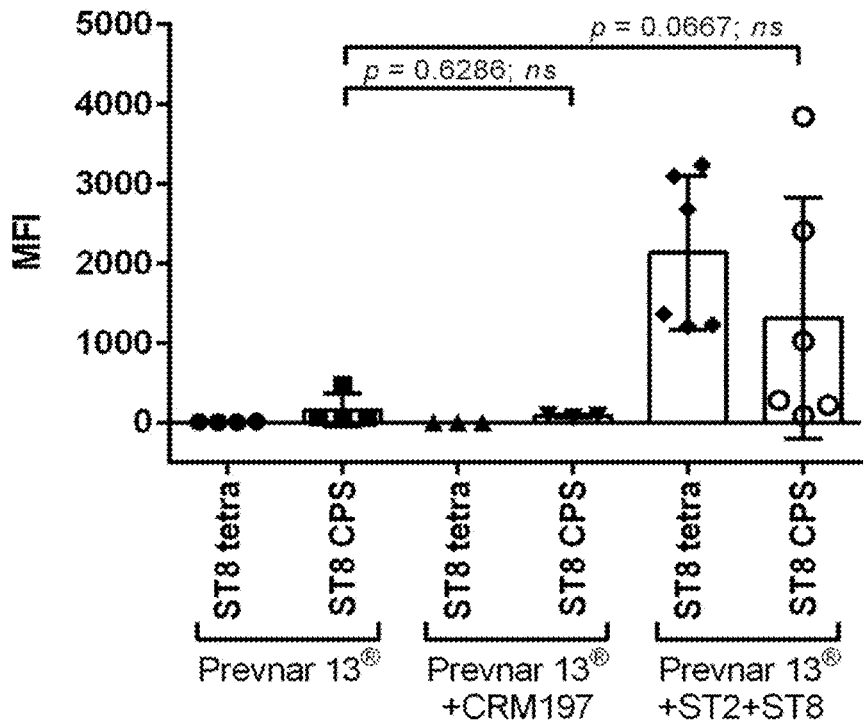
FIG. 7 shows a glycan microarray analysis comparing capsular poly-saccharide of serotype 8 recognition by antisera produced by immunization with a coformulation of Prevnar13® with conjugate 1 and conjugate 41, Prevnar13® alone or Prevnar13® with additional CRM197. A significant immune response was induced by the coformulation of Prevnar13® with conjugate 1 and conjugate 41 against *S. pneumoniae* of serotype 8, as demonstrated by the binding of the raised antibodies to tetrasaccharide as well as capsular polysaccharide of serotype 8.
Figure 8:
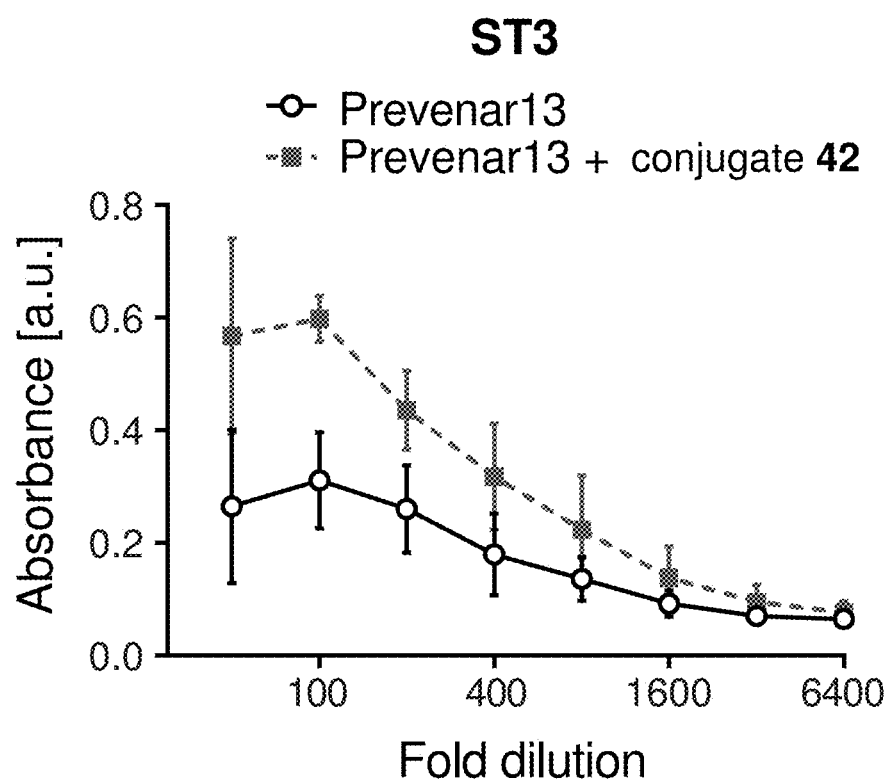
FIG. 8 shows the effect of coformulation of conjugate 42 with Prevnar13® on the immune response against the capsular polysaccharides of *S. pneumoniae* serotype 3 as assessed by polysaccharide ELISA as described in example E.
Figure 9:
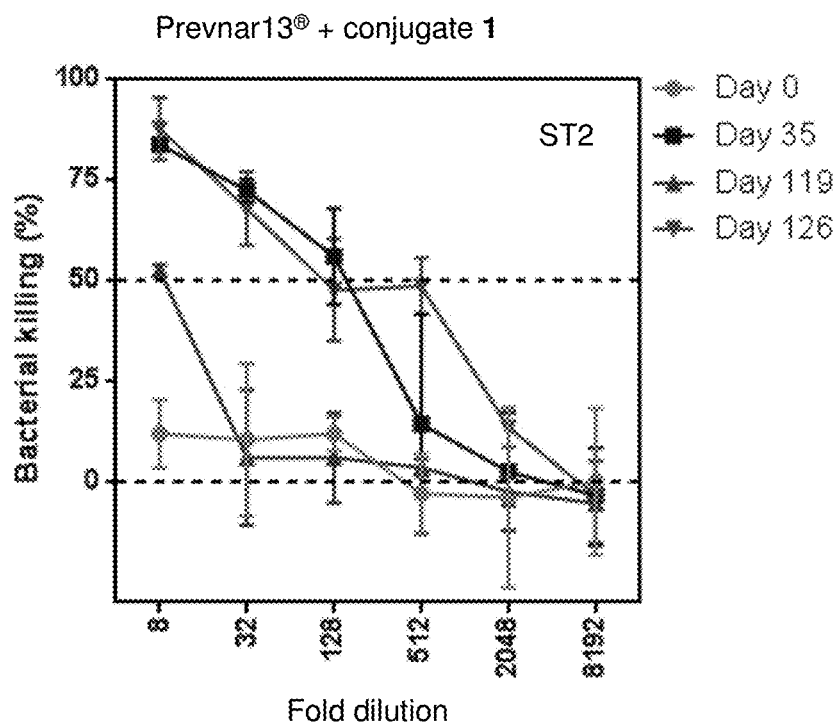
FIG. 9 shows opsonophagocytic activity of antibodies elicited by coformulation of (A) Prevnar13® with conjugate 1, (B) Synflorix® with conjugate 1, (C) Prevnar13® with conjugate 41, and (D) Synflorix® with conjugate 41 after 0 days, 35 days, 119 days and 126 days.
Figure 9:
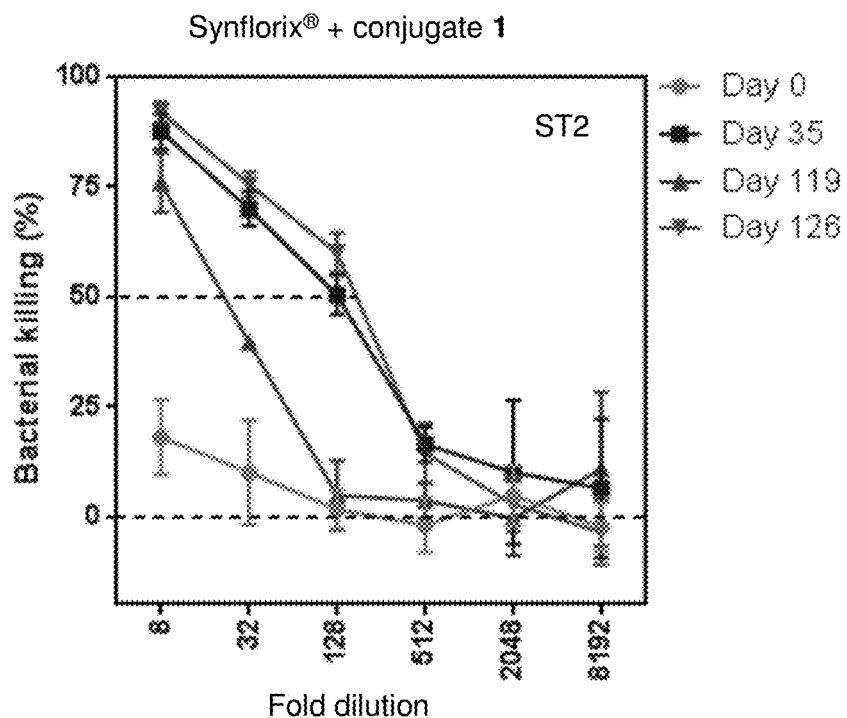
Figure 9:
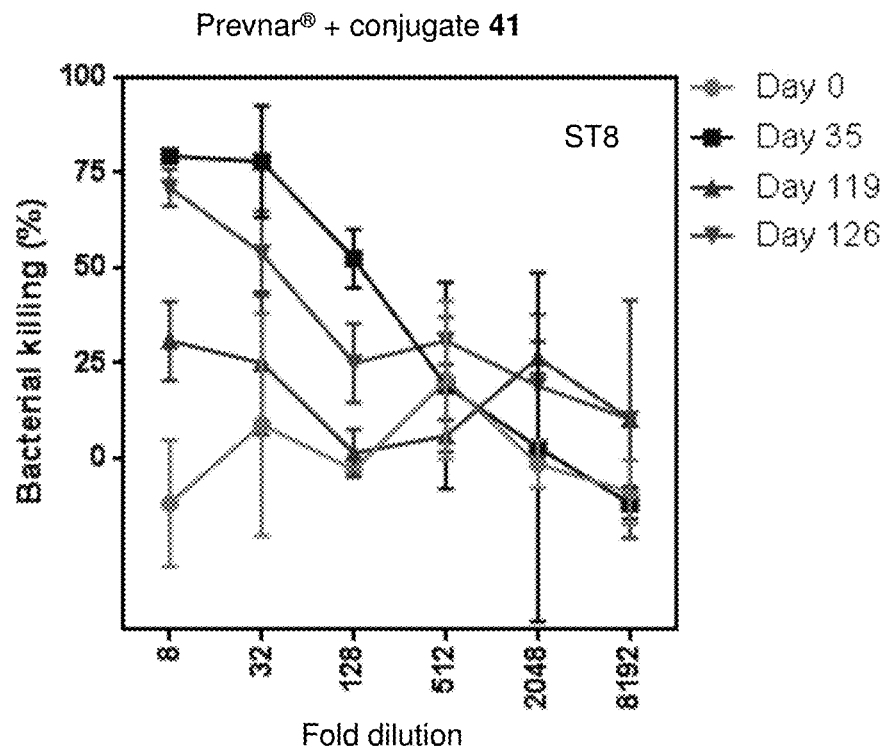
Figure 9:
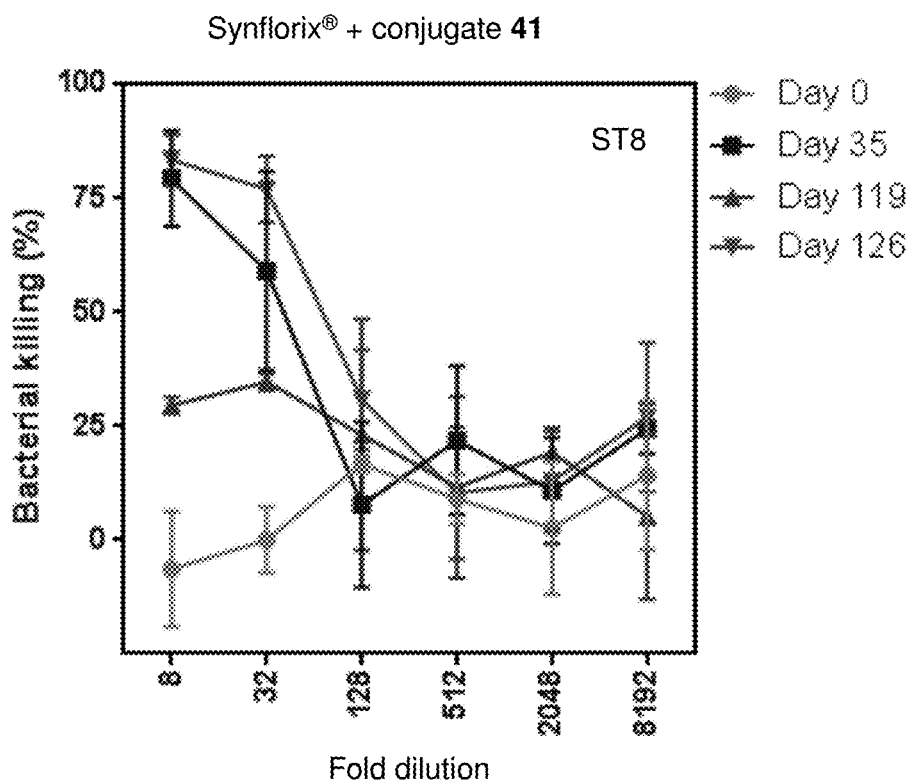
Figure 10:
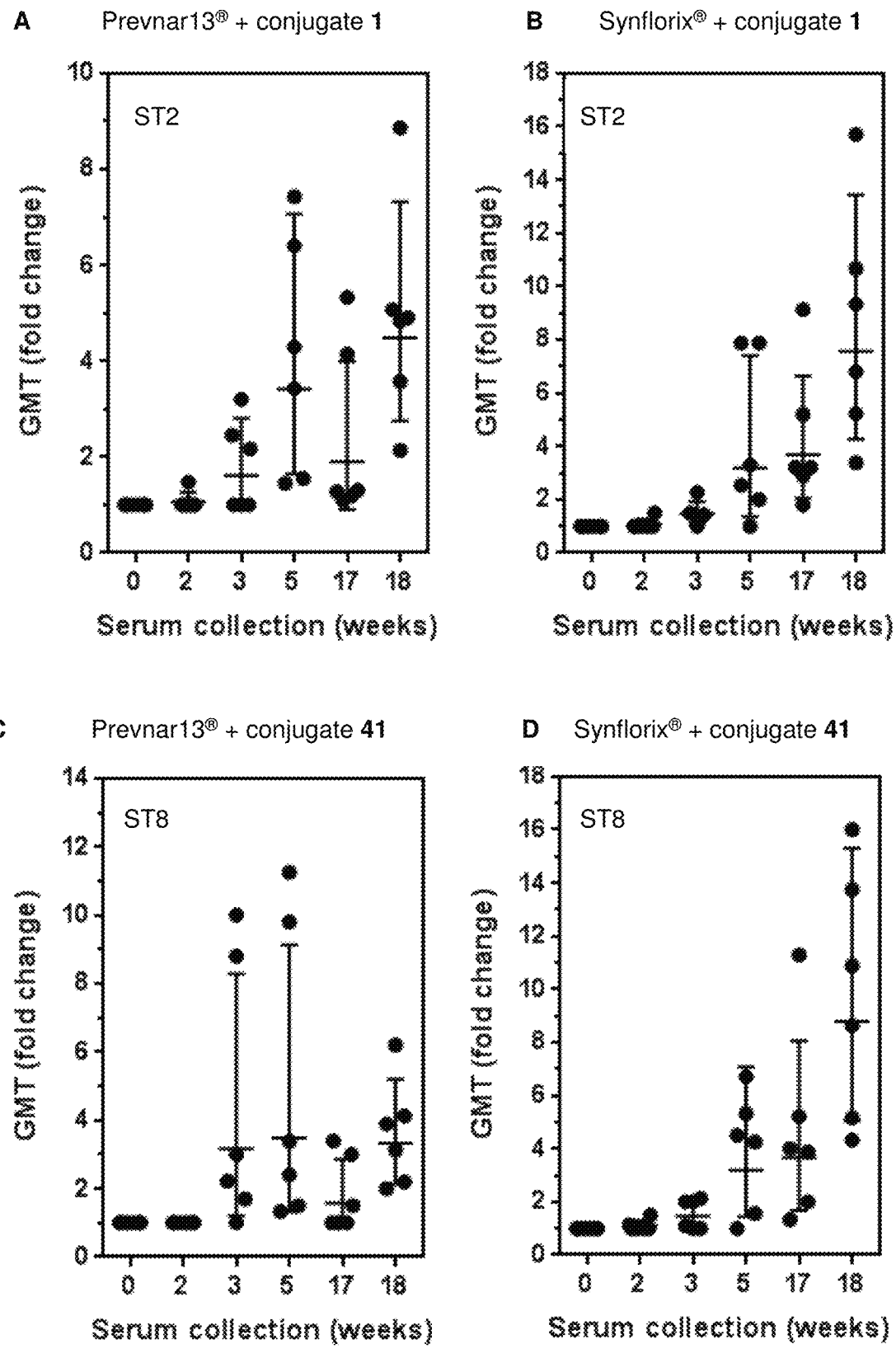
FIG. 10 shows the effect of coformulation of coformulation of (A) Prevnar13® with conjugate 1, (B) Synflorix® with conjugate 1, (C) Prevnar13® with conjugate 41, and (D) Synflorix® with conjugate 41 on the immune response against *S. pneumoniae* capsular polysaccharides of serotype 2 (A+B) and serotype 8 (B+C) after 0, 2, 3, 5, 17 and 18 weeks, as assessed by polysaccharide ELISA (GMT: Geometric Mean Titer). Sera were diluted by 1:500 and pre-adsorbed to pneumococcal cell wall polysaccharides (CWPs) and *S. pneumoniae* serotype 22F CPS before application. Bars depict mean±SD of polysaccharide binding of three rabbits per group and each dot represents an individual rabbit.

Results are shown in FIG. 7.

The invention claimed is:

1. An immunogenic composition comprising:
a conjugate of an oligosaccharide from *Streptococcus pneumoniae* serotype 8 and a carrier protein;
a mixture of conjugated capsular polysaccharides from *Streptococcus pneumoniae* consisting of capsular polysaccharides from *Streptococcus pneumoniae* serotypes 1, 3, 4, 5, 6A, 6B, 7F, 9V, 14, 18C, 19A, 19F and 23F individually conjugated to $CRM_{197}$ carrier protein; and
optionally an adjuvant, wherein the adjuvant is selected from the group consisting of an aluminum salt, an oil-in-water emulsion formulation and a saponin based adjuvant.

2. The immunogenic composition according to claim 1, wherein the conjugate of an oligosaccharide from *Streptococcus pneumoniae* serotype 8 and a carrier protein is of the following general formula (I):

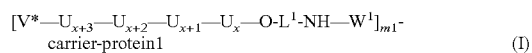

(I)

wherein
x is an integer selected from 1, 2, 3 and 4;

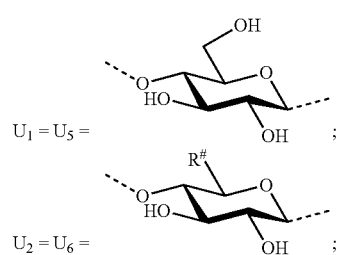

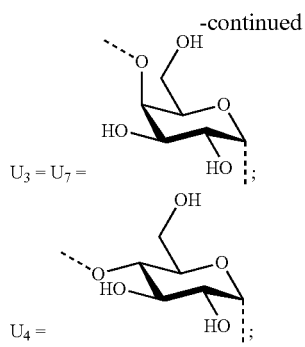

$U_3 = U_7 =$ $U_4 =$

V*— represents H—, H—$U_x$— or H—$U_{x+1}$—$U_x$—;
$R^\#$ represents —COOH or —CH$_2$OH;
$L^1$ represents a linker;
m1 is comprised between 2 and 18;
—$W^1$— is selected from:

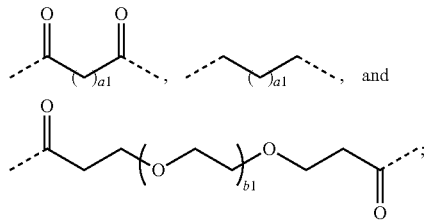

a1 represents an integer from 1 to 10;
b1 represents an integer from 1 to 4; and
carrier-protein1 is selected from CRM$_{197}$, protein D, tetanus toxoid and diphtheria toxoid.

3. The immunogenic composition according to claim 2, wherein x represents 3 and/or V*— represents H—.

4. A method for raising a protective immune response in a human or animal host comprising administering to the human or animal host the immunogenic composition according to claim 1.

5. The method according to claim 4 wherein the protective immune response is raised against *Streptococcus pneumoniae* serotype 8.

6. A vaccine comprising the immunogenic composition according to claim 1, a physiologically acceptable vehicle and an adjuvant, wherein the adjuvant is selected from the group consisting of an aluminum salt, an oil-in-water emulsion formulation and a saponin based adjuvant.

7. The vaccine according to claim 6, wherein the adjuvant is aluminium phosphate.

8. An immunogenic composition comprising:
a conjugate of an oligosaccharide from *Streptococcus pneumoniae* serotype 8 and a carrier protein; and
a conjugate of an oligosaccharide from *Streptococcus pneumoniae* serotype 2; and
a mixture of conjugated capsular polysaccharides from *Streptococcus pneumoniae* consisting of capsular polysaccharides from *Streptococcus pneumoniae* serotypes 1, 3, 4, 5, 6A, 6B, 7F, 9V, 14, 18C, 19A, 19F and 23F individually conjugated to CRM$_{197}$ carrier protein; and
optionally an adjuvant, wherein the adjuvant is selected from the group consisting of an aluminum salt, an oil-in-water emulsion formulation and a saponin based adjuvant.

9. The immunogenic composition according to claim 8, wherein the conjugate of an oligosaccharide from *Streptococcus pneumoniae* serotype 8 and a carrier protein is of following general formula (I):

$$[V^*—U_{x+3}—U_{x+2}—U_{x+1}—U_x—O-L^1-NH—W^1]_{m1}\text{-carrier-protein1} \quad (I)$$

wherein
x is an integer selected from 1, 2, 3 and 4;

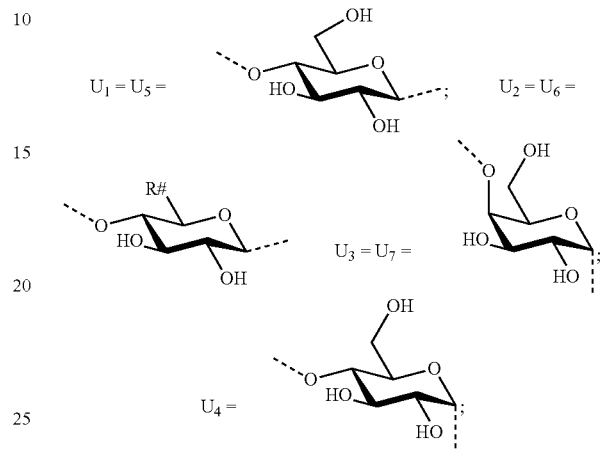

V*— represents H—, H—$U_x$— or H—$U_{x+1}$—$U_x$—;
$R^\#$ represents —COOH or —CH$_2$OH;
$L^1$ represents a linker;
m1 is comprised between 2 and 18;
—$W^1$— is selected from:

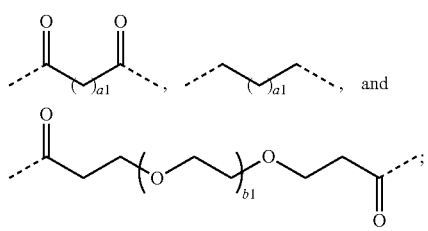

a1 represents an integer from 1 to 10;
b1 represents an integer from 1 to 4; and
carrier-protein1 is selected from CRM$_{197}$, protein D, tetanus toxoid and diphtheria toxoid.

10. The immunogenic composition according to claim 9, wherein x represents 3 and/or V*— represents H—.

11. The immunogenic composition according to claim 8, wherein the conjugate of an oligosaccharide from *Streptococcus pneumoniae* serotype 2 has following general formula (II-C)

$$[B^*-A_{y+3}-A_{y+2}-A_{y+1}-A_y-O-L^2-NH—W^2]_{m2}\text{-carrier-protein2} \quad (II\text{-}C)$$

wherein
y is an integer selected from 1, 2, 3 and 4;

$A_1 = A_5 =$ 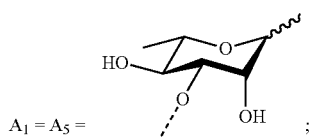 ;

-continued $A_2 = A_6 =$ 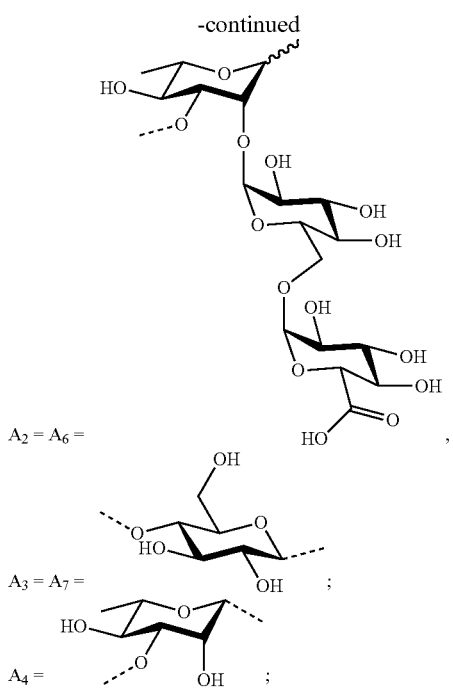  , $A_3 = A_7 =$ 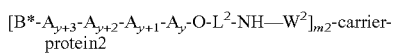  ;

$A_4 =$   ;

B*— represents H—, H-$A_y$-, H-$A_{y+1}$-$A_y$-, H-$A_{y+2}$-$A_{y+1}$-$A_y$- or H-$A_{y+3}$-$A_{y+2}$-$A_{y+1}$-$A_y$-;

$L^2$ represents a linker;

m2 is comprised between about 2 and about 18;

—$W^2$— is selected from:

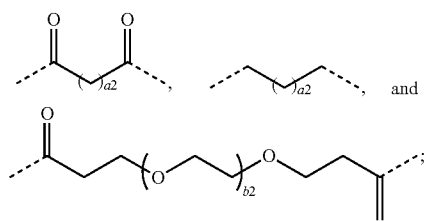

a2 represents an integer from 1 to 10;

b2 represents an integer from 1 to 4; and carrier-protein2 is selected from CRM$_{197}$, protein D, tetanus toxoid and diphtheria toxoid.

12. The immunogenic composition according to claim 11, wherein the conjugate of an oligosaccharide from *Streptococcus pneumoniae* serotype 2 has following general formula (II)

[B*-$A_{y+3}$-$A_{y+2}$-$A_{y+1}$-$A_y$-O-$L^2$-NH—$W^2$]$_{m2}$-carrier-protein2    (II)

wherein $A_1 = A_5 =$ 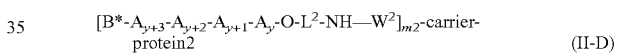  ;

-continued $A_2 = A_6 =$ 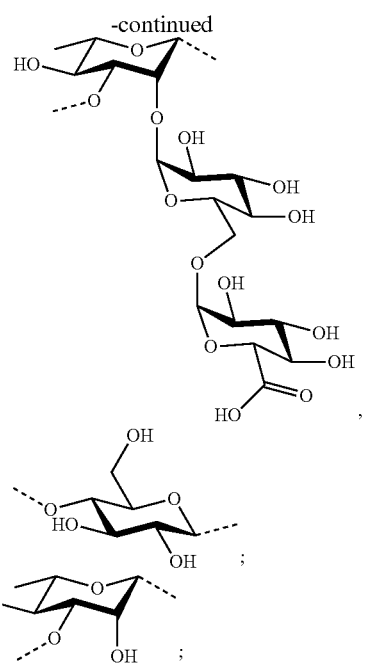  , $A_3 = A_7 =$ 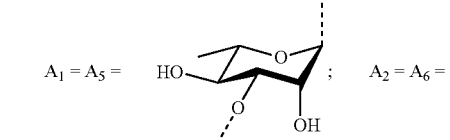  ;

$A_4 =$ ;

and y, B*—, $L^2$, m2, —$W^2$— and carrier-protein2 have the meanings as defined in claim 11.

13. The immunogenic composition according to claim 11, wherein the conjugate of an oligosaccharide from *Streptococcus pneumoniae* serotype 2 has the following general formula (II-D)

[B*-$A_{y+3}$-$A_{y+2}$-$A_{y+1}$-$A_y$-O-$L^2$-NH—$W^2$]$_{m2}$-carrier-protein2    (II-D)

wherein

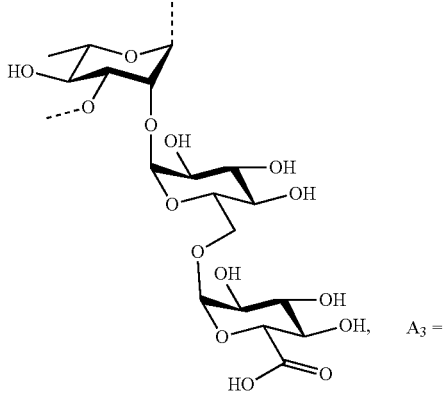

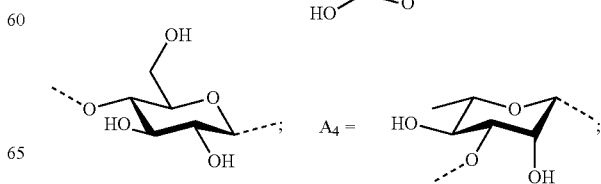

-continued

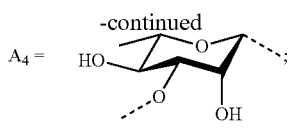

and y, $B^*$—, $L^2$, m2, —$W^2$— and carrier-protein2 have the meanings as defined in claim 11.

14. The immunogenic composition according to claim 11, wherein y represents 1 and/or $B^*$— represents H—.

15. The immunogenic composition according to claim 12, wherein y is 1 and/or $B^*$— represents H—.

16. The immunogenic composition according to claim 13, wherein y is 1 and/or $B^*$— represents H—.

17. A vaccine comprising the immunogenic composition according to claim 8, a physiologically acceptable vehicle and an adjuvant.

18. The vaccine according to claim 17, wherein the adjuvant is aluminium phosphate.

* * * * *